(12) United States Patent
Peddi et al.

(10) Patent No.: US 8,507,493 B2
(45) Date of Patent: Aug. 13, 2013

(54) AMIDE AND AMIDINE DERIVATIVES AND USES THEREOF

(75) Inventors: Sridhar Peddi, Grayslake, IL (US); Meena V. Patel, Green Oaks, IL (US); Jeffrey J. Rohde, Evanston, IL (US)

(73) Assignee: AbbVie Inc., North Chicago, IL (US)

( * ) Notice: Subject to any disclaimer, the term of this patent is extended or adjusted under 35 U.S.C. 154(b) by 523 days.

(21) Appl. No.: 12/763,808

(22) Filed: Apr. 20, 2010

(65) Prior Publication Data

US 2010/0267738 A1 Oct. 21, 2010

Related U.S. Application Data

(60) Provisional application No. 61/170,943, filed on Apr. 20, 2009, provisional application No. 61/187,500, filed on Jun. 16, 2009.

(51) Int. Cl.
| | |
|---|---|
| A61K 31/496 | (2006.01) |
| A61K 31/155 | (2006.01) |
| A61K 31/277 | (2006.01) |
| A61K 31/165 | (2006.01) |
| C07D 401/02 | (2006.01) |
| C07D 401/04 | (2006.01) |
| C07D 213/84 | (2006.01) |
| C07C 255/00 | (2006.01) |
| C07C 327/38 | (2006.01) |
| C07C 257/10 | (2006.01) |

(52) U.S. Cl.
USPC ...... 514/253.01; 514/343; 514/520; 514/599; 514/637; 544/360; 546/286; 546/276.4; 558/303; 564/305; 564/244

(58) Field of Classification Search
USPC ............... 514/253.01, 343, 520, 599, 637; 558/303; 546/286, 276.4; 564/305, 244; 544/360
See application file for complete search history.

(56) References Cited

U.S. PATENT DOCUMENTS

| | | | |
|---|---|---|---|
| 2,450,386 A * | 9/1948 | Short et al. ............... 546/229 |
| 5,308,869 A * | 5/1994 | Keana et al. ............... 514/637 |
| 5,338,745 A | 8/1994 | Fukazawa et al. |
| 7,087,400 B2 | 8/2006 | Walker et al. |
| 7,122,531 B2 | 10/2006 | Walker et al. |
| 7,217,838 B2 | 5/2007 | Rohde et al. |
| 7,435,833 B2 | 10/2008 | Yeh et al. |
| 7,511,013 B2 | 3/2009 | Molino et al. |
| 7,511,175 B2 | 3/2009 | Patel et al. |
| 7,514,068 B2 | 4/2009 | Tung |
| 7,521,421 B2 | 4/2009 | Naicker et al. |
| 7,528,131 B2 | 5/2009 | Persichetti et al. |
| 7,528,282 B2 | 5/2009 | Rohde et al. |
| 7,531,685 B2 | 5/2009 | Czarnik |
| 7,534,814 B2 | 5/2009 | Ascher et al. |
| 7,538,189 B2 | 5/2009 | Naicker et al. |
| 2005/0277647 A1 | 12/2005 | Link et al. |
| 2005/0277747 A1 | 12/2005 | McLaughlin et al. |
| 2006/0025614 A1 | 2/2006 | Carroll et al. |
| 2006/0149070 A1 | 7/2006 | Rohde et al. |
| 2006/0281773 A1 | 12/2006 | Patel et al. |
| 2007/0066584 A1 | 3/2007 | Yao et al. |
| 2007/0088088 A1 | 4/2007 | Inada et al. |
| 2007/0129345 A1 | 6/2007 | Zhuo et al. |
| 2007/0167622 A1 | 7/2007 | Gillespie et al. |
| 2007/0208001 A1 | 9/2007 | Zhuo et al. |
| 2008/0076819 A1 | 3/2008 | Yeh et al. |
| 2008/0312214 A1 | 12/2008 | Yeh et al. |
| 2009/0054426 A1 | 2/2009 | Bitner et al. |
| 2009/0082471 A1 | 3/2009 | Czarnik |
| 2009/0088416 A1 | 4/2009 | Czarnik |
| 2009/0093422 A1 | 4/2009 | Tung et al. |
| 2009/0105147 A1 | 4/2009 | Masse |
| 2009/0105307 A1 | 4/2009 | Galley et al. |
| 2009/0105338 A1 | 4/2009 | Czarnik |
| 2009/0111840 A1 | 4/2009 | Herold et al. |
| 2009/0118238 A1 | 5/2009 | Czarnik |
| 2009/0131363 A1 | 5/2009 | Harbeson |
| 2009/0131485 A1 | 5/2009 | Liu et al. |
| 2009/0137457 A1 | 5/2009 | Harbeson |
| 2010/0267738 A1 | 10/2010 | Peddi et al. |

FOREIGN PATENT DOCUMENTS

| | | |
|---|---|---|
| EP | 0333522 A2 | 9/1989 |
| EP | 0418065 A2 | 3/1991 |
| EP | 1889842 A1 | 2/2008 |
| WO | WO9507271 A1 | 3/1995 |
| WO | WO9710223 A1 | 3/1997 |
| WO | WO2004011310 A1 | 2/2004 |
| WO | WO2005099353 A2 | 10/2005 |
| WO | WO2006008754 A1 | 1/2006 |
| WO | WO2006024628 A1 | 3/2006 |
| WO | WO2006048750 A2 | 5/2006 |

(Continued)

OTHER PUBLICATIONS

Anstead, G., "Steroids, Retinoids, and Wound Healing," Advanced Wound Care, 1998, vol. 11, pp. 277-285. Armaly, et al., "Dexamethasone Ocular Hypertension and Eosinopenia, and Glucose Tolerance Test," Archives of Ophthalmology, 1967, vol. 78, pp. 193-197.
Baxter, J. "Glucocorticoid Hormone Action," Pharmacology and Therapeutics, 1976, vol. 2, pp. 605-659.
Becker, et al., "A Convergent Process for the Preparation of Adamantane 11β-HSD-1 Inhibitors," Organic Process Research & Development, 2008, vol. 12 (6), pp. 1114-1118.
Becker, et al., "A Short Synthesis of 1-Azaadamantan-4-One and the 4r and 4s Isomers of 4-Amino-1-Azaadarnantane," Synthesis, 1992, vol. 11, pp. 1080-1082.

(Continued)

*Primary Examiner* — Kristin Bianchi
(74) *Attorney, Agent, or Firm* — Lisa V. Mueller; Michael Best & Friedrich LLP

(57) ABSTRACT

The present invention relates to inhibitors of 11-β-hydroxysteroid dehydrogenase type 1 enzyme and their use in treatment of non-insulin dependent type 2 diabetes, insulin resistance, obesity, lipid disorders, metabolic syndrome, central nervous system disorders, and diseases and conditions that are related to excessive glucocorticoids.

7 Claims, No Drawings

(56) References Cited

FOREIGN PATENT DOCUMENTS

| WO | WO2007051810 A2 | 5/2007 |
|---|---|---|
| WO | WO2007051811 A2 | 5/2007 |
| WO | WO2007058346 A1 | 5/2007 |
| WO | WO2007084314 A2 | 7/2007 |
| WO | WO2007101270 A1 | 9/2007 |
| WO | WO2007107470 A2 | 9/2007 |
| WO | WO2007107550 A1 | 9/2007 |
| WO | WO2007111921 A1 | 10/2007 |
| WO | WO2007114124 A1 | 10/2007 |
| WO | WO2007114125 A1 | 10/2007 |
| WO | WO2007115935 A1 | 10/2007 |
| WO | WO2007118185 A2 | 10/2007 |
| WO | WO2007124254 A2 | 11/2007 |
| WO | WO2007124329 A1 | 11/2007 |
| WO | WO2007124337 A1 | 11/2007 |
| WO | WO2007127688 A2 | 11/2007 |
| WO | WO2007127693 A1 | 11/2007 |
| WO | WO2007127704 A1 | 11/2007 |
| WO | WO2007127726 A2 | 11/2007 |
| WO | WO2007127763 A2 | 11/2007 |
| WO | WO2007127765 A1 | 11/2007 |
| WO | WO2007127901 A1 | 11/2007 |
| WO | WO2007144394 A2 | 12/2007 |
| WO | WO2007145834 A2 | 12/2007 |
| WO | WO2007145835 A2 | 12/2007 |
| WO | WO2008006702 A1 | 1/2008 |
| WO | WO2008006703 A1 | 1/2008 |
| WO | WO2008011453 A2 | 1/2008 |
| WO | WO2008012532 A2 | 1/2008 |
| WO | WO2008024892 A2 | 2/2008 |
| WO | WO2008052638 A1 | 5/2008 |
| WO | WO2008053194 A2 | 5/2008 |
| WO | WO2008069313 A1 | 6/2008 |
| WO | WO2008074384 A1 | 6/2008 |
| WO | WO2008088540 A2 | 7/2008 |
| WO | WO2008099145 A1 | 8/2008 |
| WO | WO2008101885 A1 | 8/2008 |
| WO | WO2008101886 A1 | 8/2008 |
| WO | WO2008101907 A1 | 8/2008 |
| WO | WO2008101914 A2 | 8/2008 |
| WO | WO2008110196 A1 | 9/2008 |
| WO | WO2008119017 A1 | 10/2008 |
| WO | WO2008127924 A1 | 10/2008 |
| WO | WO2008134221 A1 | 11/2008 |
| WO | WO2008142859 A1 | 11/2008 |
| WO | WO2008142986 A1 | 11/2008 |
| WO | WO2008157752 A1 | 12/2008 |

OTHER PUBLICATIONS

Becker, "Inhibitors of the 11β-hydroxysteroid dehydrogenase type 1 enzyme," Prin. and Pract. of Endocrin. and Metabolism, 2001, pp. 723-738.
Beer, et al., "Glucocorticoid-Regulated Gene Expression During Cutaneous Wound Repair," Vitamins and Hormones, 2000, vol. 59, pp. 217-239.
Belanoff, et al., "Corticosteroids and Cognition," Journal of Psychiatric Research, 2001, vol. 35, pp. 127-145.
Bellows, et al., "Osteoprogenitor Cells in Cell Populations Derived from Mouse and Rat Calvaria Differ in Their Response to Corticosterone, Cortisol, and Cortisone," Bone, 1998, vol. 23 (2), pp. 119-125.
Bertagna, X., "Cushing's Disease," The Pituitary, 2002, pp. 496-612, Chap. 13 Sec. 3.
Beylot, et al., "In Vivo Studies of Intrahepatic Metabolic Pathways," Diabetes Metabolism, 1997, vol. 23 (3), pp. 251-257.
Billaudel, et al., "Direct Effect of Corticostrone upon Insuline Secretion Studied by Three Different Techniques," Hormone and Metabolic Research, 1979, vol. 11, pp. 555-560.
Billaudel, et al., "Immediate in-Vivo Effect of Corticosterone on Glucose-Induced Insulin Secretion in the Rat," Journal of Endocrinology, 1982, vol. 95, pp. 315-320.
Blagojevic, et al., "Role of heavy water in Boron Neutron Capture Therapy," Topics in Dosimetry & Treatment Planning for Neutron Capture Therapy, 1994, pp. 125-134.

Blake, et al., "Studies With Deuterated Drugs," Journal of Pharmaceutical Sciences, 1975, vol. 64 (3), pp. 367-391.
Bland, et al., "Characterization of 11β-hydroxysteroid Dehydrongenase Activity and Corticosteroid Receptor Expression in Human Osterosarcoma Cell Lines," Journal of Endocrinology, 1999, vol. 161, pp. 455-464.
Boscaro, et al., "Cushing's Syndrome," The Lancet, 2001, vol. 357, pp. 783-791.
Bremner, et al., "The Synthesis of Thienopyridines from ortho-Halogenated Pyridine Dderivates," Synthesis, 1992, vol. 6, pp. 528-530.
Brickner, et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.
Budziszewska, B., "Effect of Antidepressant Drugs on the Hypothalamic-Pituitary-Adrenal Axis Activity and Glucocorticoid Receptor Function," Polish Journal of Pharmacology and Pharmacy, 2002, vol. 54, pp. 343-349.
Cooper, et al., "Expression and Functional Consequences of 11β-Hydroxysteroid Dehydrogenase Activity in Human Bone," Bone, 2000, vol. 27 (3), pp. 375-381.
Cooper, et al., "Modulation of 11β-Hydroxysteroid Dehydrogenase Enzymes by Proinflammatory Cytokines in Osteoblasts: An Autocrine Switch from Glucocorticoid Inactivation to Activation," Journal of Bone and Mineral Research, 2001, vol. 16 (6), pp. 1037-1044.
Cooper, et al., "Osteoblastic 11β-Hydroxysteroid Dehydrogenase Type 1 Activity Increases With Age and Glucocorticoid Exposure," Journal of Bone and Mineral Research, 2002, vol. 17 (6), pp. 979-986.
Cross, et al., "IUPAC Commission on Nomenclature of Organic Chemistry: Rules for the Nomenclature of Organic Chemistry, Section E: Stereochemistry," Pure and Applied Chemistry, 1976, vol. 45, pp. 11-30.
Czajka, et al., "Effect of Deuterium Oxide on the Reproductive Potential of Mice," Annals of the New York Academy of Sciences, 1960, vol. 84, pp. 770-779.
Czajka, et al., "Physiological Effects of Deuterium on Dogs," American Journal of Physiology, 1961, vol. 201 (2), pp. 357-362.
Davani, et al., "Type 1 11β-Hydroxysteroid Dehydrogenase Mediates Glucocorticoid Activation and Insulin Release in Pancreatic Islets," Journal of Biological Chemistry, 2000, vol. 275 (45), pp. 34841-34844.
De Quervain, et al., "Glucocorticoid-Related Genetic Susceptibility for Alzheimer's Disease," Human Molecular Genetics, 2004, vol. 13 (1), pp. 47-52.
Debattista, et al., "The Use of Mifepristone in the Treatment of Neuropsychiatric Disorders," Trends in Endocrinology & Metabolism, 2006, vol. 17 (3), pp. 117-120.
Della, et al., "Synthesis of Bridgehead-Substituted Bicyclo[2.2.1]heptanes. Radical Cyclization of an Oxime Ether and an αβ Unsaturated Ester," Australian Journal of Chemistry, 1994, vol. 47, pp. 1833-1841.
Eliel, et al., "Stereochemistry of Organic Compounds," 1994, pp. 119-120, 1206, John Wiley & Sons, Inc. New York. Table of Contents.
European Search Report for EP Application No. 10004195.3-2103 completed search on Aug. 19, 2010.
Foster, et al., "Deuterium Isotope Effects in the Metabolism of Drugs and Xenobiotics: Implications for Drug Design," Advances in Drug Research, 1985, vol. 14, pp. 2-36.
Furniss, et al., Vogel's Textbook of Practical Organic Chemistry, 5th Edition, Longman Scientific & Technical, 1989, Table of Contents.
Greene, et al., Protective Groups in Organic Synthesis, 3rd Edition, John Wiley and Sons, Inc., 1999, Table of Contents.
Hammami, et al., "Regulation of 11β-Hydroxysteroid Dehydrogenase Activity in Human Skin Fibroblasts: Enzymatic Modulation of Glucocorticoid Action," Journal of Clinical Endocrinology & Metabolism, 1991, vol. 73 (2), pp. 326-334.
Harris, et al., "Intracellular Regeneration of Glucocorticoids by 11β-Hydroxysteroid Dehydrogenase (11β-Hsd)-1 Plays a Key Role in Regulation of the Hypothalamic-Pituitary-Adrenal Axis: Analysis of 11β-Hsd-1-Deficient Mice," Endocrinology, 2001, vol. 142 (1), pp. 114-120.

Higuchi, et al., eds., Pro-drugs as Novels Delivery Systems, vol. 14, ACS Symposium Series, 1975, Table of Contents.

International Search Report for Application No. PCT/US2010/031660, mailed Dec. 21, 2010, 5 pages.

Issa, et al., "Hypothalamic-Pituitary-Adrenal Activity in Aged, Cognitively Impaired and Cognitively Unimpaired Rats," Journal of Neuroscience, 1990, vol. 10 (10), pp. 3247-3254.

Jaroskova, et al., "An Expeditious Preparation of E-2-amino-5-hydroxyadamantane and its Z-isomer," Tetrahedron Letters, 2006, vol. 47, pp. 8063-8067.

Kato, et al., "Synthesis of Deuterated Mosapride Citrate," Journal of Labelled Compounds and Radiopharmaceuticals, 1995, vol. 36 (10), pp. 927-932.

Kerr, et al., "Modulation of Hippocampal Long-Term Potentiation and Long-Term Depression by Corticosteroid Receptor Activation," Psychobiology, 1994, vol. 22 (2), pp. 123-133.

Kershaw, et al., "Adipocyte-Specific Glucocorticoid Inactivation Protects Against Diet-Induced Obesity," Diabetes, 2005, vol. 54 (4), pp. 1023-1031.

Kim, et al., "Effects of Dexamethasone on Proliferation, Activity, and Cytkine Secretion of Normal Human Bone Marrow Stromal Cells: Possible Mechanisms of Glucocorticoidinduced Bone Loss," Journal of Endocrinology, 1999, vol. 162 (3), pp. 371-379.

Kornel, et al., "Steroids Mechanism of the Effects of Glucocorticoids and mineralocorticoids on Vascular Smooth Muscle Contractility," Steroids, 1993, vol. 58 (12), pp. 580-587.

Korolkovas, A., "Development of Drugs" in: Essentials of Medicinal Chemistry, Second Edition, John Wiley and Sons, 1988, pp. 97-118.

Krasutsky, et al., "Heterolytic Decarboxylation Involving Acyltrifluoroacetyl Peroxide Intermediates," Tetrahedron Letters, 2002, vol. 43, pp. 8687-8791.

Kushner, et al., "Pharmacological uses and perspectives of heavy water and deuterated compounds," Canadian Journal of Physiology and Pharmacology, 1999, vol. 77 (2), pp. 79-88.

Lakshmi, et al., "Regional Distribution of 11β-Hydroxysteroid Dehydrogenase in Rat Brain," Endocrinology, 1991, vol. 128 (4), pp. 1741-1748.

Landfield, et al., "Hippocampal Cell Death," Science, 1996, vol. 272 (5266), pp. 1249-1251.

Lima, et al., "Bioisosterism: A Useful Strategy for Molecular Modification and Drug Design," Current Medicinal Chemistry, 2005, vol. 12 (1), pp. 23-49.

Link, J., "Pharmacological Regulation of Hepatic Glucose Production," Current Opinion in Investigational Drugs, 2003, vol. 4 (4), pp. 421-429.

Lizondo, et al., "Linezolid: Oxazolidinone antibacterial," Drugs of the Future, 1996, vol. 21 (11), pp. 1116-1123.

Loeffler, et al., "Bridged Bicyclic and Polycyclic Amino Acids, Potent New Inhibitors of the Fibrinolytic Process," Journal of Medicinal Chemistry, 1970, vol. 13 (5), pp. 926-935.

Lupien, S., "Cortisol Levels during Human aging Predict Hippocampal Atrophy and Memory Deficits," Nature Neuroscience, 1998, vol. 1 (1), pp. 69-73.

Mallesham, B, et al., "Highly Efficient Cui-Catalyzed Coupling of Aryl Bromides With Oxazolidinones Using Buchwald's Protocol: A Short Route to Linezolid and Toloxatone," Organic Letters, 2003, vol. 5 (7), pp. 963-965.

Mason, D., "Genetic Variation in the Stress Response: Susceptibility to Experimental Allergic Encephalomyelitis and Implications for Human Inflammatory Disease," Immunology Today, 1991, vol. 12 (2), pp. 57-60.

Masuzaki, et al., "A Transgenic Model of Fisceral Obesity and the Metabolic Syndrome," Science, 2001, vol. 294, pp. 2166-2170.

McEwen, B., "Glucocorticoids, Depression, and Mood Disorders: Structural Remodeling in the Brain," Metabolism—Clinical and Experimental, 2005, vol. 54 (5 Supp1), pp. 20-23.

Moisan, et al., "11β-Hydroxysteroid Dehydrogenase Bioactivity and Messenger RNA Expression in Rat Forebrain: Localization in Hypothalamus, Hippocampus, and Cortex," Endocrinology, 1990, vol. 127 (3), pp. 1450-1455.

Montague, et al., "The Perils of Portliness: Causes and Consequences of Fisceral Adiposity," Diabetes, 2000, vol. 49 (6), pp. 883-888.

Norman, et al., "Emerging Treatments for Major Depression," Expert Review of Neurotherapeutics, 2007, vol. 7 (2), pp. 203-213.

Orth, D., "Cushing's Syndrome," The New England Journal of Medicine, 1995, vol. 332 (12), pp. 791-803.

Patel, et al., "Discovery of Adamantane Ethers as Inhibitors of 11β-HSD-1: Synthesis and Biological Evaluation," Bioorganic and Medicinal Chemistry Letters, 2007, vol. 17 (3), pp. 750-755.

Paterson, et al., "Metabolic Syndrome without Obesity: Hepatic over Expression of 11β-Hydroxysteroid Dehydrogenase Type 1 in Transgenic Mice," The Proceedings of the National Academy of Sciences of the United States of America, 2004, vol. 101 (18), pp. 7088-7093.

Pirpiris, M., "Hypertension Pressor Responsiveness in Corticosteroid-Induced Hypertension in Humans," Hypertension, 1992, vol. 19 (6 pt 1), pp. 567-574.

Poste, et al., "Lipid Vesicles as Carriers for Introducing Biologically Active Materials into Cells," Methods in Cell Biology, 1976, vol. 14, pp. 33-71.

Rajan, et al., "11β-Hydroxysteroid Dehydrogenase in Cultured Hippocampal Cells Reactivates Inert 11-dehydrocorticosterone, Potentiating Neurotoxicity," Journal of Neuroscience, 1996, vol. 16 (1), pp. 65-70.

Rauz, et al., "Expression and Putative Role of 11β-Hydroxysteroid Dehydrogenase Isozymes within the Human Eye," Investigative Ophthalmology & Visual Science, 2001, vol. 42 (9), pp. 2037-2042.

Rauz, et al., "Inhibition of 11β-Hydroxysteroid Dehydrogenase type 1 lowers Intraocular Pressure in Patients with Ocular Hypertension," QJM Monthly Journal of the Association of Physicians, 2003, vol. 96 (7), pp. 481-490.

Rehman, et al., "Effect of Glucocorticoids on Bone Density," Medical and Pediatric Oncology, 2003, vol. 41 (3), pp. 212-216.

Roberts, et al., "Syntheses of Some 4-Substituted Bicyclo [2.2.2]octane-1-carboxylic Acids," Journal of the American Chemical Society, 1953, vol. 75, pp. 637-640.

Roche, E., ed., Bioreversible Carries in Drug Design Theory and Application, Pergamon Press, 1987, Table of Contents.

Rohde, et al., "Discovery and Metabolic Stabilization of Potent and Selective 2-Amino-N-(Adamant-2-YI) Acetamide 11β-Hydroxysteroid Dehydrogenase Type 1 Inhibitors," Journal of Medicinal Chemistry, 2007, vol. 50 (1), pp. 149-164.

Rook, G., "Glucocorticoids and Immune Function," Baillieres Best Practice and Research Clinical Endocrinology Metabolism, 1999, vol. 13 (4), pp. 567-581.

Sakai, et al., "Immunocytochemical Localization of 11β-Hydroxysteroid Dehydrogenase in Hippocampus and Other Brain Regions of the Rat," Journal of Neuroendocrinology, 1992, vol. 4 (1), pp. 101-106.

Sandeep, et al., "11β-Hydroxysteroid Dehydrogenase Inhibition Improves Cognitive Function in Healthy Elderly Men and Type 2 Diabetics," Proceedings of the National Academy of Sciences, 2004, vol. 101 (17), pp. 6734-6739.

Seckl, et al., "11β-Hydroxysteroid Dehydrogenase Type 1-A Tissue Specific Amplifier of Glucocorticoid Action," Endocrinology Minireview, 2001, vol. 142, pp. 1371-1376.

Seckl, et al., "The 11-β-Hydroxysteroid Dehydrogenase Inhibitor Glycyrrhetinic Acid Affects Corticosteroid Feedback Regulation of Hypothalamic Corticotrophin-releasing Peptides in Rats," Journal of Endocrinology, 1993, vol. 136 (3), pp. 471-477.

Sorensen, et al., "Adamantane Sulfone and Sulfonamide 11β-HSD1 Inhibitors," Bioorganic and Medicinal Chemistry Letters, 2007, vol. 17 (2), pp. 527-532.

Stokes, et al., "Altered Peripheral Sensitivity to Glucocorticoids in Primary Open-Angle Glaucoma," Investigative Ophthalmology & Visual Science, 2003, vol. 44 (12), pp. 5163-5167.

Strohle, et al., "Stress Responsive Neurohormones in Depression and Anxiety," Pharmacopsychiatry, 2003, vol. 36 supp1, pp. S207-S214.

Su, et al., "Inhibitors of 11β-hydroxysteroid Dehydrogenase Type 1," Progress in Medicinal Chemistry, 2008, vol. 46, pp. 29-130.

Tadayyon, M., "Insulin Sensitization in the Treatment of Type 2 Diabetes," Expert Opinion on Investigational Drugs, 2003, vol. 12 (3), pp. 307-324.

Thomson, J., "Physiological Effects of D20 in Mammals," Annals of the New York Academy of Sciences, 1960, vol. 84, pp. 736-744.
Turner, et al., "Prednisone Inhibits Formation of Cortical Bone in Sham-Operated and Ovariectomized Female Rats," Calcified Tissue International, 1995, vol. 56, pp. 311-315.
Walker, et al., "Corticosteroids and Vascular Tone: Mapping the Messenger Maze," Clinical Science, 1992, vol. 82 (6), pp. 597-605.
Wang, M., "Glucocorticoid Antagonists and 11β-HSD1 Inhibitors," Drug Discovery Today: Therapeutic Strategies, 2007, vol. 4 (2), pp. 117-122.
Webster, et al., "11β-Hydroxysteroid Dehydrogenase Type 1 Inhibitors as Therapeutic Agents," Expert Opinion on Therapeutic Patents, 2007, vol. 17 (12), pp. 1407-1422.
Wilcox, et al., "The Preparation of 4-Substituted Bicyclo[2.2.1]heptane-1-Carboxylic Acids," Journal of Organic Chemistry, 1968, vol. 88 (2), pp. 877-880.
Wilcox, et al., "The Synthesis of 1,4-Dichlorobicyclo[2.2.1]heptane," Journal of Organic Chemistry, 1964, vol. 29, pp. 2209-2211.
Wolkowitz, et al., "The Steroid Dementia Syndrome: An Unrecognized Complication of Glucocorticoid Treatment," Annals of the New York Academy of Sciences, 2004, vol. 1032, pp. 191-194.
Woolley, et al., "Exposure to Excess Glucocorticoids Alters Dendritic Morphology of Adult Hippocampal Pyramidal Neurons," Brain Research, 1990, vol. 531, pp. 225-231.
Yau, et al., "Glucocorticoids, Hippocampal Corticosteroid Receptor Gene Expression and Antidepressant Treatment: Relationship with Spatial learning in Young and Aged Rats," Neuroscience, 1995, vol. 66 (3), pp. 571-581.
Yeh, et al., "Discovery of Orally Active Butyrolactann11β-Hsd1 Inhibitors," Bioorganic and Medicinal Chemistry Letters, 2006, vol. 16 (21), pp. 5555-5560.
Yeh, et al., "Synthesis and Biological Evaluation of Heterocycle Containing Adamantane 11β-HSD1 Inhibitors," Bioorganic and Medicinal Chemistry Letters, 2006, vol. 16 (20), pp. 5414-5419.
Yeh, et al., "Synthesis and Structural Activity Relationship of 11β-HSD1 Inhibitors with Novel Adamantane Replacements," Bioorganic and Medicinal Chemistry Letters, 2006, vol. 16 (20), pp. 5408-5413.

* cited by examiner

AMIDE AND AMIDINE DERIVATIVES AND USES THEREOF

This application claims priority to provisional application Ser. No. 61/170,943 filed Apr. 20, 2009 and provisional application 61/187,500 filed Jun. 16, 2009, which are incorporated herein by reference.

FIELD OF THE INVENTION

The present invention relates to novel amide, cyanoamidine, thioamide, amidine, hydroxyimideamide, alkoxyimideamide, aryloxyimideamide and related compounds, which are inhibitors of the 11-β-hydroxysteroid dehydrogenase type 1 (11β-HSD1) enzyme. The present invention further relates to the use of inhibitors of 11β-HSD1 enzyme for the treatment of humans in need thereof.

BACKGROUND OF THE INVENTION

Glucocorticoids circulate in the blood in an active form (i.e., cortisol in humans) and an inactive form (i.e., cortisone in humans). Many studies have shown that 11β-HSD1 functions primarily as a reductase in vivo and in intact cells. It converts inactive 11-ketoglucocorticoids (i.e., cortisone or dehydrocorticosterone) to active 11-hydroxyglucocorticoids (i.e., cortisol or corticosterone), and thereby amplifies glucocorticoid action in a tissue-specific manner leading to higher local concentration of cortisol Inhibition of 11β-HSD1 prevents or decreases the tissue specific amplification of glucocorticoid action thus imparting beneficial effects.

11β-HSD1 is a low affinity enzyme with $K_m$ for cortisone in the micromolar range that prefers NADPH/NADP$^+$ (nicotinamide adenine dinucleotide phosphate) as cofactors. 11β-HSD1 is widely expressed in various tissues such as liver, bone, brain, lung, adipose, and vascular smooth muscle cells.

Excessive glucocorticoid action in liver and adipose tissues leads to insulin resistance, type 2 diabetes, dyslipidemia, increased abdominal obesity, and hypertension (Su et al., *Progress in Medicinal Chemistry*, 46, 29-130 (2008); Webster et al., *Expert Opin. Ther. Patents*, 17 (12), 1407-1422 (2007); Wang, *Drug Discovery Today: Ther. Strategies*, 4(2), 117-122 (2007); Link, *Current Opin. In Invest. Drugs*, 4 (4), 421-429 (2003); Seckl et al., *Endocrinology*, 142, 1371-1376 (2001) and references cited therein). Accordingly, the 11-β HSD1 inhibitor class has been recognized as one of the highly promising therapeutic classes (Norman P., *Insight Pharma Reports*, 103-110 (April 2007)).

Published data indicates that elevated levels of glucocorticoids in mammalian brain may cause neuronal degeneration and dysfunction, particularly in the aged (de Quervain et al., *Hum Mol. Genet.*, 13, 47-52 (2004); Belanoff et al. *J. Psychiatr Res.*, 35, 127-35, (2001)). Evidence in rodents and humans suggests that prolonged elevation of plasma glucocorticoid levels impairs cognitive function that becomes more profound with aging. (Issa et al., *J. Neurosci.*, 10, 3247-3254 (1990); Lupien et al., *Nat. Neurosci.*, 1, 69-73 (1998); Yau et al., *Neuroscience*, 66, 571-581 (1995)). Chronic excessive cortisol levels in the brain may result in neuronal loss and neuronal dysfunction. (Kerr et al., *Psychobiology*, 22, 123-133 (1994); Woolley, *Brain Res.*, 531, 225-231, (1990); Landfield, *Science*, 272, 1249-1251 (1996)).

Furthermore, glucocorticoid-induced acute psychosis exemplifies a more pharmacological induction of this response, and is of major concern to physicians when treating patients with these steroidal agents (Wolkowitz et al., *Ann NY Acad. Sci.*, 1032, 191-194 (2004)). It has been recently shown that 11β-HSD1 mRNA is expressed in human hippocampus, frontal cortex and cerebellum, and that treatment of elderly diabetic individuals with the non-selective 11β-HSD1 and 11β-HSD2 inhibitor carbenoxolone improved verbal fluency and memory (Thekkapat et al., *Proc Natl Acad Sci USA*, 101, 6743-6749 (2004)). Excessive glucocorticoid levels also affects psychopathology, as shown in animal models, it leads to increased anxiety and aggression. Chronic elevation of cortisol has been also associated with depression in Cushing's disease (McEwen, *Metab. Clin. & Exp.*, 54, 20-23 (2005)). A number of animal and clinical studies have provided evidence for the correlation between increases in glucocorticoid levels and neuropsychiatric disorders such as major depressive disorder, psychotic depression, anxiety, panic disorder, post traumatic stress disorder, and depression in Cushing's syndrome (Budziszewska, *Polish J. of Pharmacol.*, 54, 343-349, (2002); Ströhle et al., *Pharmacopsychiatry*, 36, S207-S214 (2003); DeBattista et al., *TRENDS in Endocr. Metab.*, 17, 117-120 (2006); Norman et al., *Expert Rev. Neurotherapeutics*, 7, 203-213 (2007)).

Thus, inhibiting 11β-HSD1 benefits patients suffering from non-insulin dependent type 2 diabetes, insulin resistance, obesity, lipid disorders, metabolic syndrome, central nervous system disorders, age-related or glucocorticoid-related declines in cognitive function such as those seen in Alzheimer's disease and associated dementias, major depressive disorder, psychotic depression, anxiety, panic disorder, post traumatic stress disorder, depression in Cushing's syndrome, treatment resistant depression, and other diseases and conditions mediated by excessive glucocorticoid action.

SUMMARY OF THE INVENTION

One embodiment is directed to a compound of formula (I)

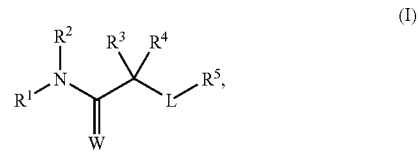

wherein

L is —(CH$_2$)$_n$—, —(CR$^{38}$R$^{39}$)$_m$—X—(CR$^{38}$R$^{39}$)$_n$— or —(CR$^{38}$R$^{39}$)$_m$—X—(CR$^{38}$R$^{39}$)$_n$—Y—;

m is independently at each occurrence 0, 1, or 2;

n is independently at each occurrence 0, 1, or 2;

R$^1$ is cycloalkyl or heterocycle;

R$^2$ is hydrogen, alkyl, or aryl; or R$^1$ and R$^2$ together with the atoms to which they are attached form a heterocycle; or R$^2$ and R$^3$ together with the atoms to which they are attached form a heterocycle;

R$^3$ and R$^4$ are independently hydrogen, alkyl or cycloalkyl; or R$^3$ and R$^4$ together with the atom to which they are attached form a cycloalkyl, heterocycle, heteroaryl or aryl;

R$^5$ is hydrogen, alkyl, amino, aryl, cycloalkyl, heteroaryl, or heterocycle provided R$^5$ is other than amino when L is —(CR$^{38}$R$^{39}$)$_m$—X—(CR$^{38}$R$^{39}$)$_n$—Y—; or R$^4$ and R$^5$ together with the atoms to which they are attached form a cycloalkyl or heterocycle;

X is —O—, —S—, —S(O)—, —S(O)$_2$—, —NR$^{36}$—, or —CR$^{36}$R$^{37}$—;

Y is O or Ne;

R$^{36}$ and R$^{37}$ are independently at each occurrence hydrogen or alkyl; or R$^{36}$ and R$^2$ together with the atoms to which they are attached form a heterocycle;

$R^{38}$, $R^{39}$ and $R^{40}$ are independently at each occurrence hydrogen or alkyl;

W is O, N—CN, N—$OR^6$, N—$R^6$, or S; and $R^6$ is hydrogen, alkyl or aryl; or a pharmaceutically acceptable salt, ester, amide, N-oxide or prodrug thereof.

Another embodiment encompasses the use of the compounds of formula (I) for the treatment of disorders that are mediated by 11β-HSD1 enzyme, such as non-insulin dependent type 2 diabetes, insulin resistance, obesity, lipid disorders, metabolic syndrome, age-related or glucocorticoid-related declines in cognitive function such as those seen in Alzheimer's disease and associated dementias, major depressive disorder, psychotic depression, anxiety, panic disorder, post traumatic stress disorder, depression in Cushing's syndrome, treatment resistant depression, and other diseases and conditions that are mediated by excessive glucocorticoid action.

Another embodiment is directed to a pharmaceutical composition comprising a therapeutically effective amount of a compound of formula (I) in combination with a pharmaceutically suitable carrier.

DETAILED DESCRIPTION OF THE INVENTION

Definition of Terms

For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

As used throughout this specification and the appended claims, the following terms have the following meanings:

The term "acetyl" means a —C(O)CH$_3$ group.

The term "acyl" means an alkyl group appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "acyloxy" means an acyl group appended to the parent molecular moiety through an oxygen atom. Representative examples of acyloxy include, but are not limited to, acetyloxy, propionyloxy, and isobutyryloxy.

The term "alkenyl" means a straight or branched chain hydrocarbon containing from 2 to 10 carbons, and preferably 2, 3, 4, 5, or 6 carbons, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" refers to an alkyl group appended to the parent molecular moiety through an oxygen atom. Representative examples of alkoxy include, but are not limited to, methoxy, ethoxy, propoxy, 2-propoxy, butoxy, tent-butoxy, pentyloxy, hexyloxy and the like.

The term "alkoxyalkoxy" means an alkoxy group appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" means an alkoxy group appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" means an alkoxy group appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxyimideamide" means a

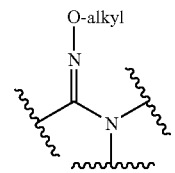

group.

The term "alkoxyimino" means an alkoxy group appended to the parent molecular moiety through a —C(=NH)— group, which also is defined as an imino group. Representative examples of alkoxyimino include, but are not limited to, imino(methoxy)methyl, ethoxy(imino)methyl and tert-butoxy(imino)methyl.

The term "alkoxysulfonyl" means an alkoxy group appended to the parent molecular moiety through a sulfonyl group, as defined herein. Representative examples of alkoxysulfonyl include, but are not limited to, methoxysulfonyl, ethoxysulfonyl, and propoxysulfonyl.

The term "alkyl" means a straight or branched chain hydrocarbon containing from 1 to 6 carbon atoms. Representative examples of alkyl include, but are not limited to, methyl, ethyl, n-propyl, iso-propyl, n-butyl, sec-butyl, iso-butyl, tent-butyl, n-pentyl, isopentyl, neopentyl, and n-hexyl.

In some instances, the number of carbon atoms in a hydrocarbyl substituent (e.g., alkyl, alkenyl, alkynyl, or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_6$-cycloalkyl means a saturated hydrocarbyl ring containing from 3 to 6 carbon ring atoms.

The term "alkyl-NH-alkyl" refers to an alkyl group appended to a second alkyl group, as defined herein through an —NH— group. Said second alkyl group is appended to the parent molecular moiety.

The term "alkylcarbonyl" refers to an alkyl group appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcycloalkyl" means an alkyl group appended to the parent molecular moiety through a cycloalkyl group, as defined herein. Representative examples of alkylcycloalkyl include, but are not limited to, 4-ethylcyclohexyl, 3-methylcyclopentyl, and 2-isopropylcyclopropyl.

The term "alkylsulfonyl" means an alkyl group appended to the parent molecular moiety through a sulfonyl group, as defined herein. Representative examples of alkylsulfonyl include, but are not limited to, methylsulfonyl and ethylsulfonyl.

The term "alkylthio" means an alkyl group appended to the parent molecular moiety through a sulfur atom. Representative examples of alkylthio include, but are not limited, methylthio, ethylthio, tert-butylthio, and hexylthio.

The term "amino" is —NR$^{90}$R$^{91}$, wherein R$^{90}$ and R$^{91}$ are each independently hydrogen, alkyl, alkoxy, alkylsulfonyl, aryl, arylalkyl, aryloxy, aryloxyalkyl, arylsulfonyl, alkyl-NH-alkyl, aryl-NH-alkyl, arylalkyl, aryl-heterocycle, carboxy, carboxyalkyl, carboxycycloalkyl, cycloalkyl, cycloalkyloxy, cycloalkylsulfonyl, heteroaryl, heteroarylalkyl, heteroaryloxyalkyl, heteroaryloxy, heteroarylsulfonyl, heterocycle, heterocycle-NH-alkyl, heterocyclealkyl, heterocycle-heterocycle, heterocycleoxyalkyl, heterocycleoxy, heterocyclesulfonyl, or hydroxyl.

The term "alkynyl" means a straight or branched chain hydrocarbon group containing from 2 to 10 carbon atoms, and preferably 2, 3, 4, or 5 carbons, and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "amidine" or "imideamide" means a

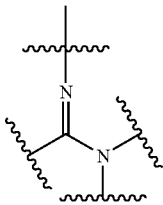 [SMILES: *N=C(*)N(*)*]

group.

The term "amido" means an amino, alkylamino, or dialkylamino group appended to the parent molecular moiety through a carbonyl group, as defined herein. Representative examples of amido include, but are not limited to, aminocarbonyl, methylaminocarbonyl, dimethylaminocarbonyl, and ethylmethylaminocarbonyl.

The term "aryl" means phenyl, a bicyclic aryl, or a tricyclic aryl. The bicyclic aryl is naphthyl, a phenyl fused to a cycloalkyl, cycloalkenyl, heteroaryl or heterocycle, as defined herein. The bicyclic aryl must be attached to the parent molecular moiety through any available carbon atom contained within the phenyl ring. Representative examples of the bicyclic aryl include, but are not limited to, dihydroindenyl, indenyl, naphthyl, dihydronaphthalenyl, and tetrahydronaphthalenyl. Tricyclic fused ring systems are exemplified by a bicyclic aryl fused to a cycloalkyl, phenyl, heteroaryl, or heterocycle, as defined herein. The tricyclic aryl is attached to the parent molecular moiety through any carbon atom contained within a phenyl ring. Representative examples of aryl include, but are not limited to, anthracenyl, phenanthrenyl, azulenyl, fluorenyl, indanyl, indenyl, naphthyl, phenyl and tetrahydronaphthyl.

The aryl groups of this invention may be substituted with 0, 1, 2, 3, 4 or 5 substituents independently selected from alkenyl, alkoxy, alkoxyalkoxy, alkoxyalkyl, alkoxycarbonyl, alkoxycarbonylalkyl, alkyl, alkylcarbonyl, alkylsulfonyl, alkynyl, aryl, arylalkoxy, arylcarbonyl, aryloxy, arylsulfonyl, carboxy, carboxyalkyl, cyano, cyanoalkyl, ethylenedioxy, formyl, haloalkoxy, haloalkyl, halogen, heteroaryl, heteroarylalkoxy, heteroarylalkyl, heteroarylcarbonyl, heterocycle, heterocyclealkoxy, heterocyclecarbonyl, heterocycleoxy, heterocyclesulfonyl, hydroxy, hydroxyalkyl, methylenedioxy, nitro, —C(O)N(H)S(O)$_2$alkyl, —R$_f$R$_g$N—, R$_f$R$_g$Nalkyl, R$_f$R$_g$Ncarbonyl, —N(H)C(O)N(H)(alkyl), and R$_f$R$_g$Nsulfonyl, wherein R$_f$ and R$_g$ are independently selected from the group consisting of hydrogen, alkyl, alkoxyalkyl, alkoxycarbonyl, alkylsulfonyl, cycloalkyl, haloalkyl, haloalkylcarbonyl and cycloalkylalkyl wherein the cycloalkyl, the cycloalkyl of cycloalkylalkyl as represented by R$_f$ and R$_g$ are each independently unsubstituted or substituted with 1, 2 or 3 substituents independently selected from the group consisting of halogen, alkyl and haloalkyl. The substituent aryl, the aryl of arylalkoxy, the aryl of arylcarbonyl, the aryl of aryloxy, the aryl of arylsulfonyl, the substituent heteroaryl, the heteroaryl of heteroarylalkyl, the heteroaryl of heteroarylcarbonyl, the substituent heterocycle, the heterocycle of heterocyclecarbonyl, the heterocycle of heterocycleoxy, the heterocycle of heterocyclesulfonyl may be optionally substituted with 1, 2 or 3 substituents independently selected from the group consisting of alkoxy, alkoxyalkyl, alkoxycarbonyl, alkyl, alkylcarbonyl, alkynyl, carboxy, carboxyalkyl, cyano, haloalkyl, halogen, hydroxy, hydroxyalkyl, nitro, R$_f$R$_g$N—, R$_f$R$_g$Nalkyl, R$_f$R$_g$Ncarbonyl and R$_f$R$_g$Nsulfonyl wherein R$_f$ and R$_g$ are as described herein.

The term "arylalkoxy" means an aryl group appended to the parent molecular moiety through an alkoxy group, as defined herein. Representative examples of arylalkoxy include, but are not limited to, 2-phenylethoxy, 3-naphth-2-ylpropoxy, and 5-phenylpentyloxy.

The term "arylalkoxycarbonyl" means an arylalkoxy group appended to the parent molecular moiety through a carbonyl group, as defined herein. Representative examples of arylalkoxycarbonyl include, but are not limited to, benzyloxycarbonyl and naphth-2-ylmethoxycarbonyl.

The term "arylalkyl" means an aryl group appended to the parent molecular moiety through an alkyl group, as defined herein. Representative examples of arylalkyl include, but are not limited to, benzyl, 2-phenylethyl and 3-phenylpropyl.

The term "arylcarbonyl" means an aryl group appended to the parent molecular moiety through a carbonyl group, as defined herein. Representative examples of arylcarbonyl include, but are not limited to, benzoyl and naphthoyl.

The term "aryloxy" means an aryl group appended to the parent molecular moiety through an oxygen atom. Representative examples of aryloxy include, but are not limited to, phenoxy and tolyloxy.

The term "aryloxyalkyl" refers to an aryloxy group appended to the parent molecular moiety through an alkyl group, as defined herein.

The term "aryloxyimideamide" means a

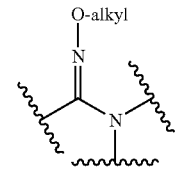

group.

The term "arylsulfonyl" refers to an aryl group appended to the parent molecular moiety through a sulfonyl group, as defined herein. Representative examples of arylsulfonyl include, but are not limited to, phenylsulfonyl, 4-bromophenylsulfonyl and naphthylsulfonyl.

The term "carbonyl" means a —C(O)— group.

The term "carboxy" means a —CO$_2$H group.

The term "carboxyalkyl" means a carboxy group appended to the parent molecular moiety through an alkyl group, as defined herein. Representative examples of carboxyalkyl include, but are not limited to, carboxymethyl, 2-carboxyethyl, and 3-carboxypropyl.

The term "carboxycycloalkyl" as used herein refers to a carboxy group as defined herein, appended to the parent molecular moiety through a cycloalkyl group as defined herein.

The term "combination therapy" is defined as the administration of a single pharmaceutical dosage formulation, which comprises two or more therapeutic agents.

The term "cyano" means a —CN group, attached to the parent molecular moiety through the carbon.

The term "cyanoalkyl" means a —CN group attached to the parent molecular moiety through an alkyl group. Representative examples of "cyanoalkyl" include, but are not limited to, 3-cyanopropyl, and 4-cyanobutyl.

The term "cyanoamidine" means a

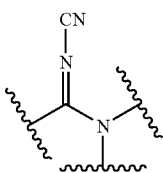 [SMILES: *C(=NC#N)N(*)*]

group.

The term "cycloalkoxy" means a cycloalkyl group appended to the parent molecular moiety through an oxygen atom. Representative examples of cycloalkoxy include, but are not limited to, cyclohexyloxy and cyclopropoxy.

The term "cycloalkoxyalkyl" means a cycloalkoxy group appended to the parent molecular moiety through an alkyl group, wherein alkyl is as defined herein. Representative examples of cycloalkoxylalkyl include, but are not limited to, cyclobutoxymethyl, cyclopentyloxymethyl, 2-(cyclopentyloxy)ethyl and cyclohexyloxymethyl.

The term "cycloalkyl" means a monocyclic, bicyclic, or tricyclic ring system. Monocyclic ring systems are exemplified by a saturated cyclic hydrocarbon group containing from 3 to 4 carbon atoms (($C_3$-$C_4$)cycloalkyl), 5 to 6 carbon atoms (($C_5$-$C_6$)cycloalkyl), 3 to 6 carbon atoms (($C_3$-$C_6$)cycloalkyl), from 7 to 8 carbon atoms (($C_7$-$C_8$)cycloalkyl), or from 3 to 8 carbon atoms (($C_3$-$C_8$)cycloalkyl). Examples of monocyclic ring systems include cyclopropyl, cyclobutyl, cyclopentyl, cyclohexyl, cycloheptyl, and cyclooctyl. Bicyclic ring systems are exemplified by a bridged monocyclic ring system in which two non-adjacent carbon atoms of the monocyclic ring are linked by an alkylene bridge of between one and three additional carbon atoms. Representative examples of bicyclic ring systems include, but are not limited to, bicyclo[3.1.1]heptanyl, bicyclo[2.2.1]heptanyl, bicyclo[2.2.2]octanyl, bicyclo[5.1.0]octanyl, bicyclo[3.2.2]nonanyl, bicyclo[3.3.1]nonanyl, and bicyclo[4.2.1]nonanyl. Bicyclic ring systems are also exemplified by a monocyclic ring system fused to a phenyl or heteroaryl ring. Representative examples of bicyclic ring systems include, but are not limited to, 1,2,3,4-tetrahydronaphthalenyl, indanyl, and 6,7-dihydro-5H-cyclopenta[c]pyridinyl. The bicyclic cycloalkyl is connected to the parent molecular moiety through any carbon atom contained within the unsaturated cycloalkyl ring. Tricyclic ring systems are exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, octahydro-2,5-methanopentalene, tricyclo[3.3.1.0$^{3,7}$]nonanyl and tricyclo[3.3.1.1$^{3,7}$]decanyl(adamantanyl).

The cycloalkyl groups of the present invention are substituted with 0, 1, 2, 3 or 4 substituents selected from the group consisting of alkyl, alkenyl, alkyl-NH-alkyl, alkylcarbonyl, alkylsulfonyl, alkylthio, aryl, arylalkyl, aryloxyalkyl, arylcarbonyl, arylsulfonyl, carboxyalkyl, carboxycycloalkyl, cyano, cyanoalkyl, cycloalkyl, cycloalkylcarbonyl, cycloalkylsulfonyl, halogen, haloalkyl, heterocyclecarbonyl, heterocyclesulfonyl, heteroaryl, heteroarylalkyl, heterocycle, heterocyclealkyl, heterocycleoxyalkyl, —$NO_2$, —$NR^8$—[C($R^9R^{10}$)]$_p$—C(O)—$R^{11}$, —[C($R^{12}R^{13}$)]$_q$—$CR^{12}$(OH)—$R^{14}$, —[C($R^{12}R^{13}$)]$_q$C(O)—$R^{14}$, —$CR^{12}$=$R^{13}$—C(O)—$R^{14}$, —[C($R^{12}R^{13}$)]$_q$S(O)$_2$—$R^{14}$, —[C($R^{12}R^{13}$)]$_q$S(O)—$R^{14}$, —[C($R^{12}R^{13}$)]$_q$S—$R^{14}$, —O—[C($R^{12}R^{13}$)]$_q$—C(O)—$R^{14}$, —$OR^{15}$, —N($R^{16}R^{17}$), $NR^8$C(O)N($R^{19}R^{20}$), —$CO_2R^{18}$, —C(O)—N($R^{19}R^{20}$), —[C($R^{12}R^{13}$)]$_p$—C(O)—N($R^{19}R^{20}$), —C(NH)$NH_2$, —C($R^{21}R^{22}$)—$OR^{23}$, and —C($R^{24}R^{25}$)—N($R^{26}R^{27}$), —C(=NOH)—N(H)$_2$, —C($R^{28}R^{29}$)—C(O)N($R^{30}R^{31}$), —S(O)—N($R^{32}R^{33}$), —S(O)$_2$—[C($R^9R^{10}$)]$_p$—C(O)N($R^{32}R^{33}$), and —C($R^{28}R^{29}$)—S(O)$_2$—N($R^{32}R^{33}$), wherein p is 1, 2, 3, 4, 5 or 6;

q is 0, 1, 2, 3, 4, 5 or 6;

$R^8$ is hydrogen, alkyl, carboxyalkyl, cycloalkyl, carboxycycloalkyl, aryl, arylalkyl, aryloxyalkyl, aryloxy, hydroxy, alkoxy, cycloalkyloxy, heterocycleoxy, heterocycle, heterocyclealkyl, or heterocycleoxyalkyl;

$R^9$ and $R^{10}$ are each independently hydrogen, alkyl, carboxy, carboxyalkyl, cycloalkyl, carboxycycloalkyl, aryl, arylalkyl, aryloxyalkyl, heterocycle, heterocyclealkyl, or heterocycleoxyalkyl, or $R^9$ and $R^{10}$ together with the atom to which they are attached form cycloalkyl or heterocycle;

$R^{11}$ is hydrogen, alkyl, carboxy, carboxyalkyl, cycloalkyl, carboxycycloalkyl, aryl, aryloxy, arylalkyl, aryloxyalkyl, hydroxy, alkoxy, cycloalkyloxy, heterocycleoxy, heterocycle, heterocyclealkyl, heterocycleoxyalkyl, or —N($R^{28}R^{29}$);

$R^{12}$ and $R^{13}$ are each independently hydrogen, alkyl, carboxy, carboxyalkyl, cycloalkyl, carboxycycloalkyl, aryl, arylalkyl, aryloxyalkyl, heterocycle, heterocyclealkyl, heterocycleoxyalkyl or —N($R^{28}R^{29}$), or $R^{12}$ and $R^{13}$ together with the atom to which they are attached form cycloalkyl or heterocycle;

$R^{14}$ is hydrogen, alkyl, carboxy, carboxyalkyl, cycloalkyl, carboxycycloalkyl, aryl, arylalkyl, aryloxy, aryloxyalkyl, hydroxy, alkoxy, cycloalkyloxy, heterocycleoxy, heterocycle, heterocyclealkyl, heterocycleoxyalkyl, or —N($R^{39}R^{31}$);

$R^{15}$ is hydrogen, alkyl, alkylcarbonyl, carboxyalkyl, cycloalkyl, carboxycycloalkyl, aryl, arylalkyl, aryloxyalkyl, haloalkyl, heterocycle, heterocyclealkyl, or heterocycleoxyalkyl;

$R^{16}$ and $R^{17}$ are each independently hydrogen, alkyl, alkylcarbonyl, carboxyalkyl, cycloalkyl, carboxycycloalkyl, aryl, arylalkyl, aryloxyalkyl, haloalkyl, heterocycle, heterocyclealkyl, heterocycleoxyalkyl, alkylsulfonyl, cycloalkylsulfonyl, arylsulfonyl, formyl, or heterocyclesulfonyl, or $R^{16}$ and $R^{17}$ together with the atom to which they are attached form a heterocycle;

$R^{18}$ is hydrogen, alkyl, carboxyalkyl, cycloalkyl, carboxycycloalkyl, aryl, arylalkyl, aryloxyalkyl, heterocycle, heterocyclealkyl, or heterocycleoxyalkyl;

$R^{19}$ and $R^{20}$ are each independently hydrogen, alkyl, carboxy, carboxyalkyl, cycloalkyl, cycloalkyloxy, carboxycycloalkyl, aryl, arylalkyl, aryloxy, aryloxyalkyl, heteroarylalkyl, heterocycle, heterocyclealkyl, heterocycleoxyalkyl, heterocycleoxy, hydroxy, alkoxy, alkylsulfonyl, cycloalkylsulfonyl, arylsulfonyl, heterocyclesulfonyl, or —[C($R^{12}R^{13}$)]$_q$C(O)$R^{14}$, or $R^{19}$ and $R^{20}$ together with the atom to which they are attached form a heterocycle;

$R^{21}$, $R^{22}$ and $R^{23}$ are each independently hydrogen, alkyl, carboxyalkyl, carboxycycloalkyl, cycloalkyl, haloalkyl, aryl, heterocycle, or heterocyclealkyl;

$R^{24}$ and $R^{25}$ are each independently hydrogen, alkyl, alkylcarbonyl, alkylsulfonyl, carboxyalkyl, carboxycycloalkyl, cycloalkylcarbonyl, cycloalkylsulfonyl, arylcarbonyl, arylsulfonyl, heterocyclecarbonyl, heterocyclesulfonyl, cycloalkyl, aryl, or heterocycle;

$R^{26}$ and $R^{27}$ are each independently hydrogen, alkyl, alkylcarbonyl, alkylsulfonyl, carboxyalkyl, carboxycycloalkyl, cycloalkylcarbonyl, cycloalkylsulfonyl, arylcarbonyl, arylsulfonyl, heterocyclecarbonyl, heterocyclesulfonyl, hydroxy, alkoxy, cycloalkyloxy, aryloxy, heterocycleoxy, cycloalkyl, aryl, or heterocycle, or $R^{26}$ and $R^{27}$ together with the atom to which they are attached form a heterocycle;

$R^{28}$ and $R^{29}$ are each independently at each occurrence hydrogen or alkyl;

$R^{30}$ and $R^{31}$ are each independently at each occurrence hydrogen, alkyl, alkylcarbonyl, alkoxy, alkylsulfonyl, aryl, arylcarbonyl, aryloxy, arylsulfonyl, carboxyalkyl, carboxycycloalkyl, cycloalkyl, cycloalkylcarbonyl, cycloalkyloxy, cycloalkylsulfonyl, heteroaryl, heteroarylcarbonyl, heteroaryloxy, heteroarylsulfonyl, heterocycle, heterocyclecarbonyl, heterocycleoxy, heterocyclesulfonyl, or hydroxy, or $R^{30}$ and $R^{31}$ taken together with the atom to which they are attached form heteroaryl or heterocycle; and $R^{32}$ and $R^{33}$ are each independently at each occurrence selected from the group consisting of hydrogen, alkyl, alkoxy, alkylsulfonyl, aryl, arylalkyl, aryloxy, aryloxyalkyl, arylsulfonyl, alkyl-NH-alkyl, aryl-NH-alkyl, arylalkyl, haloalkyl, aryl-heterocycle, carboxy, carboxyalkyl, carboxycycloalkyl, cycloalkyl, cycloalkyloxy, cycloalkylsulfonyl, heteroaryl, heteroarylalkyl, heteroaryloxyalkyl, heteroaryloxy, heteroarylsulfonyl, heterocycle, heterocycle-NH-alkyl, heterocyclealkyl, heterocycle-heterocycle, heterocycleoxyalkyl, heterocycleoxy, heterocyclesulfonyl, and hydroxy, or $R^{32}$ and $R^{33}$ taken together with the atom to which they are attached form a heterocycle.

The term "cycloalkylalkyl" means a cycloalkyl group appended to the parent molecular moiety through an alkyl group, as defined herein. Representative examples of cycloalkylalkyl include, but are not limited to, cyclopropylmethyl, cyclopentylmethyl, cyclohexylmethyl, and cycloheptylmethyl.

The term "cycloalkylcarbonyl" means cycloalkyl group appended to the parent molecular moiety through a carbonyl group, as defined herein. Representative examples of cycloalkylcarbonyl include, but are not limited to, cyclopropylcarbonyl, 2-cyclobutylcarbonyl, and cyclohexylcarbonyl.

The term "cycloalkylsulfonyl" refers to cycloalkyl group appended to the parent molecular moiety through a sulfonyl group, as defined herein. Representative examples of cycloalkylsulfonyl include, but are not limited to, cyclohexylsulfonyl and cyclobutylsulfonyl.

The term "formyl" means a —C(O)H group.

The term "halo" or "halogen" means —Cl, —Br, —I or —F.

The term "haloalkoxy" means at least one halogen appended to the parent molecular moiety through an alkoxy group, as defined herein. Representative examples of haloalkoxy include, but are not limited to, fluoroalkoxy, chloroalkoxy, bromoalkoxy and iodoalkoxy, such as fluoromethoxy, difluoromethoxy, trifluoromethoxy, 2-fluoroethoxy, trifluoromethoxy, 2,2,2-trifluoroethoxy, and pentafluoroethoxy.

The term "haloalkyl" means at least one halogen appended to the parent molecular moiety through an alkyl group, as defined herein. Representative examples of haloalkyl include, but are not limited to, difluoromethyl, chloromethyl, 2-fluoroethyl, trifluoromethyl, 2,2,2-trifluoroethyl, pentafluoroethyl, and 2-chloro-3-fluoropentyl.

The term "halocycloalkyl" means at least one halogen appended to the parent molecular moiety through a cycloalkyl group, as defined herein. Representative examples of halocycloalkyl include, but are not limited to, fluorocyclohexyl, bromocyclopropyl, and trans-2,3-dichlorocyclopentyl.

The term "halocycloalkylalkyl" means a halocycloalkyl group as defined herein, attached to the parent molecular moiety through an alkyl group. Representative examples of halocycloalkylalkyl include, but are not limited to, (4-fluorocyclohexyl)methyl, (2,2-difluorocyclobutyl)methyl and the like.

The term "halothioalkoxy" means at least one halogen appended to the parent molecular moiety through a thioalkoxy group, as defined herein. Representative examples of halothioalkoxy include, but are not limited to, 2-chloroethylsulfane and trifluoromethylsulfane.

The term "heteroaryl" means a monocyclic heteroaryl or a bicyclic heteroaryl. The monocyclic heteroaryl is a 5 or 6 membered ring that contains at least one heteroatom selected from the group consisting of nitrogen, oxygen and sulfur. The 5 membered ring contains two double bonds and the 6 membered ring contains three double bonds. The 5 or 6 membered heteroaryl is connected to the parent molecular moiety through any carbon atom or any substitutable nitrogen atom contained within the heteroaryl, provided that proper valance is maintained. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, or a monocyclic heteroaryl fused to a cycloalkyl, or a monocyclic heteroaryl fused to a cycloalkenyl, or a monocyclic heteroaryl fused to a monocyclic heteroaryl. The bicyclic heteroaryl is connected to the parent molecular moiety through any carbon atom or any substitutable nitrogen atom contained within the bicyclic heteroaryl, provided that proper valance is maintained. Representative examples of bicyclic heteroaryl include, but are not limited to, azaindolyl, benzimidazolyl, benzofuranyl, benzoxadiazolyl, benzoisoxazole, benzoisothiazole, benzooxazole, 1,3-benzothiazolyl, benzothiophenyl, cinnolinyl, furopyridine, indolyl, indazolyl, isobenzofuran, isoindolyl, isoquinolinyl, naphthyridinyl, oxazolopyridine, 1H-pyrrolo[2,3-b]pyridinyl, quinolinyl, quinoxalinyl and thienopyridinyl.

The heteroaryl groups are optionally substituted with 1, 2, 3 or 4 substituents independently selected from the group consisting of aryloxy, alkenyl, alkoxy, alkoxycarbonyl, alkyl, alkylcarbonyl, alkylsulfonyl, alkylthio, alkynyl, amido, aryl, aryloxy, carboxy, carboxyalkyl, cyano, cyanoalkyl, cycloalkyl, cycloalkoxy, formyl, haloalkoxy, haloalkyl, halogen, halothioalkoxy, heteroaryl, thioalkoxy, thiocycloalkoxy, thioaryloxy, nitro, and —NR$^{96}$R$^{97}$, wherein R$^{96}$ and R$^{97}$ are independently hydrogen, alkoxyalkyl, alkoxycarbonyl, alkyl, alkylcarbonyl, alkylsulfonyl, aryl, cycloalkyl, haloalkyl, heteroaryl, or heterocycle, or R$^{96}$ and R$^{97}$ together with the nitrogen to which they are attached form a heterocycle. In addition, the nitrogen heteroatoms can be optionally quaternized or oxidized to the corresponding N-oxide.

The term "heteroarylalkoxy" as used herein, means a heteroaryl group appended to the parent molecular moiety through an alkoxy group, as defined herein. Representative examples of heteroarylalkoxy include, but are not limited to, fur-3-ylmethoxy, 1H-imidazol-2-ylmethoxy, 1H-imidazol-4-ylmethoxy, 1-(pyridin-4-yl)ethoxy, pyridin-3-ylmethoxy, 6-chloropyridin-3-ylmethoxy, pyridin-4-ylmethoxy, (6-(trifluoromethyl)pyridin-3-yl)methoxy, (6-(cyano)pyridin-3-yl)methoxy, (2-(cyano)pyridin-4-yl)methoxy, (5-(cyano)pyridin-2-yl)methoxy, (2-(chloro)pyridin-4-yl)methoxy, pyrimidin-5-ylmethoxy, 2-(pyrimidin-2-yl)propoxy, 1,3-thiazol-4-ylmethoxy, thien-2-ylmethoxy, and thien-3-ylmethoxy.

The term "heteroarylalkyl" means a heteroaryl appended to the parent molecular moiety through an alkyl group, as defined herein.

The term "heteroarylcarbonyl" means a heteroaryl group appended to the parent molecular moiety through a carbonyl group, as defined herein. Representative examples of heteroarylcarbonyl include, but are not limited to, fur-3-ylcarbonyl, 1H-imidazol-2-ylcarbonyl, 1H-imidazol-4-ylcarbonyl, pyridin-3-ylcarbonyl, 6-chloropyridin-3-ylcarbonyl, pyridin-4-ylcarbonyl, (6-(trifluoromethyl)pyridin-3-yl)carbonyl, (6-(cyano)pyridin-3-yl)carbonyl, (2-(cyano)pyridin-4-yl)carbonyl, (5-(cyano)pyridin-2-yl)carbonyl, (2-(chloro)pyridin-4-yl)carbonyl, pyrimidin-5-ylcarbonyl, pyrimidin-2-ylcarbonyl, thien-2-ylcarbonyl, and thien-3-ylcarbonyl.

The term "heterocycle" or "heterocyclic" means a monocyclic heterocycle, a bicyclic heterocycle, or tricyclic heterocycle. The monocyclic heterocycle is a 3, 4, 5, 6 or 7 membered ring containing at least one heteroatom independently selected from the group consisting of O, N, and S. The 3- or 4-membered ring contains 1 heteroatom selected from the group consisting of O, N and S. The 5-membered ring contains zero or one double bond and one, two or three heteroatoms selected from the group consisting of O, N and S. The 6- or 7-membered ring contains zero, one, or two double bonds provided that the ring, when taken together with a substituent, does not tautomerize with a substituent to form an aromatic ring and one, two, three, or four heteroatoms selected from the group consisting of O, N and S. The monocyclic heterocycle is connected to the parent molecular moiety through any carbon atom or any nitrogen atom contained within the monocyclic heterocycle.

Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl(thiomorpholine sulfone), thiopyranyl, and trithianyl. The bicyclic heterocycle is a monocyclic heterocycle fused to a phenyl group, a monocyclic heterocycle fused to a cycloalkyl, a monocyclic heterocycle fused to a cycloalkenyl, or a monocyclic heterocycle fused to a monocyclic heterocycle. The bicyclic heterocycle is connected to the parent molecular moiety through any carbon atom or any nitrogen atom contained within the monocyclic heterocycle. Representative examples of bicyclic heterocycle include, but are not limited to, azabicyclo[3.2.0]hept-3-yl, 1-azabicyclo[2.2.2]octyl(quinuclidinyl), 1,3-benzodioxolyl, 1,3-benzodithiolyl, 2,3-dihydro-1,4-benzodioxinyl, 3,7-diazabicyclo[3.3.1]nonanyl, 3,9-diazabicyclo[4.2.1]nonanyl, 2,3-dihydro-1-benzofuranyl, 2,3-dihydro-1-benzothienyl, 2,3-dihydro-1H-indolyl, hexahydropyrrolo[3,4-b]pyrrol-1(2H)-yl, indolinyl, isoindolinyl, 2,3,4,5-tetrahydro-1H-3-benzazepinyl, octahydropyrrolo[3,4-c]pyrrolyl, tetrahydro-1H-pyrrolo[3,4-b]pyridin-6(2H,7H,7aH)-yl, 3-azabicyclo[3.2.0]heptane, quinuclidine and 1,2,3,4-tetrahydroquinolinyl. Representative examples of tricyclic heterocyclic systems include, but are not limited to, aza-adamantanyl, oxa-adamantanyl, and 7,8,9,10-tetrahydro-6H-[1,3]dioxolo[4,5-g][3]benzazepinyl.

The heterocycles are substituted with 0, 1, 2, 3, 4, 5, 6, 7, 8, or 9 substituents independently selected from acyl, aryloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkylthio, alkynyl, amido, aryl, arylalkoxycarbonyl, arylalkyl, aryloxy, aryloxyalkyl, carboxy, cyano, cyanoalkyl, cycloalkyl, formyl, haloalkoxy, haloalkyl, halogen, heteroaryl, heteroarylalkyl, heteroarylcarbonyl, heteroaryloxyalkyl, hydroxy, hydroxyalkyl, mercapto, nitro, oxo, -alkylNR$^{98}$R$^{99}$, —NR$^{98}$R$^{99}$, (NR$^{98}$R$^{99}$)carbonyl, —SO$_2$N(R$^{98}$)(R$^{99}$), —SO$_2$R$^{98}$, —NR$^{98}$(C=O)NR$^{98}$R$^{99}$, —NR and —N(R$^{98}$)SO$_2$(R$^{99}$), wherein R$^{98}$ and R$^{99}$ each are each independently selected from the group consisting of acyl, alkoxyalkyl, alkoxycarbonyl, alkyl, alkylcarbonyl, alkylcycloalkyl, alkylsulfonyl, amido, aryl, cyanoalkyl, cycloalkoxyalkyl, cycloalkyl, haloalkyl, halocycloalkyl, halocycloalkylalkyl, heteroaryl, heterocycle, hydrogen, formyl, hydroxy, and hydroxyalkyl. In addition, the nitrogen heteroatoms can be optionally quaternized or oxidized to the corresponding N-oxide.

The term "heterocyclealkoxy" as used herein, refers to a heterocycle appended to the parent molecular moiety through an alkoxy group, as defined herein. Representative examples of heterocyclealkoxy include, but are not limited, 2-morpholin-4-ylethoxy, 2-morpholin-4-ylethoxy, and (tetrahydrofuran-2-yl)methoxy.

The term "heterocyclealkyl" means a heterocycle appended to the parent molecular moiety through an alkyl group, as defined herein. Representative examples of heterocyclealkyl include, but are not limited, (pyrrolidin-2-yl)methyl, 2-(morpholin-4-yl)ethyl, and (tetrahydrofuran-3-yl)methyl.

The term "heterocyclecarbonyl" refers to a heterocycle appended to the parent molecular moiety through a carbonyl group, as defined herein. Representative examples of heterocyclecarbonyl include, but are not limited to, 1-piperidinylcarbonyl, 4-morpholinylcarbonyl, pyridin-3-ylcarbonyl and quinolin-3-ylcarbonyl.

The term "heterocycle-heterocycle" means a heterocycle appended to the parent molecular moiety through a second heterocycle, as defined herein.

The term "heterocycleoxyalkyl" refers to a heterocycleoxy appended to the parent molecular moiety through an alkyl group, as defined herein.

The term "heterocyclesulfonyl" refers to a heterocycle appended to the parent molecular moiety through a sulfonyl group, as defined herein. Representative examples of heterocyclesulfonyl include, but are not limited to, 1-piperidinylsulfonyl, 4-morpholinylsulfonyl, pyridin-3-ylsulfonyl and quinolin-3-ylsulfonyl.

The term "hydroxy" or "hydroxyl" means an —OH group.

The term "hydroxyalkyl" means at least one hydroxy group appended to the parent molecular moiety through an alkyl group, as defined herein. Representative examples of hydroxyalkyl include, but are not limited to, hydroxymethyl, 2-hydroxyethyl, 2-methyl-2-hydroxyethyl, 3-hydroxypropyl, 2,3-dihydroxypentyl, and 2-ethyl-4-hydroxyheptyl.

The term "hydroxyimideamide" means a

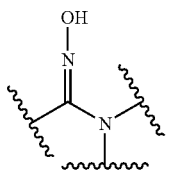 [SMILES: *C(=NO)N(*)*]

group.

The term "imino" means a —C(=NH)— group.
The term "mercapto" means a —SH group.
The term "nitro" means a —NO$_2$ group.
The term "oxo" means (=O).
The term "parenterally" refers to modes of administration, including intravenous, intramuscular, intraperitoneal, intrasternal, subcutaneous, intraarticular injection and infusion.

The term "pharmaceutically acceptable salt" or "salt" refers to those salts which are, within the scope of sound medical judgment, suitable for use in contact with the tissues of humans and lower animals without undue toxicity, irritation, allergic response, and the like, and are commensurate with a reasonable benefit/risk ratio and effective for their intended use. Pharmaceutically acceptable salts are well-known in the art. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulfuric acid and phosphoric acid and such organic acids as oxalic acid, maleic acid, succinic acid, and citric acid. Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, ethylammonium and the like. Other representative organic amines useful for the formation of base addition salts include ethylenediammonium, ethanolammonium, diethanolammonium, piperidinium, and piperazinium.

The term "pharmaceutically acceptable ester" or "ester" refers to esters of compounds of the invention which hydrolyze in vivo and include those that break down readily in the human body to leave the parent compound or a salt thereof. Examples of pharmaceutically acceptable, non-toxic esters of the invention include, but are not limited to, $C_1$-$C_6$ alkyl esters and $C_5$-$C_7$ cycloalkyl esters. Esters of the compounds of formula (I) can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, for example with methyl iodide, benzyl iodide, cyclopentyl iodide or alkyl triflate. They also can be prepared by reaction of the compound with an acid such as hydrochloric acid and an alcohol such as ethanol or methanol.

The term "pharmaceutically acceptable amide" or "amide" refers to non-toxic amides of the invention derived from ammonia, primary $C_1$-$C_3$ alkyl amines, primary $C_4$-$C_6$ alkyl amines, secondary $C_1$-$C_2$ dialkyl amines and secondary $C_3$-$C_6$ dialkyl amines. In the case of secondary amines, the amine can also be in the form of a 5- or 6-membered heterocycle containing one nitrogen atom. Amides of the compounds of formula (I) can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable amides are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, and piperidine. They also can be prepared by reaction of the compound with an acid such as sulfuric acid and an alkylcarboxylic acid such as acetic acid, or with acid and an arylcarboxylic acid such as benzoic acid under dehydrating conditions such as with molecular sieves added. The composition can contain a compound of the invention in the form of a pharmaceutically acceptable prodrug.

The term "pharmaceutically acceptable prodrug" or "prodrug" represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of formula (I), for example, by hydrolysis. A thorough discussion is provided in Higuchi et al., Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The term "pharmaceutically acceptable carrier" or "carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions; as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The term "sulfonyl" means a —$SO_2$— group.

The phrase "therapeutically effective amount" means a sufficient amount of the compound to treat disorders, at a reasonable benefit/risk ratio applicable to any medical treatment.

The term "therapeutically suitable excipient" generally refers to pharmaceutically suitable, solid, semi-solid or liquid fillers, diluents, encapsulating material, formulation auxiliary and the like.

The term "therapeutically suitable metabolite" generally refers to a pharmaceutically active compound formed by the in vivo biotransformation of compounds of formula I.

The term "thioalkoxy" refers to an alkyl group appended to the parent molecular moiety through a sulfur atom. Representative examples of thioalkoxy include, but are not limited to, methylthio, ethylthio, tert-butylthio, and hexylthio.

The term "thioamide" means a

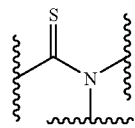 [SMILES: *C(=S)N(*)*]

group.

The term "thiocyloalkoxy" refers to a cycloalkyl group appended to the parent molecular moiety through a sulfur atom. Representative examples of thiocycloalkoxy include, but are not limited to, cyclopentylsulfane and cyclohexylsulfane.

The term "thioaryloxy" means an aryl group appended to the parent molecular moiety through a sulfur atom. Representative examples of thioaryloxy include, but are not limited to, thiophenoxy and tolylsulfane.

Compounds of the Invention

An embodiment is directed toward a compound of formula (I)

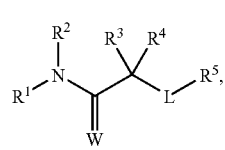

wherein

L is —$(CH_2)_n$—, —$(CR^{38}R^{39})_m$—X—$(CR^{38}R^{39})_n$— or —$(CR^{38}R^{39})_m$—X—$(CR^{38}R^{39})_n$—Y—;

m is independently at each occurrence 0, 1, or 2;

n is independently at each occurrence 0, 1, or 2;

$R^1$ is cycloalkyl or heterocycle;

$R^2$ is hydrogen, alkyl, or aryl; or $R^1$ and $R^2$ together with the atoms to which they are attached form a heterocycle; or $R^2$ and $R^3$ together with the atoms to which they are attached form a heterocycle;

$R^3$ and $R^4$ are independently hydrogen, alkyl or cycloalkyl; or $R^3$ and $R^4$ together with the atom to which they are attached form a cycloalkyl, heterocycle, heteroaryl, or aryl;

$R^5$ is hydrogen, alkyl, amino, aryl, cycloalkyl, heteroaryl, or heterocycle provided $R^5$ is other than amino when L is —$(CR^{38}R^{39})_m$—X—$(CR^{38}R^{39})_n$—Y—; or $R^4$ and $R^5$ together with the atoms to which they are attached form a cycloalkyl or heterocycle;

X is —O—, —S—, —S(O)—, —$S(O)_2$—, —$NR^{36}$—, or —$CR^{36}R^{37}$—;

Y is O or $N^{40}$;

$R^{36}$ and $R^{37}$ are independently at each occurrence hydrogen or alkyl; or $R^{36}$ and $R^2$ together with the atoms to which they are attached form a heterocycle;

$R^{38}$, $R^{39}$ and $R^{40}$ are independently at each occurrence hydrogen or alkyl;

W is N—CN, N—$OR^6$, N—$R^6$, or S; and $R^6$ is hydrogen, alkyl or aryl; or a pharmaceutically acceptable salt, ester, amide, N-oxide or prodrug thereof.

Another embodiment is a compound of formula (I), wherein $R^1$ is cycloalkyl.

Another embodiment is a compound of formula (I), wherein $R^1$ is heterocycle.

Another embodiment is a compound of formula (I), wherein $R^1$ is a cycloalkyl or heterocycle selected from the group consisting of

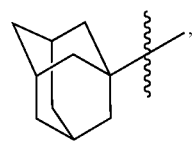

(i)

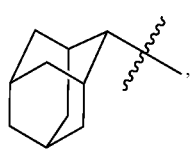

(ii)

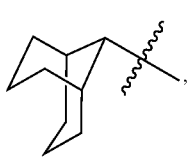

(iii)

-continued
(iv) 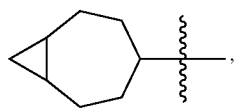
(v) 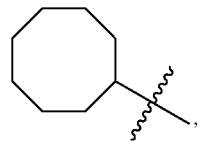
(vi) 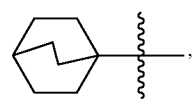
(vii) 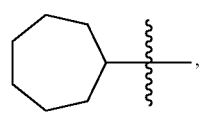
(viii) 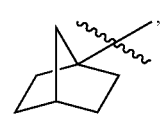
(ix) 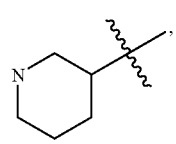
(x) 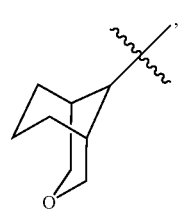
(xi) 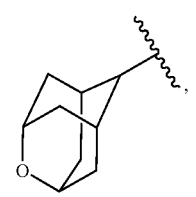
(xii) 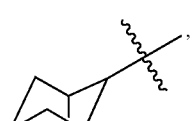
(xiii) 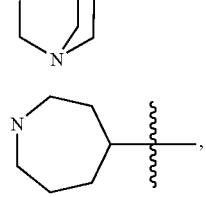
(xiv) 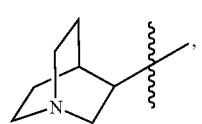
-continued
(xv) 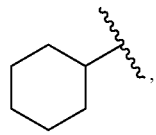
(xvi) 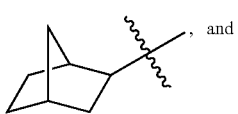, and
(xvii) 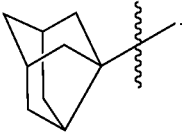.
Another embodiment is a compound of formula (I), wherein $R^1$ is a cycloalkyl or heterocycle selected from the group consisting of
(i) 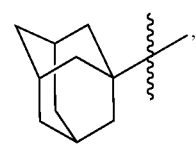
(ii) 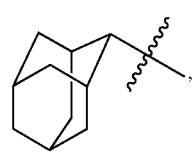
(v) 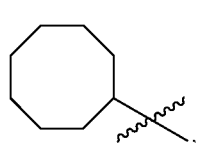
(vi) 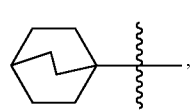
(viii) 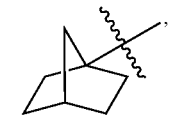
(ix) 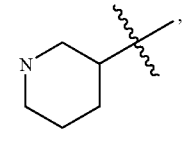
(xii) 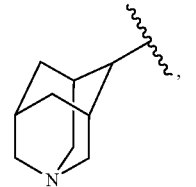, -continued

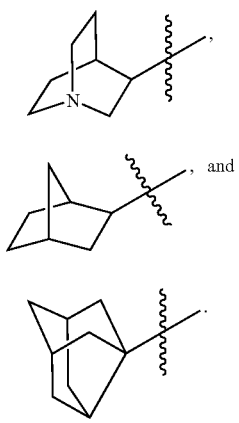

Another embodiment is a compound of formula (I), wherein R¹ is a cycloalkyl or heterocycle selected from the group consisting of

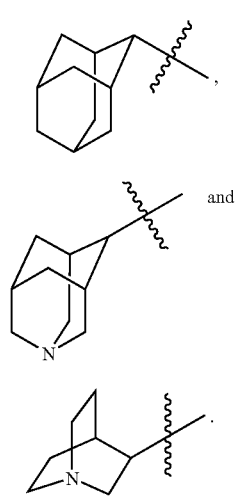

Another embodiment is a compound of formula (I), wherein R¹ is a cycloalkyl selected from the group consisting of

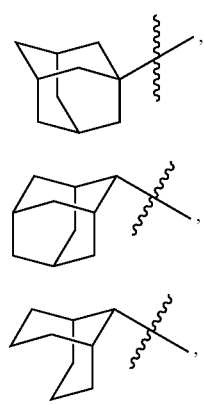

-continued

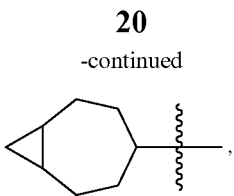

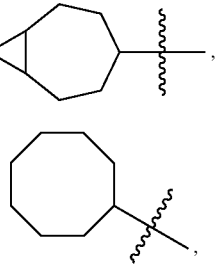

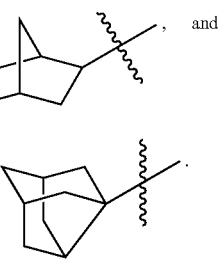

Another embodiment is a compound of formula (I), wherein R¹ is a cycloalkyl selected from the group consisting of -continued

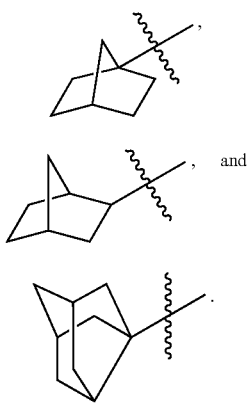

(viii)

(xvi) and (xvii)

Another embodiment is a compound of formula (I), wherein R¹ is a cycloalkyl selected from the group consisting of

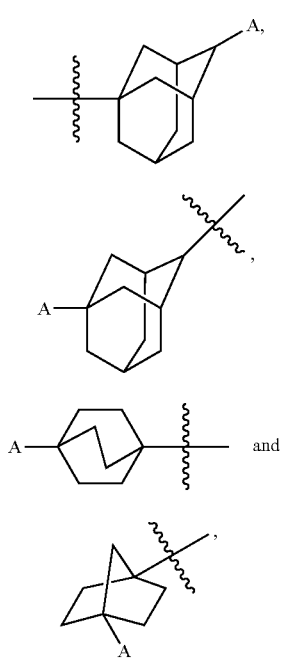

(ia)

(iia)

(via)

A— and (viiia)

wherein A is a substitution as defined in "cycloalkyl" in the Definition of Terms section.

Another embodiment is a compound of formula (I), wherein R¹ is a cycloalkyl that is (ii)

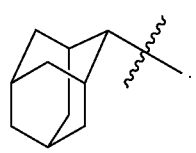

Another embodiment is a compound of formula (I), wherein R¹ is a cycloalkyl that is formula (iia)

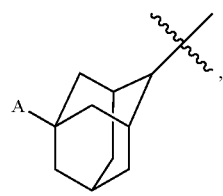

(iia)

wherein A is a substitution as defined in the definition of "cycloalkyl" in the Definition of Terms section.

Another embodiment is a compound of formula (I), wherein R¹ is a heterocycle selected from the group consisting of (ix)

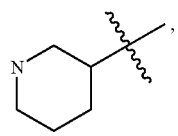

(x)

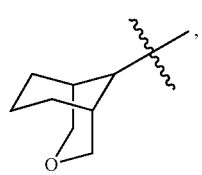

(xi)

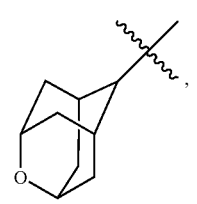

(xii)

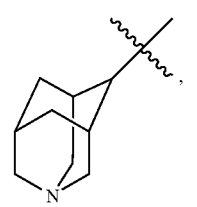

(xiii)

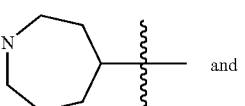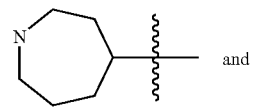 and

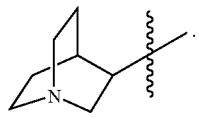

(xiv)

Another embodiment is a compound of formula (I), wherein $R^1$ is a heterocycle selected from the group consisting of

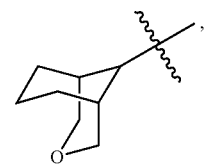

(x)

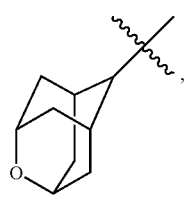

(xi)

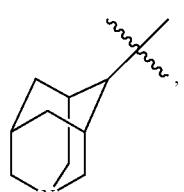

(xii)

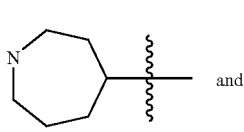

(xiii)
and

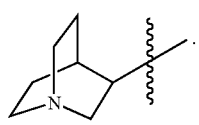

(xiv)

Another embodiment is a compound of formula (I), wherein $R^1$ is a heterocycle selected from the group consisting of

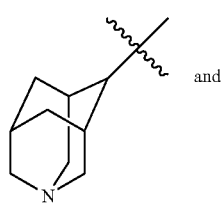

(xii)
and

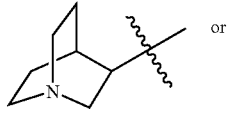

(xiv)
or the corresponding N-oxides (xvi) and (xvii)

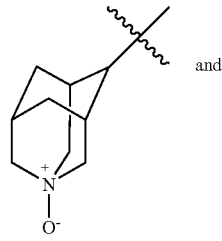

(xvi)
and

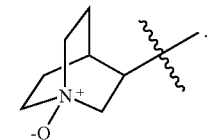

(xvii)

Another embodiment is a compound of formula (I), wherein $R^1$ is a heterocycle that is azaadamantane.

Another embodiment is a compound of formula (I), wherein $R^1$ is cycloalkyl substituted with 0, 1, 2, 3 or 4 substituents selected from the group consisting of alkyl, alkenyl, alkyl-NH-alkyl, alkylcarbonyl, alkylsulfonyl, alkylthio, aryl, arylalkyl, aryloxyalkyl, arylcarbonyl, arylsulfonyl, carboxyalkyl, carboxycycloalkyl, cyano, cyanoalkyl, cycloalkyl, cycloalkylcarbonyl, cycloalkylsulfonyl, halogen, haloalkyl, heterocyclecarbonyl, heterocyclesulfonyl, heteroaryl, heteroarylalkyl, heterocycle, heterocyclealkyl, heterocycleoxyalkyl, —$NO_2$, —$NR^8$—$[C(R^9R^{10})]_p$—C(O)—$R^{11}$, —$[C(R^{12}R^{13})]_q$—$CR^{12}(OH)$—$R^{14}$, —$[C(R^{12}R^{13})]_q$—C(O)—$R^{14}$, —$CR^{12}$=$R^{13}$—C(O)—$R^{14}$, —$[C(R^{12}R^{13})]_q$—$S(O)_2$—$R^{14}$, —$[C(R^{12}R^{13})]_q$—S(O)—$R^{14}$, —$[C(R^{12}R^{13})]_q$—S—$R^{14}$, —O—$[C(R^{12}R^{13})]_q$—C(O)—$R^{14}$, —$OR^{15}$, —$N(R^{16}R^{17})$, $NR^8C(O)N(R^{19}R^{20})$, —$CO_2R^{18}$, —C(O)—$N(R^{19}R^{20})$, —$[C(R^{12}R^{13})]_p$—C(O)—$N(R^{19}R^{20})$, —$C(NH)NH_2$, —$C(R^{21}R^{22})$—$OR^{23}$, and —$C(R^{24}R^{25})$—N($R^{26}R^{27}$), —C(=NOH)—$N(H)_2$, —$C(R^{28}R^{29})$—C(O)N($R^{30}R^{31}$), —$S(O)_2$—$N(R^{32}R^{33})$, —$S(O)_2$—$[C(R^9R^{10})]_p$—C(O)N($R^{32}R^{33}$), and —$C(R^{28}R^{29})$—$S(O)_2$—$N(R^{32}R^{33})$; wherein p, q, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$ and $R^{33}$ are as described in the definition of "cycloalkyl" in the Definition of Terms.

Another embodiment is a compound of formula (I), wherein $R^1$ is substituted with 0, 1, 2, 3 or 4 substituents selected from the group consisting of alkylsulfonyl, cyano, halogen, —$C(R^{12}R^{13})$—C(O)—$R^{14}$, —$OR^{15}$, —$CO_2R^{18}$, —C(O)—$N(R^{19}R^{20})$, and —$S(O)_2$—$N(R^{32}R^{33})$.

Another embodiment is a compound of formula (I), wherein $R^1$ is substituted with 0, 1 or 2 substituents selected from the group consisting of fluorine, methylsulfonyl, cyano, —OH, —$OCH_3$, —$OCF_3$, —$OCHF_2$, —$CO_2H$, —$CH_2$—$CO_2H$, —$CH(CH_3)$—$CO_2H$, —$C(CH_3)_2$—$CO_2H$, —$CHF_2$, —$CH(CH_3)(OH)$, —$C(CH_3)_2(OH)$, —$CH_2OH$, —C(O)—$NH_2$, and —$S(O)_2$—$NH_2$.

Another embodiment is a compound of formula (I), wherein $R^1$ is substituted with at least one substituent selected from the group consisting of fluorine, methylsulfonyl, cyano, —OH, —CO$_2$H, —CH$_2$—CO$_2$H, —CH(CH$_3$)—CO$_2$H, —C(CH$_3$)$_2$—CO$_2$H, —CH(CH$_3$)(OH), —C(O)—NH$_2$, and —S(O)$_2$—NH$_2$.

Another embodiment is a compound of formula (I), wherein $R^1$ is substituted with 0, 1, 2, 3 or 4 substituents selected from the group consisting of alkylsulfonyl, cyano, —OR$^{15}$, —CO$_2$R$^{18}$, —C(O)—N(R$^{19}$R$^{20}$), and —S(O)$_2$—N(R$^{32}$R$^{33}$).

Another embodiment is a compound of formula (I), wherein $R^2$ is hydrogen, alkyl or aryl.

Another embodiment is a compound of formula (I), wherein $R^2$ is hydrogen.

Another embodiment is a compound of formula (I), wherein $R^2$ is alkyl.

Another embodiment is a compound of formula (I), wherein $R^2$ is aryl.

Another embodiment is a compound of formula (I), wherein $R^1$ and $R^2$ together with the atoms to which they are attached form a heterocycle.

Another embodiment is a compound of formula (I), wherein $R^3$ and $R^4$ are each hydrogen.

Another embodiment is a compound of formula (I), wherein $R^3$ and $R^4$ are each alkyl.

Another embodiment is a compound of formula (I), wherein $R^3$ is hydrogen and $R^4$ is alkyl.

Another embodiment is a compound of formula (I), wherein $R^2$ and $R^3$ together with the atoms to which they are attached form a heterocycle.

Another embodiment is a compound of formula (I), wherein $R^2$ and $R^3$ together with the atoms to which they are attached form a 5-membered heterocycle, and $R^4$ is hydrogen; and is represented by formula (II):

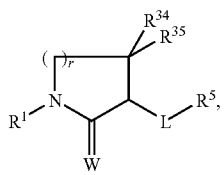

(II)

wherein
$R^{34}$ and $R^{35}$ are independently hydrogen or alkyl; or $R^{34}$ and $R^{35}$ together with the atom to which they are attached form a cycloalkyl, and
r is 1 or 2.

Another embodiment is a compound of formula (I), wherein $R^3$ and $R^4$ together with the atom to which they are attached form a cycloalkyl, heterocycle, heteroaryl or aryl.

Another embodiment is a compound of formula (I), wherein $R^3$ and $R^4$ together with the atom to which they are attached form a cycloalkyl, heterocycle, heteroaryl or aryl; and L is a bond (i.e., n is 0, when L is —(CH$_2$)$_n$—).

Another embodiment is a compound of formula (I), wherein $R^3$ and $R^4$ together with the atom to which they are attached form a cycloalkyl or heterocycle.

Another embodiment is a compound of formula (I), wherein $R^3$ and $R^4$ together with the atom to which they are attached form a cycloalkyl, wherein cycloalkyl is (C$_3$-C$_6$) cycloalkyl.

Another embodiment is a compound of formula (I), wherein $R^3$ and $R^4$ together with the atom to which they are attached form a heteroaryl or aryl.

Another embodiment is a compound of formula (I), wherein $R^4$ and $R^5$ together with atoms to which they are attached form a cycloalkyl or heterocycle.

Another embodiment is a compound of formula (I), wherein $R^3$ is hydrogen, $R^4$ and $R^5$ together with atoms to which they are attached form a cycloalkyl or heterocycle.

Another embodiment is a compound of formula (I), wherein $R^3$ is hydrogen, $R^4$ and $R^5$ together with atoms to which they are attached form a heterocycle.

Another embodiment is a compound of formula (I), wherein L is —(CR$^{38}$R$^{39}$)$_m$—X—(CR$^{38}$R$^{39}$)$_n$— or —(CR$^{38}$R$^{39}$)$_m$—X—(CR$^{38}$R$^{39}$)$_n$—Y—; wherein m is 0, X is —CR$^{36}$R$^{37}$—, and R$^{36}$ and $R^2$ together with the atoms to which they are attached form a heterocycle, and is represented by formulas (III) and (IV):

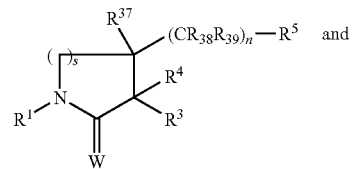

(III)

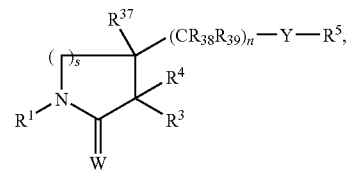

(IV)

wherein s is independently 1 or 2.

Another embodiment is a compound of formula (III), wherein n is 0, and $R^5$ is aryl or heteroaryl.

Another embodiment is a compound of formula (IV), wherein $R^5$ is aryl or heteroaryl.

Another embodiment is a compound of formula (I), wherein L is —(CR$^{38}$R$^{39}$)$_m$—X—(CR$^{38}$R$^{39}$)$_n$— or —(CR$^{38}$R$^{39}$)$_m$—X—(CR$^{38}$R$^{39}$)$_n$—Y—; wherein m is 0, X is —NR$^{36}$—, and R$^{36}$ and $R^2$ together with the atoms to which they are attached form a heterocycle, and is represented by formulas (Va) and (Vb):

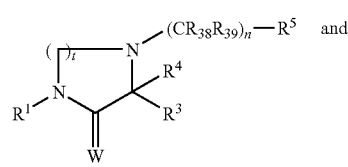

(Va)

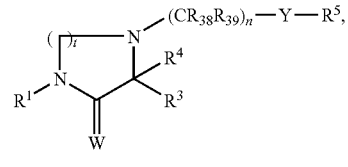

(Vb)

wherein t is 1 or 2.

Another embodiment is a compound of formula (I), wherein $R^5$ is amino, aryl, cycloalkyl, heteroaryl, or heterocycle.

Another embodiment is a compound of formula (I), wherein $R^5$ is cycloalkyl, wherein the cycloalkyl is optionally substituted with 1, 2, or 3 substituents independently selected from the group consisting of alkoxy, alkyl, aryloxy, aryl, carboxy, carboxyalkyl, cycloalkyl, cycloalkoxy, halogen, haloalkoxy, haloalkyl, halothioalkoxy, heteroaryl, hydroxyl, mercapto, thioalkoxy, thiocycloalkoxy, and thioaryloxy.

Another embodiment is a compound of formula (I), wherein $R^5$ is amino.

Another embodiment is a compound of formula (I), wherein $R^5$ is aryl optionally substituted with 1, 2, or 3 substituents independently selected from the group consisting of alkoxy, alkyl, aryloxy, carboxy, carboxyalkyl, cycloalkyl, cycloalkoxy, cyano, halogen, haloalkoxy, haloalkyl, halothioalkoxy, heteroaryl, hydroxyl, mercapto, thioalkoxy, thiocycloalkoxy, and thioaryloxy.

Another embodiment is a compound of formula (I), wherein $R^5$ is phenyl optionally substituted with 1, 2 or 3 substituents independently selected from the group consisting of alkyl, cyano, halogen, haloalkyl and heteroaryl.

Another embodiment is a compound of formula (I), wherein $R^5$ is heteroaryl selected from pyridinyl, pyridazinyl, pyrimidinyl, pyrazinyl, wherein the heteroaryl is optionally substituted with 1, 2, or 3 substituents independently selected from the group consisting of alkoxy, alkyl, aryl, aryloxy, carboxy, carboxyalkyl, cycloalkyl, cycloalkoxy, cyano, halogen, haloalkoxy, haloalkyl, halothioalkoxy, hydroxyl, mercapto, thioalkoxy, thiocycloalkoxy, and thioaryloxy.

Another embodiment is a compound of formula (I), wherein $R^5$ is pyridinyl, wherein the pyridinyl is optionally substituted with 1, 2, or 3 substituents independently selected from the group consisting of alkyl, cyano, halogen, and haloalkyl.

Another embodiment is a compound of formula (I), wherein $R^5$ is heterocycle selected from azabicyclo[3.2.0]hept-3-yl, piperazinyl, piperidinyl, morpholinyl, thiomorpholinyl, wherein the heterocycle is optionally substituted with 1, 2, or 3 substituents independently selected from the group consisting of alkoxy, alkyl, aryl, cyano, halogen, haloalkyl, and heteroaryl, wherein the aryl and heteroaryl groups are optionally substituted with halogen or haloalkyl.

Another embodiment is a compound of formula (I), wherein $R^5$ is heterocycle selected from piperazinyl or piperidinyl, wherein the heterocycle is optionally substituted with 1, 2, or 3 substituents independently selected from the group consisting of alkyl, aryl, cyano, halogen, haloalkyl, and heteroaryl, wherein the aryl is phenyl and the heteroaryl is pyridinyl each optionally substituted with halogen or haloalkyl.

Another embodiment is a compound of formula (I), wherein L is —$(CH_2)_n$—, wherein n is 0, 1, or 2.

Another embodiment is a compound of formula (I), wherein L is —$(CH_2)_n$—, wherein n is 0.

Another embodiment is a compound of formula (I), wherein L is —$(CH_2)_n$—, wherein n is 1.

Another embodiment is a compound of formula (I), wherein L is —$(CH_2)_m$—X—$(CH_2)_n$—, wherein m is 0 and n is 0.

Another embodiment is a compound of formula (I), wherein L is —$(CH_2)_m$—X—$(CH_2)_n$—, wherein m is 0 and n is 1.

Another embodiment is a compound of formula (I), wherein L is —$(CH_2)_m$—X—$(CH_2)_n$—, wherein m is 0 and n is 2.

Another embodiment is a compound of formula (I), wherein L is —$(CH_2)_m$—X—$(CH_2)_n$—, wherein m is 1 and n is 0.

Another embodiment is a compound of formula (I), wherein L is —$(CH_2)_m$—X—$(CH_2)_n$—, wherein m is 1 and n is 1.

Another embodiment is a compound of formula (I), wherein L is —$(CH_2)_m$—X—$(CH_2)_n$—, wherein m is 1 and n is 2.

Another embodiment is a compound of formula (I), wherein L is —$(CH_2)_m$—X—$(CH_2)_n$—, wherein m is 2 and n is 0.

Another embodiment is a compound of formula (I), wherein L is —$(CH_2)_m$—X—$(CH_2)_n$—, wherein m is 2 and n is 1.

Another embodiment is a compound of formula (I), wherein L is —$(CH_2)_m$—X—$(CH_2)_n$—, wherein m is 2 and n is 2.

Another embodiment is a compound of formula (I), wherein L is —$(CH_2)_m$—X—$(CH_2)_n$—, wherein X is —O—.

Another embodiment is a compound of formula (I), wherein L is —$(CH_2)_m$—X—$(CH_2)_n$—, wherein X is —S—.

Another embodiment is a compound of formula (I), wherein L is —$(CH_2)_m$—X—$(CH_2)_n$—, wherein X is —S(O)—.

Another embodiment is a compound of formula (I), wherein L is —$(CH_2)_m$—X—$(CH_2)_n$—, wherein X is —$S(O)_2$—.

Another embodiment is a compound of formula (I), wherein L is —$(CH_2)_m$—X—$(CH_2)_n$—, wherein X is —$NR^{36}$—.

Another embodiment is a compound of formula (I), wherein L is —$(CH_2)_m$—X—$(CH_2)_n$—, wherein X is —$CR^{36}R^{37}$—.

Another embodiment is a compound of formula (I), wherein L is —$(CH_2)_m$—X—$(CH_2)_n$—, wherein X is —$NR^{36}$—; wherein $R^{36}$ is hydrogen or alkyl.

Another embodiment is a compound of formula (I), wherein L is —$(CH_2)_m$—X—$(CH_2)_n$—, wherein X is —$CR^{36}R^{37}$—; wherein $R^{36}$ and $R^{37}$ are independently hydrogen or alkyl.

Another embodiment is a compound of formula (I), wherein L is a bond (i.e., n is 0, when L is —$(CH_2)_n$—) and $R^5$ is amino. In a further embodiment, $R^5$ is aryl or heteroaryl. In a further embodiment, $R^5$ is heterocycle.

Another embodiment is a compound of formula (I), wherein L is —$(CH_2)_m$—X—$(CH_2)_n$—Y—, wherein X is —$CR^{36}R^{37}$— and Y is O or $NCH_3$, n is 1, and $R^5$ is aryl or heteroaryl.

Another embodiment is a compound of formula (I), wherein W is N—CN.

Another embodiment is a compound of formula (I), wherein W is S.

Another embodiment is a compound of formula (I), wherein W is N—$R^6$, wherein $R^6$ is hydrogen, alkyl or aryl.

Another embodiment is a compound of formula (I), wherein W is N—$R^6$, wherein $R^6$ is hydrogen or alkyl.

Another embodiment is a compound of formula (I), wherein W is N—$OR^6$, wherein $R^6$ is hydrogen, alkyl or aryl.

Another embodiment is a compound of formula (I), wherein W is N—$OR^6$, wherein $R^6$ is hydrogen, or alkyl.

Another embodiment is a compound of formula (I), wherein $R^1$ is adamantyl (ii), $R^2$ is hydrogen, $R^3$ and $R^4$ are each methyl, $R^5$ is phenyl optionally substituted with 1 or 2 substituents independently selected from halogen, cyano, methoxy or haloalkyl, W is N—CN, and L is —$(CH_2)_m$—X—$(CH_2)_n$—, wherein m and n are both 0 and X is O.

Another embodiment is a compound of formula (I), wherein $R^1$ is adamantyl (ii) optionally substituted with —$OR^{15}$ wherein $R^{15}$ is hydrogen, $R^2$ is hydrogen, $R^3$ and $R^4$ are each methyl, $R^5$ is phenyl optionally substituted with 1 or 2 substituents independently selected from halogen, cyano, methoxy or haloalkyl, W is N—CN, and L is —$(CH_2)_m$—X—$(CH_2)_n$—, wherein m and n are both 0 and X is O.

Another embodiment is a compound of formula (I), wherein $R^1$ is adamantyl (ii) optionally substituted with —$OR^{15}$ wherein $R^{15}$ is hydrogen, $R^2$ is hydrogen, $R^3$ and $R^4$ are each alkyl, $R^5$ is phenyl optionally substituted with 1 or 2 substituents independently selected from halogen, haloalkyl, cyano, methoxy or haloalkyl, W is N—$R^6$, $R^6$ is hydrogen, and L is —$(CH_2)_m$—X—$(CH_2)_n$—, wherein m is 0 and n is 0 or 1 and X is O.

Another embodiment is a compound of formula (I), wherein $R^1$ is adamantyl (ii) optionally substituted with —$OR^{15}$ wherein $R^{15}$ is hydrogen, $R^2$ is hydrogen, $R^3$ and $R^4$ are both hydrogen, $R^5$ is phenyl optionally substituted with 1 or 2 substituents independently selected from alkyl, halogen, cyano, methoxy or haloalkyl, W is N—CN, and L is —$(CH_2)_n$—, wherein n is 1.

Another embodiment is a compound of formula (I), wherein $R^1$ is adamantyl (ii) optionally substituted with —$OR^{15}$ wherein $R^{15}$ is hydrogen, $R^2$ is hydrogen, $R^3$ and $R^4$ are each alkyl, $R^5$ is phenyl optionally substituted with 1 or 2 substituents independently selected from halogen, cyano, methoxy or haloalkyl, W is N—CN, and L is —$(CH_2)_n$—, wherein n is 1.

Another embodiment is a compound of formula (I), wherein $R^1$ is adamantyl (ii) optionally substituted with —$OR^{15}$ wherein $R^{15}$ is hydrogen, $R^2$ is hydrogen, $R^3$ and $R^4$ are each alkyl, $R^5$ is phenyl optionally substituted with 1 or 2 substituents independently selected from halogen, cyano, methoxy or haloalkyl, $R^6$ is hydrogen, W is $NR^6$, and L is —$(CH_2)_n$—, wherein n is 1.

Another embodiment is a compound of formula (I), wherein $R^1$ is adamantyl (ii) optionally substituted with —$OR^{15}$ wherein $R^{15}$ is hydrogen, $R^2$ is hydrogen, $R^3$ and $R^4$ are each methyl, $R^5$ is phenyl optionally substituted with 1 or 2 substituents independently selected from halogen, cyano, methoxy or haloalkyl, W is N—CN, and L is —$(CH_2)_m$—X—$(CH_2)_n$—, wherein m and n are each 0 and X is O.

Another embodiment is a compound of formula (I), wherein $R^1$ is adamantyl (ii) optionally substituted with —$OR^{15}$ wherein $R^{15}$ is hydrogen, $R^2$ is hydrogen, $R^3$ and $R^4$ are each hydrogen, $R^5$ is phenyl optionally substituted with 1 or 2 substituents independently selected from halogen, cyano, methoxy or haloalkyl, W is N—CN, and L is —$(CH_2)_m$—X—$(CH_2)_n$—, wherein m and n are each 0 and X is O.

Another embodiment is a compound of formula (I), wherein $R^1$ is adamantyl (ii) optionally substituted with —$OR^{15}$ wherein $R^{15}$ is hydrogen, $R^2$ is hydrogen, $R^3$ and $R^4$ are each hydrogen, $R^5$ is pyridinyl optionally substituted with halogen, W is N—CN, and L is —$(CH_2)_n$—, wherein n is 1.

Another embodiment is a compound of formula (I), wherein $R^1$ is adamantyl (ii) optionally substituted with —$OR^{15}$ wherein $R^{15}$ is hydrogen, $R^2$ is hydrogen, $R^3$ and $R^4$ taken together with the atom to which they are attached are ($C_3$-$C_6$)cycloalkyl, $R^5$ is phenyl optionally substituted with 1 or 2 substituents independently selected from halogen, cyano, methoxy or haloalkyl, W is N—CN, and L is —$(CH_2)_n$—, wherein n is 0.

Another embodiment is a compound of formula (I), wherein $R^1$ is adamantyl (ii) optionally substituted with —$OR^{15}$ wherein $R^{15}$ is hydrogen, $R^2$ is hydrogen, $R^3$ and $R^4$ taken together with the atom to which they are attached are ($C_3$-$C_6$)cycloalkyl, $R^5$ is phenyl optionally substituted with 1 or 2 substituents independently selected from halogen, cyano, methoxy or haloalkyl, W is N—CN, and L is —$(CH_2)_m$—X—$(CH_2)_n$—, wherein m and n are each 0 and X is O.

Another embodiment is a compound of formula (I), wherein $R^1$ is adamantyl (ii) optionally substituted with —$OR^{15}$ wherein $R^{15}$ is hydrogen, $R^2$ is hydrogen, $R^3$ and $R^4$ are each alkyl, $R^5$ is heteroaryl optionally substituted with halogen or haloalkyl, W is N—CN, and L is —$(CH_2)_m$—X—$(CH_2)_n$—, wherein m is 0 and n is 0, and X is O.

Another embodiment is a compound of formula (I), wherein $R^1$ is adamantyl (ii) optionally substituted with alkylsulfonyl, $R^2$ is hydrogen, $R^3$ and $R^4$ are each alkyl, $R^5$ is phenyl optionally substituted with 1 or 2 substituents independently selected from halogen, cyano, methoxy or haloalkyl, W is S, and L is —$(CH_2)_m$—X—$(CH_2)_n$—, wherein m and n are each 0 and X is O.

Another embodiment is a compound of formula (I), wherein $R^1$ is adamantyl (ii) optionally substituted with alkylsulfonyl, $R^2$ is hydrogen, $R^3$ and $R^4$ are each alkyl, $R^5$ is phenyl optionally substituted with 1 or 2 substituents independently selected from halogen, cyano, methoxy or haloalkyl, $R^6$ is alkyl, W is N—$OR^6$, and L is —$(CH_2)_m$—X—$(CH_2)_n$—, wherein m and n are each 0 and X is O.

Another embodiment is a compound of formula (I), wherein $R^1$ is adamantyl (ii) optionally substituted with alkylsulfonyl, $R^2$ is hydrogen, $R^3$ and $R^4$ are each alkyl, $R^5$ is phenyl optionally substituted with 1 or 2 substituents independently selected from halogen, cyano, methoxy or haloalkyl, W is N—CN, and L is —$(CH_2)_m$—X—$(CH_2)_n$—, wherein m and n are each 0 and X is O.

Another embodiment is a compound of formula (I), wherein $R^1$ is adamantyl (ii) optionally substituted with alkylsulfonyl, $R^2$ is hydrogen, $R^3$ and $R^4$ are each alkyl, $R^5$ is heteroaryl optionally substituted with halogen or haloalkyl, W is N—CN, and L is —$(CH_2)_m$—X—$(CH_2)_n$—, wherein m is 0 and n is 0, and X is O.

Another embodiment is a compound of formula (I), wherein $R^1$ is adamantyl (ii) optionally substituted with —$S(O)_2$—N($R^{32}R^{33}$), $R^2$ is hydrogen, $R^3$ and $R^4$ are each alkyl, $R^5$ is phenyl optionally substituted with 1 or 2 substituents independently selected from halogen, cyano, methoxy or haloalkyl, W is N—CN, and L is —$(CH_2)_m$—X—$(CH_2)_n$—, wherein m and n are each 0 and X is O.

Another embodiment is a compound of formula (I), wherein $R^1$ is adamantyl (ii) optionally substituted with —$S(O)_2$—N($R^{32}R^{33}$), $R^2$ is hydrogen, $R^3$ and $R^4$ are each alkyl, $R^5$ is phenyl optionally substituted with 1 or 2 substituents independently selected from halogen, cyano, haloalkoxy, methoxy or haloalkyl, W is N—CN or S, and L is —$(CH_2)_m$—X—$(CH_2)_n$—, wherein m and n are each 0 and X is O.

Another embodiment is a compound of formula (I), wherein $R^1$ is adamantyl (ii) optionally substituted with —$S(O)_2$—N($R^{32}R^{33}$), $R^2$ is hydrogen, $R^3$ and $R^4$ are each alkyl, $R^5$ is phenyl optionally substituted with 1 or 2 substituents independently selected from halogen, cyano, methoxy or haloalkyl, W is N—$R^6$, $R^6$ is hydrogen, and L is —$(CH_2)_m$—X—$(CH_2)_n$—, wherein m is 0 and n is 0 or 1 and X is O.

Another embodiment is a compound of formula (I), wherein $R^1$ is adamantyl (ii) optionally substituted with —$S(O)_2$—N($R^{32}R^{33}$), $R^2$ is hydrogen, $R^3$ and $R^4$ are each alkyl, $R^5$ is heteroaryl optionally substituted with halogen or haloalkyl, W is N—CN, and L is —$(CH_2)_m$—X—$(CH_2)_n$—, wherein m is 0 and n is 0, and X is O.

Another embodiment is a compound of formula (I), wherein $R^1$ is adamantyl (ii) optionally substituted with —$CO_2R^{18}$ wherein $R^{18}$ is alkyl, $R^2$ is hydrogen, $R^3$ and $R^4$ are each alkyl, $R^5$ is phenyl optionally substituted with 1 or 2 substituents independently selected from halogen, cyano, haloalkoxy, methoxy or haloalkyl, W is N—CN, and L is —(CH$_2$)$_m$—X—(CH$_2$)$_n$—, wherein m and n are each 0 and X is O.

Another embodiment is a compound of formula (I), wherein R$^1$ is adamantyl (ii) optionally substituted with —CO$_2$R$^{18}$ wherein R$^{18}$ is alkyl, R$^2$ is hydrogen, R$^3$ and R$^4$ are each alkyl, R$^5$ is phenyl optionally substituted with 1 or 2 substituents independently selected from halogen, cyano, methoxy or haloalkyl, W is N—CN, and L is —(CH$_2$)$_m$—X—(CH$_2$)$_n$—, wherein m and n are each 0 and X is O.

Another embodiment is a compound of formula (I), wherein R$^1$ is adamantyl (ii) optionally substituted with —CO$_2$R$^{18}$ wherein R$^{18}$ is alkyl, R$^2$ is hydrogen, R$^3$ and R$^4$ are each alkyl, R$^5$ is phenyl optionally substituted with 1 or 2 substituents independently selected from halogen, cyano, methoxy or haloalkyl, W is N—CN, and L is —(CH$_2$)$_m$—X—(CH$_2$)$_n$—, wherein m is 0 and n is 1 and X is O.

Another embodiment is a compound of formula (I), wherein R$^1$ is adamantyl (ii) optionally substituted with —CO$_2$R$^{18}$ wherein R$^{18}$ is alkyl, R$^2$ is hydrogen, R$^3$ and R$^4$ are each alkyl, R$^5$ is phenyl optionally substituted with 1 or 2 substituents independently selected from halogen, cyano, methoxy or haloalkyl, W is S, and L is —(CH$_2$)$_m$—X—(CH$_2$)$_n$—, wherein m is 0 and n is 1 and X is O.

Another embodiment is a compound of formula (I), wherein R$^1$ is adamantyl (ii) optionally substituted with —CO$_2$R$^{18}$ wherein R$^{18}$ is alkyl, R$^2$ is hydrogen, R$^3$ and R$^4$ are each alkyl, R$^5$ is heterocycle optionally substituted with heteroaryl that is optionally substituted with haloalkyl, W is S, and L is —(CH$_2$)$_n$—, wherein n is 0.

Another embodiment is a compound of formula (I), wherein R$^1$ is adamantyl (ii) optionally substituted with —CO$_2$R$^{18}$ wherein R$^{18}$ is hydrogen, R$^2$ is hydrogen, R$^3$ and R$^4$ are each alkyl, R$^5$ is phenyl optionally substituted with 1 or 2 substituents independently selected from halogen, cyano, methoxy or haloalkyl, W is N—CN, and L is —(CH$_2$)$_m$—X—(CH$_2$)$_n$—, wherein m is 0 and n is 1 and X is O.

Another embodiment is a compound of formula (I), wherein R$^1$ is adamantyl (ii) optionally substituted with —CO$_2$R$^{18}$ wherein R$^{18}$ is alkyl, R$^2$ is hydrogen, R$^3$ and R$^4$ are each alkyl, R$^5$ is heterocycle, W is N—CN, and L is —(CH$_2$)$_n$—, wherein n is 0.

Another embodiment is a compound of formula (I), wherein R$^1$ is adamantyl (ii) optionally substituted with —C(O)—N(R$^{19}$R$^{20}$), R$^2$ is hydrogen, R$^3$ and R$^4$ are each alkyl, R$^5$ is phenyl optionally substituted with 1 or 2 substituents independently selected from halogen, cyano, methoxy or haloalkyl, W is N—CN, and L is —(CH$_2$)$_m$—X—(CH$_2$)$_n$—, wherein m is 0 and n is 0 or 1 and X is O.

Another embodiment is a compound of formula (I), wherein R$^1$ is adamantyl (ii) optionally substituted with —C(O)—N(R$^{19}$R$^{20}$), R$^2$ is hydrogen, R$^3$ and R$^4$ are each alkyl, R$^5$ is phenyl optionally substituted with 1 or 2 substituents independently selected from halogen, cyano, methoxy or haloalkyl, W is N—R$^6$, R$^6$ is hydrogen, and L is —(CH$_2$)$_m$—X—(CH$_2$)$_n$—, wherein m is 0 and n is 0 or 1 and X is O.

Another embodiment is a compound of formula (I), wherein R$^1$ is adamantyl (ii) optionally substituted with —C(O)—N(R$^{19}$R$^{20}$), R$^2$ is hydrogen, R$^3$ and R$^4$ are each alkyl, R$^5$ is heteroaryl optionally substituted with halogen or haloalkyl, W is N—CN, and L is —(CH$_2$)$_m$—X—(CH$_2$)$_n$—, wherein m is 0 and n is 0 or 1 and X is O.

Another embodiment is a compound of formula (I), wherein R$^1$ is adamantyl (ii) optionally substituted with cyano, R$^2$ is hydrogen, R$^3$ and R$^4$ are each alkyl, R$^5$ is phenyl optionally substituted with 1 or 2 substituents independently selected from halogen, cyano, methoxy or haloalkyl, W is N—CN, and L is —(CH$_2$)$_m$—X—(CH$_2$)$_n$—, wherein m is 0 and n is 0, and X is O.

Another embodiment is a compound of formula (I), wherein R$^1$ is adamantyl (ii) optionally substituted with cyano, R$^2$ is hydrogen, R$^3$ and R$^4$ are each alkyl, R$^5$ is heteroaryl optionally substituted with halogen or haloalkyl, W is N—CN, and L is —(CH$_2$)$_m$—X—(CH$_2$)$_n$—, wherein m is 0 and n is 0, and X is O.

Another embodiment is a compound of formula (I), wherein R$^1$ is adamantyl (i), R$^2$ is hydrogen, R$^3$ and R$^4$ are each alkyl, R$^5$ is phenyl optionally substituted with 1 or 2 substituents independently selected from halogen, cyano, methoxy or haloalkyl, W is N—CN, and L is —(CH$_2$)$_m$—X—(CH$_2$)$_n$—, wherein m is 0 and n is 0, and X is O.

Another embodiment is a compound of formula (I), wherein R$^1$ is bicyclo[2.2.2]octanyl (vi) optionally substituted with —CO$_2$R$^{18}$ wherein R$^{18}$ is hydrogen or alkyl, R$^2$ is hydrogen, R$^3$ and R$^4$ are each alkyl, R$^5$ is phenyl optionally substituted with 1 or 2 substituents independently selected from halogen, cyano, methoxy or haloalkyl, W is N—CN, and L is —(CH$_2$)$_m$—X—(CH$_2$)$_n$—, wherein m is 0 and n is 0, and X is O.

Another embodiment is a compound of formula (I), wherein R$^1$ is bicyclo[2.2.2]octanyl (vi) optionally substituted with —C(O)—N(R$^{19}$R$^{20}$), R$^2$ is hydrogen, R$^3$ and R$^4$ are each alkyl, R$^5$ is phenyl optionally substituted with 1 or 2 substituents independently selected from halogen, cyano, methoxy or haloalkyl, W is N—CN, and L is —(CH$_2$)$_m$—X—(CH$_2$)$_n$—, wherein m is 0 and n is 0, and X is O.

Another embodiment is a compound of formula (I), wherein R$^1$ is bicyclo[2.2.2]octanyl (vi) optionally substituted with cyano, R$^2$ is hydrogen, R$^3$ and R$^4$ are each alkyl, R$^5$ is phenyl optionally substituted with 1 or 2 substituents independently selected from halogen, cyano, methoxy or haloalkyl, W is N—CN, and L is —(CH$_2$)$_m$—X—(CH$_2$)$_n$—, wherein m is 0 and n is 0, and X is O.

Another embodiment is a compound of formula (I), wherein R$^1$ is bicyclo[2.2.2]octanyl (vi) optionally substituted with —OR$^{15}$ wherein R$^{15}$ is hydrogen, alkyl or haloalkyl, R$^2$ is hydrogen, R$^3$ and R$^4$ are each alkyl, R$^5$ is phenyl optionally substituted with 1 or 2 substituents independently selected from halogen, cyano, methoxy or haloalkyl, W is N—CN, and L is —(CH$_2$)$_m$—X—(CH$_2$)$_n$—, wherein m is 0 and n is 0, and X is O.

Another embodiment is a compound of formula (I), wherein R$^1$ is bicyclo[2.2.2]octanyl (vi) optionally substituted with —CHF$_2$, R$^2$ is hydrogen, R$^3$ and R$^4$ are each alkyl, R$^5$ is phenyl optionally substituted with 1 or 2 substituents independently selected from halogen, cyano, methoxy or haloalkyl, W is N—CN, and L is —(CH$_2$)$_m$—X—(CH$_2$)$_n$—, wherein m is 0 and n is 0, and X is O.

Another embodiment is a compound of formula (I), wherein R$^1$ is cyclooctanyl (v), R$^2$ is hydrogen, R$^3$ and R$^4$ are each methyl, R$^5$ is phenyl optionally substituted with 1 or 2 substituents independently selected from halogen, cyano, methoxy or haloalkyl, W is N—CN, and L is —(CH$_2$)$_m$—X—(CH$_2$)$_n$—, wherein m and n are both 0 and X is O.

Another embodiment is a compound of formula (I), wherein R$^1$ is exo-bicyclo[2.2.1]heptyl (xvi), R$^2$ is hydrogen, R$^3$ and R$^4$ are each methyl, R$^5$ is phenyl optionally substituted with 1 or 2 substituents independently selected from halogen, cyano, methoxy or haloalkyl, W is N—CN, and L is —(CH$_2$)$_m$—X—(CH$_2$)$_n$—, wherein m and n are both 0 and X is O.

Another embodiment is a compound of formula (I), wherein R$^1$ is octahydro-2,5-methanopentalenyl (xvii), R$^2$ is hydrogen, R$^3$ and R$^4$ are each methyl, R$^5$ is phenyl optionally substituted with 1 or 2 substituents independently selected from halogen, cyano, methoxy or haloalkyl, W is N—CN, and L is —(CH$_2$)$_m$—X—(CH$_2$)$_n$—, wherein m and n are both 0 and X is O.

Another embodiment is a compound of formula (I), wherein R$^1$ is 1-azabicyclo[2.2.2]octyl (xvii), R$^2$ is hydrogen, R$^3$ and R$^4$ are each methyl, R$^5$ is phenyl optionally substituted with 1 or 2 substituents independently selected from halogen, cyano, methoxy or haloalkyl, W is N—CN, and L is —(CH$_2$)$_m$—X—(CH$_2$)$_n$—, wherein m and n are both 0 and X is O.

Another embodiment is a compound of formula (I), wherein R$^1$ is bicyclo[2.2.1]heptane-(viii) optionally substituted with —C(O)—N(R$^{19}$R$^{20}$), R$^2$ is hydrogen, R$^3$ and R$^4$ are each alkyl, R$^5$ is phenyl optionally substituted with 1 or 2 substituents independently selected from halogen, cyano, methoxy or haloalkyl, W is N—CN, and L is —(CH$_2$)$_m$—X—(CH$_2$)$_n$—, wherein m is 0 and n is 0, and X is O.

Another embodiment is a compound of formula (I), wherein R$^1$ is bicyclo[2.2.1]heptane-(viii) optionally substituted with cyano, R$^2$ is hydrogen, R$^3$ and R$^4$ are each alkyl, R$^5$ is phenyl optionally substituted with 1 or 2 substituents independently selected from halogen, cyano, methoxy or haloalkyl, W is N—CN, and L is —(CH$_2$)$_m$—X—(CH$_2$)$_n$—, wherein m is 0 and n is 0, and X is O.

Another embodiment is a compound of formula (I), wherein R$^1$ is bicyclo[2.2.1]heptane-(viii) optionally substituted with —CHF$_2$, R$^2$ is hydrogen, R$^3$ and R$^4$ are each alkyl, R$^5$ is phenyl optionally substituted with 1 or 2 substituents independently selected from halogen, cyano, methoxy or haloalkyl, W is N—CN, and L is —(CH$_2$)$_m$—X—(CH$_2$)$_n$—, wherein m is 0 and n is 0, and X is O.

Another embodiment is a compound of formula (I), wherein R$^1$ is bicyclo[2.2.1]heptane-(viii) optionally substituted with —OH, R$^2$ is hydrogen, R$^3$ and R$^4$ are each alkyl, R$^5$ is phenyl optionally substituted with 1 or 2 substituents independently selected from halogen, cyano, methoxy or haloalkyl, W is N—CN, and L is —(CH$_2$)$_m$—X—(CH$_2$)$_n$—, wherein m is 0 and n is 0, and X is O.

Exemplary compounds of various embodiments include, but are not limited to:

(1E)-2-(2-chloro-4-fluorophenoxy)-N'-cyano-N-[(E)-5-hydroxy-2-adamantyl]-2-methylpropanimidamide;
(1E)-N'-cyano-N-[(E)-5-hydroxy-2-adamantyl]-2-(2-methylphenyl)ethanimidamide;
1-(4-chlorophenyl)-N'-cyano-N-[(E)-5-hydroxy-2-adamantyl]cyclobutane carboximidamide;
(1E)-N'-cyano-2-(2,4-difluorophenyl)-N-[(E)-5-hydroxy-2-adamantyl]ethanimidamide;
(1E)-N'-cyano-2-(2-fluorophenyl)-N-[(E)-5-hydroxy-2-adamantyl]ethanimidamide;
(1E)-2-(2-chloropyridin-3-yl)-N'-cyano-N-[(E)-5-hydroxy-2-adamantyl]ethanimidamide;
(1E)-2-(4-chlorophenoxy)-N'-cyano-N-[(E)-5-hydroxy-2-adamantyl]ethanimidamide;
(1E)-2-(4-chlorophenoxy)-N'-cyano-N-[(E)-5-hydroxy-2-adamantyl]-2-methyl propanimidamide;
2-(4-chlorophenoxy)-2-methyl-N-[(E)-5-(methylsulfonyl)-2-adamantyl]propanethioamide;
(1E)-N-[(E)-5-(aminosulfonyl)-2-adamantyl]-2-(4-chlorophenoxy)-N'-cyano-2-methyl propanimidamide;
methyl(E)-4-{[(1E)-2-(4-chlorophenoxy)-N-cyano-2-methylpropanimidoyl]amino}adamantane-1-carboxylate;
2-(2-chloro-4-fluorophenoxy)-2-methyl-N-[(E)-5-(methylsulfonyl)-2-adamantyl]propanethioamide;
(1E)-2-(4-chlorophenoxy)-N'-methoxy-2-methyl-N-[(E)-5-(methylsulfonyl)-2-adamantyl]propanimidamide;
(E)-4-{[(1E)-2-(4-chlorophenoxy)-N-cyano-2-methylpropanimidoyl]amino}adamantane-1-carboxamide;
1-(3-chlorophenoxy)-N'-cyano-N-[(E)-5-hydroxy-2-adamantyl]cyclobutane carboximidamide;
methyl(E)-4-[(2-methyl-2-{[4-(trifluoromethyl)benzyl]oxy}propanethioyl)amino]adamantane-1-carboxylate;
methyl(E)-4-[((1E)-N-cyano-2-methyl-2-{[4-(trifluoromethyl)benzyl]oxy}propanimidoyl)amino]adamantane-1-carboxylate;
(1E)-2-(2-chloro-4-fluorophenoxy)-N-cyano-2-methyl-N-[(E)-5-(methylsulfonyl)-2-adamantyl]propanimidamide;
(1E)-2-(4-chlorophenoxy)-N-cyano-2-methyl-N-[(E)-5-(methylsulfonyl)-2-adamantyl]propanimidamide;
N-[(E)-5-(aminosulfonyl)-2-adamantyl]-2-methyl-2-[2-(trifluoromethoxy)phenoxy]propanethioamide;
methyl(E)-4-[(2-methyl-2-{4-[5-(trifluoromethyl)pyridin-2-yl]piperazin-1-yl}propanethioyl)amino]adamantane-1-carboxylate;
3-(4-chlorophenyl)-N-[(E)-5-hydroxy-2-adamantyl]-2,2-dimethylpropanimidamide;
(1E)-3-(4-chlorophenyl)-N'-cyano-N-[(E)-5-hydroxy-2-adamantyl]-2,2-dimethyl propanimidamide;
(E)-4-[((1E)-N-cyano-2-methyl-2-{[4-(trifluoromethyl)benzyl]oxy}propanimidoyl)amino]adamantane-1-carboxylic acid;
(E)-4-[((1E)-N-cyano-2-methyl-2-{[4-(trifluoromethyl)benzyl]oxy}propanimidoyl)amino]adamantane-1-carboxamide;
(E)-4-[(2-methyl-2-{4-[5-(trifluoromethyl)pyridin-2-yl]piperazin-1-yl}propanethioyl)amino]adamantane-1-carboxylic acid;
(1E)-N'-cyano-N-[(E)-5-cyano-2-adamantyl]-2-methyl-2-{[4-(trifluoromethyl)benzyl]oxy}propanimidamide;
methyl(E)-4-({(1E)-N-cyano-2-[(4-methoxybenzyl)oxy]-2-methylpropanimidoyl}amino)adamantane-1-carboxylate;
methyl(E)-4-[((1E)-N-cyano-2-methyl-2-{4-[5-(trifluoromethyl)pyridin-2-yl]piperazin-1-yl}propanimidoyl)amino]adamantane-1-carboxylate;
(E)-4-[((1E)-N-cyano-2-methyl-2-{4-[5-(trifluoromethyl)pyridin-2-yl]piperazin-1-yl}propanimidoyl)amino]adamantane-1-carboxylic acid;
(E)-4-[((1E)-N-cyano-2-methyl-2-{4-[5-(trifluoromethyl)pyridin-2-yl]piperazin-1-yl}propanimidoyl)amino]adamantane-1-carboxamide;
6-({4,4-dimethyl-1-[(E)-5-(methylsulfonyl)-2-adamantyl]-5-thioxopyrrolidin-3-yl}methoxy)nicotinonitrile;
(2Z)-4-{[(5-cyanopyridin-2-yl)oxy]methyl}-3,3-dimethyl-1-[(E)-5-(methylsulfonyl)-2-adamantyl]pyrrolidin-2-ylidenecyanamide;
(3S)-1-[(3-chloro-2-methylphenyl)sulfonyl]-N-cyclohexylpiperidine-3-carbothioamide;
(3S)-1-[(3-chloro-2-methylphenyl)sulfonyl]-N'-cyano-N-cyclohexylpiperidine-3-carboximidamide;
(E)-4-{[(1E)-2-(4-chlorophenoxy)-N-cyano-2-methylpropanimidoyl]amino}adamantane-1-carboxylic acid;
(1E)-2-(4-chlorophenoxy)-N'-cyano-N-[(E)-5-cyano-2-adamantyl]-2-methylpropanimidamide;
(1E)-2-(4-chlorophenoxy)-N'-cyano-N-hexahydro-2,5-methanopentalen-3a(1H)-yl-2-methylpropanimidamide;
(1E)-N-[(4s)-1-azatricyclo[3.3.1.1$^{3,7}$]dec-4-yl]-2-(4-chlorophenoxy)-N'-cyano-2-methylpropanimidamide;
N-1-azabicyclo[2.2.2]oct-3-yl-2-(4-chlorophenoxy)-N'-cyano-2-methylpropanimidamide;
2-(4-chlorophenoxy)-N'-cyano-N-cyclooctyl-2-methylpropanimidamide;
N-[exo-bicyclo[2.2.1]hept-2-yl]-2-(4-chlorophenoxy)-N'-cyano-2-methylpropanimidamide;

(1E)-N-1-adamantyl-2-(4-chlorophenoxy)-N-cyano-2-methylpropanimidamide;
(1E)-N'-cyano-2-(2-fluorophenoxy)-2-methyl-N-[(E)-5-(methylsulfonyl)adamantan-2-yl]propanimidamide;
2-(2-fluorophenoxy)-2-methyl-N-[(E)-5-(methylsulfonyl)adamantan-2-yl]propanethioamide;
(1E)-N'-cyano-2-(2,4-difluorophenoxy)-2-methyl-N-[(E)-5-(methylsulfonyl)adamantan-2-yl]propanimidamide;
2-(2,4-difluorophenoxy)-2-methyl-N-[(E)-5-(methylsulfonyl)adamantan-2-yl]propanethioamide;
4-{[2-(4-chlorophenoxy)-N-cyano-2-methylpropanimidoyl]amino}bicyclo[2.2.2]octane-1-carboxylic acid;
4-{[2-(4-chlorophenoxy)-N-cyano-2-methylpropanimidoyl]amino}bicyclo[2.2.2]octane-1-carboxamide;
methyl(E)-4-({(1E)-2-[(1R*,5S*,6R*)-6-(4-chlorophenyl)-3-azabicyclo[3.2.0]hept-3-yl]-N-cyano-2-methylpropanimidoyl}amino)adamantane-1-carboxylate;
methyl(E)-4-({2-[(1R*,5S*,6R*)-6-(4-chlorophenyl)-3-azabicyclo[3.2.0]hept-3-yl]-2-methylpropanethioyl}amino)adamantane-1-carboxylate;
(1E)-N'-cyano-N-[(E)-5-hydroxyadamantan-2-yl]-2-methyl-2-phenoxypropanimidamide;
(E)-4-{[(1E)-N-cyano-2-methyl-2-phenoxypropanimidoyl]amino}adamantane-1-carboxamide;
(1E)-N'-cyano-2-(2,4-difluorophenoxy)-N-[(E)-5-hydroxyadamantan-2-yl]-2-methylpropanimidamide;
(1E)-N'-cyano-N-[(E)-5-cyano adamantan-2-yl]-2-(2,4-difluorophenoxy)-2-methylpropanimidamide;
(1E)-2-(4-chloro-2-fluorophenoxy)-Y-cyano-N-[(E)-5-cyano adamantan-2-yl]-2-methylpropanimidamide;
(1E)-2-(4-chloro-2-fluorophenoxy)-Y-cyano-2-methyl-N-[(E)-5-sulfamoyladamantan-2-yl]propanimidamide;
(1E)-2-(4-chloro-2-fluorophenoxy)-Y-cyano-N-[(E)-5-hydroxyadamantan-2-yl]-2-methylpropanimidamide;
N-[(exo)-bicyclo[2.2.1]hept-2-yl]-N-cyano-2-(2,4-difluorophenoxy)-2-methylpropanimidamide;
(1E)-N'-cyano-2-(2,4-difluorophenoxy)-2-methyl-N-[(E)-5-sulfamoyladamantan-2-yl]propanimidamide;
(1E)-2-[(5-chloropyridin-2-yl)oxy]-N'-cyano-N-[(E)-5-hydroxyadamantan-2-yl]-2-methylpropanimidamide;
(1E)-2-[(5-chloropyridin-2-yl)oxy]-N'-cyano-N-[(E)-5-cyanoadamantan-2-yl]-2-methylpropanimidamide;
(1E)-N-(adamantan-1-yl)-2-(4-chloro-2-fluorophenoxy)-N-cyano-2-methylpropanimidamide;
2-(4-chloro-2-fluorophenoxy)-N'-cyano-N-cyclooctyl-2-methylpropanimidamide;
(1E)-N-[(E)-adamantan-2-yl]-2-(4-chloro-2-fluorophenoxy)-N'-cyano-2-methylpropanimidamide;
methyl(E)-4-{[(1E)-2-(4-chloro-2-fluorophenoxy)-N-cyano-2-methylpropanimidoyl]amino}adamantane-1-carboxylate;
(1E)-N'-cyano-2-methyl-N-[(E)-5-(methylsulfonyl)adamantan-2-yl]-2-phenoxypropanimidamide;
N'-cyano-N-cyclooctyl-2-(2,4-difluorophenoxy)-2-methylpropanimidamide;
N-(exo-bicyclo[2.2.1]hept-2-yl)-2-(4-chloro-2-fluorophenoxy)-N-cyano-2-methylpropanimidamide;
(1E)-2-[(5-chloropyridin-2-yl)oxy]-N-cyano-2-methyl-N-[(E)-5-(methylsulfonyl)adamantan-2-yl]propanimidamide;
(1E)-2-[(5-chloropyridin-2-yl)oxy]-N'-cyano-2-methyl-N-[(E)-5-sulfamoyladamantan-2-yl]propanimidamide;
N'-cyano-2-(2,4-difluorophenoxy)-N-(hexahydro-2,5-methanopentalen-3a(1H)-yl)-2-methylpropanimidamide;
(E)-4-{[(1E)-N'-cyano-2-(2,4-difluorophenoxy)-2-methylpropanimidoyl]amino}adamantane-1-carboxamide;
(1E)-N-[(3R,5R)-adamantan-1-yl]-N-cyano-2-(2,4-difluorophenoxy)-2-methylpropanimidamide;
(1E)-N-(1-azabicyclo[2.2.2]oct-3-yl)-2-(4-chloro-2-fluorophenoxy)-N'-cyano-2-methylpropanimidamide;
2-(4-chloro-2-fluorophenoxy)-N'-cyano-N-(hexahydro-2,5-methanopentalen-3a(1H)-yl)-2-methylpropanimidamide;
(E)-4-{[(1E)-2-(4-chloro-2-fluorophenoxy)-N-cyano-2-methylpropanimidoyl]amino}adamantane-1-carboxamide;
(E)-4-({(1E)-2-[(5-chloropyridin-2-yl)oxy]-N-cyano-2-methylpropanimidoyl}amino)adamantane-1-carboxamide;
(E)-4-[(2-methyl-2-phenoxypropanimidoyl)amino]adamantane-1-carboxamide;
(1E)-N'-cyano-2-methyl-N-[(E)-5-(methylsulfonyl)adamantan-2-yl]-2-(pyridin-2-yloxy)propanimidamide;
(1E)-N'-cyano-N-[(E)-5-cyano adamantan-2-yl]-2-(2-fluorophenoxy)-2-methylpropanimidamide;
(1E)-N'-cyano-2-(2-fluorophenoxy)-2-methyl-N-[(E)-5-sulfamoyladamantan-2-yl]propanimidamide;
(1E)-N'-cyano-2-(2-fluorophenoxy)-N-[(E)-5-hydroxyadamantan-2-yl]-2-methylpropanimidamide;
4-{[N-cyano-2-methyl-2-phenoxypropanimidoyl]amino}bicyclo[2.2.1]heptane-1-carboxamide;
4-{[N-cyano-2-methyl-2-phenoxypropanimidoyl]amino}bicyclo[2.2.2]octane-1-carboxamide;
N'-cyano-N-(4-cyanobicyclo[2.2.1]hept-1-yl)-2-methyl-2-phenoxypropanimidamide;
N'-cyano-N-(4-cyanobicyclo[2.2.2]oct-1-yl)-2-methyl-2-phenoxypropanimidamide;
2-(4-chlorophenoxy)-N'-cyano-N-[4-(difluoromethyl)bicyclo[2.2.2]oct-1-yl]-2-methylpropanimidamide;
N'-cyano-N-[4-(difluoromethyl)bicyclo[2.2.2]oct-1-yl]-2-methyl-2-phenoxypropanimidamide;
4-{[N-cyano-2-methyl-2-phenoxypropanimidoyl]amino}bicyclo[2.2.2]octane-1-carboxylic acid;
4-{[2-(4-chlorophenoxy)-N-cyano-2-methylpropanimidoyl]amino}bicyclo[2.2.1]heptane-1-carboxamide;
N'-cyano-N-[4-(difluoromethyl)bicyclo[2.2.1]hept-1-yl]-2-methyl-2-phenoxypropanimidamide;
2-(2-fluorophenoxy)-2-methyl-N-[(E)-5-sulfamoyladamantan-2-yl]propanimidamide;
2-(2-fluorophenoxy)-N-[(E)-5-hydroxyadamantan-2-yl]-2-methylpropanimidamide;
N-[(E)-5-hydroxy adamantan-2-yl]-2-methyl-2-phenoxypropanimidamide;
5-chloro-N'-cyano-N-[(E)-5-hydroxyadamantan-2-yl]-2-methoxybenzenecarboximidamide;
2-(4-chlorophenoxy)-N'-cyano-N-(4-hydroxybicyclo[2.2.2]oct-1-yl)-2-methylpropanimidamide;
N-cyano-N-(4-hydroxybicyclo[2.2.2]oct-1-yl)-2-methyl-2-phenoxypropanimidamide;
2-(4-chlorophenoxy)-N'-cyano-N-(4-cyanobicyclo[2.2.2]oct-1-yl)-2-methylpropanimidamide; and
N'-cyano-N-(4-hydroxybicyclo[2.2.1]hept-1-yl)-2-methyl-2-phenoxypropanimidamide.

Isomers

Compounds of the invention may exist as stereoisomers wherein, asymmetric or chiral centers are present. These stereoisomers are "R" or "S" depending on the configuration of substituents around the chiral element. The terms "R" and "S" used herein are configurations as defined in IUPAC 1974 Recommendations for Section E, Fundamental Stereochemistry, Pure Appl. Chem., 1976, 45: 13-30. The invention contemplates various stereoisomers and mixtures thereof and are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

On occasion, the relative stereochemistry of an enantiomeric pair is known, however, the absolute configuration is not known. In that circumstance, the relative stereochemistry descriptor terms "R*" and "S*" are used. The terms "R*" and "S*" used herein are defined in Eliel, E. L.; Wilen, S. H. Stereochemistry of Organic Compounds; John Wiley & Sons, Inc.: New York, 1994; pp 119-120 and 1206.

Compounds including geometric isomers of carbon-carbon double bonds and carbon-nitrogen double bonds are included in the present invention. Substituents around a carbon-carbon or a carbon-nitrogen double bond are designated as being of Z or E configuration and substituents around a cycloalkyl or heterocycle are designated as being of cis or trans configuration. All geometric isomeric forms and mixtures thereof of the compounds described herein are encompassed within the scope of the present invention.

The aza-adamantane portion of Example 39 is not chiral, however the C-4 carbon at which oxygen is attached is considered pseudoasymmetric. The configurational assignment of structures of the aminoaza-adamantane portion of Example 39 is assigned 4s in accordance with that described in Synthesis, 1992, 1080, Becker, D. P.; Flynn, D. L. and as defined in Stereochemistry of Organic Compounds, E. L. Eliel, S. H Wilen; John Wiley and Sons, Inc. 1994.

Isotope Enriched or Labeled Compounds

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to $^2$H, $^3$H, $^{13}$C, $^{14}$C, $^{15}$N, $^{18}$O, $^{32}$P, $^{35}$S, $^{18}$F, $^{36}$Cl, and $^{125}$I. Compounds that contain other isotopes of these and/or other atoms are within the scope of this invention.

In another embodiment, the isotope-labeled compounds contain deuterium ($^2$H), tritium ($^3$H) or $^{14}$C isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4$/$D_2O$. In addition to the above, relevant procedures and intermediates are disclosed, for instance, in Lizondo, J et al., *Drugs Fut*, 21(11), 1116 (1996); Brickner, S J et al., *J Med Chem*, 39(3), 673 (1996); Mallesham, B et al., *Org Lett*, 5(7), 963 (2003); PCT publications WO1997010223, WO2005099353, WO1995007271, WO2006008754; U.S. Pat. Nos. 7,538,189; 7,534,814; 7531685; 7528131; 7521421; 7514068; 7511013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of 11-β-HSD1 inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., *J. Labelled Comp. Radiopharmaceut.*, 36(10):927-932 (1995); Kushner et al., *Can. J. Physiol. Pharmacol.*, 77, 79-88 (1999).

In addition, non-radio active isotope containing drugs, such as deuterated drugs called "heavy drugs," can be used for the treatment of diseases and conditions related to 11-β-HSD1 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D Metal., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmcokinetic profile or efficacy relative to the non-istopic compound.

Amides, Esters and Prodrugs

Prodrugs are derivatives of an active drug designed to ameliorate some identified, undesirable physical or biological property. The physical properties are usually solubility (too much or not enough lipid or aqueous solubility) or stability related, while problematic biological properties include too rapid metabolism or poor bioavailability which itself may be related to a physicochemical property.

Prodrugs are usually prepared by: a) formation of ester, hemi esters, carbonate esters, nitrate esters, amides, hydroxamic acids, carbamates, imines, Mannich bases, and enamines of the active drug, b) functionalizing the drug with azo, glycoside, peptide, and ether functional groups, c) use of polymers, salts, complexes, phosphoramides, acetals, hemiacetals, and ketal forms of the drug. For example, see Andrejus Korolkovas's, "Essentials of Medicinal Chemistry", John Wiley-Interscience Publications, John Wiley and Sons, New York (1988), pp. 97-118, which is incorporated in its entirety by reference herein.

Esters can be prepared from substrates of formula (I) containing either a hydroxyl group or a carboxy group by general methods known to persons skilled in the art. The typical reactions of these compounds are substitutions replacing one of the heteroatoms by another atom, for example:

Scheme 1

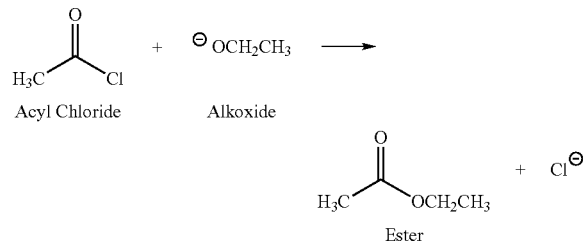

Amides can be prepared from substrates of formula (I) containing either an amino group or a carboxy group in similar fashion. Esters can also react with amines or ammonia to form amides.

Scheme 2

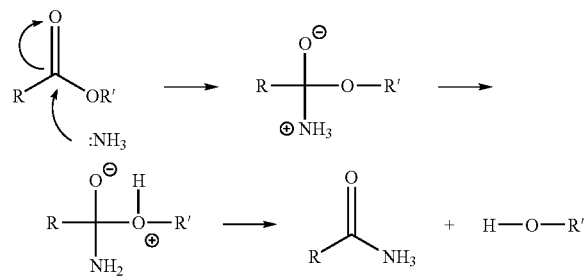

Another way to make amides from compounds of formula (I) is to heat carboxylic acids and amines together.

Scheme 3

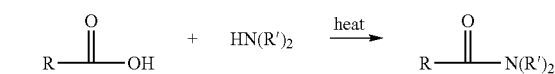

In Schemes 2 and 3, R and R' are independently substrates of formula (I), alkyl or hydrogen. Various embodiments of formula (I) that are substrates for prodrugs and esters include, but not limited to, Examples 1, 2, 3, 4, 5, 6, 7, 8, 15, 22, 23, 24, 26, 30, 46, 49, 51, 55, 58, 80, 87, and 91. Examples 11, 16, 17, 21, 28, 29, 48, and 63 are representative of esters of the invention. Examples 14, 25, 31, 47, 50, 70, 74, 75, 76, 81, 82, and 88 are representative of amides of the invention.

Compositions of the Invention

The invention also provides pharmaceutical compositions comprising a therapeutically effective amount of a compound of formula (I) in combination with a pharmaceutically acceptable carrier.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or in a certain part of the intestinal tract in a delayed manner. Examples of materials useful for delaying release of the active agent can include polymeric substances and waxes.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, eardrops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds and compositions of the invention also can be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. In one embodiment of the invention, lipids are the natural and synthetic phospholipids and phosphatidylcholines (lecithins) used separately or together. Methods to form liposomes are known in the art. See, for example, Prescott, Ed., Methods in Cell Biology, Volume XIV, Academic Press, New York, N.Y., (1976), p 33 et seq., which is incorporated herein by reference.

Dosage forms for topical administration of a compound of this invention include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this invention. Aqueous liquid compositions of the invention also are particularly useful.

In another embodiment of the invention, compositions for rectal or vaginal administration are suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Compositions comprise an effective amount of a compound of the invention formulated with one or more therapeutically suitable excipients. Examples of therapeutically suitable excipients include, but are not limited to, sugars, cellulose and derivatives thereof, oils, glycols, solutions, buffers, colorants, releasing agents, coating agents, sweetening agents, flavoring agents, perfuming agents, and the like.

The effective dosage of active ingredient employed may vary depending on the particular compound employed, the mode of administration, the condition being treated and the severity of the condition being treated. Such dosage may be ascertained readily by a person skilled in the art.

When treating or preventing diseases for which compounds of formula (I) are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligram to about 50 milligrams. In the case of a 70 kg adult human, the total daily dose will generally be from about 7 milligrams to about 350 milligrams. This dosage regimen may be adjusted to provide the optimal therapeutic response.

Methods of the Invention

Glucocorticoids are steroid hormones that play an important role in regulating multiple physiological processes in a wide range of tissues and organs. For example, glucocorticoids are potent regulators of glucose and lipid metabolism. Excess glucocorticoid action may lead to insulin resistance, type-2 diabetes, dyslipidemia, visceral obesity and hypertension. Cortisol and cortisone are the major active and inactive forms of glucocorticoids in humans, respectively, while corticosterone and dehydrocorticosterone are the major active and inactive forms in rodents.

Glucocorticoid action is initiated by the binding of glucocorticoids to receptors, such as glucocorticoid receptors and mineralocorticoid receptors. Through binding to its receptor, the main mineralocorticoid aldosterone controls the water and electrolyte balance in the body. However, the mineralocorticoid receptors have a high affinity for both cortisol and aldosterone.

Although cortisol is an important and well-recognized anti-inflammatory agent (J. Baxer, *Pharmac. Ther.*, 2, 605-659 (1976)), if present in large amount, it also has detrimental effects. For example, cortisol antagonizes the effects of insulin in the liver resulting in reduced insulin sensitivity and increased gluconeogenesis. Therefore, patients who already have impaired glucose tolerance have a greater probability of developing type 2 diabetes in the presence of abnormally high levels of cortisol.

Since glucocorticoids are potent regulators of glucose and lipid metabolism, excessive glucocorticoid action may lead to insulin resistance, type 2 diabetes, dyslipidemia, visceral obesity and hypertension. The present invention relates to the administration of a therapeutically effective dose of an 11β-HSD1 inhibitor for the treatment, control, amelioration, and/or delay of onset of diseases and conditions that are mediated by excess or uncontrolled, amounts or activity of cortisol and/or other corticosteroids. Inhibition of the 11β-HSD1 enzyme limits the conversion of inactive cortisone to active cortisol. Cortisol may cause, or contribute to, the symptoms of these diseases and conditions if it is present in excessive amounts.

Dysregulation of glucocorticoid activity has been linked to metabolic disorders, including type 2 diabetes, metabolic syndrome, Cushing's Syndrome, Addison's Disease, and others. Glucocorticoids upregulate key glucoeneogenic enzymes in the liver such as phosphoenolpyruvate carboxykinase (PEPCK) and glucose-6-phosphatase (G6 Pase), and therefore lowering local glucocorticoid levels in this tissue is expected to improve glucose metabolism in type 2 diabetics. 11β-HSD1 receptor whole-body knockout mice, and mice overexpressing 11β-HSD2 in fat (resulting in lower levels of active glucocorticoid in fat) have better glucose control than their wild type counterparts (Masuzaki, et al., *Science*, 294, 2166-2170 (2001); Harris, et al., *Endocrinology*, 142, 114-120 (2001); Kershaw et al., *Diabetes*, 54, 1023-1031 (2005)). Therefore, specific 11β-HSD1 inhibitors could be used for the treatment or prevention of type 2 diabetes and/or insulin resistance.

By reducing insulin resistance and maintaining serum glucose at normal concentrations, compounds of this invention may also have utility in the treatment and prevention of the numerous conditions that often accompany type 2 diabetes and insulin resistance, including the metabolic syndrome, obesity, reactive hypoglycemia, and diabetic dyslipidemia. The following diseases, disorders and conditions are related to type 2 diabetes, and some or all of these may be treated, controlled, prevented and/or have their onset delayed, by treatment with the compounds of this invention: hyperglycemia, low glucose tolerance, insulin resistance, obesity, lipid disorders, dyslipidemia, hyperlipidemia, hypertriglyceridemia, hypercholesterolemia, low HDL levels, high LDL levels, atherosclerosis and its sequelae, vascular restenosis, pancreatitis, abdominal obesity, neurodegenerative disease, retinopathy, nephropathy, neuropathy, metabolic syndrome and other disorders where insulin resistance is a component.

Abdominal obesity is closely associated with glucose intolerance (Montague et al., Diabetes, 49, 883-888 (2000)), hyperinsulinemia, hypertriglyceridemia, and other factors of metabolic syndrome (also known as Syndrome X), such as high blood pressure, elevated LDL, and reduced HDL. Animal data supporting the role of HSD1 in the pathogenesis of the metabolic syndrome is extensive (Masuzaki, et al., *Science*, 294, 2166-2170 (2001); Paterson et al., *Proc Natl. Acad. Sci. USA*, 101, 7088-93, (2004); Montague et al., *Diabetes*, 49, 883-888 (2000)). Thus, administration of an effective amount of an 11β-HSD1 inhibitor may be useful in the treatment or control of the metabolic syndrome. Furthermore, administration of an 11β-HSD1 inhibitor may be useful in the treatment or control of obesity by controlling excess cortisol, independent of its effectiveness in treating or prophylactically treating NIDDM. Long-term treatment with an 11β-HSD1 inhibitor may also be useful in delaying the onset of obesity, or perhaps preventing it entirely if the patients use an 11β-HSD1 inhibitor in combination with controlled diet and exercise. Potent, selective 11β-HSD1 inhibitors should also have therapeutic value in the treatment of the glucocorticoid-related effects characterizing the metabolic syndrome, or any of the following related conditions: hyperglycemia, low glucose tolerance, insulin resistance, obesity, lipid disorders, dyslipidemia, hyperlipidemia, hypertriglycidemia, hypercholesterolemia, low HDL levels, high LDL levels, atherosclerosis, vascular restenosis, pancreatitis, obesity, neurodegenerative disease, retinopathy, nephropathy, hepatic steatosis or related liver diseases, and Syndrome X, and other disorders where insulin resistance is a component.

11β-HSD1 is expressed in pancreatic islet cells, where active glucocorticoids have a negative effect on glucose stimulated insulin secretion (Davani et al., *Biol. Chem.*, 10, 34841-34844 (2000); Tadayyon et al., *Expert Opin. Investig. Drugs*, 12, 307-324 (2003); Billaudel et al., *J. Endocrinol.*, 95, 315-20 (1982)). It has been reported that the conversion of dehydrocorticosterone to corticosterone by 11β-HSD1 inhibits insulin secretion from isolated murine pancreatic beta cells. Incubation of isolated islets with an 11β-HSD1 inhibitor improves glucose stimulated insulin secretion. An earlier study suggested that glucocorticoids reduce insulin secretion in vivo (B. Billaudel et al., *Horm. Metab. Res.*, 11, 555-560 (1979)). Therefore, inhibition of 11β-HSD1 enzyme in the pancreas may improve glucose stimulated insulin release.

Glucocorticoids may bind to and activate glucocorticoid receptors (and possibly mineralocorticoid receptors) to potentiate the vasoconstrictive effects of both catecholamines and angiotensin II (Pirpiris et al., *Hypertension*, 19, 567-574 (1992); Kornel et al., *Steroids*, 58, 580-587 (1993): Walker et al., *Clin. Sci.*, 82, 597-605 (1992)). The 11β-HSD1 enzyme is present in vascular smooth muscle, which is believed to control the contractile response together with 11β-HSD2. High levels of cortisol in tissues where the mineralocorticoid receptor is present may lead to hypertension. Therefore, administration of a therapeutic dose of an 11β-HSD1 inhibitor should be effective in treating or prophylactically treating, controlling, and ameliorating the symptoms of hypertension.

Cushing's syndrome is a life-threatening metabolic disorder characterized by chronically elevated glucocorticoid levels caused by either excessive endogenous production of cortisol from the adrenal glands, or by the administration of high doses of exogenous glucocorticoids, such as prednisone or dexamethasone, as part of an anti-inflammatory treatment regimen. Typical Cushingoid characteristics include central obesity, diabetes and/or insulin resistance, dyslipidemia, hypertension, reduced cognitive capacity, dementia, osteoporosis, atherosclerosis, moon faces, buffalo hump, skin thinning, and sleep deprivation among others (Principles and Practice of Endocrinology and Metabolism. Edited by Kenneth Becker, Lippincott Williams and Wilkins Publishers, Philadelphia, 723-8 (2001)). It is therefore expected that potent, selective 11β-HSD1 inhibitors would be effective for the treatment of Cushing's disease.

The effects of elevated levels of cortisol are also observed in patients who have Cushing's syndrome (Orth, et al., *J. Med.*, 332, 791-803 (1995); Boscaro, et al., *Lancet*, 357, 783-791 (2001); Bertagna, et al., Cushing's Disease, In: Melmed, Ed., The Pituitary, $2^{nd}$ ed. Blackwell, 592-612 (2002), which is a disease characterized by high levels of cortisol in the blood stream. Patients with Cushing's syndrome often develop many of the symptoms of type 2 diabetes, obesity, metabolic syndrome and dyslipidemia including insulin resistance, central obesity, hypertension, glucose intolerance, etc.

As described above, 11β-HSD1 inhibitors may be effective in the treatment of many features of the metabolic syndrome including hypertension and dyslipidemia. The combination of hypertension and dyslipidemia contribute to the development of atherosclerosis, and therefore it would be expected that administration of a therapeutically effective amount of an 11β-HSD1 inhibitor would treat, control, delay the onset of, and/or prevent atherosclerosis and other metabolic syndrome-derived cardiovascular diseases.

One significant side effect associated with topical and systemic glucocorticoid therapy is corticosteroid-induced glaucoma. This condition results in serious increases in intraocular pressure, with the potential to result in blindness (Armaly et al., *Arch Opthalmol*, 78, 193-7 (1967); Stokes et al., *Invest Opthalmol V is Sci.*, 44, 5163-7 (2003)). The cells that produce the majority of aqueous humor in the eye are the non-pigmented epithelial cells (NPE). These cells have been demonstrated to express 11β-HSD1, and consistent with the expression of 11β-HSD1, is the finding of elevated ratios of cortisol:cortisone in the aqueous humor (Rauz et al., *Invest Opthalmol Vis Sci.*, 42, 2037-2042 (2001)). Furthermore, it has been shown that patients who have glaucoma, but who are not taking exogenous steroids, have elevated levels of cortisol vs. cortisone in their aqueous humor (Rauz et al., *QJM*, 96, 481-490 (2003)). Treatment of patients with the nonselective 11β-HSD1 and 11β-HSD2 inhibitor carbenoxolone for 4 and 7 days significantly lowered intraocular pressure by 10% and 17% respectively, and lowered local cortisol generation within the eye (Rauz et al., *QJM*, 96, 481-490 (2003)). Therefore, administration of 11β-HSD1 specific inhibitors could be used for the treatment of glaucoma.

In certain disease states, such as tuberculosis, psoriasis, and stress in general, high glucocorticoid activity shifts the immune response to a humoral response, when in fact a cell based response may be more beneficial to the patients. Inhibition of 11β-HSD1 activity may reduce glucocorticoid levels, thereby shifting the immune response to a cell based response. (Mason, *Immunology Today*, 12, 57-60 (1991); Rook, *Baillier's Clin. Endocrinol. Metab.*, 13, 576-581 (1999)). Therefore, administration of 11β-HSD1 specific inhibitors could be used for the treatment of tuberculosis, psoriasis, stress in general, and diseases or conditions where high glucocorticoid activity shifts the immune response to a humoral response.

Glucocorticoids are known to cause a variety of skin related side effects including skin thinning, and impairment of wound healing (Anstead, *Adv Wound Care*, 11, 277-85 (1998); Beer et al., *Vitam Horm.*, 59, 217-39 (2000)). 11β-HSD1 is expressed in human skin fibroblasts, and it has been shown that the topical treatment with the non-selective 11β-HSD1 and 11β-HSD2 inhibitor glycerrhetinic acid increases the potency of topically applied hydrocortisone in a skin vasoconstrictor assay (Hammami, et al., *J. Clin. Endocrinol. Metab.*, 73, 326-34 (1991)). Advantageous effects of selective 11β-HSD1 inhibitors on wound healing have also been published (International Publication No. WO 2004/11310). It is therefore expected that potent, selective 11β-HSD1 inhibitors would treat wound healing or skin thinning due to excessive glucocorticoid activity.

Excess glucocorticoids decrease bone mineral density and increase fracture risk. This effect is mainly mediated by inhibition of osteoblastic bone formation, which results in a net bone loss (Kim et al., *J. Endocrinol.*, 162, 371-379 (1999); Bellows et al., *Bone*, 23, 119-125 (1998); Cooper et al., *Bone*, 27, 375-381 (2000)). Glucocorticoids are also known to increase bone resorption and reduce bone formation in mammals (Turner et al., *Calcif. Tissue Int.*, 54, 311-5 (1995); Lane et al., *Med. Pediatr. Oncol.*, 41, 212-6 (2003)). 11β-HSD1 mRNA expression and reductase activity have been demonstrated in primary cultures of human osteoblasts in homogenates of human bone (Bland et al., *J. Endocrinol.*, 161, 455-464 (1999); Cooper et al., *Bone*, 23, 119-125 (2000); Cooper et al., *J. Bone Miner. Res.*, 17, 979-986 (2002)). In surgical explants obtained from orthopedic operations, 11β-HSD1 expression in primary cultures of osteoblasts was found to be increased approximately 3-fold between young and old donors (Cooper et al., *J. Bone Miner. Res.*, 17, 979-986 (2002)). Glucocorticoids such as prednisone and dexamethasone are also commonly used to treat a variety of inflammatory conditions including arthritis, inflammatory bowel disease, and asthma. These steroidal agents have been shown to increase expression of 11β-HSD1 mRNA and activity in human osteoblasts (Cooper et al., *J. Bone Miner. Res.*, 17, 979-986 (2002)). Similar results have been shown in primary osteoblast cells and MG-63 osteosarcoma cells where the inflammatory cytokines TNF alpha and IL-1 β increase 11β-HSD1 mRNA expression and activity (Cooper et al, *J. Bone Miner. Res.*, 16, 1037-1044 (2001)). These studies suggest that 11β-HSD1 plays a potentially important role in the development of bone-related adverse events as a result of excessive glucocorticoid levels or activity. Bone samples taken from healthy human volunteers orally dosed with the non-selective 11β-HSD1 and 11β-HSD2 inhibitor carbenoxolone showed a significant decrease in markers of bone resorption (Cooper et al., *Bone*, 27, 375-81 (2000)). Therefore, administration of an 1113-HSD1 specific inhibitor may be useful for preventing bone loss due to glucocorticoid-induced or age-dependent osteroporosis.

Studies have shown that in homogenates of hippocampus, both dehydrogenation and reduction occur (Lakshmi et al., *Endocrinol*, 128, 1741-1748 (1991) and that 11β-HSD1 is expressed in mammalian brain, and published data indicates that glucocorticoids may cause neuronal degeneration and dysfunction (de Quervain et al., *Hum Mol. Genet.*, 13, 47-52 (2004); Belanoff et al., *J. Psychiatr. Res.*, 35, 127-35 (2001)). Several studies have demonstrated 11β-HSD activity, immunoreactivity and mRNA expression in hippocampal neurons (Moisan et al., *Endocrinol*, 127, 1450-1455 (1990); Lakshmi et al., *Endocrinol*, 128, 1741-1748 (1991); Sakai et al., *J. Neuroendocrinol.*, 4, 101-106 (1992)). Administration of 11β-HSD inhibitors alters functional activity in the hippocampus in vivo (Seckl et al., *J. Endocrinol.*, 136, 471-477 (1993)). Evidence in rodents and humans suggests that prolonged elevation of plasma glucocorticoid levels impairs cognitive function that becomes more profound with aging (Issa et al., *J. Neurosci.*, 10, 3247-3254 (1990); Lupien et al., *Nat. Neurosci.*, 1, 69-73 (1998): Yau et al., *Neuroscience*, 66, 571-581 (1995)). Chronic excessive cortisol levels in the brain may result in neuronal loss and neuronal dysfunction (Kerr et al., *Psychobiology*, 22, 123-133 (1994); Woolley, *Brain Res.*, 531, 225-231 (1990); Landfield, *Science*, 272, 1249-1251 (1996)). Furthermore, glucocorticoid-induced acute psychosis exemplifies a more pharmacological induction of this response, and is of major concern to physicians when treating patients with these steroidal agents (Wolkowitz et al., *Ann NY Acad. Sci.*, 1032, 191-4 (2004)). Thekkapat et al. have recently shown that 11β-HSD1 mRNA is expressed in human hippocampus, frontal cortex and cerebellum, and that treatment of elderly diabetic individuals with the non-selective 11β-HSD1 and 11β-HSD2 inhibitor carbenoxolone improved verbal fluency and memory (Thekkapat et al., *Proc Natl Acad Sci USA.* 101, 6743-9 (2004)). In addition, Walker et al. have examined 11β-HSD activity and its function in primary cultures of fetal hippocampus cells (U.S. Pat. No. 7,122,531; U.S. Pat. No. 7,087,400; Rajan et al., *J. Neurosci.*, 16, 65-70 (1996)).

Therefore, the CNS diseases, disorders and conditions can be treated, controlled, prevented or delayed, by treatment with the compounds of this invention. Administration of a therapeutic dose of an 11β-HSD1 inhibitor may reduce, ameliorate, control and/or prevent disorders such as stress in general, neurodegeneration, the cognitive impairment associated with aging, neuronal dysfunction, dementia, steroid-induced acute psychosis, decline in cognitive function in Alzheimer's and associated dementias, cognitive deficits associated with aging and neurodegeneration, dementia, senile dementia, AIDS dementia, depression, major depressive disorder, psychotic depression, treatment resistant depression, anxiety, panic disorder, post traumatic stress disorder, decline in cognitive function in Cushing's syndrome, depression in Cushing's syndrome, steroid-induced acute psychosis, cognitive deficits associated with diabetes, attention deficit disorder in general, attention deficit hyperactivity disorder (ADHD), mild cognitive impairment, steroid-induced acute psychosis and schizophrenia.

Accordingly, an embodiment is a method of inhibiting 11β-HSD1, comprising administering to a mammal, a therapeutically effective amount of a compound of formula (I). Another embodiment is treating or prophylactically treating the above disorders in a mammal. The disorders may be mediated by excessive glucocorticoid action in a mammal.

Another embodiment is a method of treating disorders including, but are not limited to, Cushing's syndrome, non-insulin dependent type 2 diabetes, insulin resistance, obesity, lipid disorders (dyslipidemia), metabolic syndrome, hyperglycemia, low glucose tolerance, hyperlipidemia, hypertriglyceridemia, hypercholesterolemia, low HDL levels, high LDL levels, atherosclerosis and its sequelae, vascular restensosis, pancreatitis, abdominal obesity, retinopathy, nephropather, neuropathy, hypertension, other disorders where insulin resistance is a component, glaucoma, arthritis, osteoporosis, neuronal dysfunction, neurodegeneration, cognitive impairment associated with aging, dementia, Alzheimer's disease, decline in cognitive function in Alzheimer's disease and associated dementias, cognitive deficits associated with aging and neurodegeneration, dementia, senile dementia, AIDS dementia, anxiety, panic disorder, post traumatic stress disorder, steroid-induced acute psychosis, cognitive deficits associated with diabetes, attention deficit disorder in general, attention deficit hyperactivity disorder (ADHD), mild cognitive impairment, decline in cognitive function in Cushing's syndrome, schizophrenia, depression, major depressive disorder, psychotic depression, depression in Cushing's syndrome, treatment resistant depression, steroid-induced acute psychosis, and other diseases related to cortisol or glucocorticoids.

Another embodiment provides a method for treating Alzheimer's disease in a subject such that signs and symptoms are reduced.

For treating a neurodegenerative or a neuropsychiatric disorder, the method comprises administering to the subject in need of treatment thereof (e.g., a mammal, such as a human) a therapeutically effective amount of any of the compounds as described herein, or a pharmaceutically acceptable salt thereof. Alternatively, the method comprises administering to the subject a therapeutically effective amount of any of the compounds as described herein, or a pharmaceutically acceptable salt thereof, in combination with a therapeutically effective amount of at least one cognitive enhancing drug. A "cognitive enhancing drug", as defined herein, is a drug that improves impaired human cognitive abilities of the brain (namely, thinking, learning, and memory). Cognitive enhancing drugs work by altering the availability of neurochemicals (e.g., neurotransmitters, enzymes, and hormones), by improving oxygen supply, by stimulating nerve growth, or by inhibiting nerve damage. Examples of cognitive enhancing drugs include a compound that increases the activity of acetylcholine such as, but not limited to, an acetylcholine receptor agonist (e.g., a nicotinic α-7 receptor agonist or allosteric modulator, an α4β2 nicotinic receptor agonist or allosteric modulators), an acetylcholinesterase inhibitor (e.g., donepezil, rivastigmine, and galantamine), a butyrylcholinesterase inhibitor, an N-methyl-D-aspartate (NMDA) receptor antagonist (e.g., memantine), an activity-dependent neuroprotective protein (ADNP) agonist, a serotonin 5-HT1A receptor agonist (e.g., xaliproden), a 5-HT$_4$ receptor agonist, a 5-HT$_6$ receptor antagonist, a serotonin 1A receptor antagonist, a histamine H$_3$ receptor antagonist, a calpain inhibitor, a vascular endothelial growth factor (VEGF) protein or agonist, a trophic growth factor, an anti-apoptotic compound, an AMPA-type glutamate receptor activator, a L-type or N-type calcium channel blocker or modulator, a potassium channel blocker, a hypoxia inducible factor (HIF) activator, a HIF prolyl 4-hydroxylase inhibitor, an anti-inflammatory agent, an inhibitor of amyloid Aβ peptide or amyloid plaque, an inhibitor of tau hyperphosphorylation, a phosphodiesterase 5 inhibitor (e.g., tadalafil, sildenafil), a phosphodiesterase 4 inhibitor, a monoamine oxidase inhibitor, or pharmaceutically acceptable salt thereof. Specific examples of such cognitive enhancing drugs include, but are not limited to, cholinesterase inhibitors such as donepezil (Aricept®), rivastigmine (Exelon®), galanthamine (Reminyl®), N-methyl-D-aspartate antagonists such as memantine (Namenda®). At least one cognitive enhancing drug can be administered simultaneously with the compounds of the present invention or sequentially with the compounds of the present invention (and in any order). Additionally, it is believed that the combinations described herein may have additive or synergistic effects when used in the above-described treatment.

In still yet another embodiment, the present invention relates to a method for preventing (the development of) a disease condition, such as a neurodegeneration disorder or a neuropsychiatric disorder. As used herein, the term "prevent" a disease condition, such as a neurodegenerative disorder or a neuropsychiatric disorder by administration of any of the compounds described herein means that the detectable physical characteristics or symptoms of the disease or condition do not develop following the administration of the compound described herein. Specifically, the method of the present invention comprises administering to the subject in need of treatment thereof (e.g., a mammal, such as a human) a therapeutically effective amount of any of the compounds as described herein, or a pharmaceutically acceptable salt thereof. Alternatively, the method comprises administering to the subject a therapeutically effective amount of any of the compounds as described herein, or a pharmaceutically acceptable salt thereof, in combination with a therapeutically effective amount of at least one cognitive enhancing drug.

In still yet another embodiment, the present invention relates to a method for preventing the progression (e.g., worsening) of a disease condition, such as a neurodegeneration disorder or a neuropsychiatric disorder. The method comprises administering to the subject in need of treatment thereof (e.g., a mammal, such as a human) a therapeutically effective amount of any of the compounds as described herein, or a pharmaceutically acceptable salt thereof. Alternatively, the method comprises administering to the subject a therapeutically effective amount of any of the compounds as described herein, or a pharmaceutically acceptable salt thereof, in combination with a therapeutically effective amount of at least one cognitive enhancing drug.

In the above described methods for preventing the development or progression of a neurodegeneration disorder or a neuropsychiatric disorder one or more biomarkers, diagnostic tests or combination of biomarkers and diagnostic tests known to those skilled the art can be used to determine whether or not (1) a subject is at risk of developing one or more of neurodegeneration disorders or neuropsychiatric disorders; or (2) the neurodegeneration disorders or neuropsychiatric disorders in the subject previously diagnosed with one or more of the aforementioned disorders is progressing (e.g., worsening).

Another embodiment provides methods for determining whether an 11β-HSD1 inhibitor is effective at treating a subject in need thereof. Such methods may be used to determine the efficacy of an 11β-HSD1 inhibitor, including those which are unknown or unconfirmed to have such efficacy.

Preparation of Compounds of Formula (I)

Abbreviations

Ac for acetyl; AcSH for thioacetic acid; Bu for butyl; Cbz for benzyloxycarbonyl; CbzCl for benzyloxycarbonyl chloride; DAST for (diethylamino)sulfur trifluoride; DMSO for dimethyl sulfoxide; DPPA for diphenyl phosphoryl azide; Et for ethyl; Et$_3$N for triethylamine; EtOH for ethanol; HPLC for high performance liquid chromatography; LCMS for liquid chromatography/mass sprectrometry; mCPBA for meta-chloroperoxybenzoic acid; Me for methyl; MeOH for methanol; Ms for methanesulfonyl; MsCl for methanesulfonyl chloride; NaOMe for sodium methoxide; NaSMe for sodium methylthiolate; t-Bu for tent-butyl; and t-BuOH for tent-butanol.

The methods described below can entail use of various enantiomers. The compounds of this invention can be prepared according to the synthetic methods described in this section, Methods of the Invention and Examples sections. Certain groups described in the Scheme are meant to illustrate certain substituents contained within the invention and are not intended to limit the scope of the invention. Representative procedures are shown in, but are not limited to, Schemes 4-13.

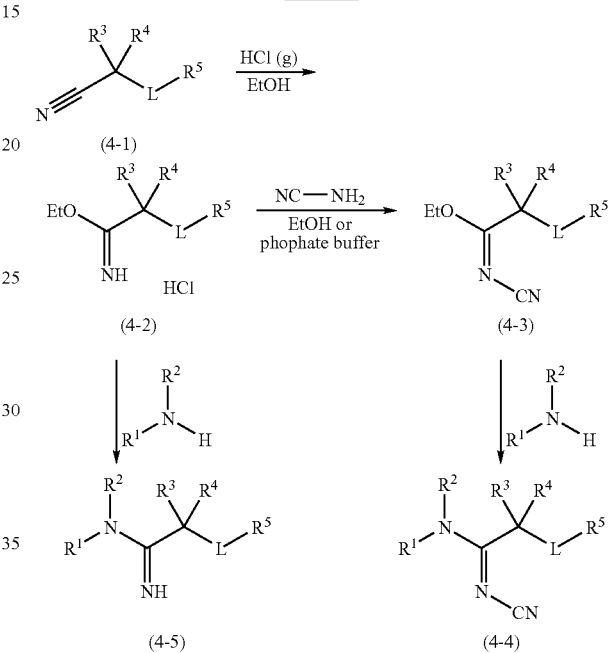

As depicted in Scheme 4, compounds of formulas (4-4) and (4-5), wherein R$^1$, R$^2$, R$^3$, R$^4$, R$^5$, and L are as defined in the Summary of the Invention can be prepared from compounds of formula (4-1). Accordingly nitriles of formula (4-1) can be converted to the corresponding imidates of formula (4-2) upon treatment with HCl in a solvent such as ethanol. Further exemplification of the preparation of compounds of formula (4-2) can be found in U.S. patent application Pub. No. US2006/0025614. Compounds of formula (4-2) can then be treated with cyanamide in either ethanol or phosphate buffer to supply compounds of formula (4-3). Compounds of formula (4-3) can then be treated with an amine, (R$^1$)(R$^2$)NH, in an optionally heated solvent such as ethanol to give compounds of formula (4-4). Amines, (R$^1$)(R$^2$)NH, are either commercially available, prepared as described in the following schemes, or as described in: *J. Med. Chem.*, 50, 149-164 (2007); *Bioorg. Med. Chem. Lett.*, 17, 527-532 (2007); *Bioorg. Med. Chem. Lett.*, 16, 5555-5560 (2006); *Bioorg. Med. Chem. Lett.*, 16, 5414-5419 (2006); *Bioorg. Med. Chem. Lett.*, 16, 5408-5413 (2006); *J. Am. Chem. Soc.*, 75, 637-640 (1953); *J. Med. Chem.*, 13, 926-935 (1970); *Australian J. Chem.*, 47, 1833-1841 (1994); *J. Org. Chem.*, 33, 877-880 (1968). In a similar transformation, compounds of formula (4-2) can be converted to compounds of formula (4-5). Compounds of formulas (4-4) and (4-5) are representative of compounds of formula (I).

Scheme 5

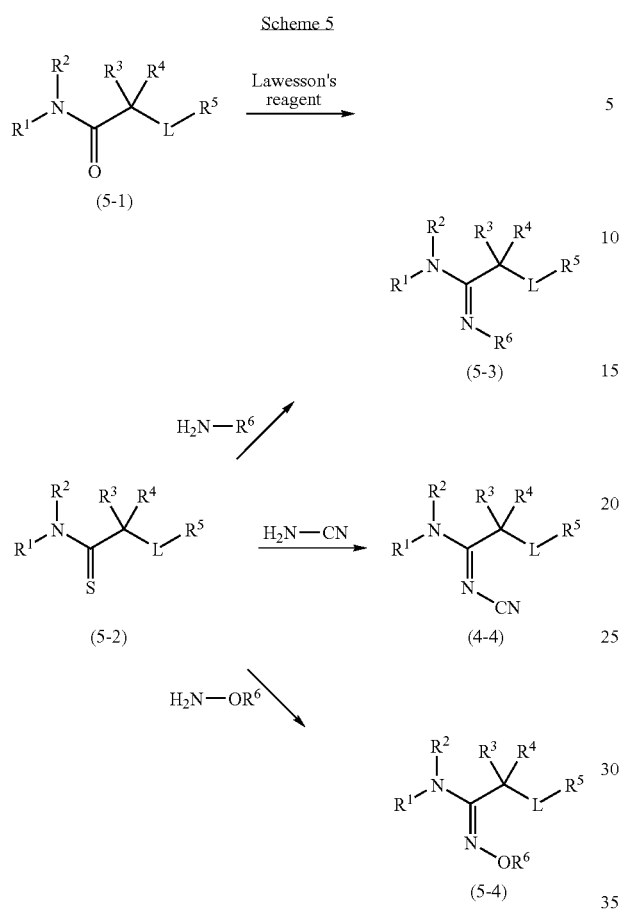

As depicted in Scheme 5, compounds of formulas (4-4), (5-3), and (5-4), wherein $R^1$, $R^2$, $R^3$, $R^4$, $R^5$, $R^6$ and L are as defined in the Summary of the Invention can be prepared from compounds of formula (5-1). Compounds of formula (5-1) can be prepared as described in Sorensen et al., *Bioorg. Med. Chem. Lett.* 17, 527-532 (2007). Additionally, preparation of compounds of formula (5-1) are described in U.S. Pat. Nos. 7,528,282; 7,511,175; 7,435,833 and 7,217,838; U.S. application publication Nos. 2009/0054426, 2008/0312214, 2008/0076819, 2006/0281773, 2005/0277747, 2006/0149070, 2007/0208001, 2007/0129345, 2007/0167622, 2007/0066584, 2007/0088088; International Publication Nos. WO 2007118185, WO 2007111921, WO 2007145834, WO 2007145835, WO 2008088540, WO 2008011453, WO 2008099145, WO 2008012532, WO 2008053194, WO 2008024892, WO 2008074384, WO 2008052638, WO 2007124337, WO 2007127765, WO 2007127726, WO 2007127693, WO 2007127704, WO 2007127688, WO 2007127901, WO 2007127763, WO 2007124329, WO 2007124254, WO 2007107470, WO 2007101270, WO 2008069313, WO 2007084314, WO 2008157752, WO 2008142859, WO 2008006703, WO 2008006702, WO 2007107550, WO 2007115935, WO 2007051810, WO 2007051811, WO 2008110196, WO 2007144394, WO 2008134221, WO 2008127924, WO 2006048750, WO 2007058346, WO 2007114124, WO 2008142986, WO 2007114125, WO 2008101886, WO 2008101907, WO 2008101885, WO 2008101914, WO 2008119017, and in U.S. patent application Ser. No. 11/697,044, which are incorporated herein by reference in entirety. Compounds of formula (5-1) can be transformed to thioamides of formula (5-2) upon exposure to Lawesson's reagent in a heated solvent such as toluene. Compounds of formula (5-2) can then be treated with amines of formula $H_2N$—$R^6$, $H_2N$—CN, or $H_2N$—$OR^6$ in the presence of mercury(II) acetate and optionally in the presence of a base such as triethylamine in an optionally heated solvent such as acetonitrile to supply compounds of formulas (5-3), (4-4), and (5-4), respectively. Compounds of formulas (5-3), (4-4), and (5-4) are representative of compounds of formula (I).

Scheme 6

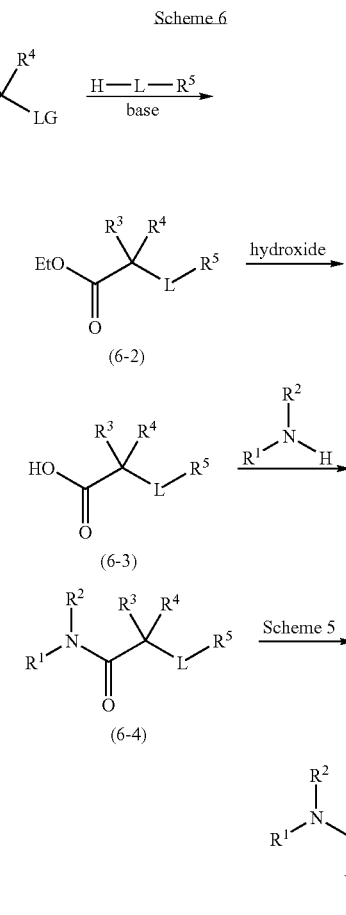

As shown in Scheme 6, compounds of formula (6-5), wherein $R^1$, $R^2$, $R^3$, $R^4$, $R^5$, L and W are as defined in the Summary of the Invention can be prepared from compounds of formula (6-1). Compounds of formula (6-1), wherein LG is a leaving group such as chlorine, bromine, iodine, trifluoromethanesulfonate, or p-toluenesulfonate, can be treated with H-L-$R^5$, wherein L is O or S, in the presence of a base such as cesium carbonate in an optionally heated solvent such as N,N-dimethylformamide to give compounds of formula (6-2). Subsequent hydrolysis under conditions known in the art deliver compounds of formula (6-3). Coupling of compounds of formula (6-3) with amines, $(R^1)(R^2)NH$, using amide bond forming conditions known in the art gives compounds of formula (6-4). Compounds of formula (6-4) are converted to compounds of formula (6-5) using the methodology described in Scheme 5. Compounds of formula (6-5) are representative of compounds of formula (I).

53

Scheme 7

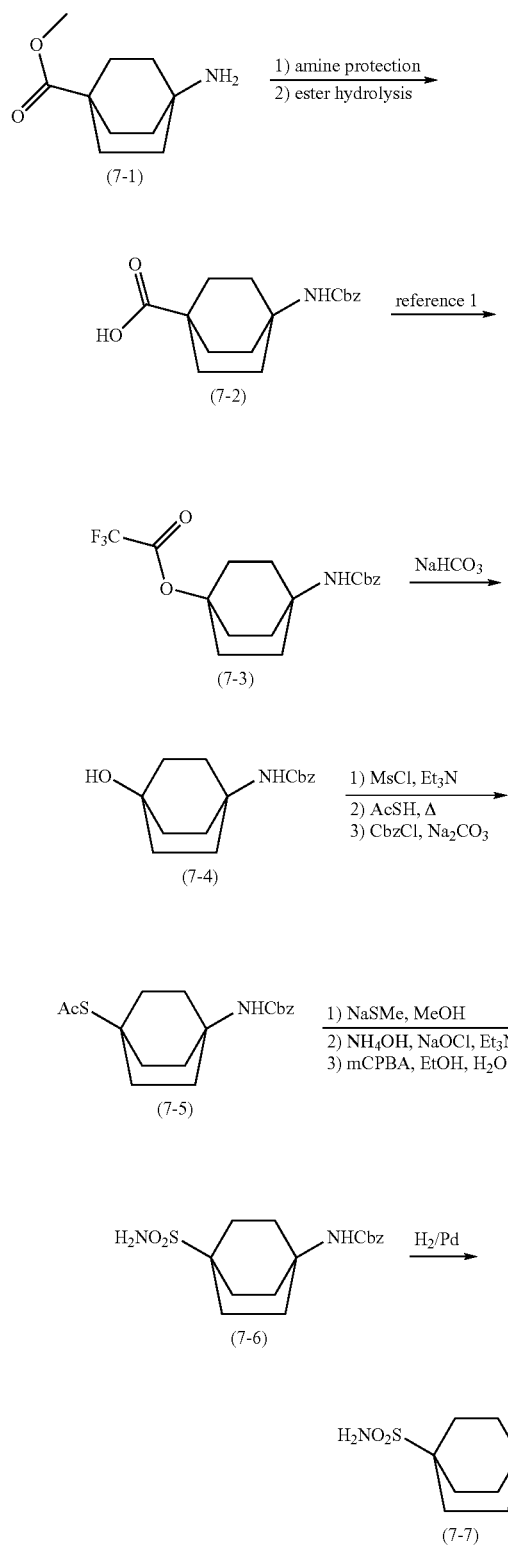

As shown in Scheme 7, compound (7-7) can be prepared from compound (7-1). Compound (7-1) can be transformed in two steps to compound (7-2). Initially the amine is protected,

54 in this instance, benzyloxycarbonyl is shown. Then the ester is hydrolyzed by methodology known in the art. Compound (7-2) is treated as described in *Tetrahedron Lett.*, 43, 8687-8691 (2002) to give compound (7-3). Compound (7-3) can then be hydrolyzed to give compound (7-4). Compound (7-4) can then be converted in three steps to compound (7-5) (*Bioorg. Med. Chem. Lett.*, 17, 527-532 (2002)). In the first step, the tertiary alcohol is sulfonylated. This is followed by displacement with thioacetic acid. Reinstallation of the protecting group gives compound (7-5). The acetate group of compound (7-5) can then be removed with sodium methanethiolate. Reaction with chloramine and subsequent oxidation with meta-chloroperoxybenzoic acid give compound (7-6). Removal of the amine protecting group using methods known in the art give compound (7-7). Compound (7-7) is representative of $(R^1)(R^2)NH$ and can be used in Schemes 4 and 6.

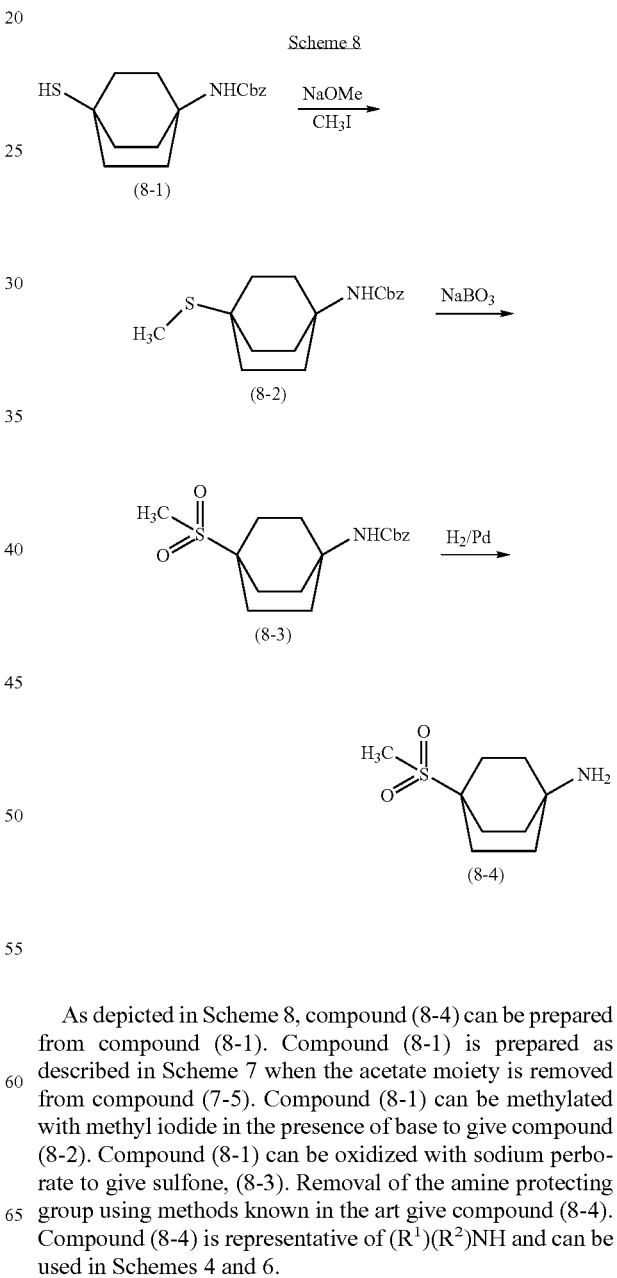

As depicted in Scheme 8, compound (8-4) can be prepared from compound (8-1). Compound (8-1) is prepared as described in Scheme 7 when the acetate moiety is removed from compound (7-5). Compound (8-1) can be methylated with methyl iodide in the presence of base to give compound (8-2). Compound (8-1) can be oxidized with sodium perborate to give sulfone, (8-3). Removal of the amine protecting group using methods known in the art give compound (8-4). Compound (8-4) is representative of $(R^1)(R^2)NH$ and can be used in Schemes 4 and 6.

Scheme 9

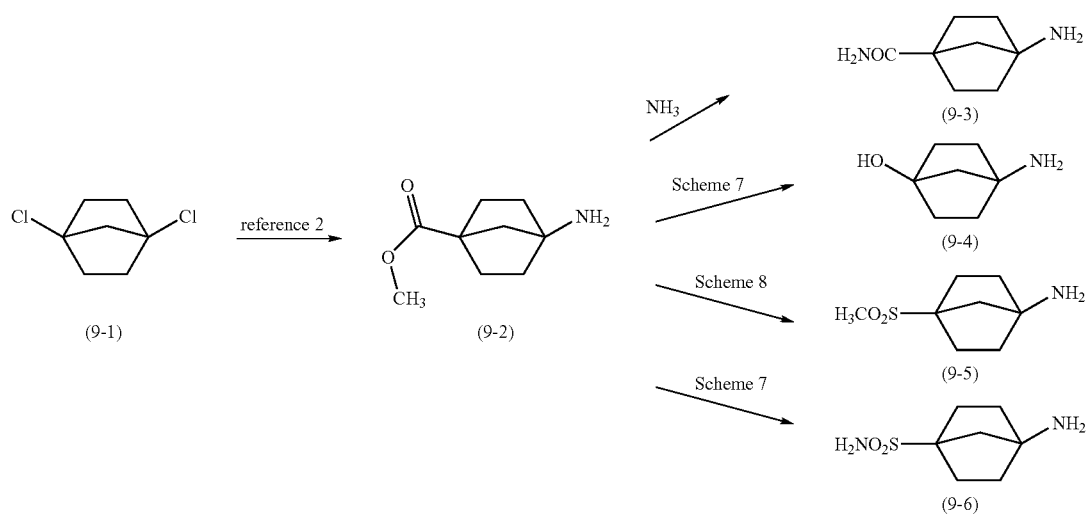

Compound (9-1) can be prepared as described in Wilcox et al., *J. Org. Chem.*, 29, 2209-2211 (1964). Compound (9-1) can then be converted to compound (9-2) by the procedures described in Wilcox et al., *J. Org. Chem.*, 33, 877-880 (1968). Compound (9-2) can then be converted to compound (9-3) upon treatment with ammonia. Alternatively, compound (9-2) can be transformed to compounds of formulas (9-4) and (9-6) using the methodologies described in Scheme 7. Also, using the methodologies in Scheme 8 convert compound (9-2) into compound (9-5). Compounds (9-3), (9-4), (9-5), and (9-6) are representative of $(R^1)(R^2)NH$ and can be used in Schemes 4 and 6.

As depicted in Scheme 10, compounds of formulas (5-3), (4-4), and (5-4) can be prepared from compounds of formula (5-2). Compounds of formula (5-2) can be treated with triethyloxonium tetrafluoroborate in a solvent such as heated dichloromethane to give compounds of formula (10-1). Compounds of formula (10-1) can then be treated as described in Scheme 5 to give compounds of formulas (5-3), (4-4), and (5-4). Compounds of formulas (5-3), (4-4), and (5-4) are representative of compounds of formula (I).

Scheme 10

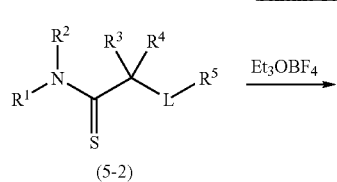

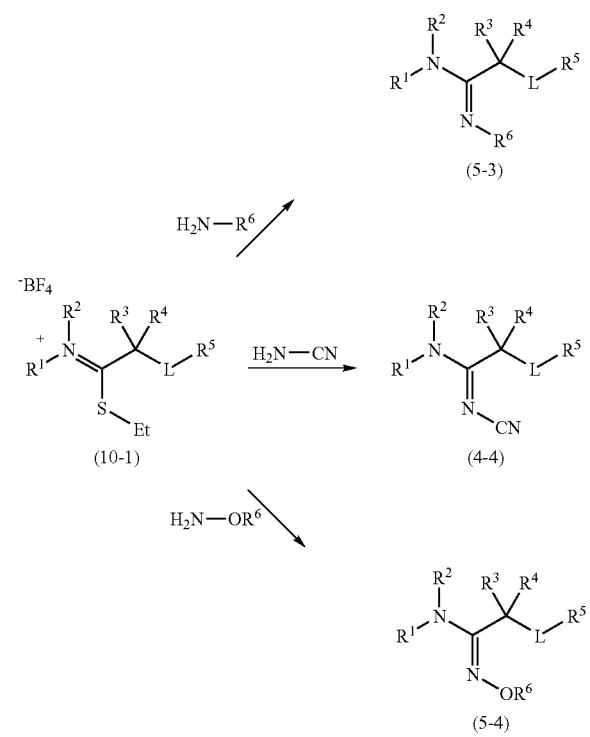

Scheme 11

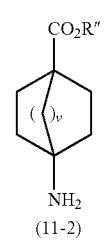

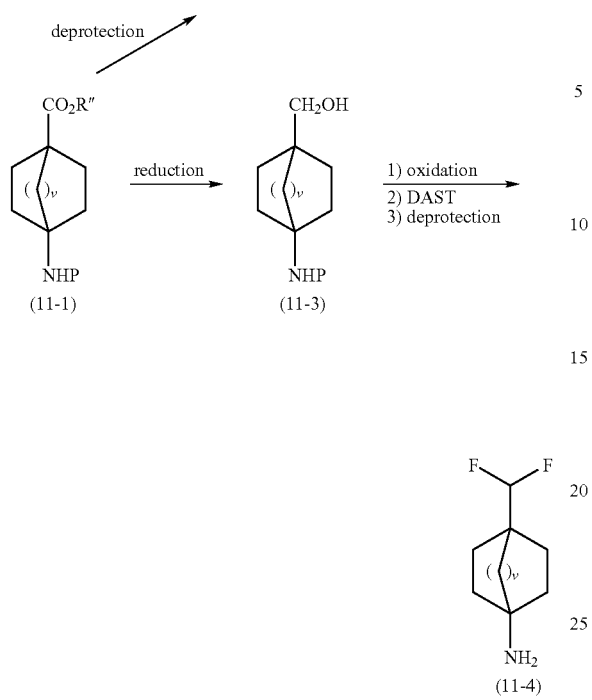

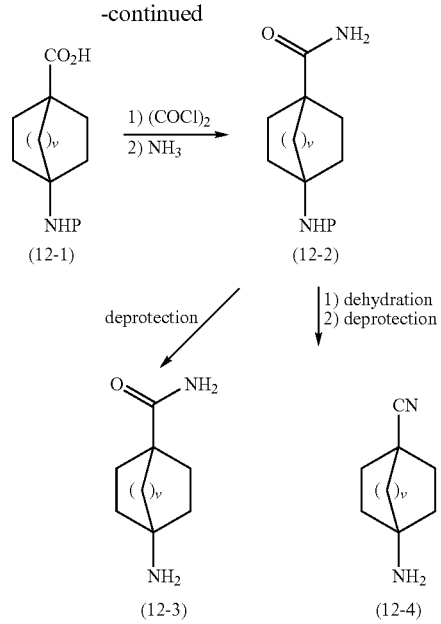

As described in Scheme 11, compounds of formula (11-2) and (11-4) can be prepared from compounds of formula (11-1). Compounds of (11-1), wherein v is 1 or 2, R" is alkyl, and P is a nitrogen protecting group can be converted to compounds of formula (11-2) by removal of said protecting group. One skilled in the art will match the deprotecting reaction conditions to the protecting group used. For example, when P is benzyloxycarbonyl, hydrogenation in the presence of a palladium catalyst will affect removal of P.

Compounds of (11-1) can also be reduced to the corresponding alcohols of formula (11-3). The ester moiety of compounds of formula (11-1) can be reduced using such reagents as borane-tetrahydrofuran complex to give the hydroxymethyl group found in compounds of (11-3). Compounds of formula (11-3) can be oxidized with reagents such as the Dess-Martin periodinane to produce an intermediate aldehyde. Subsequent treatment with (diethylamino)sulfur trifluoride (DAST) converts the aldehyde to a difluoromethyl moiety. Removal of the protecting group, P, under appropriate reaction conditions delivers compounds of formula (11-4).

Compounds of formulas (11-2) and (11-4) are representative of $(R^1)(R^2)NH$ and can be used in Schemes 4 and 6.

Scheme 12

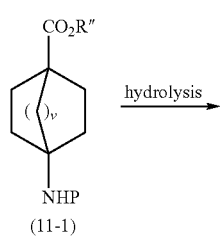

As shown in Scheme 12, compounds of formula (11-1) can also be converted to compounds of formulas (12-3) and (12-4). Compounds of formula (11-2), wherein v is 1 or 2, R" is alkyl, and P is a nitrogen protecting group can be converted to compounds of formula (12-1) by hydrolysis of the ester moiety. Compounds of formula (12-1) can be converted to the corresponding acid chloride by treatment with a reagent such as oxalyl chloride. The intermediate acid chloride can then be reacted with ammonia to give carboxamides of formula (12-2). Removal of the protecting group under conditions known to one skilled in the art supplies compounds of formula (12-3). Compounds of formula ((12-2) can also be dehydrated with reagents such as trifluoroacetic anhydride to convert the carboxamide moiety to a cyano group. Removal of the protecting group supplies compounds of formula (12-4). Compounds of formulas (12-2) and (12-4) are representative of $(R^1)(R^2)NH$ and can be used in Schemes 4 and 6.

Scheme 13

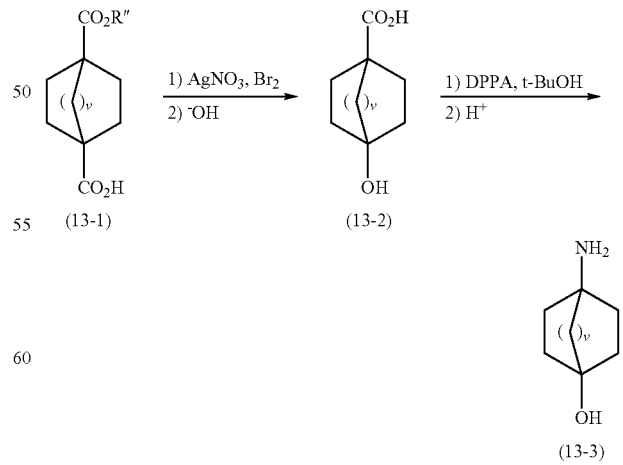

As depicted in Scheme 13, compounds of formula (13-1), wherein R" is alkyl and v is 1 or 2, can be converted to compounds of formula (13-3). Accordingly, compounds of formula (13-1) can be treated under Hunsdiecker reaction conditions to convert the carboxylic acid moiety to the corresponding bromide. Subsequent exposure to hydroxide transforms the bromide to the corresponding alcohol and also hydrolyzes the ester to the carboxylic acids of formula (13-2). Curtius rearrangement of compounds of formula (13-2) by treatment with diphenyl phosphoryl azide in the presence of an alcohol such as t-butanol delivers the intermediate t-butyl-carbamate. Removal of the t-butoxycarbonyl group by treatment with an acid such as hydrochloric acid or trifluoroacetic acid gives compounds of formula (13-3). Compounds of formula (13-3) are representative of $(R^1)(R^2)NH$ and can be used in Schemes 4 and 6.

In addition, nitrogen protecting groups can be used for protecting amine groups during the synthesis of compounds of formula (I). Such methods, and some suitable nitrogen protecting groups, are described in Greene and Wuts (Protective Groups In Organic Synthesis, Wiley and Sons, 1999). For example, suitable nitrogen protecting groups include, but are not limited to, tert-butoxycarbonyl (Boc), benzyloxycarbonyl (Cbz), benzyl (Bn), acetyl, and trifluoroacetyl. More particularly, the Boc protecting group may be removed by treatment with an acid such as trifluoroacetic acid or hydrochloric acid. The Cbz and Bn protecting groups may be removed by catalytic hydrogenation and acetyl and trifluoroacetyl protecting groups may be removed by variety of conditions including the use of sodium, potassium or lithium hydroxide in aqueous organic or alcoholic solvents.

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss et al., pub. Longman Scientific & Technical, Essex CM20 2JE, England.

Some compounds of the invention have at least one basic site whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic acid, atrolactic acid, methanesulfonic acid, ethanesulfonic acid, toluenesulfonic acid, naphthalenesulfonic acid, carbonic acid, fumaric acid, gluconic acid, acetic acid, propionic acid, salicylic acid, hydrochloric acid, hydrobromic acid, phosphoric acid, sulfuric acid, citric acid, or hydroxybutyric acid, camphorsulfonic acid, malic acid, phenylacetic acid, aspartic acid, glutamic acid, and the like.

The invention contemplates pharmaceutically active compounds either chemically synthesized or formed by in vivo biotransformation to compounds of formula (I).

The compounds, compositions, and methods of the invention will be better understood by reference to the following examples and reference examples, which are intended as an illustration of and not a limitation upon the scope of the invention.

EXAMPLES

Preparation of Bicyclic Amines

Bicyclic Amine Intermediate 1 (BAI-1) dimethyl 1-(2-chloroethyl)cyclohexane-1,4-dicarboxylate Freshly prepared lithium diisopropylamide (110.0 mL of n-butyllithium (2.5 M solution in hexane) and 41.0 mL of diisopropylamine were mixed at −30° C. in 300 mL of tetrahydrofuran) was cooled to −78° C. under nitrogen and stirred for 30 minutes. Dry hexamethylphosphoramide (180 mL, 1.0 mol) was added dropwise over 30 minutes. To the resulting mixture was added dimethyl cyclohexane-1,4-dicarboxylate (50 g, 0.25 mol) over 30 minutes. After stirring for 1 hour, 1-bromo-2-chloroethane (21 mL, 0.25 mol) was added over 1 hour. The mixture was then stirred for 3 hours at −78° C. and then stirred overnight allowing warming to room temperature. To the reaction mixture was added HCl (3 N, 100 mL), and the mixture was stirred for 10 minutes. The solvent was removed by evaporation under reduced pressure. The aqueous layer was extracted with ethyl acetate (3×150 mL). The combined extracts were washed with HCl (3 N, 2×100 mL), water (200 mL), saturated aqueous $NaHCO_3$ (100 mL), brine (2×100 mL) and dried over $Na_2SO_4$. Concentration gave the titled compound which was used in the next step without further purification.

Preparation of Bicyclic Amine Intermediate 2 (BAI-2) dimethyl bicyclo[2.2.2]octane-1,4-dicarboxylate Freshly prepared lithium diisopropylamide (110.0 mL of n-butyllithium (2.5 M solution in hexane) and 41.0 mL of diisopropylamine were mixed at −30° C. in 150 mL of tetrahydrofuran) was cooled to −78° C. under nitrogen and stirred for 30 minutes. A mixture of dimethyl 1-(2-chloroethyl)cyclohexane-1,4-dicarboxylate (BAI-1, 70 g, 0.25 mol) and dry hexamethylphosphoramide (180 mL, 1.0 mol) in tetrahydrofuran (500 mL) was stirred at −78° C. for 30 minutes under a nitrogen atmosphere. To this solution was added the above lithium diisopropylamide solution through a transfer line over 1 hour. The resulting mixture was stirred at −78° C. for 2 hours and then warmed to room temperature. After stirring overnight at room temperature, saturated aqueous $NH_4Cl$ was added. The mixture was concentrated to ½ volume followed by dilution with 500 mL of water and extracted with hexane (3×300 mL). The combined extracts were washed with brine, dried with sodium sulfate and concentrated. The crude product was crystallized from hexane to give the titled compound. $^1H$ NMR (400 MHz, $CDCl_3$), δ ppm 3.65 (s, 6H), 1.81 (s, 12H); LCMS (ESI+) m/z 227 $(M+H)^+$.

Preparation of Bicyclic Amine Intermediate 3 (BAI-3) dimethyl bicyclo[2.2.1]heptane-1,4-dicarboxylate Freshly prepared lithium diisopropylamide (15 mL of n-butyllithium (2.5 M solution in hexane) and 5 mL of diisopropylamine were mixed at −30° C. in 50 mL of tetrahydrofuran) was cooled to −78° C. under nitrogen and stirred for 30 minutes. To a solution of dimethyl cyclopentane-1,3-dicarboxylate (2.67 g, 14.37 mmol) in tetrahydrofuran (12 mL) was drop added above freshly lithium diisopropylamide solution over 10 minutes (−75° C.--−70° C.). The cold bath was then removed and the mixture was allowed to warm to 0° C.

and maintained at that temperature for 20 minutes before being cooled to −80° C. A solution of 1-bromo-2-chloroethane (2 mL, 24 mmol) in tetrahydrofuran (25 mL) was added slowly to the reaction mixture over 35 minutes (−75° C.~−70° C.). The reaction solution was then allowed to stir overnight with gradual warming to room temperature. The reaction was quenched by addition of saturated NH$_4$Cl solution (20 mL). After removal of the solvent, 200 mL of ethyl acetate was added. The organic phase was washed with 2 N HCl (120 mL×2), washed with brine and then dried over Na$_2$SO$_4$. After filtration and concentration, the residue was purified by chromatography on a silica gel column (eluted with ethyl acetate/petroleum ether=1/10) to afford the titled compound. $^1$H NMR (400 MHz, CDCl$_3$), δ (ppm): 3.68 (s, 6H), 2.02~2.03 (m, 4H), 1.91 (s, 2H), 1.68 (s, 4H); LCMS (ESI+) m/z 213.1 (M+H)$^+$.

Preparation of Bicyclic Amine Intermediate 4 (BAI-4) 4-(methoxycarbonyl)bicyclo[2.2.2]octane-1-carboxylic acid A solution of dimethyl bicyclo[2.2.2]octane-1,4-dicarboxylate (BAI-2, 22 g, 0.1 mol) in methanol (500 mL) was heated to a slight reflux. To this solution was added a solution of KOH (5.6 g, 0.1 mol) in methanol (100 mL) and water (10 mL) over 30 minutes. The reaction mixture was then refluxed for 24 hours. After cooling to room temperature, the solvent was removed and diluted with water. The aqueous solution was extracted with ethyl acetate (100 mL×2) to remove starting material BAI-2, and then the aqueous layer as acidified to pH~3 by addition of concentrated HCl. A precipitate was formed and extracted with ethyl acetate (250 mL×3). The combined extracts were washed with brine, dried over Na$_2$SO$_4$ and evaporated to give the titled compound. $^1$H NMR (400 MHz, DMSO-d$_6$) δ ppm 12.09 (s, 1H), 3.57 (s, 3H), 1.70 (s, 12H); LCMS (ESI+) m/z 213 (M+H)$^+$.

Preparation of Bicyclic Amine Intermediate 5 (BAI-5) 4-(methoxycarbonyl)bicyclo[2.2.1]heptane-1-carboxylic acid The titled compound was prepared from dimethyl bicyclo[2.2.1]heptane-1,4-dicarboxylate (BAI-3) using the methodology described for the preparation of BAI-4. $^1$H NMR (400 MHz, DMSO-d$_6$), δ ppm 11.99 (br, 1H), 3.60 (s, 3H), 1.90~1.92 (m, 4H), 1.76 (s 2H), 1.57~1.60 (m, 4H); LCMS (ESI+) m/z 199.1 (M+H)$^+$.

Preparation of Bicyclic Amine Intermediate 6 (BAI-6) methyl 4-{[(benzyloxy)carbonyl]amino}bicyclo[2.2.2]octane-1-carboxylate To a mixture of 4-(methoxycarbonyl)bicyclo[2.2.2]octane-1-carboxylic acid (BAI-4, 11.0 g, 0.05 mol), triethylamine (7.5 g, 0.075 mol) in toluene (200 mL) was added diphenyl phosphoryl azide (16.5 g, 0.06 mol). After stirring for 2 hours at reflux, benzyl alcohol (8.1 g, 0.075 mol) was added, and the mixture was refluxed overnight. After removal of the solvent, the residue was dissolved in ethyl acetate and washed with saturated aqueous NaHCO$_3$. After concentration, the residue was purified by reverse-phase flash chromatography (30-60% methanol in water) to give the titled compound. $^1$H NMR (400 MHz, CDCl$_3$), δ ppm 7.27~7.37 (m, 5H), 5.02 (s, 2H), 4.68 (s, 1H), 3.63 (s, 3H), 1.87 (s, 12H); LCMS (ESI+) m/z 318 (M+H)$^+$.

Preparation of Bicyclic Amine Intermediate 7 (BAI-7) methyl 4-{[(benzyloxy)carbonyl]amino}bicyclo[2.2.1]heptane-1-carboxylate The titled compound was prepared from 4-(methoxycarbonyl)bicyclo[2.2.1]heptane-1-carboxylic acid (BAI-5) using the methodology using the methodology used to prepare BAI-6. LCMS (ESI+) m/z 304.1 (M+H)$^+$.

Preparation of Bicyclic Amine Intermediate 8 (BAI-8) 4-{[(benzyloxy)carbonyl]amino}bicyclo[2.2.2]octane-1-carboxylic acid To a solution of methyl 4-{[(benzyloxy)carbonyl]amino}bicyclo[2.2.2]octane-1-carboxylate (BAI-6, 10.3 g, 32.5 mmol) in methanol (200 mL) was added aqueous NaOH solution (50 mL, 0.1 mol). The reaction mixture was refluxed for 2 hours. After removal of the solvent, the residue was extracted with ethyl acetate (50 mL×2). The aqueous layer was adjusted to pH=2 with concentrated HCl and extracted with ethyl acetate (200 mL×4). The combined extracts were washed with brine, dried with sodium sulfate and concentrated to give the titled compound. $^1$H NMR (400 MHz, CDCl$_3$), δ ppm 7.33~7.36 (m, 5H), 5.03 (s, 2H), 4.61 (s, 1H), 1.89 (s, 12H); LCMS (ESI+) m/z 304 (M+H)$^+$.

Preparation of Bicyclic Amine Intermediate 9 (BAI-9) 4-{[(benzyloxy)carbonyl]amino}bicyclo[2.2.1]heptane-1-carboxylic acid The titled compound was prepared from methyl 4-{[(benzyloxy)carbonyl]amino}bicyclo[2.2.1]heptane-1-carboxylate (BAI-7) using the methodology using the methodology used to prepare BAI-8. $^1$H NMR (400 MHz, DMSO-d$_6$), δ ppm 12.14 (br, 1H), 7.57 (br, 1H), 7.31~7.37 (m, 5H), 4.99 (s, 2H), 1.83~1.93 (m, 4H), 1.79 (s, 2H), 1.55~1.64 (m, 4H); LCMS (ESI+) m/z 290.1 (M+H)$^+$.

Preparation of Bicyclic Amine Intermediate 10 (BAI-10) benzyl (4-carbamoylbicyclo[2.2.2]oct-1-yl)carbamate Under a nitrogen atmosphere, to a solution of 4-{[(benzyloxy)carbonyl]amino}bicyclo[2.2.2]octane-1-carboxylic acid (BAI-8, 3.03 g, 0.01 mol) in dry CH$_2$Cl$_2$ (80 mL) cooled with an ice-water bath was added oxalyl chloride (1.9 g, 0.015 mol). The mixture was stirred for 1 hour at room temperature. The solvent and excess oxalyl chloride were removed under reduced pressure. The resulting residue was dissolved in dry CH$_2$Cl$_2$ (50 mL) and NH$_3$ gas was bubbled into this solution cooled with an ice bath. The resulting mixture was stirred for 5 minutes at room temperature and diluted with CH$_2$Cl$_2$. The solution was washed with water, brine and dried with sodium sulfate. Concentration gave the titled compound. $^1$H NMR (400 MHz, CDCl$_3$) δ ppm 7.31~7.36 (m, 5H), 5.51 (br, 2H), 5.03 (s, 2H), 4.63 (s, 1H), 1.89 (s, 12H); LCMS (ESI+) m/z 303 (M+H)$^+$.

Preparation of Bicyclic Amine Intermediate 11 (BAI-11) benzyl (4-carbamoylbicyclo[2.2.1]hept-1-yl)carbamate The titled compound was prepared from 4-{[(benzyloxy)carbonyl]amino}bicyclo[2.2.1]heptane-1-carboxylic acid (BAI-9) using the methodology used in the preparation of BAI-10. $^1$H NMR (400 MHz, CDCl$_3$), δ ppm 7.30~7.36 (m, 5H), 5.74 (br, 1H), 5.59 (br, 1H), 5.07 (s, 2H), 1.99~2.02 (m, 6H), 1.75~1.77 (m, 4H); LCMS (ESI+) m/z 289.1 (M+H)+.

Preparation of Bicyclic Amine Intermediate 12 (BAI-12) benzyl (4-cyanobicyclo[2.2.2]oct-1-yl)carbamate To a solution of benzyl (4-carbamoylbicyclo[2.2.2]oct-1-yl)carbamate (BAI-10, 3.0 g, 0.01 mol) in dry $CH_2Cl_2$ (50 mL) and triethylamine (3.03 g, 0.03 mol) at 0° C. was added trifluoroacetic anhydride (3.15 g, 0.015 mol). After the addition was complete, the solution was allowed to warm to room temperature and stirring was continued. overnight. After dilution with $CH_2Cl_2$ (100 mL), the solution was washed with saturated aqueous $NaHCO_3$ (50 mL×3), water, brine and dried with sodium sulfate. Evaporation gave the titled compound. $^1H$ NMR (400 MHz, $CDCl_3$) δ ppm 7.33~7.36 (m, 5H), 5.02 (s, 2H), 4.60 (s, 1H), 2.01~2.05 (m, 6H), 1.88~1.92 (m, 6H); LCMS (ESI+) m/z 285 (M+H)+.

Preparation of Bicyclic Amine 1 (BA-1) 4-aminobicyclo[2.2.2]octane-1-carbonitrile To a solution of benzyl (4-cyanobicyclo[2.2.2]oct-1-yl) carbamate (BAI-12, 2.1 g, 7.4 mmol) in methanol (100 mL) was added $Pd(OH)_2/C$ (100 mg). Hydrogen gas was bubbled through the stirred reaction mixture for 1 hour at room temperature. After filtration, the filtrate was concentrated to give the titled compound. $^1H$ NMR (400 MHz, DMSO-$d_6$) δ ppm 8.08 (s, 2H), 1.98~2.02 (m, 6H), 1.70~1.74 (m, 6H); LCMS (ESI+) m/z 151 (M+H)+.

Preparation of Bicyclic Amine 2 (BA-2) methyl 4-aminobicyclo[2.2.2]octane-1-carboxylate To a solution of methyl 4-{[(benzyloxy)carbonyl]amino}bicyclo[2.2.2]octane-1-carboxylate (BAI-6, 951 mg, 3 mmol) in methanol (50 mL) was added $Pd(OH)_2/C$ (100 mg). Hydrogen gas was bubbled through the stirred reaction mixture for 1 hour at room temperature. After filtration, the filtrate was concentrated to give the titled compound. $^1H$ NMR (400 MHz, $CDCl_3$) δ ppm 3.64 (s, 3H), 1.84~1.88 (m, 6H), 1.73 (s, 2H), 1.53~1.57 (m, 6H); LCMS (ESI+) m/z 184 (M+H)+.

Preparation of Bicyclic Amine 3 (BA-3) methyl 4-aminobicyclo[2.2.1]heptane-1-carboxylate The titled compound was prepared from methyl 4-{[(benzyloxy)carbonyl]amino}bicyclo[2.2.1]heptane-1-carboxylate (BAI-7) using the methodology described for the preparation of BA-2. LCMS (ESI+) m/z 170.1 (M+H)+.

Preparation of Bicyclic Amine Intermediate 13 (BAI-13) benzyl[4-(hydroxymethyl)bicyclo[2.2.2]oct-1-yl] carbamate To a solution of 4-{[(benzyloxy)carbonyl]amino}bicyclo [2.2.2]octane-1-carboxylic acid (BAI-8, 1.0 g, 3.3 mmol) in dry tetrahydrofuran (10 mL) cooling with an ice bath was added dropwise borane solution in tetrahydrofuran (1 M, 1 mL). Hydrogen was evolved, and the resulting clear solution was stirred at room temperature for 1 hour. The reaction was quenched with water, the aqueous phase was treated with aqueous $K_2CO_3$ and extracted with ethyl acetate (50 mL×3). The combined organic phases were washed with brine, dried over sodium sulfate and concentrated to give the titled compound. LCMS (ESI+) m/z 290 (M+H)+.

Preparation of Bicyclic Amine Intermediate 14 (BAI-14) benzyl[4-(hydroxymethyl)bicyclo[2.2.1]hept-1-yl]carbamate The titled compound was prepared from methyl 4-{[(benzyloxy)carbonyl]amino}bicyclo[2.2.1]heptane-1-carboxylate (BAI-7) using the methodology described for the preparation of BAI-13. $^1H$ NMR (400 MHz, $CDCl_3$) δ ppm 7.31~7.36 (m, 5H), 5.06 (s, 2H), 3.64 (s, 2H), 1.92~1.93 (m, 2H), 1.67~1.78 (m, 4H), 1.43 (s, 2H), 1.38~1.41 (m, 2H); LCMS (ESI+) m/z 275.1 (M+H)+.

Preparation of Bicyclic Amine Intermediate 15 (BAI-15) benzyl (4-formylbicyclo[2.2.2]oct-1-yl)carbamate To a solution of benzyl[4-(hydroxymethyl)bicyclo[2.2.2] oct-1-yl]carbamate (BAI-13, 1.00 g, 3.5 mmol) in dry $CH_2Cl_2$ (25 mL) was added in portions Dess-Martin periodinane (1.7 g, 4.0 mmol). The clear solution became cloudy and was stirred for 2 hours. The reaction mixture was diluted with $CH_2Cl_2$ (100 mL) and then aqueous NaOH solution (1 N, 10 equivalents) was added. The resulting suspension was stirred for 30 minutes. The aqueous layer was extracted with $CH_2Cl_2$ and the combined organic phase was washed with 1 N aqueous NaOH solution, water, brine and dried over sodium sulfate. Concentration gave the titled compound. $^1H$ NMR (400 MHz, $CDCl_3$) δ ppm 9.44 (s, 1H) 7.31~7.37 (m, 5H), 5.03 (s, 2H), 4.66 (s, 1H), 1.88~1.92 (m, 6H), 1.71~1.75 (m, 6H); LCMS (ESI+) m/z 288 (M+H)+.

Preparation of Bicyclic Amine Intermediate 16 (BAI-16) benzyl (4-formylbicyclo[2.2.1]hept-1-yl)carbamate The titled compound was prepared from benzyl[4-(hydroxymethyl)bicyclo[2.2.1]hept-1-yl]carbamate (BAI-14) using the methodology used to prepare BAI-15. LCMS (ESI+) m/z 274.1 (M+H)+.

Preparation of Bicyclic Amine Intermediate 17 (BAI-17) benzyl[4-(difluoromethyl)bicyclo[2.2.2]oct-1-yl] carbamate To a solution of benzyl (4-formylbicyclo[2.2.2]oct-1-yl) carbamate (BAI-15, 920 mg, 3.2 mmol) in dry $CH_2Cl_2$ (10 mL) was added (diethylamino)sulfur trifluoride (516 mg, 3.2 mmol). The reaction mixture was stirred for 2 hours at room temperature and poured into water (10 mL). The resulting mixture was stirred for 30 minutes. The organic layer was separated and washed with saturated aqueous $NaHCO_3$ solution, water, and brine and dried with sodium sulfate. Concentration gave the titled compound. $^1H$ NMR (400 MHz, $CDCl_3$) δ ppm 7.32~7.35 (m, 5H), 5.36 (t, J=56.8 Hz, 1H) 5.03 (s, 2H), 4.60 (s, 1H), 1.85~1.89 (m, 6H), 1.62~1.66 (m, 6H); LCMS (ESI+) m/z 310 (M+H)+.

Preparation of Bicyclic Amine Intermediate 18 (BAI-18) benzyl[4-(difluoromethyl)bicyclo[2.2.1]hept-1-yl]carbamate The titled compound was prepared from benzyl (4-formylbicyclo[2.2.1]hept-1-yl)carbamate (BAI-16) using the methodology described for the preparation of BAI-17. $^1H$ NMR (400 MHz, CDCl$_3$) δ ppm 7.33~7.36 (m, 5H), 5.78 (t, J=56.7 Hz, 1H), 5.07 (s, 2H), 1.83~1.96 (m, 5H), 1.73~1.77 (m, 5H); LCMS (ESI+) m/z 296.1 (M+H)$^+$.

Preparation of Bicyclic Amine 4 (BA-4) 4-(difluoromethyl)bicyclo[2.2.2]octan-1-amine To a solution of benzyl[4-(difluoromethyl)bicyclo[2.2.2]oct-1-yl]carbamate (BAI-17, 600 mg, 2 mmol) in methanol (100 mL) was added Pd(OH)$_2$/C (100 mg). Hydrogen gas was bubbled through the stirred reaction mixture for 0.5 hour at room temperature. After filtration, the filtrate was concentrated to give the titled compound. $^1$H NMR (400 MHz, CDCl$_3$) δ ppm 5.37 (t, J=56.8 Hz, 1H), 1.60~1.64 (m, 6H), 1.52-1.56 (m, 6H), 1.45 (s, 2H).

Preparation of Bicyclic Amine 5 (BA-5) 4-(difluoromethyl)bicyclo[2.2.1]heptan-1-amine The titled compound was prepared from benzyl[4-(difluoromethyl)bicyclo[2.2.1]hept-1-yl]carbamate (BAI-18) using the methodology described for the preparation of BA-4. $^1$H NMR (400 MHz, CDCl$_3$) δ ppm 5.76 (t, J=56.7 Hz, 1H), 2.01 (s, 2H, 1.81~1.88 (m, 2H), 1.61~1.65 (m, 4H), 1.48-1.55 (m, 2H), 1.44 (s, 2H); LCMS (ESI+) m/z 162.1 (M+H)$^+$.

Preparation of Bicyclic Amine 6 (BA-6) 4-aminobicyclo[2.2.2]octane-1-carboxamide To a solution of benzyl (4-carbamoylbicyclo[2.2.2]oct-1-yl)carbamate (BAI-10, 780 mg, 2.58 mmol) in methanol (100 mL) was added Pd(OH)$_2$/C (100 mg). Hydrogen gas was bubbled through the stirred reaction mixture for 2 hours at room temperature. After filtration, the filtrate was concentrated to give the titled compound. $^1$H NMR (400 MHz, CDCl$_3$) δ ppm 5.57 (br, 2H), 1.84~1.88 (m, 6H), 1.53~1.59 (m, 6H).

Preparation of Bicyclic Amine 7 (BA-7) 4-aminobicyclo[2.2.1]heptane-1-carboxamide The titled compound was prepared from benzyl (4-carbamoylbicyclo[2.2.1]hept-1-yl)carbamate (BAI-11) using the methodology described for the preparation of BA-6. $^1$H NMR (400 MHz, DMSO-d$_6$) δ ppm 6.96 (s, 1H), 6.74 (s, 1H), 1.76~1.83 (m, 2H), 1.50~1.55 (m, 4H), 1.44 (s, 2H), 1.40~1.42 (m, 2H); LCMS (ESI+) m/z 155.1 (M+H)$^+$.

Preparation of Bicyclic Amine Intermediate 19 (BAI-19) methyl 4-bromobicyclo[2.2.2]octane-1-carboxylate To a suspension of 4-(methoxycarbonyl)bicyclo[2.2.2]octane-1-carboxylic acid (BAI-4, 0.424 mg, 2 mmol) in acetone (3 mL) was added phenolphthaleine. To this mixture was added 1 M aqueous NaOH solution (about 2 mL, 1 equivalent) until the color of the solution turned red. Then a solution of AgNO$_3$ (340 mg, 2 mmol) in H$_2$O (0.5 mL) was added. The formed precipitate was collected by filtration, washed with H$_2$O, acetone and diethyl ether and dried in vacuo at 100° C. for 6 hours. The obtained solid was suspended in hexane (5 mL), then bromine (260 mg, 1.62 mmol) was added dropwise to the reaction mixture at room temperature. After the addition was complete, the reaction mixture was stirred at room temperature for 30 minutes. The reaction mixture was filtered to remove the solid, and the filter cake was washed with hexane (100 mL). The combined organic filtrates were washed with saturated NaHCO$_3$, dried over MgSO$_4$, filtered and concentrated to afford the titled compound. $^1$H NMR (400 MHz, CDCl$_3$) δ ppm 3.64 (s, 3H), 2.18~2.27 (m, 6H), 1.94~1.98 (m, 6H); GCMS m/z 248 (M+H)$^+$.

Preparation of Bicyclic Amine Intermediate 20 (BAI-20) 4-hydroxybicyclo[2.2.2]octane-1-carboxylic acid Methyl 4-bromobicyclo[2.2.2]octane-1-carboxylate (BAI-19, 0.246 g, 0.001 mol) was refluxed in 25 mL of 1% sodium hydroxide solution for 24 hours. After cooling, the reaction solution was acidified with 6 N hydrochloric acid and extracted with ether (50 mL×6). The combined ether layers were dried over magnesium sulfate and concentrated to small volume. Recrystallization from n-hexane and diethyl ether (40:10 mL) gave the titled compound. $^1$H NMR (400 MHz, DMSO-d$_6$) δ ppm 1. 1.68-1.78 (m, 6H), 1.48-1.52 (m, 6H), 4.00 (s, 1H), 12.00 (s, 1H).

Preparation of Bicyclic Amine Intermediate 21 (BAI-21) tent-butyl (4-hydroxybicyclo[2.2.2]oct-1-yl)carbamate To a solution of 4-hydroxybicyclo[2.2.2]octane-1-carboxylic acid (BAI-20, 340 mg, 2 mol) in dioxane (5 mL) was added triethylamine (202 m g, 2 mmol), diphenyl phosphoryl azide (550 mg, 2 mmol) and tent-butanol (3 g, 40 mmol). The reaction mixture was stirred for 45 minutes at 80° C. overnight. Then the mixture was concentrated under reduced pressure. The residue was dissolved in 30 mL of ethyl acetate and then washed with saturated NaHCO$_3$ and brine. The organic layer was dried over anhydrous Na$_2$SO$_4$ and concentrated to afford the crude titled compound which was used in the next step without further purification.

Preparation of Bicyclic Amine 8 (BA-8) 4-aminobicyclo[2.2.2]octan-1-ol

To a solution of tent-butyl (4-hydroxybicyclo[2.2.2]oct-1-yl)carbamate (BAI-21, 241 mg, 1 mmol) in CH$_2$Cl$_2$ (5 mL) was added 1.14 g of trifluoroacetic acid (10 mmol). The mixture was stirred overnight at room temperature. Removal of the solvent under reduced pressure afforded the titled compound as the trifluoroacetic acid salt. LCMS (ESI+) m/z 142 (M+H)$^+$.

Preparation of ethyl N-cyano-2-methyl-2-phenoxypropanimidoate (CI-1)

Step A ethyl 2-methyl-2-phenoxypropanoate

To a mixture of phenol (0.01 mol) and ethyl 2-bromo-2-methylpropanoate (0.01 mol) in acetonitrile was added Cs$_2$CO$_3$ (0.015 mol), and the reaction mixture was refluxed overnight. After removal of the solvent, the residue was partitioned between ethyl acetate and water. The organic layer was washed with 1 N aqueous NaOH solution, water, and brine, and then dried sodium sulfate. Concentration gave the titled compound. $^1$H NMR (400 MHz, CDCl$_3$) δ ppm 7.21~7.25 (m, 2H), 6.98 (t, J=7.2 Hz 1H), 6.83~6.86 (m, 2H), 4.23 (q, J=7.2 Hz 4H), 1.60 (s, 6H), 1.24 (t, J=7.2 Hz 3H); LCMS (ESI+) m/z 209 (M+H)$^+$.

Step B

2-methyl-2-phenoxypropanoic acid

To a solution of 2-methyl-2-phenoxypropanoic acid from Step A (0.05 mmol) in methanol (200 mL) was added aqueous LiOH (150 mL, 1 mol). The reaction mixture was refluxed for 3 hours. After removal of the solvent, the residue was extracted with ethyl acetate (50 mL×2). The aqueous layer was adjusted to pH=2 with concentrated HCl and extracted with ethyl acetate (200 mL×4). The combined extracts were washed with brine, dried with sodium sulfate and concentrated to give the titled compound. $^1$H NMR (400 MHz, CDCl$_3$) δ ppm 7.26~7.30 (m, 2H), 7.06 (t, J=7.2 Hz 1H), 6.93-6.95 (m, 2H), 1.61 (s, 6H); LCMS (ESI+) m/z 181 (M+H)$^+$.

Step C

2-methyl-2-phenoxypropanamide

Under a nitrogen atmosphere, to a solution of 2-methyl-2-phenoxypropanoic acid from Step B (0.01 mol) in dry CH$_2$Cl$_2$ (150 mL) cooled with an ice-water bath was added oxalyl chloride (1.9 g, 0.015 mol). The mixture was stirred 1 hour at room temperature. The solvent and excess oxalyl chloride were removed under reduced pressure. The resulting residue was dissolved in dry CH$_2$Cl$_2$ (50 mL) and NH$_3$ gas was bubbled into this solution which is cooled with an ice bath. The resulting mixture was stirred for 5 minutes at room temperature and diluted with CH$_2$Cl$_2$. The organic phase was washed with water and brine, dried over sodium sulfated, and concentrated to give the titled compound. $^1$H NMR (400 MHz, CDCl$_3$) δ ppm 7.27~7.31 (m, 2H), 7.08 (t, J=7.6 Hz 1H), 6.95-6.97 (m, 2H), 5.98 (s, 1H), 1.61 (s, 6H); LCMS (ESI+) m/z 180 (M+H)$^+$.

Step D

2-methyl-2-phenoxypropanenitrile

To a solution of 2-methyl-2-phenoxypropanamide from Step C (0.01 mol) in dry CH$_2$Cl$_2$ (50 mL) and triethylamine (3.03 g, 0.03 mol) at 0° C. was added trifluoroacetic anhydride (3.15 g, 0.015 mol). After the addition was complete, the solution was allowed to warm to room temperature and stirring was continued at ambient temperature overnight. The reaction mixture was then refluxed for 3 hours. After cooling to room temperature and dilution with CH$_2$Cl$_2$ (100 mL), the solution was washed with saturated aqueous NaHCO$_3$ (50 mL×3), water, and brine and dried over sodium sulfated. Evaporation gave the titled compound. $^1$H NMR (400 MHz, CDCl$_3$) δ ppm 7.32~7.36 (m, 2H), 7.14~7.20 (m, 3H), 1.71 (s, 6H).

Step E ethyl N-cyano-2-methyl-2-phenoxypropanimidoate

To a solution of sodium ethoxide in ethanol, freshly prepared from sodium (0.02 mol) and ethanol (50 mL), was added 2-methyl-2-phenoxypropanenitrile from Step D (0.05 mol). The mixture was stirred overnight at room temperature, and then acetic acid (0.07 mol) was added, followed by addition of NH$_2$CN (0.05 mol). The mixture was stirred for 3 hours and the solvent was removed. The residue was purified by column chromatography on silica gel (mobile phase: petroleum ether/ethyl acetate=4:1~1:1) to give the titled compound. $^1$H NMR (400 MHz, CDCl$_3$) δ ppm 7.27 (t, J=8.0 Hz 2H), 7.05 (t, J=7.2 Hz 1H), 6.88~6.90 (m, 2H), 4.38 (q, J=7.2 Hz, 2H), 1.61 (s, 6H), 1.39 (t, J=7.2 Hz, 3H); LCMS (ESI+) m/z 233 (M+H)$^+$.

Example 1

(1E)-2-(2-Chloro-4-fluorophenoxy)-Y-cyano-N-[(E)-5-hydroxy-2-adamantyl]-2-methylpropanimidamide

Example 1A

(1E)-2-(2-Chloro-4-fluorophenoxy)-N-[(E)-5-hydroxy-2-adamantyl]-2-methylpropanamide The titled compound was synthesized according to the methods described by Sorensen et al., *Bioorg. Med. Chem. Lett.* 2007, 17, 527-532.

Example 1B

(1E)-2-(2-Chloro-4-fluorophenoxy)-N-[(E)-5-hydroxy-2-adamantyl]-2-methylpropanethioamide To a solution of Example 1A (0.76 g, 2 mmol) in toluene (25 mL) was added Lawesson's reagent (0.81 g, 2 mmol) and then the reaction mixture was heated at 80° C. for 4 hours. The reaction mixture was concentrated under reduced pressure, and the residue was partitioned between saturated aqueous NaHCO$_3$ and ethyl acetate. The organic layers were combined, dried (MgSO$_4$), filtered and concentrated. The residue was purified by flash chromatography (SiO$_2$, 0-40% ethyl acetate in hexanes) to provide the titled compound. MS (DCI$^+$) m/z 398 (M+H)$^+$.

Example 1C

(1E)-2-(2-Chloro-4-fluorophenoxy)-N'-cyano-N-[(E)-5-hydroxy-2-adamantyl]-2-methylpropanimidamide A solution of Example 1B (0.46 g, 2.0 mmol) in acetonitrile (20 mL) was treated with cyanamide (0.12 g, 2.9 mmol), mercury(II) acetate (0.56 g, 1.7 mmol), and triethylamine (0.33 mL, 2.3 mmol) and the reaction mixture was heated at 80° C. for 18 hours. The mixture was then concentrated under reduced pressure and the residue was partitioned between saturated NaHCO$_3$ and ethyl acetate. The combined organic layers were dried (MgSO$_4$), filtered and concentrated, and the residue was purified by flash chromatography (hexane-ethyl acetate, 1:2) to afford the titled compound. $^1$H NMR (300 MHz, DMSO-d$_6$) δ ppm 1.36-1.81 (m, 16H), 1.97-2.09 (m, 1H), 2.15-2.28 (m, 2H), 4.01 (s, 1H), 4.51 (s, 1H), 7.16-7.35 (m, 2H), 7.57 (dd, J=8.5, 3.1 Hz, 1H), 7.88 (d, J=7.1 Hz, 1H); MS (DCI$^+$) m/z 406 (M+H)$^+$.

Example 2

(1E)-N-Cyano-N-[(E)-5-hydroxy-2-adamantyl]-2-(2-methylphenyl)ethanimidamide

A mixture of E-2-amino-5-hydroxyadamantane (Jaroskova et al., Tetrahedron Letters 2006, 47(46), 8063-8067) (0.35 g, 2.0 mmol) and (E)-ethyl N-cyano-2-o-tolylacetimidate (U.S. patent application Pub. No. US2006/0025614) (0.42 g, 2.0 mmol) in ethanol (1 mL) was stirred at 80° C. for 16 hours. The reaction mixture was concentrated on a rotary evaporator and purified by flash chromatography using 0-100% ethyl acetate/hexane as eluent to provide the titled compound. $^1$H NMR (300 MHz, DMSO-d$_6$) δ ppm 1.38 (d, J=12.9 Hz, 2H), 1.55-1.90 (m, 7H), 1.93-2.20 (m, 4H), 2.30 (s, 3H), 3.89 (s, 2H), 3.95 (dd, J=6.3, 3.2 Hz, 1H), 4.43-4.52 (m, 1H), 7.00 (dd, J=5.1, 3.7 Hz, 1H), 7.12-7.32 (m, 3H), 8.57 (d, J=6.8 Hz, 1H); MS (DCI$^+$) m/z 324 (M+H)$^+$. Anal. Calculated for C$_{21}$H$_{27}$ClN$_2$O$_3$S$_2$.0.5H$_2$O: C, 72.26; H, 7.88; N, 12.64. Found: C, 72.82; H, 7.65; N, 13.08.

Example 3

1-(4-Chlorophenyl)-N'-cyano-N-[(E)-5-hydroxy-2-adamantyl]cyclobutanecarboximidamide

Example 3A

Ethyl 1-(4-chlorophenyl)cyclobutanecarbimidate hydrochloride

Through a cooled solution of 1-(4-chlorophenyl)cyclobutanecarbonitrile (5.0 g, 26.1 mmol, Aldrich) and ethanol (2.3 mL, 39.1 mmol) was bubbled HCl gas at 0° C. for 30 minutes. After standing at 4° C. for 24 hours, the reaction mixture was concentrated and triturated with diethyl ether. The precipitate was collected and dried to obtain the titled compound. MS (ESI$^+$) m/z 238 (M+H)$^1$.

Example 3B

Ethyl 1-(4-chlorophenyl)-N-cyanocyclobutanecarbimidate

To a solution of Example 3A (2.5 g, 9.1 mmol) in acetonitrile (7 mL) was added a solution of sodium phosphate monobasic monohydrate (5.0 g, 36.5 mmol), sodium phosphate dibasic heptahydrate (4.9 g, 18.2 mmol), and cyanamide (0.8 g, 18.2 mmol) in water (70.0 mL). The reaction mixture was stirred at room temperature for 72 hours, and then the mixture was extracted with methylene chloride (3×30 mL). The combined organic extracts were dried over anhydrous Na$_2$SO$_4$, filtered and concentrated under reduced pressure to obtain the titled compound. MS (ESI$^+$) m/z 263 (M+H)$^+$.

Example 3C 1-(4-Chlorophenyl)-N'-cyano-N-[(E)-5-hydroxy-2-adamantyl]cyclobutanecarboximidamide A mixture of E-2-amino-5-hydroxyadamantane (Jaroskova et al., Tetrahedron Letters 2006, 47(46), 8063-8067) (0.2 g, 1.2 mmol) and Example 3B (0.3 g, 1.2 mmol) was stirred at 80° C. for 16 hours. The reaction mixture was then cooled, dissolved in dichloromethane (2 mL) and purified by column chromatography using an Analogix® Intelliflash 280™ (SiO$_2$, 0-100% of ethyl acetate in dichloromethane) to afford the titled compound. $^1$H NMR (300 MHz, DMSO-d$_6$) δ ppm 1.29-1.46 (m, 2H), 1.52-1.69 (m, 6H), 1.71-1.82 (m, 2H), 1.82-1.95 (m, 2H), 1.99-2.08 (m, 1H), 2.11-2.24 (m, 2H), 2.60-2.73 (m, 2H), 2.72-2.87 (m, 2H), 3.62-3.89 (m, 1H), 4.44 (s, 1H), 7.48 (d, J=8.3 Hz, 2H), 7.66 (d, J=5.6 Hz, 1H), 7.70 (d, J=8.7 Hz, 2H)); MS (ESI$^+$) m/z 384 (M+H)$^1$. Anal. Calculated for C$_{22}$H$_{26}$ClN$_3$O: C, 68.83; H, 6.83; N, 10.95. Found: C, 69.05; H, 7.28; N, 10.46.

Example 4

(1E)-N'-Cyano-2-(2,4-difluorophenyl)-N-[(E)-5-hydroxy-2-adamantyl]ethanimidamide

Example 4A

Ethyl 2-(2,4-difluorophenyl)acetimidate hydrochloride

Commercially available 2-(2,4-difluorophenyl)acetonitrile (Aldrich), HCl gas and ethanol were processed using the method described for Example 3A to obtain the titled compound except that the reaction time was 72 hours. MS (ESI$^+$) m/z 200 (M+H)$^+$.

Example 4B

Ethyl N-cyano-2-(2,4-difluorophenyl)acetimidate

To a solution of Example 4A (7.0 g, 29.7 mmol) in ethanol (100 mL) was added a solution of cyanamide (1.25 g, 29.7 mmol) in diethyl ether (25 mL). The reaction mixture was stirred at room temperature for 3 days. The reaction mixture was then filtered and the filtrate was concentrated to obtain the titled compound. MS (ESI$^+$) m/z 225 (M+H)$^+$.

Example 4C (1E)-N'-Cyano-2-(2,4-difluorophenyl)-N-[(E)-5-hydroxy-2-adamantyl]ethanimidamide The titled compound was synthesized according to the procedure described in Example 3C substituting Example 3B with Example 4B. $^1$H NMR (300 MHz, DMSO-d$_6$) δ ppm 1.30-1.45 (m, 2H), 1.55-1.73 (m, 6H), 1.74-1.94 (m, 2H), 1.96-2.19 (m, 3H), 3.83-3.91 (m, 1H), 3.94 (s, 2H), 4.47 (s, 1H), 7.10 (td, J=8.5, 3.4 Hz, 1H), 7.19-7.44 (m, 2H), 8.69 (d, J=6.8 Hz, 1H); MS (ESI$^+$) m/z 346 (M+H)$^+$.

Example 5

(1E)-N'-Cyano-2-(2-fluorophenyl)-N-[(E)-5-hydroxy-2-adamantyl]ethanimidamide

The titled compound was synthesized according to the procedure described in Example 3C substituting Example 3B with ethyl N-cyano-2-(2-fluorophenyl)acetimidate (U.S. patent application Pub. No. US2006/0025614). $^1$H NMR (300 MHz, DMSO-d$_6$) δ ppm 1.29-1.45 (m, 2H), 1.56-1.76 (m, 6H), 1.76-1.93 (m, 2H), 1.95-2.19 (m, 3H), 3.85-3.92 (m, 1H), 3.97 (s, 2H), 4.47 (s, 1H), 7.19 (d, 3H), 7.37 (d, 1H), 8.69 (d, J=6.8 Hz, 1H); MS (ESI$^+$) m/z 328 (M+H)$^+$. Anal. Calculated for C$_{19}$H$_{22}$FN$_3$O: C, 69.70; H, 6.77; N, 12.83 Found: C, 69.31; H, 6.87; N, 12.54.

Example 6

(1E)-2-(2-Chloropyridin-3-yl)-N'-cyano-N-[(E)-5-hydroxy-2-adamantyl]ethanimidamide

Example 6A

Ethyl 2-(2-chloropyridin-3-yl)acetimidate

Through a cooled solution of 2-(2-chloropyridin-3-yl)acetonitrile (Synthesis (6), 528-30, 1992) (1.7 g, 11.1 mmol), ethanol (1.0 mL, 16.7 mmol), and dichloromethane (25 mL) was bubbled HCl gas at 0° C. for 30 minutes. After standing at 4° C. for 24 hours, the reaction mixture was concentrated, and the residue was triturated with diethyl ether. The precipitate was collected and dried to obtain the titled compound. MS (ESI+) m/z 199 (M+H)+.

Example 6B

Ethyl 2-(2-chloropyridin-3-yl)-N-cyanoacetimidate

Example 6A and cyanamide (Aldrich) were processed using the method described for Example 4B to obtain the titled compound. MS (ESI+) m/z 224 (M+H)+.

Example 6C (1E)-2-(2-Chloropyridin-3-yl)-N'-cyano-N-[(E)-5-hydroxy-2-adamantyl]ethanimidamide The titled compound was synthesized according to the procedure described in Example 3C substituting Example 3B with Example 6B. $^1$H NMR (300 MHz, DMSO-$d_6$) δ ppm 1.30-1.47 (m, 2H), 1.56-1.73 (m, 6H), 1.76-1.92 (m, 2H), 1.97-2.19 (m, 3H), 3.90-3.98 (m, 1H), 4.05 (s, 2H), 4.48 (s, 1H), 7.46 (dd, J=7.5, 4.7 Hz, 1H), 7.62 (dd, J=7.6, 1.9 Hz, 1H), 8.36 (dd, J=4.6, 1.9 Hz, 1H), 8.74 (d, J=6.4 Hz, 1H); MS (ESI+) m/z 345 (M+H)+. Anal. Calculated for $C_{18}H_{21}ClN_4O \cdot 0.05H_2O$: C, 62.53; H, 6.15; N, 16.20. Found: C, 62.13; H, 6.02; N, 16.58.

Example 7

(1E)-2-(4-Chlorophenoxy)-N'-cyano-N-[(E)-5-hydroxy-2-adamantyl]ethanimidamide

Example 7A

Ethyl 2-(4-chlorophenoxy)acetimidate hydrochloride

Commercially available 2-(4-chlorophenoxy)acetonitrile (Aldrich), HCl gas and ethanol were processed using the method described for Example 4A to obtain the titled compound. MS (ESI+) m/z 214 (M+H)+.

Example 7B

Ethyl 2-(4-chlorophenoxy)-N-cyanoacetimidate

Example 7A and cyanamide (Aldrich) were processed using the method described for Example 4B to obtain the titled compound. MS (ESI+) m/z 239 (M+H)+.

Example 7C (1E)-2-(4-Chlorophenoxy)-N'-cyano-N-[(E)-5-hydroxy-2-adamantyl]ethanimidamide The titled compound was synthesized according to the procedure described in Example 3C substituting Example 3B with Example 7B. $^1$H NMR (300 MHz, DMSO-$d_6$) δ ppm 1.30-1.42 (m, 2H), 1.55-1.70 (m, 6H), 1.73-1.84 (m, 2H), 1.95-2.15 (m, 3H), 3.78-3.90 (m, 1H), 4.47 (s, 1H), 4.93 (s, 2H), 6.90-7.10 (m, 2H), 7.31-7.49 (m, 2H), 8.60 (d, J=5.1 Hz, 1H); MS (ESI+) m/z 360 (M+H)+. Anal. Calculated for $C_{19}H_{22}ClN_3O_2 \cdot 0.1H_2O$: C, 63.10; H, 6.19; N, 11.62. Found: C, 62.82; H, 6.32; N, 11.43.

Example 8

(1E)-2-(4-Chlorophenoxy)-N'-cyano-N-[(E)-5-hydroxy-2-adamantyl]-2-methylpropanimidamide Example 8A Ethyl 2-(4-chlorophenoxy)-2-methylpropanimidate hydrochloride Commercially available 2-(4-chlorophenoxy)-2-methylpropanenitrile (Maybridge), HCl gas and ethanol were processed using the method described for Example 4A to obtain the titled compound. MS (ESI+) m/z 242 (M+H)+.

Example 8B

Ethyl 2-(4-chlorophenoxy)-N-cyano-2-methylpropanimidate

Example 8A and cyanamide (Aldrich) were processed using the method described for Example 3B to obtain the titled compound. MS (ESI+) m/z 267 (M+H)+.

Alternative Preparation of Example 8B

Example 8B was also prepared following the procedures described for the preparation of ethyl N-cyano-2-methyl-2-phenoxypropanimidoate (CI-1) substituting 4-chlorophenol for phenol.

Example 8C (1E)-2-(4-Chlorophenoxy)-N'-cyano-N-[(E)-5-hydroxy-2-adamantyl]-2-methylpropanimidamide The titled compound was synthesized according to the procedure described in Example 3C substituting Example 3B with Example 8B. $^1$H NMR (300 MHz, DMSO-$d_6$) δ ppm 1.31-1.48 (m, 2H), 1.57-1.77 (m, 8H), 1.64 (s, 6H), 1.94-2.04 (m, 1H), 2.14-2.25 (m, 2H), 3.90-4.02 (m, 1H), 4.50 (s, 1H), 6.96-7.06 (m, 2H), 7.32-7.43 (m, 2H), 7.57 (d, J=6.8 Hz, 1H); MS (ESI+) m/z 388 (M+H)+. Anal. Calculated for $C_{21}H_{26}ClN_3O_2 \cdot 0.25H_2O$: C, 64.28; H, 6.81; N, 10.71. Found: C, 64.53; H, 6.70; N, 10.31.

Example 9

2-(4-Chlorophenoxy)-2-methyl-N-[(E)-5-(methylsulfonyl)-2-adamantyl]propanethioamide Example 9A 2-(4-Chlorophenoxy)-2-methyl-N-[(E)-5-(methylsulfonyl)-2-adamantyl]propanamide The titled compound was synthesized according to the methods described in Sorensen et al., *Bioorg. Med. Chem. Lett.*, 2007, 17, 527-532.

Example 9B 2-(4-Chlorophenoxy)-2-methyl-N-[(E)-5-(methylsulfonyl)-2-adamantyl]propanethioamide The titled compound was synthesized according to the procedure described in Example 1B substituting Example 1A with Example 9A. $^1$H NMR (300 MHz, DMSO-d$_6$) δ ppm 1.50-1.83 (m, 10H), 1.87-2.15 (m, 7H), 2.41 (s, 2H), 2.87 (s, 3H), 4.28-4.53 (m, 1H), 7.13-7.31 (m, 2H), 7.55 (dd, J=10.0, 1.9 Hz, 1H), 9.43 (d, J=7.1 Hz, 1H); MS (DCI+) m/z 460 (M+H)$^+$. Anal. Calculated for C$_{21}$H$_{27}$ClN$_2$O$_3$S$_2$: C, 57.06; H, 6.38; N, 3.17. Found: C, 57.16; H, 6.50; N, 3.05.

Example 10

(1E)-N-[(E)-5-(Aminosulfonyl)-2-adamantyl]-2-(4-chlorophenoxy)-N'-cyano-2-methylpropanimidamide Example 8B and (E)-4-aminoadamantane-1-sulfonamide (Sorensen et al., *Bioorg. Med. Chem. Lett.*, 2007, 17, 527-532) were processed using the method described for Example 2 to obtain the titled compound. $^1$H NMR (300 MHz, DMSO-d$_6$) δ ppm 1.42-1.54 (m, 2H), 1.65 (s, 6H), 1.70-1.82 (m, 2H), 1.84-2.08 (m, 7H), 2.22-2.33 (m, 2H), 3.90-4.08 (m, 1H), 6.63 (s, 2H), 7.01 (d, J=9.1 Hz, 2H), 7.38 (d, J=9.1 Hz, 2H), 7.67 (d, J=6.3 Hz, 1H); MS (ESI$^+$) m/z 451 (M+H)$^+$. Anal. Calculated for C$_{21}$H$_{27}$ClN$_4$O$_3$S: C-55.93; H-6.03; N-12.42. Found: C-56.19; H-6.05; N-12.25.

Example 11

Methyl(E)-4-{[(1E)-2-(4-chlorophenoxy)-N-cyano-2-methylpropanimidoyl]amino}adamantane-1-carboxylate

Example 11A

E-2-Amino-5-carboxyadamantane methyl ester

E-2-Amino-5-carboxyadamantane methyl ester hydrochloride salt (Becker et al., *Org. Process R & D*, 2008, 12, 1114-1118) (5 g, 20.4 mmol) was partitioned between saturated aqueous NaHCO$_3$ (60 mL) and dichloromethane (100 mL). The aqueous layer was further extracted with dichloromethane (3×50 mL). The combined organic extracts were dried over anhydrous Na$_2$SO$_4$, filtered and concentrated under reduced pressure to obtain the titled compound. MS (ESI$^+$) m/z 210 (M+H)$^+$.

Example 11B

Methyl(E)-4-{[(1E)-2-(4-chlorophenoxy)-N-cyano-2-methylpropanimidoyl]amino}adamantane-1-carboxylate Example 8B and Example 11A were processed using the method described for Example 2 to obtain the titled compound. $^1$H NMR (300 MHz, DMSO-d$_6$) δ ppm 1.46-1.58 (m, 2H), 1.62-1.68 (m, 6H), 1.68-1.84 (m, 4H), 1.85-1.96 (m, 5H), 2.10-2.23 (m, 2H), 3.59 (s, 3H), 3.98-4.11 (m, 1H), 6.96-7.07 (m, 2H), 7.32-7.44 (m, 2H), 7.65 (d, J=6.3 Hz, 1H); MS (ESI$^+$) m/z 430 (M+H)$^+$. Anal. Calculated for C$_{23}$H$_{28}$ClN$_3$O$_3$: C-64.25; H-6.56; N-9.77. Found: C-64.31; H-6.58; N-9.79.

Example 12

2-(2-Chloro-4-fluorophenoxy)-2-methyl-N-[(E)-5-(methylsulfonyl)-2-adamantyl]propanethioamide

Example 12A

2-(2-Chloro-4-fluorophenoxy)-2-methyl-N-[(1E)-5-(methylsulfonyl)-2-adamantyl]propanethioamide The titled compound was synthesized according to the methods described in Sorensen et al., *Bioorg. Med. Chem. Lett.*, 2007, 17, 527-532.

Example 12B

2-(2-Chloro-4-fluorophenoxy)-2-methyl-N-[(E)-5-(methylsulfonyl)-2-adamantyl]propanethioamide The titled compound was synthesized according to the procedure described in Example 1B substituting Example 1A with Example 12A. $^1$H NMR (300 MHz, DMSO-d$_6$) δ ppm 1.50-1.84 (m, 10H), 1.86-2.18 (m, 8H), 2.41 (s, 2H), 2.87 (s, 3H), 4.30-4.55 (m, 1H), 7.11-7.29 (m, 1H), 7.55 (dd, J=10.0, 1.9 Hz, 1H), 9.43 (d, J=7.1 Hz, 1H); MS (DCI+) m/z 460 (M+H)$^+$. Anal. Calculated for C$_{21}$H$_{27}$ClNFO$_3$S$_2$: C, 54.94; H, 5.92; N, 3.04. Found: C, 54.94; H, 6.11; N, 2.98.

Example 13

(1E)-2-(4-Chlorophenoxy)-N-methoxy-2-methyl-N-[(E)-5-(methylsulfonyl)-2-adamantyl]propanimidamide A solution of Example 9 (200 mg, 0.45 mmol) in acetonitrile (20 mL) was treated with O-methylhydroxylamine hydrochloride (94 mg, 1.1 mmol), mercury(II) acetate (216 mg, 0.67 mmol) and triethylamine (0.12 mL, 0.90 mmol). The reaction mixture was heated at 80° C. for 18 hours. The mixture was then concentrated under reduced pressure and the residue was partitioned between saturated aqueous NaHCO$_3$ and ethyl acetate. The combined organic layers were dried (MgSO$_4$), filtered and concentrated. The residue was purified by chromatography (hexane-ethyl acetate, 1:2) to afford the titled compound. $^1$H NMR (500 MHz, DMSO-d$_6$) δ ppm 1.36-1.70 (m, 10H), 1.72-2.07 (m, 9H), 2.73-2.92 (m, 3H), 3.70 (s, 3H), 4.14 (d, J=10.1 Hz, 1H), 5.32 (d, J=10.1 Hz, 1H), 6.95-7.04 (m, 2H), 7.25-7.39 (m, 2H); MS (DCI+) m/z 455 (M+H)$^+$.

Example 14

(E)-4-{[(1E)-2-(4-Chlorophenoxy)-N-cyano-2-methylpropanimidoyl]amino}adamantane-1-carboxamide

Example 14A

(E)-4-{[(1E)-2-(4-Chlorophenoxy)-N-cyano-2-methylpropanimidoyl]amino}adamantane-1-carboxylic acid To a solution of Example 11 (0.48 g, 1.1 mmol) in tetrahydrofuran (2 mL), methanol (4 mL) and water (4 mL) was added 5 N aqueous NaOH (1.1 mL, 5.6 mmol). After stirring at room temperature for 16 hours, the reaction mixture was concentrated to half the volume, the pH was adjusted to ~5, and the mixture was extracted with ethyl acetate (3×15 mL).

The combined organic extracts were dried over anhydrous $Na_2SO_4$, filtered and concentrated under reduced pressure to obtain the titled compound in crude form which was used without additional purification. MS (ESI$^+$) m/z 416 (M+H)$^+$.

Example 14B (E)-4-{[(1E)-2-(4-Chlorophenoxy)-N-cyano-2-methylpropanimidoyl]amino}adamantane-1-carboxamide To a solution of Example 14A (0.37 g, 0.9 mmol) in dichloromethane (10 mL) were added 1-hydroxy-benzotriazole hydrate (0.16 g, 1.1 mmol), N-(3-dimethylaminopropyl)-N'-ethylcarbodiimide hydrochloride (0.25 g, 1.3 mmol) and 30% aqueous ammonium hydroxide (1.0 mg, 8.9 mmol). The reaction mixture was stirred at room temperature for 16 hours and then quenched with water (10 mL). The aqueous layer was extracted with dichloromethane (3×20 mL). The combined organic extracts were dried over anhydrous $Na_2SO_4$, filtered and concentrated. The residue was purified by column chromatography using an Analogix® Intelliflash 280™ (SiO$_2$, 0-50% of methanol/ethyl acetate(1/10) in hexanes) to obtain the titled compound. $^1$H NMR (300 MHz, DMSO-d$_6$) δ ppm 1.45-1.55 (m, 2H), 1.62-1.68 (m, 6H), 1.67-1.78 (m, 4H), 1.82-1.94 (m, 5H), 2.08-2.20 (m, 2H), 3.98-4.06 (m, 1H), 6.74 (s, 1H), 6.96-7.06 (m, 3H), 7.33-7.45 (m, 2H), 7.62 (d, J=6.7 Hz, 1H); MS (ESI$^+$) m/z 415 (M+H)$^+$. Anal. Calculated for $C_{27}H_{27}ClN_4O_2$: C-63.68, H-6.56, N-13.50. Found: C-63.35; H-6.53; N-13.06.

Example 15

1-(3-Chlorophenoxy)-N'-cyano-N-[(E)-5-hydroxy-2-adamantyl]cyclobutane carboximidamide Example 15A Ethyl 1-(3-chlorophenoxy)cyclobutanecarboxylate To a solution of 3-chlorophenol (7.5 g, 58.0 mmol) in N,N-dimethylformamide (125 mL) was added cesium carbonate (28.3 g, 87 mmol) followed by the addition of ethyl 1-bromocyclobutanecarboxylate (9.8 mL, 58.0 mmol). The reaction mixture was stirred at 55° C. overnight. The solid was removed by filtration, and the filtrate was concentrated under reduced pressure. Purification by column chromatography (silica, heptane/ethyl acetate, 7:1) afforded ethyl 1-(3-chlorophenoxy)cyclobutanecarboxylate. MS (ESI$^+$) m/z 255 (M+H)$^+$.

Example 15B 1-(3-Chlorophenoxy)cyclobutanecarboxylic acid

Lithium hydroxide monohydrate (1.7 g, 40.3 mmol) was added to a suspension of Example 15A (4.7 g, 13.4 mmol) in tetrahydrofuran (320 mL) and water (160 mL) at room temperature. The reaction mixture was stirred at 55° C. overnight. The reaction was concentrated under reduced pressure to remove tetrahydrofuran, acidified to pH~3 by adding aqueous 1 M HCl while cooling. The precipitate was collected by filtration and dried in a dessicator containing KOH overnight. Recrystallization from heptane afforded the titled compound. MS (ESI$^+$) m/z 227 (M+H)$^+$.

Example 15C (1E)-2-(3-Chlorophenoxy)-N-[(E)-5-hydroxy-2-adamantyl]-2-methylpropanamide To a solution of E-2-amino-5-hydroxyadamantane (Jaroskova et al., *Tetrahedron Letters* 2006, 47(46), 8063-8067) (0.25 g, 1.5 mmol) in N,N-dimethylformamide (10 mL) were added Example 15B (0.34 g, 1.5 mmol), 2-(1H-benzo[d][1,2,3]triazol-1-yl)-1,1,3,3-tetramethylisouronium tetrafluoroborate (0.72 g, 2.2 mmol), and diisopropylethylamine (0.78 mL, 4.5 mmol). The reaction mixture was stirred at room temperature for 16 hours, and then the reaction mixture was quenched with water (10 mL). The resultant layers were separated, and the aqueous layer was extracted with ethyl acetate (3×20 mL). The combined organic extracts were dried over anhydrous $Na_2SO_4$, filtered and concentrated. The residue was purified by column chromatography using an Analogix® Intelliflash 280™ (SiO$_2$, 0-80% methanol/dichloromethane(1/10) in dichloromethane) to obtain the titled compound. MS (ESI$^+$) m/z 376 (M+H)$^+$.

Example 15D 1-(3-Chlorophenoxy)-N'-cyano-N-[(E)-5-hydroxy-2-adamantyl]cyclobutane carboximidamide The titled compound was synthesized according to the procedures described in Example 1B and Example 1C substituting Example 1A with Example 15B. $^1$H NMR (300 MHz, DMSO-d$_6$) δ ppm 1.17-1.38 (m, 2H), 1.48-1.70 (m, 7H), 1.80-2.04 (m, 6H), 2.05-2.17 (m, 2H), 2.82-2.95 (m, 2H), 3.89-4.01 (m, 1H), 4.44 (s, 1H), 6.74-6.91 (m, 2H), 7.07 (d, J=7.6 Hz, 1H), 7.32 (t, J=8.2 Hz, 1H), 7.73-7.86 (m, 1H); MS (ESI$^+$) m/z 400 (M+H)$^+$.

Example 16

Methyl(E)-4-[(2-methyl-2-{[4-(trifluoromethyl)benzyl]oxy}propanethioyl)amino]adamantane-1-carboxylate Example 16A Methyl(E)-4-[(2-methyl-2-{[4-(trifluoromethyl)benzyl]oxy}propanecarbonyl)amino]adamantane-1-carboxylate The titled compound was synthesized according to the methods described in Patel et al., *Bioorg. Med. Chem. Lett.*, 2007, 17, 750-755.

Example 16B

Methyl(E)-4-[(2-methyl-2-{[4-(trifluoromethyl)benzyl]oxy}propanethioyl)amino]adamantane-1-carboxylate The titled compound was synthesized according to the procedure described in Example 1B substituting Example 1A with Example 16A. $^1$H NMR (300 MHz, DMSO-d$_6$) δ ppm 1.35-1.66 (m, 10H), 1.74-1.96 (m, 7H), 2.15 (d, J=2.4 Hz, 2H), 3.58 (s, 3H), 4.16-4.37 (m, 1H), 4.63 (s, 2H), 7.57-7.69 (m, 2H), 7.70-7.82 (m, 2H), 9.01 (d, J=7.1 Hz, 1H); MS (DCI+) m/z 460 (M+H)$^+$.

Example 17

Methyl(E)-4-[((1E)-N-cyano-2-methyl-2-{[4-(trifluoromethyl)benzyl]oxy}propanimidoyl)amino]adamantane-1-carboxylate The titled compound was synthesized according to the procedure described in Example 1C substituting Example 1B with Example 16. $^1$H NMR (300 MHz, DMSO-$d_6$) δ ppm 1.42-1.59 (m, 4H), 1.65 (s, 6H), 1.72-1.96 (m, 7H), 2.08 (d, J=2.0 Hz, 2H), 3.58 (s, 3H), 3.98 (d, J=6.8 Hz, 1H), 4.70 (s, 2H), 7.51 (d, J=7.1 Hz, 1H), 7.57-7.69 (m, 2H), 7.71-7.82 (m, 2H); MS (DCI+) m/z 478 (M+H)$^+$. Anal. Calculated for $C_{25}H_{30}N_3F_3O_3 \cdot 0.75H_2O$: C, 61.15; H, 6.47; N, 8.56. Found: C, 61.24; H, 6.22; N, 8.20.

Example 18

(1E)-2-(2-Chloro-4-fluorophenoxy)-N-cyano-2-methyl-N-[(E)-5-(methylsulfonyl)-2-adamantyl]propanimidamide The titled compound was synthesized according to the procedure described in Example 1C substituting Example 1B with Example 12. $^1$H NMR (300 MHz, DMSO-$d_6$) δ ppm 1.52-1.64 (m, 1H), 1.69 (s, 6H), 1.75-2.19 (m, 10H), 2.33 (s, 2H), 2.86 (s, 3H), 4.08 (s, 1H), 7.17-7.36 (m, 2H), 7.58 (dd, J=8.5, 3.0 Hz, 1H), 7.96 (d, J=6.7 Hz, 1H); MS (DCI+) m/z 478 (M+H)$^+$.

Example 19

(1E)-2-(4-Chlorophenoxy)-N-cyano-2-methyl-N-[(E)-5-(methylsulfonyl)-2-adamantyl]propanimidamide The titled compound was synthesized according to the procedure described in Example 1C substituting Example 1B with Example 9. $^1$H NMR (300 MHz, DMSO-$d_6$) δ ppm 1.44-1.59 (m, 1H), 1.66 (s, 6H), 1.84-2.14 (m, 10H), 2.31 (s, 2H), 2.78-2.94 (m, 3H), 4.03 (d, J=7.1 Hz, 1H), 6.96-7.07 (m, 2H), 7.33-7.46 (m, 2H), 7.68 (d, J=6.4 Hz, 1H); MS (DCI+) m/z 450 (M+H)$^+$. Anal. Calculated for $C_{22}H_{28}N_3O_3S$: C, 58.72; H, 6.27; N, 8.59. Found: C, 58.43; H, 6.43; N, 8.59.

Example 20

N-[(E)-5-(Aminosulfonyl)-2-adamantyl]-2-methyl-2-[2-(trifluoromethoxy)phenoxy]propanethioamide

Example 20A

N-[(E)-5-(Aminosulfonyl)-2-adamantyl]-2-methyl-2-[2-(trifluoromethoxy)phenoxy]propaneamide The titled compound was synthesized according to the methods described in Sorensen et al., *Bioorg. Med. Chem. Lett.*, 2007, 17, 527-532.

Example 20B

N-[(E)-5-(Aminosulfonyl)-2-adamantyl]-2-methyl-2-[2-(trifluoromethoxy)phenoxy]propanethioamide The titled compound was synthesized according to the procedure described in Example 1B substituting Example 1A with Example 20A. $^1$H NMR (300 MHz, DMSO-$d_6$) δ ppm 1.42-1.62 (m, 3H), 1.66 (s, 6H), 1.80-2.10 (m, 8H), 2.31 (s, 2H), 4.24-4.48 (m, 1H), 6.63 (s, 2H), 7.07 (d, J=8.3 Hz, 1H), 7.13-7.22 (m, 1H), 7.30-7.39 (m, 1H), 7.44 (d, J=8.3 Hz, 1H), 9.11 (d, J=7.1 Hz, 1H); MS (DCI+) m/z 493 (M+H)$^+$.

Example 21

Methyl(E)-4-[(2-methyl-2-{4-[5-(trifluoromethyl)pyridin-2-yl]piperazin-1-yl}propanethioyl)amino]adamantane-1-carboxylate

Example 21A

Methyl(E)-4-[(2-methyl-2-{4-[5-(trifluoromethyl)pyridin-2-yl]piperazin-1-yl}propanoyl)amino]adamantane-1-carboxylate The titled compound was synthesized according to the methods described in Becker et al., *Org. Process R & D*, 2008, 12, 1114-1118.

Example 21B

Methyl(E)-4-[(2-methyl-2-{4-[5-(trifluoromethyl)pyridin-2-yl]piperazin-1-yl}propanethioyl)amino]adamantane-1-carboxylate The titled compound was synthesized according to the procedure described in Example 1B substituting Example 1A with Example 21A. $^1$H NMR (300 MHz, DMSO-$d_6$) δ ppm 1.22-1.38 (m, 6H), 1.68 (q, J=13.0 Hz, 4H), 1.81-2.06 (m, 7H), 2.19 (s, 2H), 3.32 (s, 6H), 3.52-3.76 (m, 5H), 4.24-4.42 (m, 1H), 6.98 (d, J=9.2 Hz, 1H), 7.81 (dd, J=9.2, 2.4 Hz, 1H), 8.42 (d, J=1.7 Hz, 1H), 10.23 (d, J=7.8 Hz, 1H); MS (DCI+) m/z 525 (M+H)$^+$.

Example 22

3-(4-Chlorophenyl)-N-[(E)-5-hydroxy-2-adamantyl]-2,2-dimethylpropanimidamide

Example 22A 3-(4-Chlorophenyl)-2,2-dimethylpropanenitrile

To a solution of lithium diisopropylamide (11.0 mL, 21.9 mmol, 2 Min tetrahydrofuran, Aldrich) in tetrahydrofuran (100 mL) was added isobutyronitrile (2.0 mL, 21.9 mmol) at 0-5° C. After 30 minutes of stirring, a solution of 1-(bromomethyl)-4-chlorobenzene (3.0 g, 14.6 mmol) in tetrahydrofuran (10 mL) was added at the same temperature. After stirring at room temperature for 2 hours, the reaction mixture was treated with 10% hydrochloric acid (50 mL), and concentrated under reduced pressure to remove tetrahydrofuran. The concentrate was extracted with ethyl acetate (3×50 mL). The combined organic extracts were washed successively with aqueous $NaHCO_3$ (50 mL) and brine (50 mL), dried over anhydrous $Na_2SO_4$, filtered and concentrated under reduced pressure. The residue was then purified by column chromatography using an Analogix® Intelliflash 280™ ($SiO_2$, 0-30% of ethyl acetate in hexanes) to obtain the titled compound. MS (DCI$^+$) m/z 211 (M+$NH_4$)$^+$.

Example 22B

Ethyl 3-(4-chlorophenyl)-2,2-dimethylpropanimidate hydrochloride

Example 22A, HCl gas and ethanol were processed using the method described for Example 4A to obtain the titled compound. MS (ESI$^+$) m/z 240 (M+H)$^+$.

Example 22C 3-(4-Chlorophenyl)-N-[(E)-5-hydroxy-2-adamantyl]-2,2-dimethylpropanimidamide A mixture of E-2-amino-5-hydroxyadamantane (Jaroskova et al., *Tetrahedron Letters* 2006, 47(46), 8063-8067) (59 mg, 0.36 mmol) and ethyl 3-(4-chlorophenyl)-2,2-dimethylpropanimidate (obtained after bicarbonate wash of Example 22B) (85 mg, 0.36 mmol) was stirred at 120° C. for 16 hours. The reaction mixture was cooled, dissolved in dichlorormethane (2 mL) and purified by preparative HPLC on a on a Phenomenex® Luna® C8(2) 5 um 100 Å AXIA™ column (30 mm×75 mm) using a gradient of 20% to 95% acetonitrile in 10 mM of ammonium acetate over 10 minutes at a flow rate of 50 mL/minute to provide the titled compound. $^1$H NMR (300 MHz, DMSO-d$_6$) δ ppm 1.09-1.19 (m, 2H), 1.37 (s, 6H), 1.40-1.51 (m, 2H), 1.66-1.82 (m, 4H), 1.99-2.12 (m, 7H), 3.00 (s, 2H), 3.42-3.56 (m, 1H), 4.11 (s, 1H), 7.11 (d, J=8.3 Hz, 2H), 7.17-7.28 (m, 2H); MS (ESI$^+$) m/z 361 (M+H)$^+$.

Example 23

(1E)-3-(4-Chlorophenyl)-N'-cyano-N-[(E)-5-hydroxy-2-adamantyl]-2,2-dimethyl propanimidamide

Example 23A

Ethyl 3-(4-chlorophenyl)-N-cyano-2,2-dimethylpropanimidate

Example 22A and cyanamide (Aldrich) were processed using the method described for Example 3B to obtain the titled compound. MS (ESI$^+$) m/z 265 (M+H)$^+$.

Example 23B (1E)-3-(4-Chlorophenyl)-N'-cyano-N-[(E)-5-hydroxy-2-adamantyl]-2,2-dimethyl propanimidamide The titled compound was synthesized according to the procedure described in Example 3C substituting Example 3B with Example 23A. $^1$H NMR (300 MHz, DMSO-d$_6$) δ ppm 1.18-1.32 (m, 4H), 1.35 (s, 6H), 1.50-1.70 (m, 6H), 1.80-1.91 (m, 1H), 1.94-2.04 (m, 2H), 3.11 (s, 2H), 3.77-3.87 (m, 1H), 4.44 (s, 1H), 6.36 (s, 1H), 7.13 (d, J=8.3 Hz, 2H), 7.35 (d, J=8.3 Hz, 2H); MS (ESI$^+$) m/z 386 (M+H)$^+$. Anal. Calculated for $C_{21}H_{28}ClN_3O.0.2$ ethyl acetate: C-67.86; H-7.39; N-10.41. Found C-67.48; H-7.51; N-10.17.

Example 24

(E)-4-[((1E)-N-Cyano-2-methyl-2-{[4-(trifluoromethyl)benzyl]oxy}propanimidoyl)amino]adamantane-1-carboxylic acid A solution of Example 17 (0.35 g, 0.7 mmol) in methanol:tetrahydrofuran (1:1, 10 mL) was treated with 2 NNaOH (0.5 mL, 3.5 mmol) and stirred for 30 hours. The reaction mixture was concentrated in vacuo, diluted with water, acidified to pH ~5 and then extracted with ethyl acetate. The organic layer was washed with brine, dried (MgSO$_4$) and concentrated to give the titled compound. $^1$H NMR (300 MHz, DMSO-d$_6$) δ ppm 1.32-1.61 (m, 3H), 1.65 (s, 6H), 1.71-1.96 (m, 8H), 2.06 (s, 2H), 3.89-4.04 (m, 1H), 4.70 (s, 2H), 7.51 (d, J=7.1 Hz, 1H), 7.63 (d, J=8.3 Hz, 2H), 7.69-7.87 (m, 2H), 12.12 (s, 1H); MS (DCI+) m/z 464 (M+H)$^+$.

Example 25

(E)-4-[((1E)-N-Cyano-2-methyl-2-{[4-(trifluoromethyl)benzyl]oxy}propanimidoyl)amino]adamantane-1-carboxamide A solution of Example 24 (0.34 g, 0.72 mmol) in CH$_2$Cl$_2$ (20 mL) was treated with 1H-benzo[d][1,2,3]triazol-1-ol hydrate (0.12 g, 0.8 mmol) followed by N$^1$-((ethylimino)methylene)-N$^3$,N$^3$-dimethylpropane-1,3-diamine hydrochloride (0.17 g, 0.91 mmol) and the reaction mixture was stirred for 1 hour. Then 30% aqueous NH$_4$OH (0.5 mL, 3.6 mmol) was added, and the reaction mixture was stirred for 18 hours at room temperature. The reaction mixture was concentrated in vacuo and the residue was partitioned between ethyl acetate and water. Then the combined organic layers were washed with brine, dried (MgSO$_4$) and concentrated. Purification by flash chromatography using 0-18% ethanol in ethyl acetate as eluent provided the titled compound. $^1$H NMR (300 MHz, DMSO-d$_6$) δ ppm 1.39-1.58 (m, 4H), 1.61-1.90 (m, 14H), 2.04 (s, 2H), 3.94 (s, 1H), 4.71 (s, 1H), 6.73 (s, 1H), 6.99 (s, 1H), 7.50 (d, J=7.1 Hz, 1H), 7.59-7.69 (m, 2H), 7.70-7.81 (m, 2H); MS (DCI+) m/z 463 (M+H)$^+$. Anal. Calculated for $C_{25}H_{30}N_3F_3O_3.0.2H_2O$: C, 61.84; H, 6.36; N, 12.02. Found: C, 61.64; H, 6.34; N, 11.97.

Example 26

(E)-4-[(2-Methyl-2-{4-[5-(trifluoromethyl)pyridin-2-yl]piperazin-1-yl}propanethioyl)amino]adamantane-1-carboxylic acid A stirred solution of (E)-4-{2-methyl-2-[4-(5-trifluoromethyl-pyridin-2-yl)-piperazin-1-yl]-propionylamino}-adamantane-1-carboxylic acid (0.085 mmol, U.S. patent application No. 2005/0277647), Lawesson's reagent (0.085 mmol), and toluene was heated to 120° C. for 2 hours. The reaction mixture was cooled to 23° C. and concentrated in vacuo. The resultant residue was filtered through a short flash silica gel plug, first eluting with dichloromethane and then with ethyl acetate. Collected fractions that confirmed by LCMS for the desired product were concentrated in vacuo and further purified by reverse phase HPLC (YMC ODS Guardpak column, acetonitrile/10 mM ammonium acetate in water gradient) to provide the title compound. $^1$H NMR (400 MHz, DMSO-d$_6$) δ 8.41 (s, 1H), 7.80 (m, 1H), 7.72 (m, 1H), 6.97 (d, J=8 Hz, 1H), 3.81 (m, 1H), 3.66 (m, 4H), 2.54 (m, 4H), 2.07-1.69 (m, 11H), 1.65-1.50 (m, 2H), 1.13 (s, 6H); MS (APCI) m/z 511 (M+H)$^+$.

Example 27

(1E)-N-Cyano-N-[(E)-5-cyano-2-adamantyl]-2-methyl-2-{[4-(trifluoromethyl)benzyl]oxy}propanimidamide A solution of product from Example 25 (73 mg, 0.158 mmol) in dioxane/pyridine (1.5 mL/0.15 mL) was cooled to 0° C. and treated with trifluoroacetic anhydride (0.022 mL, 0.158 mmol). The reaction mixture was stirred at room temperature for 18 hours, concentrated in vacuo and then partitioned between ethyl acetate and brine. The organic layer was washed with water (2×30 mL), dried (MgSO$_4$) and concentrated. Purification by reverse phase HPLC method using a Phenomenex® Luna® C8(2) 5 um 100 Å AXIA™ column (30 mm×75 mm). column and a gradient of 10-100% acetonitrile and 10 mM ammonium acetate in water provided the titled compound. $^1$H NMR (300 MHz, CDCl$_3$) δ ppm 1.43-1.63 (m, 9H), 1.84-2.28 (m, 10H), 3.90-4.09 (m, 1H), 4.58 (s, 2H), 6.98 (d, J=7.8 Hz, 1H), 7.45 (d, J=8.1 Hz, 2H), 7.63 (d, J=8.1 Hz, 2H); MS (DCI+) m/z 445 (M+H)$^+$.

Example 28

Methyl(E)-4-({(1E)-N-cyano-2-[(4-methoxybenzyl)oxy]-2-methylpropanimidoyl}amino)adamantane-1-carboxylate Example 28A methyl(E)-4-({2-[(4-methoxybenzyl)oxy]-2-methylpropanoyl}amino)adamantane-1-carboxylate The titled compound was synthesized according to the methods described in: Patel et al., *Bioorg. Med. Chem. Lett.*, 2007, 17, 750-755.

Example 28B

Methyl(E)-4-({2-[(4-methoxybenzyl)oxy]-2-methylpropanethioyl}amino)adamantane-1-carboxylate To a solution of Example 28A (2.1 g, 5 mmol) in tetrahydrofuran (25 mL) was added Lawesson reagent (2.04 mg, 5 mmol) and the reaction mixture was heated at 50° C. for 4 hours. The reaction mixture was concentrated under reduced pressure and the residue was partitioned between saturated NaHCO$_3$ and ethyl acetate. The combined organic layers were dried (MgSO$_4$), filtered and concentrated. The residue was purified by flash chromatography (SiO$_2$, 0-40% ethyl acetate in hexanes) to provide the titled compound. MS (DCI+) m/z 432 (M+H)$^+$.

Example 28C

Methyl(E)-4-({(1E)-N-cyano-2-[(4-methoxybenzyl)oxy]-2-methylpropanimidoyl}amino)adamantane-1-carboxylate The titled compound was synthesized according to the procedure described in Example 1C substituting Example 1B with Example 28B. $^1$H NMR (300 MHz, DMSO-d$_6$) δ ppm 1.33-1.56 (m, 4H), 1.63 (s, 6H), 1.70-2.13 (m, 9H), 3.58 (s, 3H), 3.67-3.79 (m, 3H), 3.97 (d, J=4.4 Hz, 1H), 4.50 (s, 2H), 6.90-7.01 (m, 2H), 7.28-7.39 (m, 2H), 7.55 (d, J=7.5 Hz, 1H); MS (DCI+) m/z 440 (M+H)$^+$.

Example 29

Methyl(E)-4-[((1E)-N-cyano-2-methyl-2-{4-[5-(trifluoromethyl)pyridin-2-yl]piperazin-1-yl}propanimidoyl)amino]adamantane-1-carboxylate Example 21 (366 mg, 0.7 mmol) in dichloromethane (8 mL) was treated with a 1 molar solution of triethyloxonium tetrafluoroborate in dichloromethane (1 mL, 1 mmol). The reaction mixture was stirred at 45° C. for 18 hours. The reaction mixture was concentrated in vacuo, and the residue was dissolved in ethanol and then treated with cyanamide (120 mg, 2.8 mmol) and triethylamine (0.3 mL, 2.2 mmol). The reaction mixture was heated at 80° C. for 18 hours and then concentrated in vacuo. The residue was partitioned between ethyl acetate and water. The organic layer was dried (MgSO$_4$) and concentrated in vacuo. Purification by flash chromatography (SiO$_2$, 0-10% ethanol in ethyl acetate) provided the titled compound. $^1$H NMR (300 MHz, DMSO-d$_6$) δ ppm 1.28-1.43 (m, 6H), 1.51-2.20 (m, 13H), 2.54-2.64 (m, 4H), 3.60 (s, 3H), 3.66 (s, 4H), 4.14 (s, 1H), 6.99 (d, J=9.1 Hz, 1H), 7.81 (dd, J=8.9, 2.6 Hz, 1H), 8.42 (s, 1H), 8.67 (d, J=5.6 Hz, 1H); MS (DCI+) m/z 533 (M+H)$^+$.

Example 30

(E)-4-[((1E)-N-Cyano-2-methyl-2-{4-[5-(trifluoromethyl)pyridin-2-yl]piperazin-1-yl}propanimidoyl)amino]adamantane-1-carboxylic acid The titled compound was synthesized according to the procedure described in Example 14A substituting Example 11 with Example 29. $^1$H NMR (300 MHz, DMSO-d$_6$) δ ppm 1.12-1.33 (m, 6H), 1.53 (d, J=12.5 Hz, 2H), 1.64-2.10 (m, 12H), 2.50-2.63 (m, 4H), 3.64 (s, 4H), 3.81 (s, 1H), 6.98 (d, J=8.8 Hz, 1H), 7.26 (d, J=8.5 Hz, 1H), 7.80 (dd, J=9.2, 2.7 Hz, 1H), 8.41 (s, 1H); MS (DCI+) m/z 519 (M+H)$^+$.

Example 31

(E)-4-[((1E)-N-Cyano-2-methyl-2-{4-[5-(trifluoromethyl)pyridin-2-yl]piperazin-1-yl}propanimidoyl)amino]adamantane-1-carboxamide The titled compound was synthesized according to the procedure described in Example 14B substituting Example 14A with Example 30. $^1$H NMR (300 MHz, DMSO-d$_6$) δ ppm 1.35 (s, 6H), 1.50-2.18 (m, 13H), 2.52-2.66 (m, 4H), 3.67 (s, 4H), 4.11 (s, 1H), 6.74 (s, 1H), 6.99 (d, J=9.2 Hz, 2H), 7.81 (dd, J=9.2, 2.4 Hz, 1H), 8.42 (s, 1H), 8.66 (d, J=7.5 Hz, 1H); MS (DCI+) m/z 518 (M+H)$^+$. Anal. Calculated for C$_{26}$H$_{34}$F$_3$N$_7$O: C, 60.34; H, 6.65; N, 18.94. Found: C, 60.34; H, 6.65; N, 18.55.

Example 32

6-({4,4-Dimethyl-1-[(E)-5-(methylsulfonyl)-2-adamantyl]-5-thioxopyrrolidin-3-yl}methoxy)nicotinonitrile Example 32A 6-({4,4-Dimethyl-1-[(E)-5-(methylsulfonyl)-2-adamantyl]-5-oxopyrrolidin-3-yl}methoxy)nicotinonitrile The titled compound was synthesized according to the methods described in reference: Yeh et al., *Bioorg. Med. Chem. Lett.* 2006, 16, 5555-5560.

Example 32B 6-({4,4-Dimethyl-1-[(E)-5-(methylsulfonyl)-2-adamantyl]-5-thioxopyrrolidin-3-yl}methoxy)nicotinonitrile The titled compound was synthesized according to the procedure described in Example 28 substituting Example 28A with Example 32A. $^1$H NMR (300 MHz, DMSO-d$_6$) δ ppm 0.97-1.13 (m, 3H), 1.18-1.39 (m, 3H), 1.61 (t, J=14.7 Hz, 2H), 1.75-2.23 (m, 10H), 2.76-2.97 (m, 3H), 3.87 (dd, J=10.9, 8.5 Hz, 1H), 4.13 (dd, J=11.1, 7.9 Hz, 1H), 4.28-4.64 (m, 3H), 6.85 (d, J=8.7 Hz, 1H), 8.24 (dd, J=8.7, 2.8 Hz, 1H), 8.72 (d, J=2.4 Hz, 1H), 9.51 (s, 1H), 9.84 (s, 1H); MS (DCI+) m/z 474 (M+H)$^+$.

Example 33

(2Z)-4-{[(5-Cyanopyridin-2-yl)oxy]methyl}-3,3-dimethyl-1-[(E)-5-(methylsulfonyl)-2-adamantyl]pyrrolidin-2-ylidenecyanamide The titled compound was synthesized according to the procedure described in Example 29 substituting Example 21 with Example 32. $^1$H NMR (400 MHz, DMSO-d$_6$) δ ppm 1.23-1.36 (m, 3H), 1.52 (s, 3H), 1.56 (s, 1H), 1.68-2.25 (m, 12H), 2.43 (s, 2H), 2.57-2.74 (m, 1H), 3.64-4.06 (m, 4H), 4.35-4.64 (m, 2H), 7.04 (d, J=8.5 Hz, 1H), 8.18 (dd, J=8.7, 2.3 Hz, 1H), 8.72 (d, J=2.1 Hz, 1H); MS (DCI+) m/z 482 (M+H)$^+$.

Example 34

(3S)-1-[(3-Chloro-2-methylphenyl)sulfonyl]-N-cyclohexylpiperidine-3-carbothioamide The titled compound was synthesized according to the procedures described in Example 1B substituting Example 1A with (S)-1-(3-chloro-2-methylphenylsulfonyl)-N-cyclohexylpiperidine-3-carboxamide. $^1$H NMR (300 MHz, DMSO-d$_6$) δ ppm 1.05-1.36 (m, 5H), 1.45-1.95 (m, 9H), 2.57-2.68 (m, 1H), 2.59 (s, 3H), 2.78 (t, 1H), 2.99 (t, J=11.5 Hz, 1H), 3.48-3.70 (m, 2H), 4.01-4.33 (m, 1H), 7.46 (t, J=7.9 Hz, 1H), 7.80 (t, J=8.3 Hz, 2H), 9.88 (d, J=7.5 Hz, 1H); MS (ESI$^+$) m/z 415 (M+H)$^+$.

Example 35

(3S)-1-[(3-Chloro-2-methylphenyl)sulfonyl]-N'-cyano-N-cyclohexylpiperidine-3-carboximidamide To a solution of Example 34 (200 mg, 0.48 mmol) in dichloromethane (15 mL) was added triethyloxonium tetrafluoroborate (0.96 mL, 0.96 mmol, 1 M in dichloromethane) and the mixture was stirred at room temperature for overnight. The reaction mixture was then heated to 50° C. for 3 more days with continued stirring. The reaction mixture was cooled, concentrated and triturated in ether. The obtained product was dissolved in ethanol (2 mL) and cyanamide (61 mg, 1.4 mmol) and triethylamine (0.2 mL, 1.4 mmol) were added. After stirring, at 80° C. for 16 hours, the reaction mixture was cooled, diluted with water (10 mL) and extracted with ethyl acetate (3×10 mL). The combined organic extracts were dried over anhydrous Na$_2$SO$_4$, filtered and concentrated under reduced pressure. The residue was purified by column chromatography using an Analogix® Intelliflash 280™ (SiO$_2$, 0-100% of ethyl acetate in hexanes). $^1$H NMR (300 MHz, DMSO-d$_6$) δ ppm 1.04-1.34 (m, 5H), 1.44-1.91 (m, 9H), 2.60 (s, 3H), 2.60-2.70 (m, 1H), 2.83-2.98 (m, 1H), 3.08 (t, J=11.4 Hz, 1H), 3.64 (t, 3H), 7.47 (t, J=8.3 Hz, 1H), 7.80 (dd, J=8.1, 1.0 Hz, 1H), 7.83-7.89 (m, 1H), 8.31 (d, J=7.5 Hz, 1H); MS (ESI$^+$) m/z 423 (M+H)$^+$. Anal. Calculated for C$_{20}$H$_{27}$ClN$_4$O$_2$S: C, 56.79; H, 6.43; N, 13.29. Found: C, 56.42; H, 6.41; N, 12.98.

Example 36

(E)-4-{[(1E)-2-(4-Chlorophenoxy)-N-cyano-2-methylpropanimidoyl]amino}adamantane-1-carboxylic acid An alternative preparation of Example 14A is herein described. To a solution of Example 14B (50 mg, 0.12 mmol) in 1,4-dioxane (0.5 mL) was added 5 M hydrogen chloride in water (0.5 mL, 2.5 mmol). After stirring at 60° C. for 6 hours, the reaction mixture was cooled, diluted with water (5 mL) and extracted with ethyl acetate (2×10 mL). The combined organic extracts were dried over anhydrous Na$_2$SO$_4$, filtered and concentrated under reduced pressure. The residue was purified by preparative HPLC on a Phenomenex® Luna® C8(2) 5 um 100 Å AXIA™ column (30 mm×75 mm) with a gradient of 10-95% (acetonitrile/0.1% trifluoroacetic acid in water) at a flow rate of 50 mL/min for 10 minutes to obtain the title compound. $^1$H NMR (500 MHz, DMSO-d$_6$) δ ppm 1.46-1.57 (m, 2H), 1.65 (s, 6H), 1.69-1.77 (m, 2H), 1.77-1.82 (m, 2H), 1.84-1.93 (m, 5H), 2.11-2.22 (m, 2H), 3.95-4.08 (m, 1H), 7.01 (d, J=8.8 Hz, 2H), 7.38 (d, J=8.8 Hz, 2H), 7.64 (d, J=6.1 Hz, 1H), 12.13 (s, 1H); MS (ESI$^+$) m/z 416 (M+H)$^+$.

Example 37

(1E)-2-(4-Chlorophenoxy)-N'-cyano-N-[(E)-5-cyano-2-adamantyl]-2-methylpropanimidamide The titled compound was synthesized according to the procedure described in Example 3C substituting E-2-amino-5-hydroxyadamantane and Example 3B with E-4-Amino-adamantane-1-carbonitrile (International Publication No. WO 2007/118185, filed Oct. 18, 2007) and Example 8B, respectively. $^1$H NMR (300 MHz, DMSO-d$_6$) δ ppm 1.50-1.61 (m, 2H), 1.65 (s, 6H), 1.68-1.79 (m, 2H), 1.85-1.92 (m, 1H), 1.96-2.00 (m, 2H), 2.07-2.13 (m, 4H), 2.15-2.22 (m, 2H), 4.04 (d, 1H), 6.99 (dt, 2H), 7.34-7.43 (m, 2H), 7.63 (d, J=6.1 Hz, 1H); MS (ESI$^+$) m/z 397 (M+H)$^+$. Anal. Calculated for C$_{22}$H$_{26}$ClN$_4$O: C, 66.57; H, 6.35; N, 14.12. Found: C, 66.39; H, 6.26; N, 14.22.

Example 38

(1E)-2-(4-Chlorophenoxy)-N'-cyano-N-hexahydro-2,5-methanopentalen-3a(1H)-yl-2-methylpropanimidamide A mixture of 3-noradamantanamine hydrochloride (100 mg, 0.58 mmol), triethylamine (0.24 mL, 1.73 mmol) and Example 8B (184 mg, 0.69 mmol) in ethanol (2 mL) was stirred at 80° C. for 16 hours. The reaction mixture was then cooled, concentrated, and diluted with saturated aqueous NaHCO$_3$ solution (10 mL). The aqueous mixture was extracted with ethyl acetate (3×20 mL). The combined organic extracts were dried over anhydrous Na$_2$SO$_4$, filtered and concentrated under reduced pressure. The residue was purified by preparative HPLC on a Phenomenex® Luna® C8(2) 5 um 100 Å AXIA™ column (30 mm×75 mm) with a gradient of 50-95% (acetonitrile/10 mM ammonium acetate in water) at a flow rate of 50 mL/min for 10 minutes to obtain the title compound. $^1$H NMR (300 MHz, DMSO-d$_6$) δ ppm 1.48-1.58 (m, 4H), 1.64 (s, 6H), 1.85-2.16 (m, 6H), 2.19-2.30 (m, 2H), 2.58 (t, J=6.8 Hz, 1H), 6.96 (dt, 2H), 7.37 (dt, 2H), 8.06 (s, 1H); MS (ESI$^+$) m/z 358 (M+H)$^+$.

Example 39

(1E)-N-[(4s)-1-Azatricyclo[3.3.1.1$^{3,7}$]dec-4-yl]-2-(4-chlorophenoxy)-N'-cyano-2-methylpropanimidamide A mixture of 1-azatricyclo[3.3.1.1$^{3,7}$]decan-4s-amine dihydrochloride (Synthesis, 11, 1080-2, 1992) (80 mg, 0.36 mmol), triethylamine (0.15 mL, 1.1 mmol) and Example 8B (142 mg, 0.53 mmol) in ethanol (2 mL) was stirred at 80° C. for 16 hours. The reaction mixture was then cooled, concentrated, and diluted with saturated aqueous NaHCO$_3$ solution (10 mL). The aqueous mixture was extracted with ethyl acetate (3×20 mL). The combined organic extracts were dried over anhydrous Na$_2$SO$_4$, filtered and concentrated under reduced pressure. The residue was purified by preparative HPLC on a Phenomenex® Luna® C8(2) 5 um 100 Å AXIA™ column (30 mm×75 mm) with a gradient of 10-95% (acetonitrile/0.1% trifluoroacetic acid in water) at a flow rate of 50 mL/min for 10 minutes to obtain the title compound. $^1$H NMR (300 MHz, DMSO-d$_6$) δ ppm 1.20-1.31 (m, 3H), 1.69 (s, 6H), 1.73-2.01 (m, 4H), 3.18-3.63 (m, 6H), 4.19-4.31 (m, 1H), 6.96-7.03 (m, 2H), 7.32-7.43 (m, 2H), 7.87 (d, J=5.4 Hz, 1H); MS (ESI$^+$) m/z 373 (M+H)$^+$.

Example 40

N-1-Azabicyclo[2.2.2]oct-3-yl-2-(4-chlorophenoxy)-N'-cyano-2-methylpropanimidamide The titled compound was synthesized according to the procedure described in Example 39 substituting 1-azatricyclo[3.3.1.1$^{3,7}$]decan-4s-amine dihydrochloride with quinuclidin-3-amine dihydrochloride (Aldrich). $^1$H NMR (300 MHz, DMSO-d$_6$) δ ppm 1.18-1.31 (m, 1H), 1.59-1.73 (m, 6H), 1.72-1.99 (m, 3H), 2.23-2.37 (m, 1H), 3.09-3.79 (m, 6H), 4.28-4.53 (m, 1H), 6.96-7.06 (m, 2H), 7.34-7.45 (m, 2H), 8.66-8.84 (m, 1H); MS (ESI$^+$) m/z 347 (M+H)$^+$.

Example 41

2-(4-Chlorophenoxy)-N'-cyano-N-cyclooctyl-2-methylpropanimidamide

The titled compound was synthesized according to the procedure described in Example 3C substituting E-2-amino-5-hydroxyadamantane and Example 3B with cyclooctanamine (Aldrich) and Example 8B, respectively. $^1$H NMR (300 MHz, DMSO-d$_6$) δ ppm 1.37-1.57 (m, 7H), 1.59 (s, 6H), 1.61-1.79 (m, 7H), 4.02-4.18 (m, 1H), 6.94 (d, J=9.2 Hz, 2H), 7.37 (d, J=9.2 Hz, 2H), 8.43 (d, J=8.1 Hz, 1H); MS (ESI$^+$) m/z 348 (M+H)$^+$. Anal. Calculated for C$_{19}$H$_{26}$ClN$_3$O: C, 65.60; H, 7.53; N, 12.08. Found: C, 65.70; H, 7.35; N, 11.97.

Example 42

N-[exo-Bicyclo[2.2.1]hept-2-yl]-2-(4-chlorophenoxy)-N'-cyano-2-methylpropanimidamide The titled compound was synthesized according to the procedure described in Example 3C substituting E-2-amino-5-hydroxyadamantane and Example 3B with exo-2-aminonorbornane (Aldrich) and Example 8B, respectively. $^1$H NMR (300 MHz, DMSO-d$_6$) δ ppm 1.03-1.23 (m, 3H), 1.35-1.50 (m, 3H), 1.56-1.62 (m, 6H), 1.61-1.66 (m, 2H), 2.18-2.23 (m, 1H), 2.24-2.33 (m, 1H), 3.68-3.83 (m, 1H), 6.88-7.00 (m, 2H), 7.32-7.44 (m, J=9.2 Hz, 2H), 8.13 (d, J=5.8 Hz, 1H); MS (ESI$^+$) m/z 332 (M+H)$^+$. Anal. Calculated for C$_{18}$H$_{22}$ClN$_3$O: C, 65.15; H, 6.68; N, 12.66. Found: C, 65.18; H, 6.91; N, 12.43.

Example 43

(1E)-N-1-Adamantyl-2-(4-chlorophenoxy)-N-cyano-2-methylpropanimidamide

The titled compound was synthesized according to the procedure described in Example 3C substituting E-2-amino-5-hydroxyadamantane and Example 3B with 1-admantanamine (Aldrich) and Example 8B, respectively. $^1$H NMR (300 MHz, DMSO-d$_6$) δ ppm 1.60-1.68 (m, 6H), 1.63 (s, 6H), 2.01-2.13 (m, 9H), 6.94-7.04 (m, 2H), 7.14 (s, 1H), 7.33-7.44 (m, 2H); MS (ESI$^+$) m/z 372 (M+H)$^+$. Anal. Calculated for C$_{21}$H$_{26}$ClN$_3$O: C, 67.82; H, 7.05; N, 11.30. Found: C, 67.83; H, 6.87; N, 11.09.

Example 44

(1E)-N-cyano-2-(2-fluorophenoxy)-2-methyl-N-[(E)-5-(methylsulfonyl)adamantan-2-yl]propanimidamide

Example 44A 2-(2-fluorophenoxy)-2-methyl-N-[(E)-5-(methylsulfonyl)adamantan-2-yl]propanamide The titled compound was synthesized according to the methods described in reference: Sorensen, B., et al., Bioorg. Med. Chem. Lett. 2007, 17, 527-532. MS (DCI+) m/z 410 (M+H)$^+$.

Example 44B 2-(2-fluorophenoxy)-2-methyl-N-[(E)-5-(methylsulfonyl)adamantan-2-yl]propanethioamide The titled compound was synthesized according to the methods described in Example 1B substituting Example 1A with Example 44A. $^1$H NMR (300 MHz, DMSO-d$_6$) δ ppm 1.43-1.79 (m, 10H), 1.83-2.20 (m, 7H), 2.39 (s, 2H), 2.87 (s, 3H), 4.32-4.49 (m, 1H), 7.02-7.24 (m, 3H), 7.22-7.45 (m, 1H), 9.42 (d, J=7.1 Hz, 1H); MS (DCI+) m/z 426 (M+H)$^+$.

Example 44C (1E)-N'-cyano-2-(2-fluorophenoxy)-2-methyl-N-[(E)-5-(methylsulfonyl)adamantan-2-yl]propanimidamide A solution of Example 44B (60 mg, 0.14 mmol) in dichloromethane (3 mL) at room temperature was treated dropwise with commercially available triethyloxonium tetrafluoroborate (1 M solution in tetrahydrofuran, 0.21 mL, 0.21 mmol). The reaction mixture was stirred at 45° C. for 16 hours and then concentrated in vacuo. Ethanol (3 mL) was added to the thioimidate salt, and the mixture was treated with cyanamide (24 mg, 0.57 mmol) and triethylamine (43 mg, 0.42 mmol). The reaction mixture was heated at 80° C. overnight. Purification by reverse phase HPLC method using a Phenomenex® Luna® C8, 5 μM 100 Å AXIA™ column (30 mm×75 mm) and a gradient of 10-100% acetonitrile and 10 mM ammonium acetate in water provided the titled compound. $^1$H NMR (500 MHz, CDCl$_3$) δ ppm 1.57-1.81 (m, 6H), 1.87 (d, J=13.4

Hz, 2H), 2.00-2.32 (m, 9H), 2.40 (s, 2H), 2.68-2.86 (m, 3H), 4.19 (s, 1H), 7.01-7.23 (m, 4H), 7.92 (d, J=6.7 Hz, 1H); MS (DCI+) m/z 434 (M+H)+.

Example 45

(1E)-N'-cyano-2-(2,4-difluorophenoxy)-2-methyl-N-[(E)-5-(methylsulfonyl)adamantan-2-yl]propanimidamide Example 45A 2-(2,4-difluorophenoxy)-2-methyl-N-[(E)-5-(methylsulfonyl)adamantan-2-yl]propanamide The titled compound was synthesized according to the methods described in reference: Sorensen, B., et al., Bioorg. Med. Chem. Lett. 2007, 17, 527-532.

Example 45B 2-(2,4-difluorophenoxy)-2-methyl-N-[(E)-5-(methylsulfonyl)adamantan-2-yl]propanethioamide The titled compound was synthesized according to the methods described in Example 1B substituting Example 1A with Example 45A. $^1$H NMR (300 MHz, DMSO-$d_6$) δ ppm 1.48-1.85 (m, 9H), 1.87-2.20 (m, 8H), 2.40 (s, 2H), 2.87 (s, 3H), 4.32-4.46 (m, 1H), 6.94-7.13 (m, 1H), 7.14-7.32 (m, 1H), 7.32-7.51 (m, 1H), 9.40 (d, J=7.1 Hz, 1H); MS (DCI+) m/z 444 (M+H)+. Anal. Calculated for $C_{21}H_{27}NF_2O_3S_2$: C, 56.86; H, 6.14; N, 3.16. Found: C, 57.61; H, 5.82; N, 3.11.

Example 45C (1E)-N'-cyano-2-(2,4-difluorophenoxy)-2-methyl-N-[(E)-5-(methylsulfonyl)adamantan-2-yl]propanimidamide The titled compound was synthesized according to the methods described in Example 1C substituting Example 1B with Example 45B. $^1$H NMR (500 MHz, CDCl$_3$) δ ppm 1.39-1.77 (m, 9H), 1.86 (t, J=14.0 Hz, 2H), 2.03-2.33 (m, 8H), 2.69-2.86 (m, 3H), 3.95-4.15 (m, 1H), 6.69-6.99 (m, 2H), 7.01-7.16 (m, 1H), 7.42 (d, J=7.6 Hz, 1H); MS (DCI+) m/z 452 (M+H)+.

Example 46

4-{[2-(4-chlorophenoxy)-N-cyano-2-methylpropanimidoyl]amino}bicyclo[2.2.2]octane-1-carboxylic acid Example 46A methyl 4-{[2-(4-chlorophenoxy)-N-cyano-2-methylpropanimidoyl]amino}bicyclo[2.2.2]octane-1-carboxylate Example 8B and methyl 4-aminobicyclo[2.2.2]octane-1-carboxylate (obtained by aqueous bicarbonate wash of 4-methoxycarbonyl-bicyclo[2.2.2]oct-1-yl ammonium chloride salt, Prime Organics) were processed using the method described for Example 2 to obtain the titled compound. LCMS (ESI+) m/z 404 (M+H)+.

Example 46B

4-{[2-(4-chlorophenoxy)-N-cyano-2-methylpropanimidoyl]amino}bicyclo[2.2.2]octane-1-carboxylic acid The titled compound was synthesized according to the procedures described in Example 14A substituting Example 11 with Example 46A. $^1$H NMR (300 MHz, DMSO-$d_6$) δ ppm 1.62 (s, 6H), 1.72-1.88 (m, 6H), 1.90-2.06 (m, 6H), 6.92-7.01 (m, 2H), 7.25 (s, 1H), 7.34-7.42 (m, 2H), 12.09 (s, 1H); MS (ESI+) m/z 391 (M+H)+.

Alternative Preparation of Example 46

The titled compound was also prepared using the procedure described in Example 87 substituting Example 8B for ethyl N-cyano-2-methyl-2-phenoxypropanimidoate (CI-1). Purification was achieved by preparative reverse phase HPLC [Waters 2767; Benetnach 10-C18 20×250 mm, 10 µm; 45-85% acetonitrile/water (0.05% trifluoroacetic acid), 30 mL/minute; detection at 214 and 254 nm]

Example 47

4-{[2-(4-chlorophenoxy)-N-cyano-2-methylpropanimidoyl]amino}bicyclo[2.2.2]octane-1-carboxamide The titled compound was synthesized according to the procedures described in Example 14B substituting Example 14A with Example 46B. $^1$H NMR (300 MHz, DMSO-$d_6$) δ ppm 1.62 (s, 6H), 1.69-1.83 (m, 6H), 1.89-2.05 (m, 6H), 6.73 (s, 1H), 6.92-7.01 (m, 2H), 6.95 (s, 1H), 7.24 (s, 1H), 7.33-7.44 (m, 2H); MS (ESI+) m/z 390 (M+H)+.

First Alternative Preparation of Example 47

Example 47 was also prepared using the procedure described in Example 85 substituting 4-aminobicyclo[2.2.2]octane-1-carboxamide (BA-6) for 4-(difluoromethyl)bicyclo[2.2.2]octan-1-amine (BA-4).

Second Alternative Preparation of Example 47

Example 8B (524 mg, 2 mmol) and 4-aminobicyclo[2.2.2]octane-1-carbonitrile (BA-1) (300 mg, 2 mmol) were mixed and the neat mixture was heated to 130° C. under nitrogen and stirred for 3 hours. After cooling, the mixture was dissolved in a small amount of ethanol and purified by preparative reverse phase HPLC [Waters 2767; Benetnach 10-C18 20×250 mm, 10 µm; 40-60% acetonitrile/water (0.05% trifluoroacetic acid), 30 mL/minute; detection at 214 and 254 nm] to give the titled compound. $^1$H NMR (400 MHz, CDCl$_3$) δ ppm 11.23 (br, 1H), 9.72 (s, 1H), 7.22 (d, J=8.5 Hz, 2H), 6.88 (d, J=8.6 Hz, 2H), 4.03 (s, 2H), 2.00-2.10 (m, 12H), 1.50 (s, 6H); LCMS (ESI+) m/z 389.7 (M+H)+.

Example 48 methyl(E)-4-({(1E)-2-[(1R*,5S*,6R*)-6-(4-chlorophenyl)-3-azabicyclo[3.2.0]hept-3-yl]-N-cyano-2-methylpropanimidoyl}amino)adamantane-1-carboxylate Example 48A methyl 2-[(1R*,5S*,6R*)-6-(4-chlorophenyl)-3-azabicyclo[3.2.0]hept-3-yl]-2-methylpropanoate To a solution of (1R*,5S*,6R*)-6-(4-chlorophenyl)-3-azabicyclo[3.2.0]heptane (Steiner, G., et al., Heterocycles, 1995, 40, 319-330) (1.0 g, 1.3 mmol) in N,N-dimethylformamide (40 mL) were added potassium carbonate (1.0 g, 7.5 mmol) and methyl 2-bromo-2-methylpropanoate (0.4 mL, 3.0 mmol, Aldrich). After stirring at 80° C. for 16 hours, the reaction mixture was cooled and quenched with water (30 mL). The aqueous layer was extracted with ethyl acetate (3×50 mL). The combined organic extracts were dried over anhydrous $Na_2SO_4$, filtered and concentrated under reduced pressure. The residue was then purified by column chromatography using an Analogix® Intelliflash280™ ($SiO_2$, 0-50% of ethyl acetate in hexanes) to obtain the titled compound. MS ($ESI^+$) m/z 308 $(M+H)^+$.

Example 48B methyl(E)-4-({2-[(1R*,5S*,6R*)-6-(4-chlorophenyl)-3-azabicyclo[3.2.0]hept-3-yl]-2-methylpropanoyl}amino)adamantane-1-carboxylate To a solution of Example 48A (0.44 g, 1.4 mmol) in methanol (4 mL) and water (4 mL) was added 5 N aqueous NaOH solution (1.4 mL, 7.1 mmol). After stirring at 60° C. for 16 hours, the reaction mixture was cooled, neutralized to pH~7 with 3 N HCl, and concentrated to obtain crude 2-[(1S,5R,6S)-6-(4-chlorophenyl)-3-azabicyclo[3.2.0]hept-3-yl]-2-methylpropanoic acid.
To a solution of the above acid (1.0 g, 3.4 mmol) in N,N-dimethylformamide (25 mL) and tetrahydrofuran (25 mL) were added 1-hydroxybenzotriaole hydrate (0.6 g, 3.9 mmol, Aldrich), N-(3-dimethylaminopropyl)-N-ethylcarbodimide hydrochloride (0.8 g, 4.1 mmol, Aldrich), methyl(E)-4-aminoadamantane-1-carboxylate hydrochloride salt (Becker, C. L., et al., Org. Process R & D, 2008, 12, 1114-1118) (0.8 g, 3.4 mmol) and triethylamine (0.7 mL, 5.1 mmol). The reaction mixture was stirred at room temperature for 16 hours and then quenched with water (30 mL). The aqueous layer was extracted with methylene chloride (3×50 mL). The combined organic extracts were dried over anhydrous $Na_2SO_4$, filtered and concentrated under reduced pressure. The residue was then purified by column chromatography using an Analogix® Intelliflash280™ ($SiO_2$, 0-50% of ethyl acetate in hexanes) to obtain the titled compound. MS ($ESI^+$) m/z 485 $(M+H)^+$.

Example 48C methyl(E)-4-({2-[(1R*,5S*,6R*)-6-(4-chlorophenyl)-3-azabicyclo[3.2.0]hept-3-yl]-2-methylpropanethioyl}amino)adamantane-1-carboxylate The titled compound was synthesized according to the procedure described in Example 1B substituting Example 1A with Example 48B. MS ($ESI^+$) m/z 501 $(M+H)^+$.

Example 48D methyl(E)-4-({(1E)-2-[(1R*,5S*,6R*)-6-(4-chlorophenyl)-3-azabicyclo[3.2.0]hept-3-yl]-N-cyano-2-methylpropanimidoyl}amino)adamantane-1-carboxylate To a solution of Example 48C (240 mg, 0.48 mmol) in methylene chloride (15 mL) was added triethyloxonium tetrafluoroborate (1.5 mL, 1.5 mmol, 1 M in methylene chloride, Aldrich), and the mixture was stirred at 50° C. for 3 days. The reaction mixture was then concentrated under reduced pressure and triturated in ether. The obtained precipitate was dissolved in ethanol (2 mL) and cyanamide (60 mg, 1.5 mmol) and triethylamine (0.2 ml, 1.5 mmol) were added. After stirring at 80° C. for 16 hours, the reaction mixture was cooled, concentrated under reduced pressure and diluted with water (10 mL). The aqueous layer was extracted with ethyl acetate (3×10 mL). The combined organic extracts were dried over anhydrous $Na_2SO_4$, filtered and concentrated under reduced pressure. The residue was then purified by column chromatography using an Analogix® Intelliflash280™ ($SiO_2$, 0-100% ethyl acetate in hexanes) to obtain the titled compound. $^1$H NMR (300 MHz, DMSO-$d_6$) δ ppm 1.40 (s, 3H), 1.41 (s, 3H), 1.57-1.69 (m, 2H), 1.77-1.99 (m, 10H), 2.07-2.31 (m, 4H), 2.40-2.49 (m, 2H), 2.68-2.94 (m, 4H), 3.60 (s, 3H), 4.11-4.20 (m, 1H), 7.24-7.30 (m, 2H), 7.33-7.40 (m, 2H), 8.84 (d, J=8.1 Hz, 1H); MS ($ESI^+$) m/z 510 $(M+H)^+$.

Example 49

(1E)-N'-cyano-N-[(E)-5-hydroxyadamantan-2-yl]-2-methyl-2-phenoxypropanimidamide

To a solution of Example 8 (50 mg, 0.13 mmol) in methanol (2 mL) were added ammonium formate (81 mg, 1.3 mmol) and 10% Pd/C (2 mg) under an inert atmosphere. The reaction mixtures was stirred at room temperature for 2 hours, filtered and concentrated under reduced pressure. The residue was purified by preparative HPLC on a Phenomenex® Luna® C8(2) 5 µm 100 Å AXIA™ column (30 mm×75 mm) using a gradient of 20% to 95% acetonitrile in 10 mM of ammonium acetate over 10 minutes at a flow rate of 50 mL/minute to provide the titled compound. $^1$H NMR (300 MHz, DMSO-$d_6$) δ ppm 1.34-1.47 (m, 2H), 1.55-1.78 (m, 9H), 1.64 (s, 6H), 1.94-2.02 (m, 1H), 2.13-2.25 (m, 2H), 3.89-4.05 (m, 1H), 6.98 (d, J=8.7 Hz, 2H), 7.12 (t, J=7.3 Hz, 1H), 7.27-7.41 (m, 2H), 7.59 (d, J=6.7 Hz, 1H); MS ($ESI^+$) m/z 354 $(M+H)^+$.

Example 50

(E)-4-{[(1E)-N-cyano-2-methyl-2-phenoxypropanimidoyl]amino}adamantane-1-carboxamide The titled compound was synthesized according to the procedure described in Example 49 substituting Example 8 with Example 14B. $^1$H NMR (300 MHz, DMSO-$d_6$) δ ppm 1.45-1.56 (m, 2H), 1.65 (s, 6H), 1.67-1.78 (m, 4H), 1.79-1.94 (m, 5H), 2.10-2.19 (m, 2H), 3.97-4.09 (m, 1H), 6.73 (s, 1H), 6.95-7.04 (m, 3H), 7.08-7.17 (m, 1H), 7.29-7.40 (m, 2H), 7.65 (d, J=6.8 Hz, 1H); MS (ESL') m/z 381 $(M+H)^1$.

Example 51

(1E)-N'-cyano-2-(2,4-difluorophenoxy)-N-[(E)-5-hydroxyadamantan-2-yl]-2-methylpropanimidamide Example 51A 2-(2,4-difluorophenoxy)-2-methylpropanamide To a solution of 2-(2,4-difluorophenoxy)-2-methylpropanoic acid (10.0 g, 46.3 mmol, Chembridge) in methylene chloride (200 mL) were added 1-hydroxybenzotriaole hydrate (8.5 g, 55.5 mmol, Aldrich), N-(3-dimethylaminopropyl)-N-ethylcarbodimide hydrochloride (10.6 g, 55.5 mmol, Aldrich) and ammonium hydroxide (54.0 g, 463 mmol). The reaction mixture was stirred at room temperature for 16 hours and then quenched with water (100 mL). The aqueous layer was extracted with methylene chloride (3×100 mL). The combined organic extracts were washed with brine, 5% citric acid, and brine (100 mL each), dried over anhydrous $Na_2SO_4$, filtered and concentrated under reduced pressure to obtain the titled compound. MS (ESI$^+$) m/z 233 (M+NH$_4$)$^+$.

Example 51B 2-(2,4-difluorophenoxy)-2-methylpropanenitrile

To a solution of Example 51A (0.9 g, 4.0 mmol) in methylene chloride (10 mL) and triethylamine (2.2 mL, 15.8 mmol) was added 2,2,2-trifluoroacetic anhydride (1.6 mL, 11.9 mmol) at 0° C. The reaction mixture was allowed to warm to room temperature and stirred for three hours before methanol was added to quench the reaction. The reaction mixture was washed with saturated aqueous $NaHCO_3$ solution, dried over anhydrous $Na_2SO_4$, filtered and concentrated under reduced pressure. The residue was purified by column chromatography using an Analogix® Intelliflash280™ (SiO$_2$, 0-100% methanol/ethyl acetate(1/10) in hexanes) to obtain the titled compound. $^1$H NMR (300 MHz, DMSO-d$_6$) δ ppm 1.71 (s, 6H), 7.08-7.18 (m, 1H), 7.36-7.49 (m, 2H).

Example 51C ethyl 2-(2,4-difluorophenoxy)-2-methylpropanimidate hydrochloride

Through a cooled solution of Example 51B (6.5 g, 33 mmol) and ethanol (9.6 mL, 165 mmol) in methylene chloride (10 ml) was bubbled HCl gas at 0° C. for 30 minutes. The reaction was kept in a refrigerator at 4° C. for 60 hours. The reaction mixture was then concentrated and triturated with diethyl ether to obtain a precipitate of the titled compound. MS (ESI$^+$) m/z 244 (M+H)$^+$.

Example 51D ethyl N-cyano-2-(2,4-difluorophenoxy)-2-methylpropanimidate

Example 51C and cyanamide (Aldrich) were processed using the method described for Example 3B to obtain the titled compound. MS (ESI$^+$) m/z 286 (M+NH$_4$)$^+$.

Example 51E (1E)-N'-cyano-2-(2,4-difluorophenoxy)-N-[(E)-5-hydroxyadamantan-2-yl]-2-methylpropanimidamide The titled compound was synthesized according to the procedure described in Example 3C substituting Example 3B with Example 51D. $^1$H NMR (300 MHz, DMSO-d$_6$) δ ppm 0.39-1.50 (m, 2H), 1.62 (s, 6H), 1.62-1.80 (m, 8H), 1.99-2.10 (m, 1H), 2.14-2.25 (m, 2H), 3.93-4.04 (m, 1H), 4.50 (s, 1H), 7.01-7.18 (m, 1H), 7.25-7.49 (m, 2H), 7.82 (d, J=6.4 Hz, 1H); MS (ESI$^+$) m/z 390 (M+H)$^+$.

Example 52

(1E)-N'-cyano-N-[(E)-5-cyanoadamantan-2-yl]-2-(2,4-difluorophenoxy)-2-methylpropanimidamide The titled compound was synthesized according to the procedure described in Example 3C substituting E-2-amino-5-hydroxyadamantane and Example 3B with E-4-aminoadamantane-1-carbonitrile (International Publication No. WO 2007/118185, filed Oct. 18, 2007) and Example 51D, respectively. $^1$H NMR (300 MHz, DMSO-d$_6$) δ ppm 1.52-1.69 (m, 2H), 1.63 (s, 6H), 1.72-1.83 (m, 2H), 1.87-2.25 (m, 8H), 2.42-2.61 (m, 1H), 3.99-4.15 (m, 1H), 7.02-7.15 (m, 1H), 7.23-7.35 (m, 1H), 7.35-7.46 (m, 1H), 7.88 (d, J=6.7 Hz, 1H); MS (ESI$^+$) m/z 390 (M+H)$^+$.

Example 53

(1E)-2-(4-chloro-2-fluorophenoxy)-N'-cyano-N-[(E)-5-cyanoadamantan-2-yl]-2-methylpropanimidamide Example 53A ethyl 2-(4-chloro-2-fluorophenoxy)-2-methylpropanoate A mixture of 4-chloro-2-fluorophenol (11.280 g, 77 mmol), ethyl 2-bromoisobutyrate (12.61 mL, 85 mmol) and cesium carbonate (37.6 g, 115 mmol) in N,N-dimethylformamide (100 mL) was stirred at 55° C. for 18 hours. The reaction mixture was poured into brine, and extracted with ethyl acetate (2×250 mL). The combined organic phases were washed with brine, dried (MgSO$_4$) and concentrated. The crude product was used in the next step without additional purification. MS (DCI+) m/z 278 (M+NH$_4$)$^+$.

Example 53B 2-(4-chloro-2-fluorophenoxy)-2-methylpropanoic acid

Example 53A (18 g, 70 mmol) in a mixture of tetrahydrofuran (100 mL) and water (50 mL) was treated with LiOH (4.96 g, 207 mmol). The reaction mixture was stirred at 55° C. overnight and then concentrated under reduced pressure to remove tetrahydrofuran. The basic aqueous layer was extracted with ethyl acetate (2×100 mL) to extract out the unreacted starting phenol. The aqueous layer was acidified to pH~3, extracted with ethyl acetate (2×200 mL). The combined organic layers were washed with brine, dried (MgSO$_4$) and concentrated. The crude product was used in the next step without additional purification. MS (DCI+) m/z 233 (M+H)$^+$.

Example 53C 2-(4-chloro-2-fluorophenoxy)-2-methylpropanamide

To a solution of Example 53B (14.6 g, 62.8 mmol) in dichloromethane (200 mL) was added $N^1$-((ethylimino)methylene)-$N^3$,$N^3$-dimethylpropane-1,3-diamine hydrochloride (8.50 g, 55.5 mmol), and the reaction mixture was stirred for 1 hour. Ammonium hydroxide (87 mL, 628 mmol) was added. The reaction mixture was stirred at room temperature for 16 hours and then quenched with water (100 mL). The aqueous layer was extracted with dichloromethane (3×100 mL). The combined organic layers were washed with saturated NaHCO$_3$, brine (100 mL), dried (MgSO$_4$), filtered and concentrated. The residue was triturated with hexane/ethyl acetate (95/5) to provide the titled compound. MS (DCI+) m/z 232 (M+H)$^+$.

Example 53D 2-(4-chloro-2-fluorophenoxy)-2-methylpropanenitrile

To a solution of Example 53C (8 g, 34.5 mmol) in dichloromethane (100 mL) and triethylamine (19.25 mL, 138 mmol) was added trifluoroacetic anhydride (slow addition, 14.63 mL, 104 mmol) at 0° C. After the addition, the solution was allowed to warm to room temperature and stirred for 2 hours before methanol (20 mL) was added to quench the reaction. The solution was washed with saturated NaHCO$_3$ solution, dried (Na$_2$SO$_4$), and concentrated. The residue was purified by column chromatography using an Analogix® Intelliflash280™ (SiO$_2$, 0-60% ethyl acetate in hexanes) to provide titled product. MS (DCI+) m/z 214 (M+H)$^+$.

Example 53E ethyl 2-(4-chloro-2-fluorophenoxy)-2-methylpropanimidoate hydrochloride Through a cooled solution of Example 53D (7.2 g, 33.7 mmol) in ethanol (75 mL) and dichloromethane (30 mL) was bubbled HCl gas at 0° C. for 30 minutes. The reaction was kept in a refrigerator for 24-72 hours (checked by LCMS). The reaction mixture was then concentrated and the residue was triturated with diethyl ether. The titled compound was collected by filtration.

Example 53F ethyl 2-(4-chloro-2-fluorophenoxy)-N-cyano-2-methylpropanimidoate A solution of Example 53E (9.9 g, 33.4 mmol) in acetonitrile (15 mL) was added to a solution of monosodium mono (hydrogenphosphate) hydrate (18.32 g, 134 mmol) and sodium hydrogenphosphate heptahydrate (17.92 g, 66.9 mmol) in water (70 mL) followed by the addition of cyanamide (2.81 g, 66.9 mmol). The reaction mixture was stirred at room temperature for 55 hours and then extracted with dichloromethane (3×50 mL). The combined organic extracts were dried (Na$_2$SO$_4$), filtered and concentrated to give the titled compound. MS (DCI+) m/z 302 (M+NH$_4$)$^+$.

Example 53G (1E)-2-(4-chloro-2-fluorophenoxy)-N'-cyano-N-[(E)-5-cyanoadamantan-2-yl]-2-methylpropanimidamide The titled compound was synthesized according to the methods described in Example 3C substituting Example 53F for Example 3B and E-4-aminoadamantane-1-carbonitrile (International Publication No. WO 2007/118185, filed Oct. 18, 2007) for E-5-hydroxy-2-adamantamine. $^1$H NMR (300 MHz, DMSO-d$_6$) δ ppm 1.47-1.84 (m, 9H), 1.85-2.29 (m, 10H), 4.02-4.17 (m, 1H), 7.12-7.35 (m, 2H), 7.47-7.66 (m, 1H), 7.85 (d, J=6.8 Hz, 1H); MS (DCI+) m/z 415 (M+H)$^+$. Anal. Calculated for C$_{22}$H$_{24}$N$_4$ClFO: C, 63.69; H, 5.83; N, 13.50. Found: C, 63.50; H, 5.89; N, 13.32.

Example 54

(1E)-2-(4-chloro-2-fluorophenoxy)-N-cyano-2-methyl-N-[(E)-5-sulfamoyladamantan-2-yl]propanimidamide The titled compound was synthesized according to the methods described in Example 3C substituting Example 53F for Example 3B and (E)-4-aminoadamantane-1-sulfonamide (Sorensen, B., et al., Bioorg. Med. Chem. Lett., 2007, 17, 527-532) for E-5-hydroxy-2-adamantamine. $^1$H NMR (300 MHz, DMSO-d$_6$) δ ppm 1.45-1.72 (m, 8H), 1.73-2.14 (m, 10H), 2.27 (s, 2H), 6.63 (s, 2H), 7.17-7.37 (m, 2H), 7.49-7.68 (m, 1H), 7.89 (d, J=6.7 Hz, 1H); MS (DCI+) m/z 469 (M+H)$^+$. Anal. Calculated for C$_{21}$H$_{26}$N$_4$ClFO$_3$S: C, 63.69; H, 5.83; N, 13.50. Found: C, 53.18; H, 5.95; N, 10.28.

Example 55

(1E)-2-(4-chloro-2-fluorophenoxy)-N'-cyano-N-[(E)-5-hydroxyadamantan-2-yl]-2-methylpropanimidamide The titled compound was synthesized according to the methods described in Example 3C substituting Example 53F for Example 3B. $^1$H NMR (300 MHz, DMSO-d$_6$) δ ppm 1.43 (d, J=13.2 Hz, 2H), 1.56-1.81 (m, 14H), 1.93-2.07 (m, 1H), 2.19 (s, 2H), 4.01 (d, J=7.1 Hz, 1H), 4.50 (s, 1H), 7.19-7.37 (m, 2H), 7.48-7.67 (m, 1H), 7.79 (d, J=6.8 Hz, 1H); MS (DCI+) m/z 406 (M+H)$^+$. Anal. Calculated for C$_{21}$H$_{25}$N$_3$ClFO$_2$.0.25H$_2$O: C, 61.46; H, 6.26; N, 10.24. Found: C, 61.76; H, 6.26; N, 10.17.

Example 56

N-[(exo)-bicyclo[2.2.1]hept-2-yl]-N-cyano-2-(2,4-difluorophenoxy)-2-methylpropanimidamide The titled compound was synthesized according to the procedure described in Example 3C substituting E-2-amino-5-hydroxyadamantane and Example 3B with exo-2-aminonorbornane (Aldrich) and Example 51D, respectively. $^1$H NMR (300 MHz, DMSO-d$_6$) δ ppm 1.00-1.25 (m, 4H), 1.37, 1.38 (s, 3H), 1.40-1.55 (m, 4H), 1.56, 1.58 (s, 3H), 1.61-1.67 (m, 1H), 2.08-2.31 (m, 2H), 3.51-3.60, 3.70-3.80 (m, 1H), 6.98-7.21 (m, 2H), 7.25-7.41 (m, 2H), 7.66, 8.27 (d, J=6.4 Hz, d, J=6.8 Hz, 1H); MS (ESI$^+$) m/z 334 (M+H)$^+$.

Example 57

(1E)-N-cyano-2-(2,4-difluorophenoxy)-2-methyl-N-[(E)-5-sulfamoyladamantan-2-yl]propanimidamide Example 51D and (E)-4-aminoadamantane-1-sulfonamide (Sorensen, B., et al., Bioorg. Med. Chem. Lett., 2007, 17, 527-532) were processed using the method described for Example 3C to obtain the titled compound. $^1$H NMR (300 MHz, DMSO-d$_6$) δ ppm 1.48-1.57 (m, 2H), 1.63 (s, 6H), 1.74-2.11 (m, 9H), 2.22-2.32 (m, 2H), 3.96-4.06 (m, 1H), 6.64 (s, 2H), 7.08 (t, J=7.8 Hz, 1H), 7.27-7.35 (m, 1H), 7.38-7.45 (m, 1H), 7.92 (d, J=6.1 Hz, 1H); MS (ESI$^+$) m/z 456 (M+H)$^+$.

Example 58

(1E)-2-[(5-chloropyridin-2-yl)oxy]-N'-cyano-N-[(E)-5-hydroxyadamantan-2-yl]-2-methylpropanimidamide

Example 58A 2-(5-chloropyridin-2-yloxy)-2-methylpropanamide

The titled compound was synthesized according to the procedure described in Example 51A substituting 2-(2,4-difluorophenoxy)-2-methylpropanoic acid with 2-(5-chloropyridin-2-yloxy)-2-methylpropanoic acid. (Liu, P., et al., Journal of Medicinal Chemistry, 2007, 50, 15, 3427-3430). MS (ESI+) m/z 215 (M+H)+.

Example 58B 2-(5-chloropyridin-2-yloxy)-2-methylpropanenitrile

The titled compound was synthesized according to the procedure described in Example 51B substituting Example 51A with Example 58A. MS (ESI+) m/z 197 (M+H)+.

Example 58C ethyl 2-(5-chloropyridin-2-yloxy)-2-methylpropanimidate hydrochloride The titled compound was synthesized according to the procedure described in Example 51C substituting Example 51B with Example 58B. MS (ESI+) m/z 244 (M+H)+.

Example 58D ethyl 2-(5-chloropyridin-2-yloxy)-N-cyano-2-methylpropanimidate

Example 58C and cyanamide (Aldrich) were processed using the method described for Example 3B to obtain the titled compound. MS (ESI+) m/z 268 (M+NH$_4$)+.

Example 58E (1E)-2-[(5-chloropyridin-2-yl)oxy]-N'-cyano-N-[(E)-5-hydroxyadamantan-2-yl]-2-methylpropanimidamide The titled compound was synthesized according to the procedure described in Example 3C substituting Example 3B with Example 58D. $^1$H NMR (300 MHz, DMSO-d$_6$) δ ppm 1.34-1.47 (m, 2H), 1.56-1.74 (m, 7H), 1.77 (s, 6H), 1.95-2.04 (m, 2H), 2.13-2.21 (m, 2H), 3.79-3.87 (m, 1H), 4.44 (s, 1H), 6.94 (d, J=8.8 Hz, 1H), 7.16 (d, J=6.4 Hz, 1H), 7.85 (dd, J=8.8, 2.7 Hz, 1H), 8.00 (d, J=2.4 Hz, 1H); MS (ESI+) m/z 390 (M+H)+.

Example 59

(1E)-2-[(5-chloropyridin-2-yl)oxy]-N'-cyano-N-[(E)-5-cyanoadamantan-2-yl]-2-methylpropanimidamide The titled compound was synthesized according to the procedure described in Example 3C substituting E-2-amino-5-hydroxyadamantane and Example 3B with E-4-aminoadamantane-1-carbonitrile (International Publication No. WO 2007/118185, filed Oct. 18, 2007) and Example 58D, respectively. $^1$H NMR (300 MHz, DMSO-d$_6$) δ ppm 1.51-1.64 (m, 2H), 1.78 (s, 6H), 1.80-1.94 (m, 3H), 1.98 (d, 2H), 2.06 (d, 4H), 2.17 (d, 2H), 3.92 (d, 1H), 6.94 (d, J=8.7 Hz, 1H), 7.26 (d, J=5.6 Hz, 1H), 7.86 (dd, J=8.7, 2.8 Hz, 1H), 7.99 (d, J=2.8 Hz, 1H); MS (ESI+) m/z 399 (M+H)+.

Example 60

(1E)-N-(adamantan-1-yl)-2-(4-chloro-2-fluorophenoxy)-N-cyano-2-methylpropanimidamide The titled compound was synthesized according to the methods described in Example 3C substituting Example 53F for Example 3B and 1-adamantylamine for E-5-hydroxy-2-adamantamine. $^1$H NMR (300 MHz, DMSO-d$_6$) δ ppm 1.50-1.92 (m, 12H) 2.01-2.17 (m, 9H) 7.13-7.33 (m, 2H) 7.37 (s, 1H) 7.56 (dd, J=10.71, 2.38 Hz, 1H); MS (DCI+) m/z 390 (M+H)+.

Example 61

2-(4-chloro-2-fluorophenoxy)-N'-cyano-N-cyclooctyl-2-methylpropanimidamide

The titled compound was synthesized according to the methods described in Example 3C substituting Example 53F for Example 3B and 1-cyclooctylamine for E-5-hydroxy-2-adamantamine. $^1$H NMR (300 MHz, DMSO-d$_6$) δ ppm 1.30-1.84 (m, 20H), 4.11 (d, J=5.6 Hz, 1H), 7.10 (t, J=8.9 Hz, 1H), 7.19-7.31 (m, 1H), 7.54 (dd, J=10.5, 2.6 Hz, 1H), 8.58 (d, J=7.9 Hz, 1H); MS (DCI+) m/z 366 (M+H)+.

Example 62

(1E)-N-[(E)-adamantan-2-yl]-2-(4-chloro-2-fluorophenoxy)-N-cyano-2-methylpropanimidamide The titled compound was synthesized according to the methods described in Example 3C substituting Example 53F for Example 3B and 2-adamantylamine for E-5-hydroxy-2-adamantamine. $^1$H NMR (300 MHz, DMSO-d$_6$) δ ppm 1.51-1.94 (m, 18H) 2.06 (s, 2H) 4.00-4.15 (m, 1H) 7.23-7.31 (m, 2H) 7.59 (dd, J=10.17, 1.70 Hz, 1H) 7.86 (d, J=7.12 Hz, 1H); MS (DCI+) m/z 390 (M+H)+. Anal. Calculated for C$_{21}$H$_{25}$ClN$_3$FO: C, 64.69; H, 6.46; N, 10.78. Found: C, 64.33; H, 6.34; N, 9.79.

Example 63 methyl(E)-4-{[(1E)-2-(4-chloro-2-fluorophenoxy)-N-cyano-2-methylpropanimidoyl]amino}adamantane-1-carboxylate The titled compound was synthesized according to the methods described in Example 3C substituting Example 53F for Example 3B and methyl(E)-4-aminoadamantane-1-carboxylate (Becker, C. L., et al., Org. Process R & D, 2008, 12, 1114-1118) for E-5-hydroxy-2-adamantamine. $^1$H NMR (300 MHz, DMSO-d$_6$) δ ppm 1.56 (d, J=13.22 Hz, 2H) 1.65 (s, 6H) 1.71-2.00 (m, 10H) 2.17 (s, 2H) 3.60 (s, 3H) 4.05 (dd, J=3.73, 1.36 Hz, 1H) 7.14-7.33 (m, 1H) 7.58 (dd, J=10.17, 1.70 Hz, 1H) 7.87 (d, J=7.12 Hz, 1H); MS (DCI+) m/z 390 (M+H)+. Anal. Calculated for C$_{23}$H$_{27}$N$_3$FO$_3$: C, 61.67; H, 6.08; N, 9.38. Found: C, 61.46; H, 5.89; N, 9.29.

Example 64

(1E)-N-cyano-2-methyl-N-[(E)-5-(methylsulfonyl)adamantan-2-yl]-2-phenoxypropanimidamide The titled compound was synthesized according to the methods described in Example 78 substituting Example 53 with Example 19. $^1$H NMR (300 MHz, DMSO-d$_6$) δ ppm 1.43-1.84 (m, 10H) 1.86-2.15 (m, 7H) 2.32 (s, 2H) 2.85 (s, 3H) 4.04 (d, J=1.36 Hz, 1H) 6.99 (d, J=7.80 Hz, 2H) 7.12 (t, J=7.29 Hz, 1H) 7.23-7.43 (m, 2H) 7.70 (d, J=6.44 Hz, 1H); MS(DCI+) m/z 415 (M+H)+. Anal. Calculated for C$_{22}$H$_{24}$N$_4$ClFO: C, 63.59; H, 7.03; N, 10.11. Found: C, 63.06; H, 7.03; N, 9.97.

Example 65

N'-cyano-N-cyclooctyl-2-(2,4-difluorophenoxy)-2-methylpropanimidamide

The titled compound was synthesized according to the procedure described in Example 3C substituting E-2-amino-5-hydroxyadamantane and Example 3B with cyclooctanamine (Aldrich) and Example 51D, respectively. $^1$H NMR (300 MHz, DMSO-$d_6$) δ ppm 1.38-1.56 (m, 8H), 1.55-1.61 (m, 6H), 1.62-1.82 (m, 6H), 4.02-4.20 (m, J=7.9 Hz, 1H), 7.01-7.10 (m, 1H), 7.11-7.21 (m, 1H), 7.31-7.42 (m, J=23.0 Hz, 1H), 8.58 (d, J=8.3 Hz, 1H); MS (ESI$^+$) m/z 350 (M+H)$^+$.

Example 66

N-(exo-bicyclo[2.2.1]hept-2-yl)-2-(4-chloro-2-fluorophenoxy)-N-cyano-2-methylpropanimidamide The titled compound was synthesized according to the methods described in Example 3C substituting Example 53F for Example 3B and exo-bicyclo[2.2.1]heptylamine for E-5-hydroxy-2-adamantamine. $^1$H NMR (300 MHz, DMSO-$d_6$) δ ppm 0.99-1.29 (m, 3H) 1.35-1.77 (m, 11H) 2.09-2.36 (m, 2H) 3.61-3.92 (m, 1H) 7.10 (t, J=8.82 Hz, 1H) 7.18-7.36 (m, 1H) 7.53 (dd, J=10.68, 2.54 Hz, 1H) 8.27 (d, J=6.44 Hz, 1H); MS (DCI+) m/z 349 (M+H)$^+$.

Example 67

(1E)-2-[(5-chloropyridin-2-yl)oxy]-N-cyano-2-methyl-N-[(E)-5-(methylsulfonyl)adamantan-2-yl]propanimidamide Example 58D and (E)-4-aminoadamantane-1-sulfone (Sorensen, B. et al., Bioorg. Med. Chem. Lett., 2007, 17, 527-532) were processed using the method described for Example 3C to obtain the titled compound. $^1$H NMR (300 MHz, DMSO-$d_6$) δ ppm 1.47-1.62 (m, 2H), 1.79 (s, 6H), 1.82-2.11 (m, 9H), 2.23-2.38 (m, 2H), 2.84 (s, 3H), 3.84-3.96 (m, 1H), 6.94 (d, J=9.5 Hz, 1H), 7.29 (d, J=5.8 Hz, 1H), 7.86 (dd, J=8.8, 2.7 Hz, 1H), 8.01 (d, J=2.4 Hz, 1H); MS (ESI$^+$) m/z 452 (M+H)$^+$.

Example 68

(1E)-2-[(5-chloropyridin-2-yl)oxy]-N-cyano-2-methyl-N-[(E)-5-sulfamoyladamantan-2-yl]propanimidamide Example 58D and (E)-4-aminoadamantane-1-sulfonamide (Sorensen, B. et al., Bioorg. Med. Chem. Lett., 2007, 17, 527-532) were processed using the method described for Example 3C to obtain the titled compound. $^1$H NMR (300 MHz, DMSO-$d_6$) δ ppm 1.41-1.55 (m, 2H), 1.78 (s, 6H), 1.80-2.09 (m, 9H), 2.21-2.29 (m, 2H), 3.80-3.89 (m, 1H), 6.59 (s, 2H), 6.94 (d, J=8.8 Hz, 1H), 7.29 (d, J=6.4 Hz, 1H), 7.86 (dd, J=8.8, 2.7 Hz, 1H), 8.02 (d, J=2.7 Hz, 1H); MS (ESI$^+$) m/z 453 (M+H)$^+$.

Example 69

N-cyano-2-(2,4-difluorophenoxy)-N-(hexahydro-2,5-methanopentalen-3a(1H)-yl)-2-methylpropanimidamide The titled compound was synthesized according to the procedure described in Example 38 substituting Example 8B with Example 51D, respectively. $^1$H NMR (300 MHz, DMSO-$d_6$) δ ppm 1.48-1.59 (m, J=11.9 Hz, 4H), 1.62 (s, 6H), 1.87-2.16 (m, 6H), 2.21-2.30 (m, 2H), 2.60 (t, J=6.5 Hz, 1H), 7.02-7.13 (m, 1H), 7.14-7.26 (m, 1H), 7.32-7.46 (m, 1H), 8.23 (s, 1H); MS (ESI$^+$) m/z 360 (M+H)$^+$.

Example 70

(E)-4-{[(1E)-N-cyano-2-(2,4-difluorophenoxy)-2-methylpropanimidoyl]amino}adamantane-1-carboxamide

Example 70A methyl(E)-4-{[(benzyloxy)carbonyl]amino}adamantane-1-carboxylate

Benzyl chloroformate (6.9 mL, 48.8 mmol) was added drop wise to a stirred and cooled (0° C.) solution of methyl (E)-4-aminoadamantane-1-carboxylate hydrochloride salt (Becker, C. L., et al., Org. Process R & D, 2008, 12, 1114-1118) (10.0 g, 40.7 mmol) and diisopropylethylamine (21.3 mL, 122 mmol) in dry methylene chloride (100 mL). After stirring at room temperature for 2 hours, the reaction mixture was quenched with saturated aqueous NaHCO$_3$ solution (50 mL). The organic phase was washed with 50% aqueous NaHSO$_4$ solution (50 mL) and saturated aqueous NaHCO$_3$ solution (50 mL), dried (Na$_2$SO$_4$); and concentrated under reduced pressure. The residue was triturated in hexanes and filtered to obtain the titled compound. MS (ESI$^+$) m/z 344 (M+H)$^+$.

Example 70B

(E)-4-{[(benzyloxy)carbonyl]amino}adamantane-1-carboxylic acid

The titled compound was synthesized according to the procedure described in Example 14A substituting Example 11 with Example 70A. LCMS (ESI$^+$) m/z 330 (M+H)$^+$.

Example 70C benzyl[(E)-5-carbamoyladamantan-2-yl]carbamate

The titled compound was synthesized according to the procedure described in Example 14B substituting Example 11 with Example 70B. MS (ESI$^+$) m/z 329 (M+H)$^+$.

Example 70D

(E)-4-aminoadamantane-1-carboxamide

To a solution of Example 70C (1.0 g, 3.0 mmol) in methanol (20 mL) was added Pd(OH)$_2$/C (0.2 g, 0.3 mmol). The reaction mixture was stirred at room temperature under H$_2$ atmosphere (balloon) for 4 hours. The reaction mixture was then filtered through a pad of diatomaceous earth and concentrated under reduced pressure to provide the titled compound. MS (ESI$^+$) m/z 195 (M+H)$^+$.

Example 70E

(E)-4-{[(1E)-N-cyano-2-(2,4-difluorophenoxy)-2-methylpropanimidoyl]amino}adamantane-1-carboxamide Example 51D and Example 70D were processed using the method described for Example 3C to obtain the titled compound. ¹H NMR (300 MHz, DMSO-d₆) δ ppm 1.46-1.58 (m, 2H), 1.64 (s, 6H), 1.70-2.00 (m, 9H), 2.10-2.20 (m, 2H), 3.98-4.10 (m, 1H), 6.75 (s, 1H), 7.02 (s, 1H), 7.04-7.14 (m, 1H), 7.25-7.36 (m, 1H), 7.36-7.49 (m, 1H), 7.89 (d, J=7.1 Hz, 1H); MS (ESI⁺) m/z 417 (M+H)⁺.

Example 71

(1E)-N-(adamantan-1-yl)-N-cyano-2-(2,4-difluorophenoxy)-2-methylpropanimidamide

Example 51D and 1-adamantamine were processed using the method described for Example 38 to obtain the titled compound. ¹H NMR (300 MHz, DMSO-d₆) δ ppm 1.62 (s, 6H), 1.63-1.69 (m, 6H), 2.08 (s, 9H), 7.03-7.12 (m, 1H), 7.26 (d, J=24.2 Hz, 1H), 7.35-7.45 (m, J=22.6 Hz, 1H), 7.39-7.42 (m, 1H); MS (ESI⁺) m/z 375 (M+H)⁺.

Example 72

(1E)-N-(1-azabicyclo[2.2.2]oct-3-yl)-2-(4-chloro-2-fluorophenoxy)-N'-cyano-2-methylpropanimidamide The titled compound was synthesized according to the methods described in Example 3C substituting Example 53F for Example 3B and 1-azabicyclo[2.2.2]oct-3-yl amine for E-5-hydroxy-2-adamantamine. ¹H NMR (300 MHz, DMSO-d₆) δ ppm 1.14 (t, J=7.29 Hz, 2H) 1.35-1.57 (m, 2H) 1.55-1.82 (m, 9H) 2.11 (d, J=2.71 Hz, 1H) 2.76-3.06 (m, 3H) 4.04-4.30 (m, 1H) 7.15 (t, J=8.82 Hz, 1H) 7.22-7.31 (m, 1H) 7.56 (dd, J=10.68, 2.54 Hz, 1H) 8.67 (d, J=6.10 Hz, 1H); MS (DCI+) m/z 364 (M+H)⁺.

Example 73

2-(4-chloro-2-fluorophenoxy)-Y-cyano-N-(hexahydro-2,5-methanopentalen-3a(1H)-yl)-2-methylpropanimidamide The titled compound was synthesized according to the methods described in Example 3C substituting Example 53F for Example 3B and hexahydro-2,5-methanopentalen-3a (1H)-ylamine for E-5-hydroxy-2-adamantamine. ¹H NMR (300 MHz, DMSO-d₆) δ ppm 1.43-1.71 (m, 10H) 1.83-2.16 (m, 6H) 2.25 (s, 2H) 2.60 (t, J=6.61 Hz, 1H) 7.14 (t, J=8.82 Hz, 1H) 7.21-7.36 (m, 1H) 7.54 (dd, J=10.68, 2.54 Hz, 1H) 8.21 (s, 1H); MS (DCI+) m/z 375 (M+H)⁺. Anal. Calculated for C₂₀H₂₃N₃ClFO: C, 64.08; H, 5.92; N, 11.21. Found: C, 63.17; H, 6.26; N, 10.76.

Example 74

(E)-4-{[(1E)-2-(4-chloro-2-fluorophenoxy)-N-cyano-2-methylpropanimidoyl]amino}adamantane-1-carboxamide The titled compound was synthesized according to the methods described in Example 14 substituting Example 63 for Example 11. ¹H NMR (300 MHz, DMSO-d₆) δ ppm 1.45-1.70 (m, 8H) 1.70-1.99 (m, 9H) 2.14 (s, 2H) 3.88-4.19 (m, 1H) 6.74 (s, 1H) 7.01 (s, 1H) 7.18-7.37 (m, 2H) 7.58 (dd, J=9.66, 1.86 Hz, 1H) 7.85 (d, J=7.12 Hz, 1H); MS (DCI+) m/z 430 (M+H)⁺.

Example 75

(E)-4-({(1E)-2-[(5-chloropyridin-2-yl)oxy]-N-cyano-2-methylpropanimidoyl}amino)adamantane-1-carboxamide Example 58D and Example 70D were processed using the method described for Example 3C to obtain the titled compound. ¹H NMR (300 MHz, CDCl₃) δ ppm 1.62-1.66 (m, 4H), 1.85 (s, 6H), 1.88-1.94 (m, 2H), 1.98-2.05 (m, 5H), 2.15-2.24 (m, 2H), 4.13-4.23 (m, 1H), 5.20 (s, 1H), 5.57 (s, 1H), 6.85 (d, J=9.5 Hz, 1H), 6.84-6.91 (m, 1H), 7.62 (dd, J=8.7, 2.4 Hz, 1H), 8.03 (d, J=2.8 Hz, 1H); MS (ESI⁺) m/z 417 (M+H)⁺.

Example 76

(E)-4-[(2-methyl-2-phenoxypropanimidoyl)amino]adamantane-1-carboxamide

The titled compound was obtained as a byproduct from the procedure described for Example 50. ¹H NMR (300 MHz, DMSO-d₆) δ ppm 1.30-1.42 (m, 2H), 1.50 (s, 6H), 1.69-1.88 (m, 9H), 1.93-2.13 (m, 2H), 3.44-3.54 (m, 1H), 6.66 (s, 1H), 6.87-6.99 (m, 4H), 7.17-7.27 (m, 2H)); MS (ESI⁺) m/z 356 (M+H)⁺.

Example 77

(1E)-N'-cyano-2-methyl-N-[(E)-5-(methylsulfonyl)adamantan-2-yl]-2-(pyridin-2-yloxy)propanimidamide The titled compound was synthesized according to the procedure described in Example 49 substituting Example 8 with Example 67. ¹H NMR (300 MHz, DMSO-d₆) δ ppm 1.45-1.56 (m, 2H), 1.65 (s, 6H), 1.67-1.78 (m, 4H), 1.79-1.94 (m, 5H), 2.10-2.19 (m, 2H), 3.97-4.09 (m, 1H), 6.73 (s, 1H), 6.95-7.04 (m, 3H), 7.08-7.17 (m, 1H), 7.29-7.40 (m, 2H), 7.65 (d, J=6.8 Hz, 1H); MS (ESI⁺) m/z 381 (M+H)⁺.

Example 78

(1E)-N'-cyano-N-[(E)-5-cyanoadamantan-2-yl]-2-(2-fluorophenoxy)-2-methylpropanimidamide A solution of Example 53 (50 mg, 0.111 mmol) in methanol (3 mL) was treated with ammonium formate (70.1 mg, 1.111 mmol) and palladium 10% palladium on carbon (1.182 mg, 0.011 mmol). The reaction mixture was stirred at room temperature for 18 hours. The reaction mixture was filtered and concentrated. Purification by reverse phase HPLC method using a Phenomenex® Luna® C8, 5 μM 100 Å AXIA™ column (30 mm×75 mm) and a gradient of 10-100% acetonitrile and 10 mM ammonium acetate in water provided the titled compound. ¹H NMR (300 MHz, DMSO-d₆) δ ppm 1.52-1.83 (m, 10H) 1.89-2.26 (m, 9H) 4.07 (s, 1H) 7.08-7.42 (m, 4H) 7.91 (d, J=6.35 Hz, 1H); MS (DCI+) m/z 380 (M+H)⁺.

Example 79

(1E)-N'-cyano-2-(2-fluorophenoxy)-2-methyl-N-[(E)-5-sulfamoyladamantan-2-yl]propanimidamide The titled compound was synthesized according to the methods described in Example 78 substituting Example 53 with Example 54. ¹H NMR (300 MHz, DMSO-d₆) δ ppm 1.45-1.71 (m, 8H) 1.72-2.13 (m, 9H) 2.27 (s, 2H) 4.02 (dd, J=4.92, 1.53 Hz, 1H) 6.63 (s, 2H) 7.14-7.42 (m, 4H) 7.95 (d, J=6.44 Hz, 1H); MS (DCI+) m/z 435 (M+H)⁺.

Example 80

(1E)-N'-cyano-2-(2-fluorophenoxy)-N-[(E)-5-hydroxyadamantan-2-yl]-2-methylpropanimidamide The titled compound was synthesized according to the methods described in Example 78 substituting Example 53 with Example 55. ¹H NMR (300 MHz, DMSO-d₆) δ ppm 1.45 (d, J=13.09 Hz, 2H) 1.54-1.78 (m, 14H) 1.91-2.29 (m, 3H) 3.99 (d, J=2.38 Hz, 1H) 4.51 (s, 1H) 7.06-7.44 (m, 4H) 7.86 (d, J=7.14 Hz, 1H); MS (DCI+) m/z 372 (M+H)⁺.

Example 81

4-{[N-cyano-2-methyl-2-phenoxypropanimidoyl]amino}bicyclo[2.2.1]heptane-1-carboxamide To a mixture of ethyl N-cyano-2-methyl-2-phenoxypropanimidoate (CI-1) (300 mg, 1.29 mmol) and 4-aminobicyclo[2.2.1]heptane-1-carboxamide (BA-7) (217 mg, 1.29 mmol) in ethanol (3 mL) was added 4-(dimethylamino)pyridine (47 mg, 0.387 mmol). The mixture was stirred at room temperature for 5 hours and then heated to 75° C. and stirred overnight. After concentration, the residue was purified by preparative reverse phase HPLC [Waters 2767; Benetnach 10-C18 20×250 mm, 10 μm; 35-85% acetonitrile/water (0.05% trifluoroacetic acid), 30 mL/minute; detection at 214 and 254 nm] to give the titled compound. ¹H NMR (400 MHz, CD₃OD) δ ppm 7.34 (t, J=7.8 Hz, 2H), 7.14 (t, J=7.4 Hz, 1H), 7.0 (d, J=8.4 Hz, 2H), 2.10-2.15 (m, 4H), 2.01-2.03 (m, 4H), 1.79-1.83 (m, 2H), 1.72 (s, 6H); LCMS (ESI+) m/z 341.7 (M+H)⁺.

Example 82

4-{[N-cyano-2-methyl-2-phenoxypropanimidoyl]amino}bicyclo[2.2.2]octane-1-carboxamide The titled compound was prepared using the procedure described in Example 81 substituting 4-aminobicyclo[2.2.2]octane-1-carboxamide (BA-6) for 4-aminobicyclo[2.2.1]heptane-1-carboxamide (BA-7). ¹H NMR (400 MHz, CDCl₃) δ ppm 7.32 (t, J=8.0 Hz, 2H), 7.17 (t, J=7.2 Hz, 1H), 7.06 (s, 1H), 6.91 (d, J=8.0 Hz, 2H), 6.20 (s, 1H), 5.85 (s, 1H), 4.81 (br, 1H), 2.05-2.06 (m, 6H), 1.92-1.94 (m. 6H), 1.68 (s, 6H); LCMS (ESI+) m/z 355.7 (M+H)⁺.

Example 83

N'-cyano-N-(4-cyanobicyclo[2.2.1]hept-1-yl)-2-methyl-2-phenoxypropanimidamide

The titled compound was prepared using the procedure described in Example 84 substituting Example 81 for Example 82. ¹H NMR (400 MHz, CDCl₃) δ ppm 7.47 (s, 1H), 7.34 (t, J=7.95 Hz, 2H), 7.20 (t, J=7.4 Hz, 1H), 6.93 (d, J=8.9 Hz, 2H), 2.26 (s, 2H), 2.07~2.16 (m, 4H), 1.90~1.99 (m, 4H), 1.71 (s, 6H); LCMS (ESI+) m/z 323.7 (M+H)⁺.

Example 84

N'-cyano-N-(4-cyanobicyclo[2.2.2]oct-1-yl)-2-methyl-2-phenoxypropanimidamide

To a solution of Example 82 (70 mg, 0.2 mmol) and triethylamine (120 mg, 1.2 mmol) in dichloromethane cooled in an ice bath was added trifluoroacetic anhydride (125 mg, 0.6 mmol) dropwise. After addition was complete, the mixture was stirred overnight at room temperature. After removal of the solvent, the residue was purified by preparative reverse phase HPLC [Waters 2767; Benetnach 10-C18 20×250 mm, 10 μm; 35-85% acetonitrile/water (0.05% trifluoroacetic acid), 30 mL/minute; detection at 214 and 254 nm] to give the titled compound. ¹H NMR (400 MHz, CDCl₃) δ ppm 7.33 (t, J=7.85 Hz, 2H), 7.19 (t, J=7.4 Hz, 1H), 7.01 (s, 1H), 6.91 (d, J=7.6 Hz, 2H), 2.01~2.08 (m, 12H), 1.69 (s, 6H); LCMS (ESI+) m/z 337.7 (M+H)⁺.

Example 85

2-(4-chlorophenoxy)-N'-cyano-N-[4-(difluoromethyl)bicyclo[2.2.2]oct-1-yl]-2-methylpropanimidamide 4-(Difluoromethyl)bicyclo[2.2.2]octan-1-amine (BA-4) and Example 8B were mixed, and the neat mixture was heated to 100° C. under nitrogen and stirred for 3 hours. After cooling, the mixture was dissolved in a small amount of ethanol and purified by prep-HPLC [Waters 2767; Benetnach 10-C18 20×250 mm, 10 μm; 35-85% acetonitrile/water (0.05% trifluoroacetic acid), 30 mL/minute; detection at 214 and 254 nm] to give the titled compound. ¹H NMR (400 MHz, DMSO-d₆) δ ppm 7.38 (dd, J=8.8 Hz 2H), 7.29 (s, 1H), 6.96 (d, J=8.8 Hz 2H), 5.71 (t, J=56.4 Hz 1H), 1.98 (m, 6H), 1.62 (s, 6H), 1.58 (m, 6H); LCMS (ESI+) m/z 396.7 (M+H)⁺.

Example 86

N-cyano-N-[4-(difluoromethyl)bicyclo[2.2.2]oct-1-yl]-2-methyl-2-phenoxypropanimidamide The titled compound was prepared using the procedure described in Example 85 substituting ethyl N-cyano-2-methyl-2-phenoxypropanimidoate (CI-1) for Example 8B. Purification was achieved by preparative reverse phase HPLC [Waters 2767; Benetnach 10-C18 20×250 mm, 10 μm; 58-78% acetonitrile/water (0.05% trifluoroacetic acid), 30 mL/minute; detection at 214 and 254 nm]. ¹H NMR (400 MHz, DMSO-d₆) δ ppm 7.33 (t, J=7.8 Hz, 3H), 7.10 (t, J=7.2 Hz, 1H), 6.94 (d, J=7.7 Hz, 2H), 5.70 (t, J=56.7 Hz, 1H), 1.97~2.01 (m, 6H), 1.62 (s, 6H), 1.56-1.60 (m, 6H); LCMS (ESI+) m/z 362 (M+H)⁺.

Example 87

4-{[N-cyano-2-methyl-2-phenoxypropanimidoyl]amino}bicyclo[2.2.2]octane-1-carboxylic acid Ethyl N-cyano-2-methyl-2-phenoxypropanimidoate (CI-1) (1 mmol) and methyl 4-aminobicyclo[2.2.2]octane-1-carboxylate (BA-2) (1 mmol) were mixed, and the neat mixture was heated to 100° C. under nitrogen and stirred for 5 hours. After cooling, the mixture was purified by column chromatography on silica gel (mobile phase:CH₂Cl₂/CH₃OH=50/1) to give an impure ester product which was dissolved in methanol (10 mL). To the solution was added a solution of LiOH (10 mg) in methanol (40 mL) and water (1 mL). The mixture was refluxed overnight. After removal of the solvent, the residue was dissolved in water and adjusted pH=5~6 with HCl (1 mol/L), extracted with ethyl acetate (50 mL×3). The combined extracts were washed with brine, dried over sodium sulfate and concentrated. The residue was purified by preparative reverse phase HPLC [Waters 2767; Benetnach 10-C18 20×250 mm, 10 μm; 35-60% acetonitrile/water (0.05% trifluoroacetic acid), 30 mL/minute; detection at 214 and 254 nm] to give the titled compound.

Example 88

4-{[2-(4-chlorophenoxy)-N-cyano-2-methylpropanimidoyl]amino}bicyclo[2.2.1]heptane-1-carboxamide The titled compound was prepared using the procedure described in Example 85 substituting 4-aminobicyclo[2.2.1]heptane-1-carboxamide (BA-7) for 4-(difluoromethyl)bicyclo[2.2.2]octan-1-amine (BA-4). Purification was achieved by preparative reverse phase HPLC [Waters 2767; Benetnach 10-C18 20×250 mm, 10 μm; 36-60% acetonitrile/water (0.05% trifluoroacetic acid), 30 mL/minute; detection at 214 and 254 nm]. $^1$H NMR (400 MHz, CDCl$_3$) δ ppm 7.36 (s, 1H), 7.30 (d, J=8.6 Hz, 2H), 6.88 (d, J=8.7 Hz, 2H), 5.58 (s, 1H), 5.41 (s, 1H), 1.97~2.13 (m, 8H), 1.78~1.82 (m, 2H), 1.71 (s, 6H); LCMS (ESI+) m/z 375.1 (M+H)$^+$.

Example 89

N'-cyano-N-[4-(difluoromethyl)bicyclo[2.2.1]hept-1-yl]-2-methyl-2-phenoxypropanimidamide The titled compound was prepared using the procedure described in Example 85 substituting 4-(difluoromethyl)bicyclo[2.2.1]heptan-1-amine (BA-5) for 4-(difluoromethyl)bicyclo[2.2.2]octan-1-amine (BA-4) and ethyl N-cyano-2-methyl-2-phenoxypropanimidoate (CI-1) for Example 8B. $^1$H NMR (400 MHz, CDCl$_3$) δ ppm 7.50 (s, 1H), 7.9 (t, J=7.9 Hz, 2H), 7.19 (t, J=7.6 Hz, 1H), 6.94 (d, J=7.6 Hz, 2H), 5.82 (t, J=56.4 Hz, 1H), 2.0 (m, 8H), 1.72 (s, 6H), 1.6-2.0 (m, 2H); LCMS (ESI+) m/z 348.2 (M+H)$^+$.

Example 90

2-(2-fluorophenoxy)-2-methyl-N-[(E)-5-sulfamoyladamantan-2-yl]propanimidamide

Titled compound was isolated as a byproduct from the Example 79 synthesis. $^1$H NMR (300 MHz, DMSO-d$_6$) δ ppm 1.24-1.40 (m, 2H) 1.42-1.56 (m, 6H) 1.79-2.18 (m, 12H) 3.20-3.64 (m, 2H) 6.52 (s, 2H) 6.88-7.26 (m, 4H); MS (DCI+) m/z 410 (M+H)$^+$.

Example 91

2-(2-fluorophenoxy)-N-[(E)-5-hydroxyadamantan-2-yl]-2-methylpropanimidamide

Titled compound was isolated as a byproduct from Example 80 synthesis. $^1$H NMR (300 MHz, DMSO-d$_6$) δ ppm 1.39-1.63 (m, 10H), 1.72 (s, 2H), 1.88 (s, 11H), 6.89-7.15 (m, 3H), 7.14-7.29 (m, 1H). MS (DCI+) m/z 347 (M+H)$^+$.

Example 92

N-[(E)-5-hydroxyadamantan-2-yl]-2-methyl-2-phenoxypropanimidamide

The titled compound was obtained as a byproduct from the procedure described for Example 49. $^1$H NMR (300 MHz, DMSO-d$_6$) δ ppm 1.17-1.33 (m, 2H), 1.48 (s, 6H), 1.50-1.80 (m, 6H), 1.81-2.06 (m, 6H), 4.17-4.39 (m, 1H), 6.84-7.00 (m, 3H), 7.14-7.30 (m, 2H); MS (ESI$^+$) m/z 329 (M+H)$^+$.

Example 93

5-chloro-N'-cyano-N-[(E)-5-hydroxyadamantan-2-yl]-2-methoxybenzenecarboximidamide Example 93A ethyl 5-chloro-2-methoxybenzimidate hydrochloride The titled compound was synthesized according to the procedure described in Example 51C substituting Example 51B with 5-chloro-2-methoxybenzonitrile (Maybridge). MS (ESI+) m/z 214 (M+H)$^+$.

Example 93B ethyl 5-chloro-N-cyano-2-methoxybenzimidate

Example 93A and cyanamide (Aldrich) were processed using the method described for Example 3B to obtain the titled compound. MS (ESI$^+$) m/z 239 (M+NH$_4$)$^+$.

Example 93C 5-chloro-N'-cyano-N-[(E)-5-hydroxyadamantan-2-yl]-2-methoxybenzenecarboximidamide The titled compound was synthesized according to the procedure described in Example 3C substituting Example 3B with Example 93B. $^1$H NMR (300 MHz, DMSO-d$_6$) δ ppm 1.29-1.40 (m, 2H), 1.58-1.76 (m, 6H), 1.85-2.03 (m, 3H), 2.13-2.21 (m, 2H), 3.81 (s, 3H), 3.90-3.98 (m, 1H), 4.46 (s, 1H), 7.21 (d, J=9.1 Hz, 1H), 7.35 (d, J=2.8 Hz, 1H), 7.55 (dd, J=8.9, 2.6 Hz, 1H), 8.87 (d, J=6.7 Hz, 1H); MS (ESI$^+$) m/z 361 (M+H)$^+$.

The following compounds can be prepared using knowledge known to one skilled in the art or with the procedures described for the above examples.

Example 94

2-(4-chlorophenoxy)-N'-cyano-N-(4-hydroxybicyclo[2.2.2]oct-1-yl)-2-methylpropanimidamide Example 95

N-cyano-N-(4-hydroxybicyclo[2.2.2]oct-1-yl)-2-methyl-2-phenoxypropanimidamide

Example 96

2-(4-chlorophenoxy)-N'-cyano-N-(4-cyanobicyclo[2.2.2]oct-1-yl)-2-methylpropanimidamide

Example 97

N-cyano-N-(4-hydroxybicyclo[2.2.1]hept-1-yl)-2-methyl-2-phenoxypropanimidamide

The examples listed below are prepared by the methods described in the Schemes and Examples above or by methods well known to one skilled in the art:

4-({2-[(4-chlorobenzyl)oxy]-N-cyano-2-methylpropanimidoyl}amino)adamantane-1-carboxamide;
4-[(N-cyano-2-methyl-2-{[4-(methylsulfonyl)benzyl]oxy}propanimidoyl)amino]adamantane-1-carboxamide;
4-{[N-cyano-2-methyl-2-(pyridin-2-ylmethoxy)propanimidoyl]amino}adamantane-1-carboxamide;
4-[(N-cyano-2-methyl-2-{[4-(trifluoromethoxy)benzyl]oxy}propanimidoyl)amino]adamantane-1-carboxylic acid;
4-[(N-cyano-2-methyl-2-{[4-(trifluoromethoxy)benzyl]oxy}propanimidoyl)amino]adamantane-1-carboxamide;
4-({N-cyano-2-[(4-cyanobenzyl)oxy]-2-methylpropanimidoyl}amino)adamantane-1-carboxamide;
4-({N-cyano-2-[(4-methoxybenzyl)oxy]-2-methylpropanimidoyl}amino)adamantane-1-carboxamide;
4-[(N-cyano-2-{[2-fluoro-4-(trifluoromethyl)benzyl]oxy}-2-methylpropanimidoyl)amino]adamantane-1-carboxamide;
4-[(N-cyano-2-{[4-(difluoromethoxy)benzyl]oxy}-2-methylpropanimidoyl)amino]adamantane-1-carboxylic acid;
4-[(N-cyano-2-{[4-(difluoromethoxy)benzyl]oxy}-2-methylpropanimidoyl)amino]adamantane-1-carboxamide;
4-({2-[(4-chloro-2-fluorobenzyl)oxy]-N-cyano-2-methylpropanimidoyl}amino)adamantane-1-carboxylic acid;
4-({2-[(4-chloro-2-fluorobenzyl)oxy]-N-cyano-2-methylpropanimidoyl}amino)adamantane-1-carboxamide;
4-({N-cyano-2-[(4-methoxybenzyl)oxy]-2-methylpropanimidoyl}amino)adamantane-1-carboxylic acid;
4-[(N-cyano-2-{[2-fluoro-4-(trifluoromethyl)benzyl]oxy}-2-methylpropanimidoyl)amino]adamantane-1-carboxylic acid;
4-{[N-cyano-2-methyl-2-(pyridin-2-ylmethoxy)propanimidoyl]amino}adamantane-1-carboxylic acid;
4-[(2-{[2-bromo-4-(trifluoromethyl)benzyl]oxy}-N-cyano-2-methylpropanimidoyl)amino]adamantane-1-carboxamide;
4-({N-cyano-2-[(2,6-difluorobenzyl)oxy]-2-methylpropanimidoyl}amino)adamantane-1-carboxylic acid;
4-({N-cyano-2-[(2,3-difluorobenzyl)oxy]-2-methylpropanimidoyl}amino)adamantane-1-carboxamide;
4-({N-cyano-2-[(3,4-difluorobenzyl)oxy]-2-methylpropanimidoyl}amino)adamantane-1-carboxamide;
4-{[2-(benzyloxy)-N-cyano-2-methylpropanimidoyl]amino}adamantane-1-carboxamide;
4-({N-cyano-2-[(2,5-difluorobenzyl)oxy]-2-methylpropanimidoyl}amino)adamantane-1-carboxylic acid;
4-({N-cyano-2-[(3,5-difluorobenzyl)oxy]-2-methylpropanimidoyl}amino)adamantane-1-carboxylic acid;
4-({N-cyano-2-[(3-methoxybenzyl)oxy]-2-methylpropanimidoyl}amino)adamantane-1-carboxylic acid;
4-({N-cyano-2-[(2-fluorobenzyl)oxy]-2-methylpropanimidoyl}amino)adamantane-1-carboxylic acid;
4-({N-cyano-2-[(2,6-difluorobenzyl)oxy]-2-methylpropanimidoyl}amino)adamantane-1-carboxamide;
4-({N-cyano-2-[(2-cyanobenzyl)oxy]-2-methylpropanimidoyl}amino)adamantane-1-carboxamide;
4-({N-cyano-2-[(2,3-difluorobenzyl)oxy]-2-methylpropanimidoyl}amino)adamantane-1-carboxamide;
4-({N-cyano-2-[(2-methoxybenzyl)oxy]-2-methylpropanimidoyl}amino)adamantane-1-carboxylic acid;
4-({N-cyano-2-[(4-fluorobenzyl)oxy]-2-methylpropanimidoyl}amino)adamantane-1-carboxylic acid;
4-({2-[(3-chlorobenzyl)oxy]-N-cyano-2-methylpropanimidoyl}amino)adamantane-1-carboxamide;
4-({N-cyano-2-[(4-isopropylbenzypoxy]-2-methylpropanimidoyl}amino)adamantane-1-carboxylic acid;
4-[(N-cyano-2-methyl-2-{[3-(trifluoromethyl)benzyl]oxy}propanimidoyl)amino]adamantane-1-carboxylic acid;
4-({N-cyano-2-methyl-2-[(4-methylbenzyl)oxy]propanimidoyl}amino)adamantane-1-carboxylic acid;
methyl 4-[(N-cyano-2-methyl-2-{[4-(trifluoromethyl)benzyl]oxy}propanimidoyl)amino]adamantane-1-carboxylate;
4-{[2-(1,3-benzodioxol-5-ylmethoxy)-N-cyano-2-methylpropanimidoyl]amino}adamantane-1-carboxylic acid;
4-({N-cyano-2-[(2,4-dichlorobenzyl)oxy]-2-methylpropanimidoyl}amino)adamantane-1-carboxylic acid;
4-({N-cyano-2-[(2-methoxybenzyl)oxy]-2-methylpropanimidoyl}amino)adamantane-1-carboxamide;
4-({N-cyano-2-[(3-cyanobenzyl)oxy]-2-methylpropanimidoyl}amino)adamantane-1-carboxamide;
4-({N-cyano-2-[(2-fluorobenzyl)oxy]-2-methylpropanimidoyl}amino)adamantane-1-carboxamide;
4-({2-[(4-tert-butylbenzyl)oxy]-N-cyano-2-methylpropanimidoyl}amino)adamantane-1-carboxamide;
4-({N-cyano-2-[(3-fluorobenzyl)oxy]-2-methylpropanimidoyl}amino)adamantane-1-carboxamide;
4-[(N-cyano-2-methyl-2-{[3-(trifluoromethyl)benzyl]oxy}propanimidoyl)amino]adamantane-1-carboxamide;
4-({N-cyano-2-methyl-2-[(4-methylbenzyl)oxy]propanimidoyl}amino)adamantane-1-carboxamide;
4-({N-cyano-2-[(3,5-difluorobenzyl)oxy]-2-methylpropanimidoyl}amino)adamantane-1-carboxamide;
4-({N-cyano-2-[(3-methoxybenzyl)oxy]-2-methylpropanimidoyl}amino)adamantane-1-carboxamide;
4-({N-cyano-2-methyl-2-[(6-methylpyridin-2-yl)methoxy]propanimidoyl}amino)adamantane-1-carboxylic acid;

4-({N-cyano-2-methyl-2-[(6-methylpyridin-2-yl)methoxy]propanimidoyl}amino)adamantane-1-carboxamide;
4-({N-cyano-2-[(4-fluorobenzyl)oxy]-2-methylpropanimidoyl}amino)adamantane-1-carboxamide;
4-[(N-cyano-2-methyl-2-{[3-(trifluoromethoxy)benzyl]oxy}propanimidoyl)amino]adamantane-1-carboxylic acid;
4-[(N-cyano-2-methyl-2-{[3-(trifluoromethoxy)benzyl]oxy}propanimidoyl)amino]adamantane-1-carboxamide;
4-{[N-cyano-2-methyl-2-(quinolin-2-ylmethoxy)propanimidoyl]amino}adamantane-1-carboxamide;
methyl 4-{[(cyanoimino)(1-{[4-(trifluoromethyl)benzyl]oxy}cyclobutyl)methyl]amino}adamantane-1-carboxylate;
4-({N-cyano-2-[(2,4-dichlorobenzyl)oxy]-2-methylpropanimidoyl}amino)adamantane-1-carboxamide;
4-{[N-cyano-2-methyl-2-(quinolin-2-ylmethoxy)propanimidoyl]amino}adamantane-1-carboxylic acid;
4-({N-cyano-2-[(4-isopropylbenzyl)oxy]-2-methylpropanimidoyl}amino)adamantane-1-carboxamide;
4-({N-cyano-2-methyl-2-[(3-methylbenzyl)oxy]propanimidoyl}amino)adamantane-1-carboxamide;
4-({N-cyano-2-[(2,5-difluorobenzyl)oxy]-2-methylpropanimidoyl}amino)adamantane-1-carboxamide;
4-{[(cyanoimino)(1-{[4-(difluoromethoxy)benzyl]oxy}cyclopropyl)methyl]amino}adamantane-1-carboxylic acid;
4-({(cyanoimino)[1-(quinolin-8-ylmethoxy)cyclopropyl]methyl}amino)adamantane-1-carboxylic acid;
4-{[(cyanoimino)(1-{[4-(difluoromethoxy)benzyl]oxy}cyclopropyl)methyl]amino}adamantane-1-carboxamide;
4-({(cyanoimino)[1-(quinolin-8-ylmethoxy)cyclopropyl]methyl}amino)adamantane-1-carboxamide;
4-{[(cyanoimino)(1-{[4-(trifluoromethyl)benzyl]oxy}cyclobutyl)methyl]amino}adamantane-1-carboxylic acid;
4-{[(cyanoimino)(1-{[4-(trifluoromethyl)benzyl]oxy}cyclobutyl)methyl]amino}adamantane-1-carboxamide;
N'-cyano-N-(5-hydroxy-2-adamantyl)-2-{4-[5-(trifluoromethyl)pyridin-2-yl]piperazin-1-yl}ethanimidamide;
N'-cyano-2-(2,6-dimethylmorpholin-4-yl)-N-(5-hydroxy-2-adamantyl)propanimidamide;
N'-cyano-N-(5-hydroxy-2-adamantyl)-2-{4-[5-(trifluoromethyl)pyridin-2-yl]piperazin-1-yl}propanimidamide;
N'-cyano-N-(5-hydroxy-2-adamantyl)-2-(4-hydroxypiperidin-1-yl)propanimidamide;
2-azepan-1-yl-N'-cyano-N-(5-hydroxy-2-adamantyl)propanimidamide;
4-[(N-cyano-2-{4-[5-(trifluoromethyl)pyridin-2-yl]piperazin-1-yl}ethanimidoyl)amino]-1-adamantyl carbamate;
4-[(N-cyano-2-{4-[5-(trifluoromethyl)pyridin-2-yl]piperazin-1-yl}ethanimidoyl)amino]-1-adamantyl acetate;
N'-{4-[(N-cyano-2-{4-[5-(trifluoromethyl)pyridin-2-yl]piperazin-1-yl}ethanimidoyl)amino]-1-adamantyl}acetamide;
N'-cyano-N-(5-hydroxy-2-adamantyl)-2-methyl-2-{4-[5-(trifluoromethyl)pyridin-2-yl]piperazin-1-yl}propanimidamide;
N'-cyano-N-(5-fluoro-2-adamantyl)-2-{4-[5-(trifluoromethyl)pyridin-2-yl]piperazin-1-yl}ethanimidamide;
N'-cyano-N-(5-hydroxy-2-adamantyl)-2-[4-(5-methylpyridin-2-yl)piperazin-1-yl]propanimidamide;
2-{[2-(4-chlorophenyl)ethyl]amino}-N'-cyano-N-(5-hydroxy-2-adamantyl)propanimidamide;
2-(4-benzylpiperidin-1-yl)-N'-cyano-N-(5-hydroxy-2-adamantyl)propanimidamide;
N'-cyano-N-(5-hydroxy-2-adamantyl)-2-(6,7,9,10-tetrahydro-8H-[1,3]dioxolo[4,5-g][3]benzazepin-8-yl)propanimidamide;
N'-cyano-N-(5-hydroxy-2-adamantyl)-2-(4-pyridin-2-ylpiperazin-1-yl)propanimidamide;
N'-cyano-2-[4-(4-fluorophenyl)piperazin-1-yl]-N-(5-hydroxy-2-adamantyl)propanimidamide;
N'-cyano-N-(5-hydroxy-2-adamantyl)-2-[4-(4-methoxyphenyl)piperazin-1-yl]propanimidamide;
N'-cyano-2-[4-(5-cyanopyridin-2-yl)piperazin-1-yl]-N-(5-hydroxy-2-adamantyl)propanimidamide;
N'-cyano-2-[4-(2-furoyl)piperazin-1-yl]-N-(5-hydroxy-2-adamantyl)propanimidamide;
N'-cyano-2-(1,3-dihydro-2H-isoindol-2-yl)-N-(5-hydroxy-2-adamantyl)propanimidamide;
N'-cyano-N-(5-hydroxy-2-adamantyl)-2-{4-[4-(trifluoromethyl)phenyl]piperazin-1-yl}propanimidamide;
N'-cyano-N-(5-hydroxy-2-adamantyl)-2-{4-[5-(trifluoromethyl)pyridin-2-yl]piperazin-1-yl}propanimidamide;
2-[3-(4-chlorophenoxy)azetidin-1-yl]-N'-cyano-N-(5-hydroxy-2-adamantyl)propanimidamide;
N'-cyano-2-[4-(2-fluorophenoxy)piperidin-1-yl]-N-(5-hydroxy-2-adamantyl)propanimidamide;
N'-cyano-2-[3-(2-fluorophenoxy)piperidin-1-yl]-N-(5-hydroxy-2-adamantyl)propanimidamide;
N'-cyano-2-[3-(3-fluorophenoxy)pyrrolidin-1-yl]-N-(5-hydroxy-2-adamantyl)propanimidamide;
N'-cyano-2-[[2-(3,4-dichlorophenyl)ethyl](methyl)amino]-N-(5-hydroxy-2-adamantyl)propanimidamide;
2-[[2-(4-chlorophenyl)-1-methylethyl](methyl)amino]-N'-cyano-N-(5-hydroxy-2-adamantyl)propanimidamide;
2-(5-chloro-2,3-dihydro-1H-indol-1-yl)-N'-cyano-N-(5-hydroxy-2-adamantyl)propanimidamide;
2-[4-(6-chloropyridin-3-yl)piperazin-1-yl]-N'-cyano-N-(5-hydroxy-2-adamantyl)propanimidamide;
N'-cyano-N-(5-hydroxy-2-adamantyl)-2-(3-phenylazetidin-1-yl)propanimidamide;
N'-cyano-N-[5-(hydroxymethyl)-2-adamantyl]-2-methyl-2-{4-[5-(trifluoromethyl)pyridin-2-yl]piperazin-1-yl}propanimidamide;
4-[(N-cyano-2-methyl-2-{4-[5-(trifluoromethyl)pyridin-2-yl]piperazin-1-yl}propanimidoyl)amino]-N-methyladamantane-1-carboxamide;
4-[(N-cyano-2-methyl-2-{4-[5-(trifluoromethyl)pyridin-2-yl]piperazin-1-yl}propanimidoyl)amino]-N-methoxyadamantane-1-carboxamide;
4-[(N-cyano-2-methyl-2-{4-[5-(trifluoromethyl)pyridin-2-yl]piperazin-1-yl}propanimidoyl)amino]-N-hydroxyadamantane-1-carboxamide;
N-[5-(aminomethyl)-2-adamantyl]-N-cyano-2-methyl-2-{4-[5-(trifluoromethyl)pyridin-2-yl]piperazin-1-yl}propanimidamide;
N'-cyano-N-(5-hydroxy-2-adamantyl)-1-{[4-(trifluoromethyl)benzyl]amino}cyclopropanecarboximidamide;
4-({N-cyano-2-methyl-2-[2-(trifluoromethyl)pyrrolidin-1-yl]propanimidoyl}amino)adamantane-1-carboxamide;
4-{[N-cyano-2-(3,3-difluoropiperidin-1-yl)-2-methylpropanimidoyl]amino}adamantane-1-carboxamide;
N'-cyano-N-(5-hydroxy-2-adamantyl)-1-piperidin-1-ylcyclopropanecarboximidamide;

N'-cyano-2-methyl-N-[5-(5-methyl-1,2,4-oxadiazol-3-yl)-2-adamantyl]-2-{4-[5-(trifluoromethyl)pyridin-2-yl]piperazin-1-yl}propanimidamide;
N'-cyano-2-methyl-N-[5-(2H-tetraazol-5-yl)-2-adamantyl]-2-{4-[5-(trifluoromethyl)pyridin-2-yl]piperazin-1-yl}propanimidamide;
4-[(2-{4-[[(4-chlorophenyl)sulfonyl](cyclopropyl)amino]piperidin-1-yl}-N-cyanopropanimidoyl)amino]adamantane-1-carboxamide;
4-[(N-cyano-2-{4-[5-(trifluoromethyl)pyridin-2-yl]piperazin-1-yl}propanimidoyl)amino]adamantane-1-carboxamide;
N'-cyano-N-(5-hydroxy-2-adamantyl)-2-methyl-2-[2-(trifluoromethyl)pyrrolidin-1-yl]propanimidamide;
4-{[N-cyano-2-(3-fluoropyrrolidin-1-yl)-2-methylpropanimidoyl]amino}adamantane-1-carboxamide;
4-{[N-cyano-2-(3-fluoropyrrolidin-1-yl)propanimidoyl]amino}adamantane-1-carboxamide;
4-{[N-cyano-2-(3,3-difluoropiperidin-1-yl)propanimidoyl]amino}adamantane-1-carboxamide;
4-({N-cyano-2-[2-(trifluoromethyl)pyrrolidin-1-yl]propanimidoyl}amino)adamantane-1-carboxamide;
methyl 4-{[N-cyano-2-methyl-2-(4-pyridin-2-ylpiperazin-1-yl)propanimidoyl]amino}adamantane-1-carboxylate;
4-{[N-cyano-2-methyl-2-(4-pyridin-2-ylpiperazin-1-yl)propanimidoyl]amino}adamantane-1-carboxylic acid;
4-{[N-cyano-2-methyl-2-(2-methyl-4-pyridin-2-ylpiperazin-1-yl)propanimidoyl]amino}adamantane-1-carboxylic acid;
4-({2-[4-(5-chloropyridin-2-yl)piperazin-1-yl]-N-cyano-2-methylpropanimidoyl}amino)adamantane-1-carboxylic acid;
4-{[N-cyano-2-(3,3-difluoropiperidin-1-yl)ethanimidoyl]amino}adamantane-1-carboxylic acid;
4-({N-cyano-2-[2-(trifluoromethyl)pyrrolidin-1-yl]ethanimidoyl}amino)adamantane-1-carboxylic acid;
4-{[[(cyanoimino)(1-{4-[5-(trifluoromethyl)pyridin-2-yl]piperazin-1-yl}cyclopropyl)methyl]amino}adamantane-1-carboxylic acid;
4-[(N-cyano-2-{4-[5-(trifluoromethyl)pyridin-2-yl]piperazin-1-yl}ethanimidoyl)amino]adamantane-1-carboxylic acid;
4-{[N-cyano-2-methyl-2-(4-pyridin-2-ylpiperazin-1-yl)propanimidoyl]amino}adamantane-1-carboxamide;
4-[(N-cyano-2-{4-[5-(trifluoromethyl)pyridin-2-yl]piperazin-1-yl}ethanimidoyl)amino]adamantane-1-carboxamide;
N'-cyano-2-methyl-N-[5-(4H-1,2,4-triazol-3-yl)-2-adamantyl]-2-{4-[5-(trifluoromethyl)pyridin-2-yl]piperazin-1-yl}propanimidamide;
4-{[N-cyano-2-(3,3-difluoropiperidin-1-yl)-2-methylpropanimidoyl]amino}-N-(2-furylmethyl)adamantane-1-carboxamide;
4-{[N-cyano-2-(3,3-difluoropiperidin-1-yl)-2-methylpropanimidoyl]amino}-N-(pyridin-4-ylmethyl)adamantane-1-carboxamide;
4-{[[(cyanoimino)(1-{4-[5-(trifluoromethyl)pyridin-2-yl]piperazin-1-yl}cyclopropyl)methyl]amino}adamantane-1-carboxamide;
4-({2-[4-(4-chlorophenyl)piperidin-1-yl]-N-cyano-2-methylpropanimidoyl}amino)adamantane-1-carboxylic acid;
4-{[N-cyano-2-methyl-2-(4-phenylpiperidin-1-yl)propanimidoyl]amino}adamantane-1-carboxylic acid;
4-{[N-cyano-2-methyl-2-(1,2,4,5-tetrahydro-3H-3-benzazepin-3-yl)propanimidoyl]amino}adamantane-1-carboxylic acid;
4-[(N-cyano-2-methyl-2-{4-[4-(trifluoromethyl)phenyl]piperazin-1-yl}propanimidoyl)amino]adamantane-1-carboxylic acid;
4-({N-cyano-2-[2-(trifluoromethyl)pyrrolidin-1-yl]ethanimidoyl}amino)adamantane-1-carboxamide;
4-{[N-cyano-2-(3,3-difluoropiperidin-1-yl)ethanimidoyl]amino}adamantane-1-carboxamide;
4-({N-cyano-2-methyl-2-[2-methyl-4-(5-methylpyridin-2-yl)piperazin-1-yl]propanimidoyl}amino)adamantane-1-carboxylic acid;
4-{[N-cyano-2-(3-fluoropiperidin-1-yl)propanimidoyl]amino}adamantane-1-carboxamide;
4-[(N-cyano-2-methyl-2-{[4-(trifluoromethyl)benzyl]oxy}propanimidoyl)amino]adamantane-1-carboxylic acid;
4-[(N-cyano-2-{4-[5-(trifluoromethyl)pyridin-2-yl]piperazin-1-yl}propanimidoyl)amino]adamantane-1-carboxamide;
4-[(N-cyano-2-{[4-(trifluoromethyl)benzyl]oxy}propanimidoyl)amino]adamantane-1-carboxylic acid;
4-[(N-cyano-2-{2-(trifluoromethyl)-4-[5-(trifluoromethyl)pyridin-2-yl]piperazin-1-yl}ethanimidoyl)amino]adamantane-1-carboxamide;
4-({N-cyano-2-[4-(5-fluoropyridin-3-yl)-1,4-diazepan-1-yl]-2-methylpropanimidoyl}amino)adamantane-1-carboxamide;
4-[(N-cyano-2-cyclopropyl-2-{4-[5-(trifluoromethyl)pyridin-2-yl]piperazin-1-yl}ethanimidoyl)amino]adamantane-1-carboxylic acid;
4-{[(cyanoimino)(1-{4-[5-(trifluoromethyl)pyridin-2-yl]piperazin-1-yl}cyclobutyl)methyl]amino}adamantane-1-carboxylic acid;
4-[(N-cyano-2-methyl-2-{5-[3-(trifluoromethyl)phenyl]-1,5-diazocan-1-yl}propanimidoyl)amino]adamantane-1-carboxylic acid;
4-({N-cyano-2-methyl-2-[4-(3-methylphenyl)-1,4-diazepan-1-yl]propanimidoyl}amino)adamantane-1-carboxylic acid;
4-[(N-cyano-2-methyl-2-phenoxypropanimidoyl)amino]adamantane-1-carboxamide;
4-[(N-cyano-2-methyl-2-{[4-(trifluoromethyl)benzyl]oxy}propanimidoyl)amino]adamantane-1-carboxamide;
4-({2-[7-(5-bromopyridin-2-yl)-3,7-diazabicyclo[3.3.1]non-3-yl]-N-cyano-2-methylpropanimidoyl}amino)adamantane-1-carboxamide;
4-({2-[5-(6-chloropyridin-3-yl)hexahydropyrrolo[3,4-c]pyrrol-2(1H)-yl]-N-cyano-2-methylpropanimidoyl}amino)adamantane-1-carboxamide;
4-{[N-cyano-2-methyl-2-(3-pyridin-3-yl-3,9-diazabicyclo[4.2.1]non-9-yl)propanimidoyl]amino}adamantane-1-carboxamide;
4-({[(4-{[N-cyano-2-(3,3-difluoropiperidin-1-yl)-2-methylpropanimidoyl]amino}-1-adamantyl)carbonyl]amino}methyl)benzoic acid;
4-[(N-cyano-2-{4-[5-(trifluoromethyl)pyridin-2-yl]piperazin-1-yl}butanimidoyl)amino]adamantane-1-carboxamide;
4-[(N-cyano-2-cyclopropyl-2-{4-[5-(trifluoromethyl)pyridin-2-yl]piperazin-1-yl}ethanimidoyl)amino]adamantane-1-carboxamide;
4-{[(cyanoimino)(1-{4-[5-(trifluoromethyl)pyridin-2-yl]piperazin-1-yl}cyclobutyl)methyl]amino}adamantane-1-carboxamide;
4-({N-cyano-2-methyl-2-[(2-methylcyclohexyl)oxy]propanimidoyl}amino)adamantane-1-carboxylic acid;

4-({N-cyano-2-methyl-2-[(3-methylcyclohexyl)oxy]
propanimidoyl}amino)adamantane-1-carboxylic acid;
4-{[N-cyano-2-(cycloheptyloxy)-2-methylpropanimidoyl]
amino}adamantane-1-carboxylic acid;
4-{[N-cyano-2-(cyclohexylmethoxy)-2-methylpropanimidoyl]amino}adamantane-1-carboxylic acid;
4-{[2-(benzyloxy)-N-cyanoethanimidoyl]
amino}adamantane-1-carboxylic acid;
4-{[2-(4-chlorophenoxy)-N-cyano-2-methylpropanimidoyl]
amino}adamantane-1-carboxylic acid;
4-{[N-cyano-2-(3,3-difluoropiperidin-1-yl)-2-methylpropanimidoyl]amino}-N-(1,3-thiazol-5-ylmethyl)adamantane-1-carboxamide;
4-{[N-cyano-2-(3,3-difluoropiperidin-1-yl)-2-methylpropanimidoyl]amino}-N-(2-methoxybenzyl)adamantane-1-carboxamide;
4-{[N-cyano-2-(3,3-difluoropiperidin-1-yl)-2-methylpropanimidoyl]amino}-N-(3,4-dimethoxybenzyl)adamantane-1-carboxamide;
4-({2-[9-(6-chloropyridin-3-yl)-3,9-diazabicyclo[4.2.1]non-3-yl]-N-cyano-2-methylpropanimidoyl}amino)adamantane-1-carboxamide;
4-[(2-anilino-N-cyano-2-methylpropanimidoyl)amino]adamantane-1-carboxamide;
4-({N-cyano-2-[4-(2,3-dichlorophenyl)piperazin-1-yl]-2-methylpropanimidoyl}amino)adamantane-1-carboxylic acid;
4-{[N-cyano-2-methyl-2-(4-phenylpiperazin-1-yl)propanimidoyl]amino}adamantane-1-carboxylic acid;
4-({N-cyano-2-methyl-2-[4-(4-methylphenyl)piperazin-1-yl]propanimidoyl}amino)adamantane-1-carboxylic acid;
4-({2-[4-(1,3-benzothiazol-2-yl)piperazin-1-yl]-N-cyano-2-methylpropanimidoyl}amino)adamantane-1-carboxylic acid;
4-({N-cyano-2-[4-(3,4-dichlorophenyl)piperazin-1-yl]-2-methylpropanimidoyl}amino)adamantane-1-carboxylic acid;
4-({N-cyano-2-methyl-2-[4-(3-methylphenyl)piperazin-1-yl]propanimidoyl}amino)adamantane-1-carboxylic acid;
4-[(N-cyano-2-methyl-2-{4-[2-(trifluoromethyl)phenyl]piperazin-1-yl}propanimidoyl)amino]adamantane-1-carboxylic acid;
4-({N-cyano-2-[4-(2,4-difluorophenyl)piperazin-1-yl]-2-methylpropanimidoyl}amino)adamantane-1-carboxylic acid;
4-({N-cyano-2-methyl-2-[4-(6-methylpyridin-2-yl)piperazin-1-yl]propanimidoyl}amino)adamantane-1-carboxylic acid;
4-{[N-cyano-2-methyl-2-(4-pyrimidin-2-ylpiperazin-1-yl)propanimidoyl]amino}adamantane-1-carboxylic acid;
4-({N-cyano-2-[4-(4-fluorophenyl)piperazin-1-yl]-2-methylpropanimidoyl}amino)adamantane-1-carboxylic acid;
4-[(N-cyano-2-methyl-2-{4-[3-(trifluoromethyl)phenyl]piperazin-1-yl}propanimidoyl)amino]adamantane-1-carboxylic acid;
4-[(N-cyano-2-methyl-2-{4-[3-(trifluoromethyl)pyridin-2-yl]piperazin-1-yl}propanimidoyl)amino]adamantane-1-carboxylic acid;
4-({2-[4-(3-chlorophenyl)piperazin-1-yl]-N-cyano-2-methylpropanimidoyl}amino)adamantane-1-carboxylic acid;
4-({2-[4-(4-acetylphenyl)piperazin-1-yl]-N-cyano-2-methylpropanimidoyl}amino)adamantane-1-carboxylic acid;

4-[(N-cyano-2-methyl-2-{4-[5-(trifluoromethyl)pyridin-2-yl]piperazin-1-yl}propanimidoyl)amino]-N,N-dimethyladamantane-1-carboxamide;
4-{[[1-(4-chlorophenyl)cyclobutyl](cyanoimino)methyl]
amino}adamantane-1-carboxylic acid;
4-{[(cyanoimino)(1-phenylcyclopropyl)methyl]
amino}adamantane-1-carboxylic acid;
4-[(N-cyano-2-methyl-2-phenylpropanimidoyl)amino]adamantane-1-carboxylic acid;
4-{[2-(4-chlorophenoxy)-N-cyano-2-methylpropanimidoyl]
amino}adamantane-1-carboxamide;
4-({N-cyano-2-methyl-2-[(4-methylcyclohexyl)oxy]
propanimidoyl}amino)adamantane-1-carboxamide;
N-{4-[(N-cyano-2-{4-[5-(trifluoromethyl)pyridin-2-yl]piperazin-1-yl}propanimidoyl)amino]-1-
adamantyl}acetamide;
4-{[N-cyano-2-methyl-2-(4-pyrimidin-2-ylpiperazin-1-yl)
propanimidoyl]amino}adamantane-1-carboxamide;
4-{[N-cyano-2-methyl-2-(4-pyrazin-2-ylpiperazin-1-yl)propanimidoyl]amino}adamantane-1-carboxamide;
4-({N-cyano-2-[4-(4-fluorophenyl)piperazin-1-yl]-2-methylpropanimidoyl}amino)adamantane-1-carboxamide;
4-({N-cyano-2-[4-(3-cyanopyridin-2-yl)piperazin-1-yl]-2-methylpropanimidoyl}amino)adamantane-1-carboxamide;
4-({N-cyano-2-methyl-2-[4-(6-methylpyridin-3-yl)-1,4-diazepan-1-yl]propanimidoyl}amino)adamantane-1-carboxamide;
4-[(2-{4-[3-chloro-5-(trifluoromethyl)pyridin-2-yl]piperazin-1-yl}-N-cyano-2-methylpropanimidoyl)amino]adamantane-1-carboxylic acid;
4-[(N-cyano-2-phenoxypropanimidoyl)amino]adamantane-1-carboxamide;
4-{[2-(benzyloxy)-N-cyano ethanimidoyl]
amino}adamantane-1-carboxamide;
4-(2-{[(4-{[N-cyano-2-(3,3-difluoropiperidin-1-yl)-2-methylpropanimidoyl]amino}-1-adamantyl)carbonyl]
amino}ethyl)benzoic acid;
4-{[N-cyano-2-methyl-2-(2-methylphenoxy)propanimidoyl]amino}adamantane-1-carboxylic acid;
4-{[N-cyano-2-methyl-2-(4-methylphenoxy)propanimidoyl]amino}adamantane-1-carboxylic acid;
4-{[2-(2-chlorophenoxy)-N-cyano-2-methylpropanimidoyl]
amino}adamantane-1-carboxylic acid;
4-[(N-cyano-2-methyl-2-phenylpropanimidoyl)amino]adamantane-1-carboxamide;
4-{[(cyanoimino)(1-phenylcyclopropyl)methyl]
amino}adamantane-1-carboxamide;
4-{[[1-(4-chlorophenyl)cyclobutyl](cyanoimino)methyl]
amino}adamantane-1-carboxamide;
N'-cyano-N-{5-[(methylsulfonyl)amino]-2-adamantyl}-2-
{4-[5-(trifluoromethyl)pyridin-2-yl]piperazin-1-
yl}propanimidamide;
4-{[N-cyano-2-(2-methoxyphenoxy)-2-methylpropanimidoyl]amino}adamantane-1-carboxamide;
4-{[N-cyano-2-(4-methoxyphenoxy)-2-methylpropanimidoyl]amino}adamantane-1-carboxamide;
4-({N-cyano-2-methyl-2-[3-(trifluoromethyl)phenoxy]
propanimidoyl}amino)adamantane-1-carboxamide;
N-cyano-N-[5-(1-hydroxy-1-methylethyl)-2-adamantyl]-2-
methyl-2-{4-[5-(trifluoromethyl)pyridin-2-yl]piperazin-
1-yl}propanimidamide;
4-{[N-cyano-2-methyl-2-(4-methylphenoxy)propanimidoyl]amino}adamantane-1-carboxamide;
4-{[2-(3-chlorophenoxy)-N-cyano-2-methylpropanimidoyl]
amino}adamantane-1-carboxamide;

4-{[N-cyano-2-methyl-2-(tetrahydro-2H-pyran-2-yl-methoxy)propanimidoyl]amino}adamantane-1-carboxylic acid;
4-{[N-cyano-2-methyl-2-(4-phenylpiperazin-1-yl)propanimidoyl]amino}adamantane-1-carboxamide;
4-{[N-cyano-2-(3-methoxyphenoxy)-2-methylpropanimidoyl]amino}adamantane-1-carboxamide;
4-({N-cyano-2-methyl-2-[4-(trifluoromethoxy)phenoxy]propanimidoyl}amino)adamantane-1-carboxamide;
4-({N-cyano-2-[4-(2-methoxyphenyl)piperazin-1-yl]-2-methylpropanimidoyl}amino)adamantane-1-carboxamide;
4-({N-cyano-2-methyl-2-[methyl(phenyl)amino]propanimidoyl}amino)adamantane-1-carboxamide;
4-({N-cyano-2-[4-(2,4-dimethoxyphenyl)piperazin-1-yl]-2-methylpropanimidoyl}amino)adamantane-1-carboxamide;
4-{[N-cyano-2-(cyclohexylmethoxy)-2-methylpropanimidoyl]amino}adamantane-1-carboxamide;
4-({N-cyano-2-[4-(2,3-dicyanophenyl)piperazin-1-yl]-2-methylpropanimidoyl}amino)adamantane-1-carboxamide;
N-cyano-N-[5-(cyanomethyl)-2-adamantyl]-2-methyl-2-{4-[5-(trifluoromethyl)pyridin-2-yl]piperazin-1-yl}propanimidamide;
4-({N-cyano-2-methyl-2-[4-(4-nitrophenyl)piperazin-1-yl]propanimidoyl}amino)adamantane-1-carboxylic acid;
2-(4-chlorophenoxy)-N'-cyano-N-(5-hydroxy-2-adamantyl)-2-methylpropanimidamide;
4-({N-cyano-2-[4-(2,4-dichlorophenyl)piperazin-1-yl]-2-methylpropanimidoyl}amino)adamantane-1-carboxylic acid;
N-2-adamantyl-2-(4-chlorophenoxy)-N'-cyano-2-methylpropanimidamide;
N-2-adamantyl-N'-cyano-2-methyl-2-phenylpropanimidamide;
N-2-adamantyl-N'-cyano-1-phenylcyclopropanecarboximidamide;
{4-[(N-cyano-2-methyl-2-{4-[5-(trifluoromethyl)pyridin-2-yl]piperazin-1-yl}propanimidoyl)amino]-1-adamantyl}acetic acid;
4-({2-[4-(4-chloro-2-fluorophenyl)piperazin-1-yl]-N-cyano-2-methylpropanimidoyl}amino)adamantane-1-carboxylic acid;
4-[(N-cyano-2-methyl-2-{4-[4-(trifluoromethyl)pyrimidin-2-yl]piperazin-1-yl}propanimidoyl)amino]adamantane-1-carboxylic acid;
4-({2-[4-(3-chloro-4-fluorophenyl)piperazin-1-yl]-N-cyano-2-methylpropanimidoyl}amino)adamantane-1-carboxylic acid;
4-({N-cyano-2-[4-(4-cyanophenyl)piperazin-1-yl]-2-methylpropanimidoyl}amino)adamantane-1-carboxylic acid;
4-({2-[4-(4-bromophenyl)piperazin-1-yl]-N-cyano-2-methylpropanimidoyl}amino)adamantane-1-carboxylic acid;
4-({2-[4-(5-chloro-2-methoxyphenyl)piperazin-1-yl]-N-cyano-2-methylpropanimidoyl}amino)adamantane-1-carboxylic acid;
4-({2-[4-(2-chlorophenyl)piperazin-1-yl]-N-cyano-2-methylpropanimidoyl}amino)adamantane-1-carboxylic acid;
4-({N-cyano-2-[4-(2-cyanophenyl)piperazin-1-yl]-2-methylpropanimidoyl}amino)adamantane-1-carboxylic acid;
4-({N-cyano-2-[4-(2-fluorophenyl)piperazin-1-yl]-2-methylpropanimidoyl}amino)adamantane-1-carboxylic acid;
4-({N-cyano-2-methyl-2-[4-(2-methylphenyl)piperazin-1-yl]propanimidoyl}amino)adamantane-1-carboxylic acid;
4-({2-[4-(4-chlorophenyl)piperazin-1-yl]-N-cyano-2-methylpropanimidoyl}amino)adamantane-1-carboxylic acid;
6-[(1-cycloheptyl-4,4-dimethyl-5-oxopyrrolidin-3-yl)methoxy]nicotinonitrile;
4-({2-[4-(3-chloropyridin-2-yl)piperazin-1-yl]-N-cyano-2-methylpropanimidoyl}amino)adamantane-1-carboxylic acid;
4-[(2-{4-[2-chloro-4-(trifluoromethyl)phenyl]piperazin-1-yl}-N-cyano-2-methylpropanimidoyl)amino]adamantane-1-carboxylic acid;
4-{[N-cyano-2-(3-fluoropyrrolidin-1-yl)-2-methylpropanimidoyl]amino}-N-(pyridin-3-ylmethyl)adamantane-1-carboxamide;
4-({2-[(4-chlorophenyl)thio]-N-cyano-2-methylpropanimidoyl}amino)adamantane-1-carboxylic acid;
4-{[N-cyano-2-methyl-2-(3-phenylpiperidin-1-yl)propanimidoyl]amino}adamantane-1-carboxamide;
4-({2-[4-(2-chloro-4-methylphenyl)piperazin-1-yl]-N-cyano-2-methylpropanimidoyl}amino)adamantane-1-carboxylic acid;
4-{[2-(3-bromophenoxy)-N-cyano-2-methylpropanimidoyl]amino}adamantane-1-carboxylic acid;
1-cycloheptyl-4-{[(2-fluorophenyl)(methyl)amino]methyl}-3,3-dimethylpyrrolidin-2-one;
4-({N-cyano-2-[4-(2-fluorophenyl)piperidin-1-yl]-2-methylpropanimidoyl}amino)adamantane-1-carboxylic acid;
4-({N-cyano-2-methyl-2-[4-(2-methylphenyl)piperidin-1-yl]propanimidoyl}amino)adamantane-1-carboxylic acid;
4-({2-[4-(2-chloro-4-fluorophenyl)piperazin-1-yl]-N-cyano-2-methylpropanimidoyl}amino)adamantane-1-carboxamide;
4-({[(4-{[2-(4-chlorophenoxy)-N-cyano-2-methylpropanimidoyl]amino}-1-adamantyl)carbonyl]amino}methyl)benzoic acid;
4-{[2-({1-[(benzyloxy)carbonyl]piperidin-4-yl}methoxy)-N-cyano-2-methylpropanimidoyl]amino}adamantane-1-carboxylic acid;
4-({N-cyano-2-[4-(2-furoyl)piperazin-1-yl]-2-methylpropanimidoyl}amino)adamantane-1-carboxylic acid;
4-({2-[4-(2-chloro-4-cyanophenyl)piperazin-1-yl]-N-cyano-2-methylpropanimidoyl}amino)adamantane-1-carboxylic acid;
4-({2-[4-(2-chloro-4-fluorophenyl)piperazin-1-yl]-N-cyano-2-methylpropanimidoyl}amino)adamantane-1-carboxylic acid;
1-cycloheptyl-3,3-dimethyl-4-(phenoxymethyl)pyrrolidin-2-one;
4-{[[1-(4-chlorophenyl)cyclohexyl](cyanoimino)methyl]amino}adamantane-1-carboxamide;
4-{[[1-(4-chlorophenyl)cyclopropyl](cyanoimino)methyl]amino}adamantane-1-carboxamide;
4-{[[1-(4-chlorophenyl)cyclopentyl](cyanoimino)methyl]amino}adamantane-1-carboxamide;
4-{[2-(4-chlorophenyl)-N-cyano-2-methylpropanimidoyl]amino}adamantane-1-carboxamide;
4-{[(cyanoimino)(1-phenylcyclopentyl)methyl]amino}adamantane-1-carboxamide;

4-{[N-cyano-2-(2,3-dimethylphenoxy)-2-methylpropanimidoyl]amino}adamantane-1-carboxylic acid;
4-[(N-cyano-2-methyl-2-{4-[5-(trifluoromethyl)pyridin-2-yl]piperazin-1-yl}propanimidoyl)amino]-1-adamantyl carbamate;
4-[(2-{4-[(4-chlorophenyl)sulfonyl]piperazin-1-yl}-N-cyano-2-methylpropanimidoyl)amino]adamantane-1-carboxylic acid;
4-{[2-(benzyloxy)-N-cyano-2-methylpropanimidoyl]amino}adamantane-1-carboxylic acid;
4-(4-{[(5-cyanopyridin-2-yl)oxy]methyl}-3,3-dimethyl-2-oxopyrrolidin-1-yl)azepane-1-carboxamide;
4-({N-cyano-2-[4-(2,4-difluorophenyl)piperidin-1-yl]-2-methylpropanimidoyl}amino)adamantane-1-carboxylic acid;
6-{[1-(5-hydroxycyclooctyl)-4,4-dimethyl-5-oxopyrrolidin-3-yl]methoxy}nicotinonitrile;
4-({N-cyano-2-[4-(4-cyano-2-fluorophenyl)piperazin-1-yl]-2-methylpropanimidoyl}amino)adamantane-1-carboxylic acid;
4-(2-(cyanoimino)-4-{[(5-cyanopyridin-2-yl)oxy]methyl}-3,3-dimethylpyrrolidin-1-yl)adamantane-1-carboxamide;
9-(4-{[(5-cyanopyridin-2-yl)oxy]methyl}-3,3-dimethyl-2-oxopyrrolidin-1-yl)bicyclo[3.3.1]nonane-3-carboxamide;
N-[4-(aminosulfonyl)benzyl]-4-{[2-(4-chlorophenoxy)-N-cyano-2-methylpropanimidoyl]amino}adamantane-1-carboxamide;
tert-butyl 4-[2-{[5-(aminocarbonyl)-2-adamantyl]amino}-2-(cyanoimino)-1,1-dimethylethoxy]phenylcarbamate;
ethyl 4-(4-{[(5-cyanopyridin-2-yl)oxy]methyl}-3,3-dimethyl-2-oxopyrrolidin-1-yl)bicyclo[5.1.0]octane-8-carboxylate;
N-[4-(aminocarbonyl)benzyl]-4-{[2-(4-chlorophenoxy)-N-cyano-2-methylpropanimidoyl]amino}adamantane-1-carboxamide;
[(4-{[2-(4-chlorophenoxy)-N-cyano-2-methylpropanimidoyl]amino}-1-adamantyl)carbonyl]glycine;
3-({[(4-{[2-(4-chlorophenoxy)-N-cyano-2-methylpropanimidoyl]amino}-1-adamantyl)carbonyl]amino}methyl)benzoic acid;
4-({(cyanoimino)[1-(3-fluorophenyl)cyclopentyl]methyl}amino)adamantane-1-carboxamide;
4-{[[1-(2-chloro-4-fluorophenyl)cyclopentyl](cyanoimino)methyl]amino}adamantane-1-carboxamide;
4-({(cyanoimino)[1-(4-fluorophenyl)cyclopentyl]methyl}amino)adamantane-1-carboxamide;
4-({(cyanoimino)[1-(2-fluorophenyl)cyclopentyl]methyl}amino)adamantane-1-carboxamide;
4-{[(cyanoimino)(1-methylcyclohexyl)methyl]amino}adamantane-1-carboxamide;
4-({(cyanoimino)[1-(2,4-dichlorophenyl)cyclopropyl]methyl}amino)adamantane-1-carboxamide;
4-({(cyanoimino)[1-(4-methoxyphenyl)cyclopropyl]methyl}amino)adamantane-1-carboxamide;
4-({(cyanoimino)[1-(4-methylphenyl)cyclopropyl]methyl}amino)adamantane-1-carboxamide;
4-[(N-cyano-2-methyl-2-{3-methyl-4-[5-(trifluoromethyl)pyridin-2-yl]piperazin-1-yl}propanimidoyl)amino]adamantane-1-carboxylic acid;
4-({N-cyano-2-[4-(4-cyanophenyl)-3,5-dimethyl-1H-pyrazol-1-yl]-2-methylpropanimidoyl}amino)adamantane-1-carboxylic acid;
4-({N-cyano-2-[4-(4-cyanophenyl)-3,5-dimethyl-1H-pyrazol-1-yl]-2-methylpropanimidoyl}amino)adamantane-1-carboxamide;
6-{[4,4-dimethyl-1-(4-methylbicyclo[2.2.2]oct-1-yl)-5-oxopyrrolidin-3-yl]methoxy}nicotinonitrile;
4-{[N-cyano-2-methyl-2-(4-pyridin-4-ylphenyl)propanimidoyl]amino}adamantane-1-carboxamide;
6-{[1-(5-cyanocyclooctyl)-4,4-dimethyl-5-oxopyrrolidin-3-yl]methoxy}nicotinonitrile;
4-[(N-cyano-2-methyl-2-thien-2-ylpropanimidoyl)amino]adamantane-1-carboxamide;
4-[(N-cyano-2-methyl-2-thien-3-ylpropanimidoyl)amino]adamantane-1-carboxamide;
4-({N-cyano-2-methyl-2-[5-(trifluoromethyl)pyridin-2-yl]propanimidoyl}amino)adamantane-1-carboxamide;
4-[(N-cyano-2-methyl-2-{4-[5-(trifluoromethyl)pyridin-2-yl]phenyl}propanimidoyl)amino]adamantane-1-carboxamide;
4-({2-[4-chloro-2-(pyrrolidin-1-ylsulfonyl)phenoxy]-N-cyano-2-methylpropanimidoyl}amino)adamantane-1-carboxamide;
4-({N-cyano-2-methyl-2-[4-(methylsulfonyl)phenoxy]propanimidoyl}amino)adamantane-1-carboxamide;
4-({(cyanoimino)[1-(4-methoxyphenyl)cyclopentyl]methyl}amino)adamantane-1-carboxamide;
4-({N-cyano-2-methyl-2-[(3-methylphenyl)amino]propanimidoyl}amino)adamantane-1-carboxamide;
tert-butyl 4-[2-{[5-(aminocarbonyl)-2-adamantyl]amino}-2-(cyanoimino)-1,1-dimethylethyl]piperazine-1-carboxylate;
N-cyano-2-(3-fluoropyrrolidin-1-yl)-N-(5-hydroxy-2-adamantyl)propanimidamide;
4-({N-cyano-2-methyl-2-[2-(methylsulfonyl)phenoxy]propanimidoyl}amino)adamantane-1-carboxamide;
4-({2-[4-(2-bromophenyl)piperazin-1-yl]-N-cyano-2-methylpropanimidoyl}amino)adamantane-1-carboxylic acid;
4-{[2-(4-bromophenyl)-N-cyano-2-methylpropanimidoyl]amino}adamantane-1-carboxamide;
4-({2-[(3-chlorophenyl)amino]-N-cyano-2-methylpropanimidoyl}amino)adamantane-1-carboxamide;
4-({N-cyano-2-[(3-methoxyphenyl)amino]-2-methylpropanimidoyl}amino)adamantane-1-carboxamide;
4-({N-cyano-2-[4-(4-cyanophenyl)-3,5-dimethyl-1H-pyrazol-1-yl]-2-methylpropanimidoyl}amino)-N-(1,3-thiazol-5-ylmethyl)adamantane-1-carboxamide;
4-({2-[4-(6-chloropyrimidin-4-yl)piperazin-1-yl]-N-cyano-2-methylpropanimidoyl}amino)adamantane-1-carboxylic acid;
4-({2-[4-(6-chloropyridazin-3-yl)piperazin-1-yl]-N-cyano-2-methylpropanimidoyl}amino)adamantane-1-carboxylic acid;
4-({2-[4-(2-chloropyrimidin-4-yl)piperazin-1-yl]-N-cyano-2-methylpropanimidoyl}amino)adamantane-1-carboxylic acid;
4-[(2-{4-chloro-2-[(diethylamino)sulfonyl]phenoxy}-N-cyano-2-methylpropanimidoyl)amino]adamantane-1-carboxamide;
N-[({4-[(N-cyano-2-methyl-2-{4-[5-(trifluoromethyl)pyridin-2-yl]piperazin-1-yl}propanimidoyl)amino]-1-adamantyl}amino)carbonyl]glycine;
4-({N-cyano-2-[4-(5-cyanopyridin-2-yl)piperazin-1-yl]-2-methylpropanimidoyl}amino)adamantane-1-carboxylic acid;
4-({2-[4-(3-chloro-5-cyanopyridin-2-yl)piperazin-1-yl]-N-cyano-2-methylpropanimidoyl}amino)adamantane-1-carboxylic acid;
4-({N-cyano-2-methyl-2-[4-(1,3-thiazol-2-yl)piperazin-1-yl]propanimidoyl}amino)adamantane-1-carboxylic acid;

4-({2-[(5-bromopyridin-2-yl)oxy]-N-cyano-2-methylpropanimidoyl}amino)adamantane-1-carboxamide;

1-(5-cyano-2-adamantyl)-4-{[(5-cyanopyridin-2-yl)oxy]methyl}-3,3-dimethylpyrrolidin-2-ylidenecyanamide;

4-({N-cyano-2-methyl-2-[4-(pyrrolidin-1-ylsulfonyl)phenoxy]propanimidoyl}amino)adamantane-1-carboxamide;

4-({N-cyano-2-[(4-methoxyphenyl)amino]-2-methylpropanimidoyl}amino)adamantane-1-carboxamide;

4-[(N-cyano-2-{[4-(dimethylamino)phenyl]amino}-2-methylpropanimidoyl)amino]adamantane-1-carboxamide;

4-[(N-cyano-2-methyl-2-{[4-(trifluoromethyl)phenyl]amino}propanimidoyl)amino]adamantane-1-carboxamide;

4-[(N-cyano-2-methyl-2-{[3-(trifluoromethyl)phenyl]amino}propanimidoyl)amino]adamantane-1-carboxamide;

4-({(cyanoimino)[3-methyl-1-(2-methylbenzyl)-2-oxopiperidin-3-yl]methyl}amino)adamantane-1-carboxamide;

4-{[N-cyano-2-(2-cyanophenoxy)-2-methylpropanimidoyl]amino}adamantane-1-carboxamide;

4-(2-(cyanoimino)-3,3-dimethyl-4-{[4-(1H-1,2,4-triazol-1-yl)phenoxy]methyl}pyrrolidin-1-yl)adamantane-1-carboxamide;

4-(2-(cyanoimino)-4-{[4-(1H-imidazol-1-yl)phenoxy]methyl}-3,3-dimethylpyrrolidin-1-yl)adamantane-1-carboxamide;

4-({N-cyano-2-[4-(2-hydroxyphenyl)piperazin-1-yl]-2-methylpropanimidoyl}amino)adamantane-1-carboxylic acid;

2-(2-chloro-4-fluorophenoxy)-N'-cyano-N-(5-hydroxy-2-adamantyl)-2-methylpropanimidamide;

4-[2-{[5-(aminocarbonyl)-2-adamantyl]amino}-2-(cyanoimino)-1,1-dimethylethyl]-N-(tert-butyl)piperazine-1-carboxamide;

4-{[N-cyano-2-(4-hydroxyphenoxy)-2-methylpropanimidoyl]amino}adamantane-1-carboxamide;

4-({N-cyano-2-[(4-methoxyphenyl)thio]-2-methylpropanimidoyl}amino)adamantane-1-carboxamide;

N-cyano-N-[5-(formylamino)-2-adamantyl]-2-methyl-2-{4-[5-(trifluoromethyl)pyridin-2-yl]piperazin-1-yl}propanimidamide;

4-{[(1-benzyl-3-methyl-2-oxopyrrolidin-3-yl)(cyanoimino)methyl]amino}adamantane-1-carboxamide;

4-({(cyanoimino)[3-methyl-1-(2-methylbenzyl)-2-oxopyrrolidin-3-yl]methyl}amino)adamantane-1-carboxamide;

4-{[[1-(2-chlorobenzyl)-3-methyl-2-oxopyrrolidin-3-yl](cyanoimino)methyl]amino}adamantane-1-carboxamide;

4-{[[1-(3-chlorobenzyl)-3-methyl-2-oxopyrrolidin-3-yl](cyanoimino)methyl]amino}adamantane-1-carboxamide;

2-(2-chloro-4-fluorophenoxy)-N-cyano-2-methyl-N-[5-(2H-tetraazol-5-yl)-2-adamantyl]propanimidamide;

4-({N-cyano-2-methyl-2-[4-(1-methyl-1H-pyrazol-4-yl)phenyl]propanimidoyl}amino)adamantane-1-carboxamide;

2-(2-chloro-4-fluorophenoxy)-N-cyano-2-methyl-N-[5-(methylthio)-2-adamantyl]propanimidamide;

2-(2-chloro-4-fluorophenoxy)-N-cyano-2-methyl-N-[5-(methylsulfonyl)-2-adamantyl]propanimidamide;

2-(2-chloro-4-fluorophenoxy)-N-cyano-2-methyl-N-[5-(methylsulfinyl)-2-adamantyl]propanimidamide;

4-{[2-(3-bromophenyl)-N-cyano-2-methylpropanimidoyl]amino}adamantane-1-carboxamide;

4-({N-cyano-2-[4-(3,5-dimethylisoxazol-4-yl)phenyl]-2-methylpropanimidoyl}amino)adamantane-1-carboxamide;

4-{[N-cyano-2-methyl-2-(4-pyridin-3-ylphenyl)propanimidoyl]amino}adamantane-1-carboxamide;

N-[5-(aminosulfonyl)-2-adamantyl]-2-(4-chlorophenoxy)-N-cyano-2-methylpropanimidamide;

4-{[({4-[(N-cyano-2-methyl-2-thien-2-ylpropanimidoyl)amino]-1-adamantyl}carbonyl)amino]methyl}benzoic acid;

4-({N-cyano-2-methyl-2-[4-(1H-pyrazol-4-yl)phenyl]propanimidoyl}amino)adamantane-1-carboxamide;

4-{[2-(4-chlorophenoxy)-N-cyano-2-methylpropanimidoyl]amino}-N-(4-{[(methylsulfonyl)amino]carbonyl}benzyl)adamantane-1-carboxamide;

4-({N-cyano-2-[(4-methoxyphenyl)sulfinyl]-2-methylpropanimidoyl}amino)adamantane-1-carboxamide;

4-({N-cyano-2-[(4-methoxyphenyl)sulfonyl]-2-methylpropanimidoyl}amino)adamantane-1-carboxamide;

4-({(cyanoimino)[3-methyl-1-(1-methyl-1-phenylethyl)-2-oxopyrrolidin-3-yl]methyl}amino)adamantane-1-carboxamide;

4-({(cyanoimino)[3-methyl-2-oxo-1-(1-phenylethyl)pyrrolidin-3-yl]methyl}amino)adamantane-1-carboxamide;

2-(4-{[2-(4-chlorophenoxy)-N-cyano-2-methylpropanimidoyl]amino}-1-adamantyl)acetamide;

4-{[N-cyano-2-methyl-2-(1,3-thiazol-2-yl)propanimidoyl]amino}adamantane-1-carboxamide;

4-{[[1-(4-chlorobenzyl)-3-methylpiperidin-3-yl](cyanoimino)methyl]amino}adamantane-1-carboxamide;

4-{[N-cyano-2-(4-hydroxyphenyl)-2-methylpropanimidoyl]amino}adamantane-1-carboxamide;

4-[2-(cyanoimino)-3,3-dimethyl-4-({[5-(trifluoromethyl)pyridin-2-yl]oxy}methyl)pyrrolidin-1-yl]-N'-hydroxyadamantane-1-carboximidamide;

4-[2-(cyanoimino)-3,3-dimethyl-4-({[5-(trifluoromethyl)pyridin-2-yl]oxy}methyl)pyrrolidin-1-yl]adamantane-1-carboxamide;

4-{[(1-benzyl-3-methyl-2-oxopiperidin-3-yl)(cyanoimino)methyl]amino}adamantane-1-carboxamide;

4-{[N-cyano-2-methyl-2-(4-phenoxyphenyl)propanimidoyl]amino}adamantane-1-carboxamide;

(4-{[2-(4-chlorophenoxy)-N-cyano-2-methylpropanimidoyl]amino}-1-adamantyl)acetic acid;

4-[2-(cyanoimino)-3,3-dimethyl-4-({[5-(trifluoromethyl)pyridin-2-yl]oxy}methyl)pyrrolidin-1-yl]adamantane-1-carboximidamide;

2-(4-chlorophenoxy)-N-cyano-2-methyl-N-[5-(2H-tetraazol-5-ylmethyl)-2-adamantyl]propanimidamide;

4-{[2-(1-benzothien-3-yl)-N-cyano-2-methylpropanimidoyl]amino}adamantane-1-carboxamide;

N-{5-[(aminosulfonyl)methyl]-2-adamantyl}-2-(4-chlorophenoxy)-N-cyano-2-methylpropanimidamide;

4-{[[1-(4-chlorophenoxy)cyclobutyl](cyanoimino)methyl]amino}adamantane-1-carboxamide;

4-{[2-(4-chlorophenoxy)-N-cyano-2-methylpropanimidoyl]amino}-N-hydroxyadamantane-1-carboximidamide;

4-[({[(4-{[2-(4-chlorophenoxy)-N-cyano-2-methylpropanimidoyl]amino}-1-adamantyl)methyl]sulfonyl}amino)methyl]benzoic acid;

2-(4-chlorophenoxy)-N'-cyano-N-[5-(1H-imidazol-2-yl)-2-adamantyl]-2-methylpropanimidamide;

4-{[N-cyano-2-(5-fluoropyridin-2-yl)-2-methylpropanimidoyl]amino}adamantane-1-carboxamide;

3-(4-{[2-(4-chlorophenoxy)-N-cyano-2-methylpropanimidoyl]amino}-1-adamantyl)acrylic acid;

4-[(N-cyano-2-methyl-2-{[5-(1H-pyrazol-1-yl)pyridin-2-yl]oxy}propanimidoyl)amino]adamantane-1-carboxamide;
2-(4-chlorophenoxy)-N'-cyano-N-(5-isoxazol-5-yl-2-adamantyl)-2-methylpropanimidamide;
4-[(N-cyano-2-methyl-2-quinoxalin-2-ylpropanimidoyl)amino]adamantane-1-carboxamide;
2-(4-chlorophenoxy)-N-cyano-2-methyl-N-{5-[(2-morpholin-4-ylethoxy)methyl]-2-adamantyl}propanimidamide;
N-[5-(aminosulfonyl)-2-adamantyl]-2-(2-chlorophenoxy)-N-cyano-2-methylpropanimidamide;
N-[5-(aminosulfonyl)-2-adamantyl]-N-cyano-2-methyl-2-(2-methylphenoxy)propanimidamide;
N-[5-(aminosulfonyl)-2-adamantyl]-N-cyano-2-methyl-2-(4-methylphenoxy)propanimidamide;
N-[5-(aminosulfonyl)-2-adamantyl]-N-cyano-2-methyl-2-[2-(trifluoromethyl)phenoxy]propanimidamide;
N-[5-(aminosulfonyl)-2-adamantyl]-N-cyano-2-methyl-2-[2-(trifluoromethoxy)phenoxy]propanimidamide;
N-[5-(aminosulfonyl)-2-adamantyl]-2-(2-chloro-4-fluorophenoxy)-N-cyano-2-methylpropanimidamide;
N-cyano-N-[5-(1-hydroxyethyl)-2-adamantyl]-2-methyl-2-{4-[5-(trifluoromethyl)pyridin-2-yl]piperazin-1-yl}propanimidamide;
2-{4-[(N-cyano-2-methyl-2-{4-[5-(trifluoromethyl)pyridin-2-yl]piperazin-1-yl}propanimidoyl)amino]-1-adamantyl}propanoic acid;
4-[(N-cyano-3-methyl-2-{4-[5-(trifluoromethyl)pyridin-2-yl]piperazin-1-yl}butanimidoyl)amino]adamantane-1-carboxamide;
(2R)—N-cyano-N-[5-hydroxy-2-adamantyl]-2-{4-[5-(trifluoromethyl)pyridin-2-yl]piperazin-1-yl}butanimidamide;
4-[((2R)—N-cyano-2-{4-[5-(trifluoromethyl)pyridin-2-yl]piperazin-1-yl}propanimidoyl)amino]adamantane-1-carboxylic acid;
4-[((2R)—N-cyano-2-{4-[5-(trifluoromethyl)pyridin-2-yl]piperazin-1-yl}butanimidoyl)amino]adamantane-1-carboxylic acid;
4-[((2R)—N-cyano-3-methyl-2-{4-[5-(trifluoromethyl)pyridin-2-yl]piperazin-1-yl}butanimidoyl)amino]adamantane-1-carboxylic acid;
4-[((2R)—N-cyano-2-{4-[5-(trifluoromethyl)pyridin-2-yl]piperazin-1-yl}propanimidoyl)amino]-N,N-dimethyladamantane-1-carboxamide;
4-[((2R)—N-cyano-2-{4-[5-(trifluoromethyl)pyridin-2-yl]piperazin-1-yl}butanimidoyl)amino]-N,N-dimethyladamantane-1-carboxamide;
N-{4-[((2R)—N-cyano-2-{4-[5-(trifluoromethyl)pyridin-2-yl]piperazin-1-yl}butanimidoyl)amino]-1-adamantyl}acetamide;
N-{4-[42R)—N-cyano-3-methyl-2-{4-[5-(trifluoromethyl)pyridin-2-yl]piperazin-1-yl}butanimidoyl)amino]-1-adamantyl}acetamide;
N-cyano-2-(3,3-difluoropiperidin-1-yl)-N-[5-hydroxy-2-adamantyl]propanimidamide;
N'-cyano-N-[5-hydroxy-2-adamantyl]-2-[(3S)-3-(trifluoromethyl)pyrrolidin-1-yl]ethanimidamide;
4-({N-cyano-2-[(3R)-3-fluoropiperidin-1-yl]propanimidoyl}amino)adamantane-1-carboxamide;
N-cyano-N-[5-methoxy-2-adamantyl]-2-{4-[5-(trifluoromethyl)pyridin-2-yl]piperazin-1-yl}propanimidamide;
4-[(N-cyano-2-{4-[5-(trifluoromethyl)pyridin-2-yl]piperazin-1-yl}pentanimidoyl)amino]adamantane-1-carboxamide;
4-{[N-cyano-2-methyl-2-(phenylthio)propanimidoyl]amino}adamantane-1-carboxamide;
4-({N-cyano-2-methyl-2-[methyl(phenyl)amino]propanimidoyl}amino)adamantane-1-carboxylic acid;
4-{[N-cyano-2-methyl-2-(2-methylphenoxy)propanimidoyl]amino}adamantane-1-carboxamide;
4-{[N-cyano-2-methyl-2-(3-methylphenoxy)propanimidoyl]amino}adamantane-1-carboxamide;
4-({N-cyano-2-methyl-2-[methyl(phenyl)amino]propanimidoyl}amino)adamantane-1-carboxamide;
4-({2-[(4-chlorophenyl)amino]-N-cyano-2-methylpropanimidoyl}amino)adamantane-1-carboxamide;
4-{[2-(2-chlorophenoxy)-N-cyano-2-methylpropanimidoyl]amino}adamantane-1-carboxamide;
4-{[N-cyano-2-(3,3-difluoropiperidin-1-yl)butanimidoyl]amino}adamantane-1-carboxamide;
4-[3-benzyl-2-(cyanoimino)pyrrolidin-1-yl]adamantane-1-carboxamide;
4-({2-[4-(2-chloro-4-cyanophenyl)piperazin-1-yl]-N-cyano-2-methylpropanimidoyl}amino)adamantane-1-carboxamide;
N-cyano-N-[5-hydroxy-2-adamantyl]-2-methyl-2-phenylpropanimidamide;
2-(4-chlorophenyl)-N-cyano-N-[5-hydroxy-2-adamantyl]-2-methylpropanimidamide;
N-cyano-N-[5-hydroxy-2-adamantyl]-1-phenylcyclopropanecarboximidamide;
4-{[2-(4-bromo-3,5-dimethyl-1H-pyrazol-1-yl)-N-cyano-2-methylpropanimidoyl]amino}adamantane-1-carboxamide;
4-(2-(cyanoimino)-4-{[(5-cyanopyridin-2-yl)oxy]methyl}-3,3-dimethylpyrrolidin-1-yl)adamantane-1-carboxamide;
4-{[2-(4-chlorophenoxy)-N-cyano-2-methylpropanimidoyl]amino}-N-methyladamantane-1-carboxamide;
4-{[2-(2-chloro-4-fluorophenoxy)-N-cyano-2-methylpropanimidoyl]amino}adamantane-1-carboxamide;
4-[(N-cyano-2-methyl-2-{[4'-(methylsulfonyl)-1,1'-biphenyl-4-yl]oxy}propanimidoyl)amino]adamantane-1-carboxamide;
4-{[N-cyano-2-(3-cyanopyridin-2-yl)-2-methylpropanimidoyl]amino}adamantane-1-carboxamide;
4-({N-cyano-2-methyl-2-[2-(trifluoromethoxy)phenoxy]propanimidoyl}amino)adamantane-1-carboxamide;
4-({N-cyano-2-methyl-2-[4-(trifluoromethyl)pyridin-2-yl]propanimidoyl}amino)adamantane-1-carboxamide;
4-({2-[(5-bromopyridin-2-yl)oxy]-N-cyano-2-methylpropanimidoyl}amino)adamantane-1-carboxamide;
4-({N-cyano-2-methyl-2-[2-(trifluoromethyl)phenoxy]propanimidoyl}amino)adamantane-1-carboxamide;
4-(2-(cyanoimino)-3,3-dimethyl-4-{[4-(1H-1,2,4-triazol-1-yl)phenoxy]methyl}pyrrolidin-1-yl)adamantane-1-carboxamide;
4-{[(cyanoimino)(2-methylphenyl)methyl]amino}adamantane-1-carboxamide;
4-{[2-(3-bromo-4-methoxyphenoxy)-N-cyano-2-methylpropanimidoyl]amino}adamantane-1-carboxamide;
4-{[2-(2-bromo-4-methoxyphenoxy)-N-cyano-2-methylpropanimidoyl]amino}adamantane-1-carboxamide;
4-({(cyanoimino)[3-methyl-2-oxo-1-(pyridin-2-ylmethyl)pyrrolidin-3-yl]methyl}amino)adamantane-1-carboxamide;
4-({(cyanoimino)[3-methyl-2-oxo-1-(pyridin-3-ylmethyl)pyrrolidin-3-yl]methyl}amino)adamantane-1-carboxamide;
4-({(cyanoimino)[3-methyl-2-oxo-1-(pyridin-4-ylmethyl)pyrrolidin-3-yl]methyl}amino)adamantane-1-carboxamide;

4-({(cyanoimino)[3-methyl-2-oxo-1-(2-pyridin-2-ylethyl) pyrrolidin-3-yl]methyl}amino)adamantane-1-carboxamide;
4-{[N-cyano-3-(4-methoxyphenyl)-2,2-dimethyl-3-oxopropanimidoyl]amino}adamantane-1-carboxamide;
4-[(N-cyano-2-methyl-2-{[4-(trifluoromethoxy)phenyl] amino}propanimidoyl)amino]adamantane-1-carboxamide;
4-[(N-cyano-2-methyl-2-{[4-(trifluoromethoxy)phenyl] thio}propanimidoyl)amino]adamantane-1-carboxamide;
4-[2-(cyanoimino)-3,3-dimethyl-4-({[5-(trifluoromethyl) pyridin-2-yl]oxy}methyl)pyrrolidin-1-yl]adamantane-1-carboxamide;
4-{[2-(2-chloro-4-fluorophenoxy)-N-cyano-2-methylpropanimidoyl]amino}-N,N-dimethyladamantane-1-carboxamide;
4-({(cyanoimino)[3-methyl-2-oxo-1-(1-pyridin-2-ylethyl) pyrrolidin-3-yl]methyl}amino)adamantane-1-carboxamide;
4-({N-cyano-2-methyl-2-[3-(1,3-thiazol-4-ylmethoxy)phenyl]propanimidoyl}amino)adamantane-1-carboxamide;
4-({N-cyano-2-methyl-2-[3-(2-morpholin-4-ylethoxy)phenyl]propanimidoyl}amino)adamantane-1-carboxamide;
N-[5-(5-amino-4H-1,2,4-triazol-3-yl)-2-adamantyl]-2-(4-chlorophenoxy)-Y-cyano-2-methylpropanimidamide;
4-{[N-cyano-2-(6-fluoropyridin-3-yl)-2-methylpropanimidoyl]amino}adamantane-1-carboxamide;
2-(4-chlorophenoxy)-Y-cyano-N-[5-(hydroxymethyl)-2-adamantyl]-2-methylpropanimidamide;
4-{[N-cyano-2-methyl-2-(6-morpholin-4-ylpyridin-3-yl) propanimidoyl]amino}adamantane-1-carboxamide;
4-{[N-cyano-2-(5-fluoropyridin-2-yl)-2-methylpropanimidoyl]amino}adamantane-1-carboxamide;
4-({N-cyano-2-methyl-2-[6-(methylamino)pyridin-3-yl] propanimidoyl}amino)adamantane-1-carboxamide;
4-[(N-cyano-2-{5-(1H-imidazol-1-yl)pyridin-2-yl]oxy}-2-methylpropanimidoyl)amino]adamantane-1-carboxamide;
4-[(N-cyano-2-methyl-2-{[5-(1H-pyrazol-1-yl)pyridin-2-yl] oxy}propanimidoyl)amino]adamantane-1-carboxamide;
4-[(N-cyano-2-methyl-2-quinoxalin-2-ylpropanimidoyl) amino]adamantane-1-carboxamide;
N-[5-(aminosulfonyl)-2-adamantyl]-2-(3-chlorophenoxy)-N-cyano-2-methylpropanimidamide;
N-[5-(aminosulfonyl)-2-adamantyl]-N-cyano-2-methyl-2-(3-methylphenoxy)propanimidamide;
N-[5-(aminosulfonyl)-2-adamantyl]-N-cyano-2-methyl-2-(2-methoxyphenoxy)propanimidamide;
N-[5-(aminosulfonyl)-2-adamantyl]-N-cyano-2-methyl-2-(3-methoxyphenoxy)propanimidamide;
(2S)-amino(4-{[2-(2-chloro-4-fluorophenoxy)-N-cyano-2-methylpropanimidoyl]amino}-1-adamantyl)acetic acid;
2-[(4-{[2-(2-chloro-4-fluorophenoxy)-N-cyano-2-methylpropanimidoyl]amino}-1-adamantyl)sulfonyl]acetamide;
N-cyano-N-[5-hydroxy-2-adamantyl]-2-methyl-2-(4-nitrophenyl)propanimidamide;
N-cyano-N-[5-(methylsulfonyl)-2-adamantyl]-1-phenylcyclopropanecarboximidamide;
2-[(4-bromopyridin-2-yl)oxy]-N-cyano-2-methyl-N-[5-(methylsulfonyl)-2-adamantyl]propanimidamide;
(2S)-2-(4-{[2-(2-chloro-4-fluorophenoxy)-N-cyano-2-methylpropanimidoyl]amino}-1-adamantyl)propanoic acid;
N-[5-(aminosulfonyl)-2-adamantyl]-2-(1,1'-biphenyl-2-yloxy)-N-cyano-2-methylpropanimidamide;
4-{[2-(1,1'-biphenyl-2-yloxy)-N-cyano-2-methylpropanimidoyl]amino}adamantane-1-carboxylic acid;

N'-cyano-2-(2,4-dichlorophenoxy)-2-methyl-N-[5-(methylsulfonyl)-2-adamantyl]propanimidamide;
2-(2-bromo-4-fluorophenoxy)-N-cyano-2-methyl-N-[5-(methylsulfonyl)-2-adamantyl]propanimidamide;
N'-cyano-2-methyl-2-(2-methylphenoxy)-N-[5-(methylsulfonyl)-2-adamantyl]propanimidamide;
N'-cyano-2-methyl-2-(4-methylphenoxy)-N-[5-(methylsulfonyl)-2-adamantyl]propanimidamide;
2-(2-chlorophenoxy)-N-cyano-2-methyl-N-[5-(methylsulfonyl)-2-adamantyl]propanimidamide;
2-(4-chlorophenoxy)-N-cyano-2-methyl-N-[5-(methylsulfonyl)-2-adamantyl]propanimidamide;
N-cyano-2-(4-methoxyphenoxy)-2-methyl-N-[5-(methylsulfonyl)-2-adamantyl]propanimidamide;
N-cyano-2-(2-cyanophenoxy)-2-methyl-N-[5-(methylsulfonyl)-2-adamantyl]propanimidamide;
N-cyano-2-(2-methoxyphenoxy)-2-methyl-N-[5-(methylsulfonyl)-2-adamantyl]propanimidamide;
2-[(3-bromopyridin-2-yl)oxy]-N-cyano-2-methyl-N-[5-(methylsulfonyl)-2-adamantyl]propanimidamide;
N-[5-(aminosulfonyl)-2-adamantyl]-2-(2-bromo-4-fluorophenoxy)-N-cyano-2-methylpropanimidamide;
N-cyano-N-[5-hydroxy-2-adamantyl]-3-methyl-2-oxo-1-pyridin-2-ylpyrrolidine-3-carboximidamide;
2-(4-chlorophenoxy)-N-cyano-2-methyl-N-{5-[(methylthio)methyl]-2-adamantyl}propanimidamide;
N-[5-(aminosulfonyl)-2-adamantyl]-N-cyano-2-(2,4-dichlorophenoxy)-2-methylpropanimidamide;
N-[5-(aminosulfonyl)-2-adamantyl]-N-cyano-2-(2,4-dimethylphenoxy)-2-methylpropanimidamide;
N-[5-(aminosulfonyl)-2-adamantyl]-N-cyano-2-(4-fluoro-2-methylphenoxy)-2-methylpropanimidamide;
N-[5-(aminosulfonyl)-2-adamantyl]-N-cyano-2-(2,6-dichloro-4-methylphenoxy)-2-methylpropanimidamide;
N-[5-(aminosulfonyl)-2-adamantyl]-N-cyano-2-(2,6-dichloro-4-fluorophenoxy)-2-methylpropanimidamide;
N-[5-(aminosulfonyl)-2-adamantyl]-2-(4-chloro-2-fluorophenoxy)-N-cyano-2-methylpropanimidamide;
N-[5-(aminosulfonyl)-2-adamantyl]-2-(2-chloro-4-methylphenoxy)-N-cyano-2-methylpropanimidamide;
N-[5-(aminosulfonyl)-2-adamantyl]-N-cyano-2-(mesityloxy)-2-methylpropanimidamide;
2-(4-chlorophenoxy)-N-cyano-2-methyl-N-{5-[(methylsulfonyl)methyl]-2-adamantyl}propanimidamide;
N-[5-(aminosulfonyl)-2-adamantyl]-N-cyano-2-(2,4-difluorophenoxy)-2-methylpropanimidamide;
N-[5-(aminosulfonyl)-2-adamantyl]-N-cyano-2-(4-fluorophenoxy)-2-methylpropanimidamide;
N'-cyano-2-(2,4-difluorophenoxy)-2-methyl-N-[5-(methylsulfonyl)-2-adamantyl]propanimidamide;
N'-cyano-2-(2-isopropylphenoxy)-2-methyl-N-[5-(methylsulfonyl)-2-adamantyl]propanimidamide;
N'-cyano-2-(4-fluoro-2-methylphenoxy)-2-methyl-N-[5-(methylsulfonyl)-2-adamantyl]propanimidamide;
N'-cyano-2-(2-fluorophenoxy)-2-methyl-N-[5-(methylsulfonyl)-2-adamantyl]propanimidamide;
N'-cyano-2-methyl-N-[5-(methylsulfonyl)-2-adamantyl]-2-[2-(trifluoromethyl)phenoxy]propanimidamide;
4-{[(cyanoimino)(3-methyl-2-oxo-1-pyridin-2-ylpyrrolidin-3-yl)methyl]amino}adamantane-1-carboxamide;
(2S)-2-amino-2-(4-{[2-(2-chloro-4-fluorophenoxy)-N-cyano-2-methylpropanimidoyl]amino}-1-adamantyl)acetamide;
N'-cyano-2-[4-fluoro-2-(1H-pyrazol-1-yl)phenoxy]-2-methyl-N-[5-(methylsulfonyl)-2-adamantyl]propanimidamide;

N'-cyano-2-(2,6-dichloro-4-fluorophenoxy)-2-methyl-N-[5-(methylsulfonyl)-2-adamantyl]propanimidamide;

N'-cyano-2-[4-fluoro-2-(1H-pyrazol-4-yl)phenoxy]-2-methyl-N-[5-(methylsulfonyl)-2-adamantyl]propanimidamide;

N'-cyano-2-methyl-N-[5-(methylsulfonyl)-2-adamantyl]-2-[3-(trifluoromethoxy)phenoxy]propanimidamide;

3-deutero-4-[(N-cyano-2-methyl-2-{[4-(trifluoromethyl)benzyl]oxy}propanimidoyl)amino]adamantane-1-carboxamide;

4-[(N-cyano-2-methyl-2-{[4-(trifluoromethyl)benzyl]oxy}propanimidoyl)amino]-7-deutero-adamantane-1-carboxamide;

N-[1-deutero-4-adamantyl]-N-cyano-2-methyl-2-{[4-(trifluoromethyl)benzyl]oxy}propanimidamide;

3-deutero-4-[(N-cyano-2-methyl-2-{4-[5-(trifluoromethyl)pyridin-2-yl]piperazin-1-yl}propanimidoyl)amino]adamantane-1-carboxamide;

4-[(N-cyano-2-methyl-2-{4-[5-(trifluoromethyl)pyridin-2-yl]piperazin-1-yl}propanimidoyl)amino]-7-deutero-adamantane-1-carboxamide;

N-[1-deutero-4-adamantyl]-N-cyano-2-methyl-2-{4-[5-(trifluoromethyl)pyridin-2-yl]piperazin-1-yl}propanimidamide;

3-[(N-cyano-2-methyl-2-{[4-(trifluoromethyl)benzyl]oxy}propanimidoyl)amino]adamantane-1-carboxamide;

N-1-azabicyclo[2.2.2]oct-3-yl-N-cyano-2-methyl-2-{[4-(trifluoromethyl)benzyl]oxy}propanimidamide;

N-[1-azatricyclo[3.3.1.13,7]dec-4-yl]-N-cyano-2-methyl-2-{4-[5-(trifluoromethyl)pyridin-2-yl]piperazin-1-yl}propanimidamide;

N'-cyano-N-cyclohexyl-2-methyl-2-{4-[5-(trifluoromethyl)pyridin-2-yl]piperazin-1-yl}propanimidamide;

{4-[(4-methylphenyl)sulfonyl]piperazin-1-yl}(4-nitrophenyl)methylenecyanamide;

N-cyano-N-{1-[(1-cyanocyclopropyl)methyl]piperidin-4-yl}-N-cyclopropyl-4-(2,2,2-trifluoro-1-hydroxy-1-methylethyl)benzenecarboximidamide;

[4-[{(cyanoimino)[4-(2,2,2-trifluoro-1-hydroxy-1-methylethyl)phenyl]methyl}(cyclopropyl)amino]-1-(4-fluorophenyl)cyclohexyl]methyl carbamate;

N'-cyano-N-cyclopropyl-N-[4-(2-hydroxyethyl)cyclohexyl]-4-isopropylbenzenecarboximidamide[5-(4-methylphenyl)isoxazol-4-yl](3-pyridin-3-ylpyrrolidin-1-yl)methylenecyanamide;

4-[4-[(1-adamantylamino)(cyanoimino)methyl]-5-(1-methylcyclopropyl)-1H-pyrazol-1-yl]benzoic acid;

N'-cyano-N-cyclohexyl-2-[(2-phenylethyl)thio]pyridine-3-carboximidamide;

4-[5-[(2-adamantylamino)(cyanoimino)methyl]-6-(propylthio)pyridin-2-yl]morpholine-2-carboxylic acid;

N'-cyano-N-cyclopropyl-N-(4-cyclopropyl-4-hydroxycyclohexyl)-4-(2,2,2-trifluoro-1-hydroxy-1-methylethyl)benzenecarboximidamide;

2-[2-(4-fluorophenyl)-6-hydroxy-2-adamantyl]-1-(3-hydroxyazetidin-1-yl)ethylidenecyanamide;

2-{1-[2-(2-adamantylamino)-2-(cyanoimino)ethyl]cyclopentyl}-N-isobutylacetamide;

2-{4-[(2-fluorophenyl)sulfonyl]-1,4-diazepan-1-yl}-1-octahydroquinolin-1(2H)-ylethylidenecyanamide;

1-cyclohexyl-3-[(3,5-dichloro-4'-{[4-(2-fluoro ethyl)piperazin-1-yl]carbonyl}-1,1'-biphenyl-4-yl)methyl]pyrrolidin-2-ylidenecyanamide;

3-[(3,5-dichloro-4'-{[4-(trifluoromethyl)piperidin-1-yl]carbonyl}-1,1'-biphenyl-4-yl)methyl]-1-piperidin-1-ylpyrrolidin-2-ylidenecyanamide;

3-cyclohexyl-1-[(3,5-dichloro-4'-{[4-(2-fluoro ethyl)piperazin-1-yl]carbonyl}-1,1'-biphenyl-4-yl)methyl]pyrrolidin-2-ylidenecyanamide;

3-[(3,5-dichloro-4'-{[4-(trifluoromethyl)piperidin-1-yl]carbonyl}-1,1'-biphenyl-4-yl)methyl]-1-(4,4-difluorocyclohexyl)pyrrolidin-2-ylidenecyanamide;

3-[(3,5-dichloro-4'-fluoro-1,1'-biphenyl-4-yl)methyl]-1-(4,4-difluorocyclohexyl)pyrrolidin-2-ylidenecyanamide;

3-[(3,5-dichloro-4'-{[4-(trifluoromethyl)piperidin-1-yl]carbonyl}-1,1'-biphenyl-4-yl)methyl]-1-(4-hydroxypiperidin-1-yl)pyrrolidin-2-ylidenecyanamide;

methyl 4-{2-(cyanoimino)-3-[(3,5-dichloro-4'-{[4-(trifluoromethyl)piperidin-1-yl]carbonyl}-1,1'-biphenyl-4-yl)methyl]pyrrolidin-1-yl}piperidine-1-carboxylate;

2-[(3,5-dichloro-4'-{[4-(trifluoromethyl)piperidin-1-yl]carbonyl}-1,1'-biphenyl-4-yl)methyl]-2-azaspiro[4.5]dec-1-ylidenecyanamide;

3-[(3,5-dichloro-4'-{[4-(trifluoromethyl)piperidin-1-yl]carbonyl}-1,1'-biphenyl-4-yl)methyl]-1-(4,5,6,7-tetrahydro-1H-benzimidazol-6-yl)pyrrolidin-2-ylidenecyanamide;

3-[(3,5-dichloro-4'-fluoro-1,1'-biphenyl-4-yl)methyl]-1-(4,5,6,7-tetrahydro-2H-indazol-5-yl)pyrrolidin-2-ylidenecyanamide;

N-2-adamantyl-2'-tert-butyl-N-cyano-2'H-1,3'-bipyrazole-4'-carboximidamide;

2-(4-bromo-2-fluorophenyl)-2-hydroxy-1-(3-oxo-1'H,3H-spiro[2-benzofuran-1,3'-pyrrolidin]-1'-yl)ethylidenecyanamide;

N'-cyano-N-(1-{[4-(2,5-dimethylphenyl)piperazin-1-yl]carbonyl}piperidin-3-yl)-4-hydroxyadamantane-1-carboximidamide;

1-{3-[1-(4-chlorophenyl)cyclopropyl]-1-oxa-2,7-diazaspiro[4.4]non-2-en-7-yl}ethylidenecyanamide;

7-(2-chlorophenyl)-1-isobutyl-1,7-diazaspiro[4.4]non-6-ylidenecyanamide;

8-(3-chloropyridin-2-yl)-2-cyclohexyl-2,8-diazaspiro[4.5]dec-1-ylidenecyanamide;

5-{4-[1-(cyanoimino)-2-(4-hydroxycyclohexyl)-2,7-diazaspiro[4.5]dec-7-yl]-3-fluorophenyl}-N,N-dimethylpyridine-2-carboxamide;

2-(2-acetylphenyl)-N'-cyano-N-cyclooctyl-1,3-thiazole-4-carboximidamide;

(5-cyclopropyl-1-piperidin-4-yl-1H-pyrazol-4-yl){3-[2-(trifluoromethyl)phenyl]pyrrolidin-1-yl}methylenecyanamide;

2-[4-(2-{[(4-chlorophenyl)(cyanoimino)methyl]amino}ethyl)phenoxy]-2-methylpropanoic acid;

1'-{[2-(trifluoromethyl)phenoxy]acetyl}Spiro[indole-3,4'-piperidin]-2(1H)-ylidenecyanamide;

1-{4-[(2-adamantylamino)(cyanoimino)methyl]phenyl}piperidine-4-carboxylic acid;

N-(1-{4-[3-azabicyclo[3.2.2]non-3-yl(cyanoimino)methyl]phenyl}pyrrolidin-3-yl)-N-methyl-1-phenylmethanesulfonamide;

1-adamantyl {4-[2-(1H-imidazol-2-ylthio)ethyl]piperidin-1-yl}methylenecyanamide;

N-2-adamantyl-N-cyano-4-(2-oxa-5-azabicyclo[2.2.1]hept-5-yl)benzenecarboximidamide;

N-{4-[(cyanoimino)(1,3,3-trimethyl-6-azabicyclo[3.2.1]oct-6-yl)methyl]benzyl}-1,1,1-trifluoro-N-isopropylmethanesulfonamide;

1-acetyl-N-(2-{5-[(cyanoimino)(1,3,3-trimethyl-6-azabicyclo[3.2.1]oct-6-yl)methyl]-1H-benzimidazol-1-yl}ethyl)piperidine-4-carboxamide;

ethyl 3-{4-[(cyanoimino)(1,3,3-trimethyl-6-azabicyclo[3.2.1]oct-6-yl)methyl]-1H-indol-1-yl}propanoate;

N-1-adamantyl-N-cyano-1-(thien-2-ylsulfonyl)piperidine-4-carboximidamide;

N-cyano-4-(2,4-dichlorophenoxy)-N-[4-(hydroxymethyl)-2-adamantyl]butanimidamide;

4-[(5-chloropyridin-2-yl)oxy]-N'-cyano-N-[4-(hydroxymethyl)cyclohexyl]-N-methylbenzenecarboximidamide;

N-2-adamantyl-N-cyano-2-[cyclohexyl(methyl)amino]ethanimidamide;

N-2-adamantyl-N-cyano-1-methyl-5-(2-phenylethoxy)-1H-pyrazole-4-carboximidamide;

2,4-dichloro-N-[1-({[5-{(cyanoimino) [(5-hydroxy-2-adamantyl)amino]methyl}-4-(cyclopentylthio)isoxazol-3-yl]oxy}methyl)cyclopropyl]benzamide;

4-[((cyanoimino) {1-[3-cyano-3-methylbut-1-enyl]-5-isobutoxy-1H-pyrazol-4-yl}methyl)amino]-1-adamantyl carbamate;

2-(5-hydroxy-2-adamantyl)-3-oxo-2,3-dihydro-1H-isoindol-1-ylidenecyanamide and 2-(6-hydroxy-2-adamantyl)-3-oxo-2,3-dihydro-1H-isoindol-1-ylidenecyanamide;

N'-cyano-N-(5-hydroxy-2-adamantyl)-4-[(pyridin-2-ylsulfonyl)methoxy]benzenecarboximidamide;

N'-cyano-3-(cyclohexylmethoxy)-N-[5-(hydroxymethyl)-2-adamantyl]benzenecarboximidamide;

N'-cyano-N-(3-hydroxy-1-adamantyl)-4-[(methylsulfonyl)methoxy]benzenecarboximidamide;

N'-cyano-N-(5-hydroxy-2-adamantyl)-N-methyl-3-(2-phenylethoxy)benzenecarboximidamide;

(3-hydroxy-8-azabicyclo[3.2.1]oct-8-yl)(9-methyl-9H-carbazol-3-yl)methylenecyanamide; and 1-(4-{[2-(4-chlorophenoxy)phenyl]amino}piperidin-1-yl)ethylidenecyanamide.

Determination of Biological Activity

Abbreviations

EDTA for ethylenediaminetetraacetic acid; Tris for tris(hydroxymethyl)aminomethane; NADPH for nicotinamide adenine dinucleotide phosphate.

Measurement of Inhibition Constants:

The ability of test compounds to inhibit human 11β-HSD1 enzymatic activity in vitro was evaluated in a Scintillation Proximity Assay (SPA). Tritiated-cortisone substrate, NADPH cofactor and titrated compound were incubated with truncated (24-287aa) human 11β-HSD1 enzyme at room temperature to allow the conversion to cortisol to occur. The reaction was stopped by adding a non-specific 11β-HSD inhibitor, glycyrrhetinic acid. The tritiated cortisol was captured by a mixture of an anti-cortisol monoclonal antibody and SPA beads coated with anti-mouse antibodies. The reaction plate was shaken at room temperature and the radiolabel bound to SPA beads was then measured on a scintillation counter. The 11β-HSD1 assay was carried out in 96-well microtiter plates in a total volume of 220 pt. To start the assay, 188 µL of master mix which contained 75 nM $^3$H-cortisone, 100 nM cortisone and 181 µM NADPH was added to the wells. In order to drive the reaction in the 11β-reductase direction, 1 mM glucose-6-phosphate (G-6-P) and 1 U/mL G-6-P dehydrogenase were also added as a NADPH generating system. Solid compound was dissolved in dimethyl sulfoxide to make a 10 mM stock followed by a subsequent 10-fold serial dilution with dimethyl sulfoxide. Each compound solution in dimethyl sulfoxide was 10-fold diluted in Tris/EDTA buffer (pH 7.4). 22 µL of titrated compound were then added in duplicate to the substrate. Reactions were initiated by the addition of 10 µL of 0.1 mg/mL E. coli lysates overexpressing 11β-HSD1 enzyme. After shaking and incubating plates for 30 minutes at room temperature, reactions were stopped by adding 10 µL of 1 mM glycyrrhetinic acid. The product, tritiated cortisol, was captured by adding 10 µL of 1 µM monoclonal mouse anti-cortisol antibodies and 50 µL of SPA beads coated with anti-mouse antibodies. After shaking for 30 minutes, plates were read in a Microbeta scintillation counter. Percent inhibition was calculated based on the background and the maximal signal. Wells that contained substrate without compound or enzyme were used as the background, while the wells that contained substrate and enzyme without any compound were considered as maximal signal. Percent of inhibition of each compound was calculated relative to the maximal signal and $IC_{50}$ curves were generated. Assuming competitive inhibition the Cheng-Prusoff equation was used to calculate apparent Ki values from the $IC_{50}$ values. This assay was applied to 11β-HSD2 as well, whereby 6 nM tritiated cortisol and 250 uM $NAD^+$ were used as substrate and cofactor, respectively.

Compounds of the present invention are active in the 11β-HSD1 assay described above as indicated in Table 1. The legend in the table below is as follows: A—Ki≦0.01 µM; B—0.1 µM≧Ki>0.01 µM; C—1 µM≧Ki>0.1 µM; and D—Ki>1 µM; ND—not determined.

TABLE 1

Human 11β-HSD1 enzymatic SPA assay.

| Example # | Ki 11β-HSD1 [µM] |
|---|---|
| 1 | B |
| 2 | D |
| 3 | D |
| 4 | D |
| 5 | D |
| 6 | D |
| 7 | D |
| 8 | A |
| 9 | B |
| 10 | C |
| 11 | C |
| 12 | B |
| 13 | C |
| 14 | A |
| 15 | C |
| 16 | C |
| 17 | C |
| 18 | B |
| 19 | B |
| 20 | ND |
| 21 | B |
| 22 | D |
| 23 | C |
| 24 | B |
| 25 | B |
| 27 | A |
| 28 | C |
| 29 | C |
| 30 | D |
| 31 | C |
| 33 | C |
| 35 | D |
| 36 | C |
| 37 | B |
| 38 | B |
| 39 | D |
| 40 | D |
| 41 | B |
| 42 | C |
| 43 | B |
| 45 | A |
| 46 | D |
| 47 | B |
| 48 | C |
| 49 | B |
| 50 | A |
| 51 | A |

TABLE 1-continued

Human 11β-HSD1 enzymatic SPA assay.

| Example # | Ki 11β-HSD1 [μM] |
|---|---|
| 52 | B |
| 56 | A |
| 57 | B |
| 58 | C |
| 59 | C |
| 60 | B |
| 61 | C |
| 62 | B |
| 63 | B |
| 64 | A |
| 65 | C |
| 66 | C |
| 67 | C |
| 68 | D |
| 69 | B |
| 70 | A |
| 71 | B |
| 72 | D |
| 73 | C |
| 74 | A |
| 75 | B |
| 76 | D |
| 77 | C |
| 78 | B |
| 79 | B |
| 80 | A |
| 81 | D |
| 82 | B |
| 83 | C |
| 84 | C |
| 85 | C |
| 86 | B |
| 87 | D |
| 88 | C |
| 89 | B |
| 93 | D |

The data in Table 1 indicates that the compounds of the present invention are active in the human 11β-HSD1 enzymatic SPA assay described above. The 11β-HSD1 inhibitors of this invention generally have an inhibition constant Ki of less than 600 nM, and preferably less than 50 nM.

It is understood that the foregoing detailed description and examples are merely illustrative and are not to be taken as limitations upon the scope of the invention. Various changes and modifications to the disclosed embodiments will be apparent to those skilled in the art (see for example Moreira et al., Current Med. Chem. 12, 23-49 (2005); EP 1889842). Such changes and modifications, including without limitation those relating to the chemical structures, substituents, derivatives, intermediates, syntheses, formulations and/or methods of use of the invention, may be made without departing from the spirit and scope thereof. Such modifications are intended to fall within the scope of the appended claims.

All patents, patent applications, and literature references cited herein are hereby incorporated herein by reference in their entireties.

The invention claimed is:

1. A compound of formula (I):

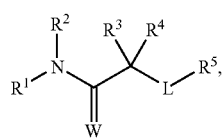

(I)

wherein

L is —$(CH_2)_n$—, or —$(CR^{38}R^{39})_m$—X—$(CR^{38}R^{39})_n$— or —$(CR^{38}R^{39})_m$—X—$(CR^{38}R^{39})_n$—Y—;

m is independently at each occurrence 0, 1, or 2;

n is independently at each occurrence 0, 1, or 2;

$R^1$ is cycloalkyl or heterocycle selected from the group consisting of

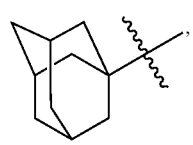

(i)

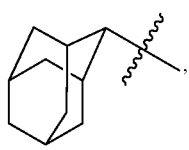

(ii)

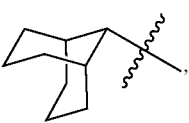

(iii)

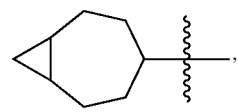

(iv)

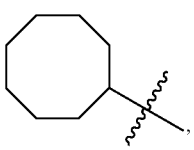

(v)

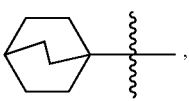

(vi)

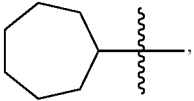

(vii)

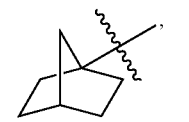

(viii)

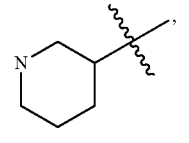

(ix)

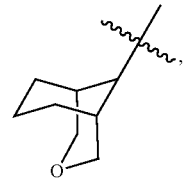

(x)

-continued

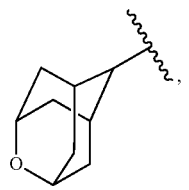 (xi),

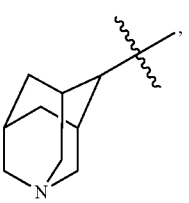 (xii),

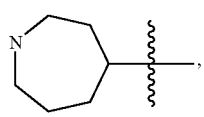 (xiii),

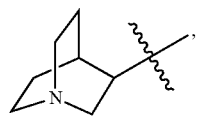 (xiv),

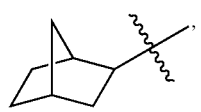 (xvi),

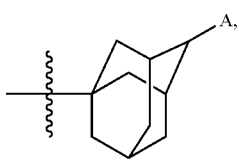 (xvii),

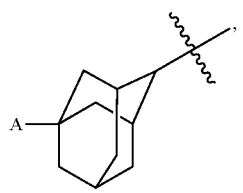 (ia),

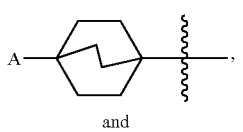 (iia),

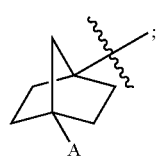 (via), and

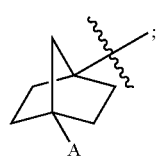 (viiia);

A is selected from the group consisting of alkyl, alkenyl, alkyl-NH-alkyl, alkylcarbonyl, alkylsulfonyl, alkylthio, aryl, arylalkyl, aryloxyalkyl, arylcarbonyl, arylsulfonyl, carboxyalkyl, carboxycycloalkyl, cyano, cyanoalkyl, cycloalkyl, cycloalkylcarbonyl, cycloalkylsulfonyl, halogen, haloalkyl, heterocyclecarbonyl, heterocyclesulfonyl, heteroaryl, heteroarylalkyl, heterocycle, heterocyclealkyl, heterocycleoxyalkyl, —NO$_2$, —NR$^8$—[C(R$^9$R$^{10}$)]$_p$—C(O)—R$^{11}$, —[C(R$^{12}$R$^{13}$)]$_q$—CR$^{12}$(OH)—R$^{14}$, —[C(R$^{12}$R$^{13}$)]$_q$C(O)—R$^{14}$, —CR$^{12}$=R$^{13}$—C(O)—R$^{14}$, —[C(R$^{12}$R$^{13}$)]$_q$S(O)$_2$—R$^{14}$, —[C(R$^{12}$R$^{13}$)]$_q$S(O)—R$^{14}$, —[C(R$^{12}$R$^{13}$)]$_q$S—R$^{14}$, —O—[C(R$^{12}$R$^{13}$)]$_q$—C(O)—R$^{14}$, —OR$^{15}$, —N(R$^{16}$R$^{17}$), NR$^8$C(O)N(R$^{19}$R$^{20}$), —CO$_2$R$^{18}$, —C(O)—N(R$^{19}$R$^{20}$), —[C(R$^{12}$R$^{13}$)]$_p$—C(O)—N(R$^{19}$R$^{20}$), —C(NH)NH$_2$, —C(R$^{21}$R$^{22}$)—OR$^{23}$, —C(R$^{24}$R$^{25}$)—N(R$^{26}$R$^{27}$), —C(=NOH)—N(H)$_2$, —C(R$^{28}$R$^{29}$)—C(O)N(R$^{30}$R$^{31}$), —S(O)$_2$—N(R$^{32}$R$^{33}$), —S(O)$_2$—[C(R$^9$R$^{10}$)]$_p$—C(O)N(R$^{32}$R$^{33}$), and —C(R$^{28}$R$^{29}$)—S(O)$_2$—N(R$^{32}$R$^{33}$), wherein p is 1, 2, 3, 4, 5 or 6, q is 0, 1, 2, 3, 4, 5 or 6, R$^8$ is hydrogen, alkyl, carboxyalkyl, cycloalkyl, carboxycycloalkyl, aryl, arylalkyl, aryloxyalkyl, aryloxy, hydroxy, alkoxy, cycloalkyloxy, heterocycleoxy, heterocycle, heterocyclealkyl, or heterocycleoxyalkyl, R$^9$ and R$^{10}$ are each independently hydrogen, alkyl, carboxy, carboxyalkyl, cycloalkyl, carboxycycloalkyl, aryl, arylalkyl, aryloxyalkyl, heterocycle, heterocyclealkyl, or heterocycleoxyalkyl, or R$^9$ and R$^{10}$ together with the atom to which they are attached form cycloalkyl or heterocycle, R$^{11}$ is hydrogen, alkyl, carboxy, carboxyalkyl, cycloalkyl, carboxycycloalkyl, aryl, aryloxy, arylalkyl, aryloxyalkyl, hydroxy, alkoxy, cycloalkyloxy, heterocycleoxy, heterocycle, heterocyclealkyl, heterocycleoxyalkyl, or —N(R$^{28}$R$^{29}$), R$^{12}$ and R$^{13}$ are each independently hydrogen, alkyl, carboxy, carboxyalkyl, cycloalkyl, carboxycycloalkyl, aryl, arylalkyl, aryloxyalkyl, heterocycle, heterocyclealkyl, heterocycleoxyalkyl or —N(R$^{28}$R$^{29}$), or R$^{12}$ and R$^{13}$ together with the atom to which they are attached form cycloalkyl or heterocycle, R$^{14}$ is hydrogen, alkyl, carboxy, carboxyalkyl, cycloalkyl, carboxycycloalkyl, aryl, arylalkyl, aryloxy, aryloxyalkyl, hydroxy, alkoxy, cycloalkyloxy, heterocycleoxy, heterocycle, heterocyclealkyl, heterocycleoxyalkyl, or —N(R$^{30}$R$^{31}$), R$^{15}$ is hydrogen, alkyl, alkylcarbonyl, carboxyalkyl, cycloalkyl, carboxycycloalkyl, aryl, arylalkyl, aryloxyalkyl, haloalkyl, heterocycle, heterocyclealkyl, or heterocycleoxyalkyl, R$^{16}$ and R$^{17}$ are each independently hydrogen, alkyl, alkylcarbonyl, carboxyalkyl, cycloalkyl, carboxycycloalkyl, aryl, arylalkyl, aryloxyalkyl, haloalkyl, heterocycle, heterocyclealkyl, heterocycleoxyalkyl, alkylsulfonyl, cycloalkylsulfonyl, arylsulfonyl, formyl, or heterocyclesulfonyl, or R$^{16}$ and R$^{17}$ together with the atom to which they are attached form a heterocycle, R$^{18}$ is hydrogen, alkyl, carboxyalkyl, cycloalkyl, carboxycycloalkyl, aryl, arylalkyl, aryloxyalkyl, heterocycle, heterocyclealkyl, or heterocycleoxyalkyl, R$^{19}$ and R$^{20}$ are each independently hydrogen, alkyl, carboxy, carboxyalkyl, cycloalkyl, cycloalkyloxy, carboxycycloalkyl, aryl, arylalkyl, aryloxy, aryloxyalkyl, heteroarylalkyl, heterocycle, heterocyclealkyl, heterocycleoxyalkyl, heterocycleoxy, hydroxy, alkoxy, alkylsulfonyl, cycloalkylsulfonyl, arylsulfonyl, heterocyclesulfonyl, or —[C(R$^{12}$R$^{13}$)$_q$]C(O)R$^{14}$, or R$^{19}$ and R$^{20}$ together with the atom to which they are attached form a heterocycle, R$^{21}$, R$^{22}$ and R$^{23}$ are each independently hydrogen, alkyl, carboxyalkyl, carboxycycloalkyl, cycloalkyl, haloalkyl, aryl, heterocycle, or heterocyclealkyl, R$^{24}$ and R$^{25}$ are each independently hydrogen, alkyl, alkylcarbonyl, alkylsulfonyl, carboxyalkyl, carboxycycloalkyl, cycloalkylcarbonyl, cycloalkylsulfonyl, arylcarbonyl, arylsulfonyl, heterocyclecarbonyl, heterocyclesulfonyl, cycloalkyl, aryl, or heterocycle, R$^{26}$ and R$^{27}$ are each independently hydrogen, alkyl, alkylcarbonyl, alkylsulfonyl, carboxyalkyl, carboxycycloalkyl, cycloalkylcarbonyl, cycloalkylsulfonyl, arylcarbonyl, arylsulfonyl, heterocyclecarbonyl, heterocyclesulfonyl, hydroxy, alkoxy, cycloalkyloxy, aryloxy, heterocycleoxy, cycloalkyl, aryl, or heterocycle, or R$^{26}$ and R$^{27}$ together with the atom to which they are attached form a heterocycle, R$^{28}$ and R$^{29}$ are each independently at each occurrence hydrogen or alkyl, R$^{30}$ and R$^{31}$ are each independently at each occurrence hydrogen, alkyl, alkylcarbonyl, alkoxy, alkylsulfonyl, aryl, arylcarbonyl, aryloxy, arylsulfonyl, carboxyalkyl, carboxycycloalkyl, cycloalkyl, cycloalkylcarbonyl, cycloalkyloxy, cycloalkylsulfonyl, heteroaryl, heteroarylcarbonyl, heteroaryloxy, heteroarylsulfonyl, heterocycle, heterocyclecarbonyl, heterocycleoxy, heterocyclesulfonyl, or hydroxy, or R$^{30}$ and R$^{31}$ taken together with the atom to which they are attached form heteroaryl or heterocycle, and R$^{32}$ and R$^{33}$ are each independently at each occurrence selected from the group consisting of hydrogen, alkyl, alkoxy, alkylsulfonyl, aryl, arylalkyl, aryloxy, aryloxyalkyl, arylsulfonyl, alkyl-NH-alkyl, aryl-NH-alkyl, arylalkyl, haloalkyl, aryl-heterocycle, carboxy, carboxyalkyl, carboxycycloalkyl, cycloalkyl, cycloalkyloxy, cycloalkylsulfonyl, heteroaryl, heteroarylalkyl, heteroaryloxyalkyl, heteroaryloxy, heteroarylsulfonyl, heterocycle, heterocycle-NH-alkyl, heterocyclealkyl, heterocycle-heterocycle, heterocycleoxyalkyl, heterocycleoxy, heterocyclesulfonyl, and hydroxy, or R$^{32}$ and R$^{33}$ taken together with the atom to which they are attached form a heterocycle;

R$^2$ is hydrogen, alkyl, or aryl;

R$^3$ and R$^4$ are independently hydrogen, alkyl or cycloalkyl;

R$^5$ is hydrogen, alkyl, amino, aryl, cycloalkyl, heteroaryl, or heterocycle provided R$^5$ is other than amino when L is —(CR$^{38}$R$^{39}$)$_m$—X—(CR$^{38}$R$^{39}$)$_n$—Y—;

X is —O—, —S—, —S(O)—, —S(O)$_2$—, —NR$^{36}$—, or —CR$^{36}$R$^{37}$—;

Y is O or NR$^{40}$;

R$^{36}$ and R$^{37}$ are independently at each occurrence hydrogen or alkyl;

R$^{38}$, R$^{39}$ and R$^{40}$ are independently at each occurrence hydrogen or alkyl;

W is N—CN, N—OR$^6$, N—R$^6$, or S; and

R$^6$ is hydrogen or alkyl; or a pharmaceutically acceptable salt thereof.

2. The compound of claim 1, wherein R$^1$ is cycloalkyl or heterocycle selected from the group consisting of

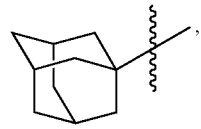  (i)

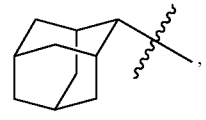  (ii)

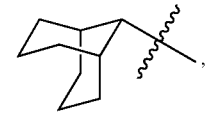  (iii)

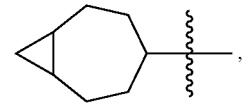  (iv)

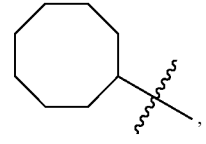  (v)

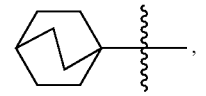  (vi)

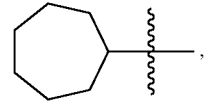  (vii)

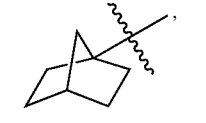  (viii)

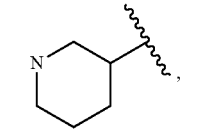  (ix)

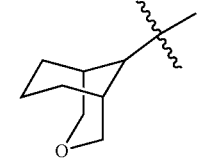  (x)

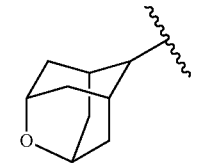  (xi)

-continued

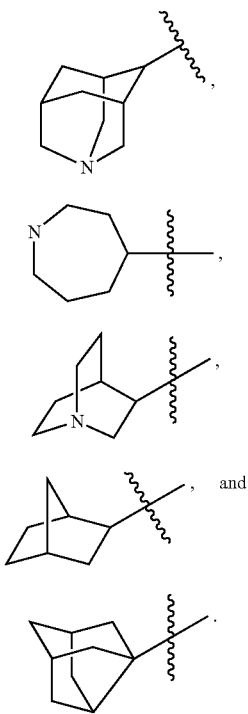

3. The compound of claim 1, wherein $R^5$ is phenyl, pyridyl, or heterocycle.

4. The compound of claim 1, wherein $R^3$ and $R^4$ are both hydrogen or both alkyl.

5. The compound of claim 1, wherein L is —$(CH_2)_n$— wherein n is 0, or —$(CR^{38}R^{39})_m$—X—$(CR^{38}R^{39})_n$— wherein both m and n are 0 and X is O.

6. The compound of claim 1, wherein $R^6$ is alkyl.

7. The compound of claim 1 selected from the group consisting of
(1E)-2-(2-chloro-4-fluorophenoxy)-N'-cyano-N-[(E)-5-hydroxy-2-adamantyl]-2-methylpropanimidamide;
(1E)-N'-cyano-N-[(E)-5-hydroxy-2-adamantyl]-2-(2-methylphenyl)ethanimidamide;
(1E)-N'-cyano-2-(2,4-difluorophenyl)-N-[(E)-5-hydroxy-2-adamantyl]ethanimidamide;
(1E)-N'-cyano-2-(2-fluorophenyl)-N-[(E)-5-hydroxy-2-adamantyl]ethanimidamide;
(1E)-2-(2-chloropyridin-3-yl)-N'-cyano-N-[(E)-5-hydroxy-2-adamantyl]ethanimidamide;
(1E)-2-(4-chlorophenoxy)-N'-cyano-N-[(E)-5-hydroxy-2-adamantyl]ethanimidamide;
(1E)-2-(4-chlorophenoxy)-N'-cyano-N-[(E)-5-hydroxy-2-adamantyl]-2-methylpropanimidamide;
2-(4-chlorophenoxy)-2-methyl-N-[(E)-5-(methylsulfonyl)-2-adamantyl]propanethioamide;
(1E)-N-[(E)-5-(aminosulfonyl)-2-adamantyl]-2-(4-chlorophenoxy)-N-cyano-2-methylpropanimidamide;
methyl(E)-4-{[(1E)-2-(4-chlorophenoxy)-N-cyano-2-methylpropanimidoyl]amino}adamantane-1-carboxylate;
2-(2-chloro-4-fluorophenoxy)-2-methyl-N-[(E)-5-(methylsulfonyl)-2-adamantyl]propanethioamide;
(1E)-2-(4-chlorophenoxy)-N'-methoxy-2-methyl-N-[(E)-5-(methylsulfonyl)-2-adamantyl]propanethioamide;
(E)-4-{[(1E)-2-(4-chlorophenoxy)-N-cyano-2-methylpropanimidoyl]amino}adamantane-1-carboxamide;
methyl(E)-4-[(2-methyl-2-{[4-(trifluoromethyl)benzyl]oxy}propanethioyl)amino]adamantane-1-carboxylate;
methyl(E)-4-[((1E)-N-cyano-2-methyl-2-{[4-(trifluoromethyl)benzyl]oxy}propanimidoyl)amino]adamantane-1-carboxylate;
(1E)-2-(2-chloro-4-fluorophenoxy)-N'-cyano-2-methyl-N-[(E)-5-(methylsulfonyl)-2-adamantyl]propanimidamide;
(1E)-2-(4-chlorophenoxy)-N'-cyano-2-methyl-N-[(E)-5-(methylsulfonyl)-2-adamantyl]propanimidamide;
N-[(E)-5-(aminosulfonyl)-2-adamantyl]-2-methyl-2-[2-(trifluoromethoxy)phenoxy]propanethioamide;
methyl(E)-4-[(2-methyl-2-{4-[5-(trifluoromethyl)pyridin-2-yl]piperazin-1-yl}propanethioyl)amino]adamantane-1-carboxylate;
3-(4-chlorophenyl)-N-[(E)-5-hydroxy-2-adamantyl]-2,2-dimethylpropanimidamide;
(1E)-3-(4-chlorophenyl)-N'-cyano-N-[(E)-5-hydroxy-2-adamantyl]-2,2-dimethylpropanimidamide;
(E)-4-[((1E)-N-cyano-2-methyl-2-{[4-(trifluoromethyl)benzyl]oxy}propanimidoyl)amino]adamantane-1-carboxylic acid;
(E)-4-[((1E)-N-cyano-2-methyl-2-{[4-(trifluoromethyl)benzyl]oxy}propanimidoyl)amino]adamantane-1-carboxamide;
(E)-4-[(2-methyl-2-{4-[5-(trifluoromethyl)pyridin-2-yl]piperazin-1-yl}propanethioyl)amino]adamantane-1-carboxylic acid;
(1E)-N'-cyano-N-[(E)-5-cyano-2-adamantyl]-2-methyl-2-{[4-(trifluoromethyl)benzyl]oxy}propanimidamide;
methyl(E)-4-({(1E)-N-cyano-2-[(4-methoxybenzyl)oxy]-2-methylpropanimidoyl}amino)adamantane-1-carboxylate;
methyl(E)-4-[((1E)-N-cyano-2-methyl-2-{4-[5-(trifluoromethyl)pyridin-2-yl]piperazin-1-yl}propanimidoyl)amino]adamantane-1-carboxylate;
(E)-4-[((1E)-N-cyano-2-methyl-2-{4-[5-(trifluoromethyl)pyridin-2-yl]piperazin-1-yl}propanimidoyl)amino]adamantane-1-carboxylic acid;
(E)-4-[((1E)-N-cyano-2-methyl-2-{4-[5-(trifluoromethyl)pyridin-2-yl]piperazin-1-yl}propanimidoyl)amino]adamantane-1-carboxamide;
(E)-4-{[(1E)-2-(4-chlorophenoxy)-N-cyano-2-methylpropanimidoyl]amino}adamantane-1-carboxylic acid;
(1E)-2-(4-chlorophenoxy)-N'-cyano-N-[(E)-5-cyano-2-adamantyl]-2-methylpropanimidamide;
(1E)-2-(4-chlorophenoxy)-N'-cyano-N-hexahydro-2,5-methanopentalen-3a(1H)-yl-2-methylpropanimidamide;
(1E)-N-[(4s)-1-azatricyclo[3.3.1.1$^{3,7}$]dec-4-yl]-2-(4-chlorophenoxy)-N'-cyano-2-methylpropanimidamide;
N-1-azabicyclo[2.2.2]oct-3-yl-2-(4-chlorophenoxy)-N-cyano-2-methylpropanimidamide;
2-(4-chlorophenoxy)-N'-cyano-N-cyclooctyl-2-methylpropanimidamide;
N-[exo-bicyclo[2.2.1]hept-2-yl]-2-(4-chlorophenoxy)-N-cyano-2-methylpropanimidamide;
(1E)-N-1-adamantyl-2-(4-chlorophenoxy)-N-cyano-2-methylpropanimidamide;
(1E)-N'-cyano-2-(2-fluorophenoxy)-2-methyl-N-[(E)-5-(methylsulfonyl)adamantan-2-yl]propanimidamide;
2-(2-fluorophenoxy)-2-methyl-N-[(E)-5-(methylsulfonyl)adamantan-2-yl]propanethioamide;
(1E)-N'-cyano-2-(2,4-difluorophenoxy)-2-methyl-N-[(E)-5-(methylsulfonyl)adamantan-2-yl]propanimidamide;

2-(2,4-difluorophenoxy)-2-methyl-N-[(E)-5-(methylsulfonyl)adamantan-2-yl]propanethioamide;
4-{[2-(4-chlorophenoxy)-N-cyano-2-methylpropanimidoyl]amino}bicyclo[2.2.2]octane-1-carboxylic acid;
4-{[2-(4-chlorophenoxy)-N-cyano-2-methylpropanimidoyl]amino}bicyclo[2.2.2]octane-1-carboxamide;
methyl(E)-4-({(1E)-2-[(1R*,5S*,6R*)-6-(4-chlorophenyl)-3-azabicyclo[3.2.0]hept-3-yl]-N-cyano-2-methylpropanimidoyl}amino)adamantane-1-carboxylate;
methyl(E)-4-({2-[(1R*,5S*,6R*)-6-(4-chlorophenyl)-3-azabicyclo[3.2.0]hept-3-yl]-2-methylpropanethioyl}amino)adamantane-1-carboxylate;
(1E)-N'-cyano-N-[(E)-5-hydroxyadamantan-2-yl]-2-methyl-2-phenoxypropanimidamide;
(E)-4-{[(1E)-N-cyano-2-methyl-2-phenoxypropanimidoyl]amino}adamantane-1-carboxamide;
(1E)-N'-cyano-2-(2,4-difluorophenoxy)-N-[(E)-5-hydroxyadamantan-2-yl]-2-methylpropanimidamide;
(1E)-N'-cyano-N-[(E)-5-cyano adamantan-2-yl]-2-(2,4-difluorophenoxy)-2-methylpropanimidamide;
(1E)-2-(4-chloro-2-fluorophenoxy)-Y-cyano-N-[(E)-5-cyano adamantan-2-yl]-2-methylpropanimidamide;
(1E)-2-(4-chloro-2-fluorophenoxy)-Y-cyano-2-methyl-N-[(E)-5-sulfamoyladamantan-2-yl]propanimidamide;
(1E)-2-(4-chloro-2-fluorophenoxy)-Y-cyano-N-[(E)-5-hydroxyadamantan-2-yl]-2-methylpropanimidamide;
N-[(exo)-bicyclo[2.2.1]hept-2-yl]-N-cyano-2-(2,4-difluorophenoxy)-2-methylpropanimidamide;
(1E)-N'-cyano-2-(2,4-difluorophenoxy)-2-methyl-N-[(E)-5-sulfamoyladamantan-2-yl]propanimidamide;
(1E)-2-[(5-chloropyridin-2-yl)oxy]-N'-cyano-N-[(E)-5-hydroxyadamantan-2-yl]-2-methylpropanimidamide;
(1E)-2-[(5-chloropyridin-2-yl)oxy]-N'-cyano-N-[(E)-5-cyano adamantan-2-yl]-2-methylpropanimidamide;
(1E)-N-(adamantan-1-yl)-2-(4-chloro-2-fluorophenoxy)-N-cyano-2-methylpropanimidamide;
2-(4-chloro-2-fluorophenoxy)-N'-cyano-N-cyclooctyl-2-methylpropanimidamide;
(1E)-N-[(E)-adamantan-2-yl]-2-(4-chloro-2-fluorophenoxy)-N-cyano-2-methylpropanimidamide;
methyl(E)-4-{[(1E)-2-(4-chloro-2-fluorophenoxy)-N-cyano-2-methylpropanimidoyl]amino}adamantane-1-carboxylate;
(1E)-N'-cyano-2-methyl-N-[(E)-5-(methylsulfonyl)adamantan-2-yl]-2-phenoxypropanimidamide;
N'-cyano-N-cyclooctyl-2-(2,4-difluorophenoxy)-2-methylpropanimidamide;
N-(exo-bicyclo[2.2.1]hept-2-yl)-2-(4-chloro-2-fluorophenoxy)-N-cyano-2-methylpropanimidamide;
(1E)-2-[(5-chloropyridin-2-yl)oxy]-N-cyano-2-methyl-N-[(E)-5-(methylsulfonyl)adamantan-2-yl]propanimidamide;
(1E)-2-[(5-chloropyridin-2-yl)oxy]-N-cyano-2-methyl-N-[(E)-5-sulfamoyladamantan-2-yl]propanimidamide;
N'-cyano-2-(2,4-difluorophenoxy)-N-(hexahydro-2,5-methanopentalen-3a(1H)-yl)-2-methylpropanimidamide;
(E)-4-{[(1E)-N-cyano-2-(2,4-difluorophenoxy)-2-methylpropanimidoyl]amino}adamantane-1-carboxamide;
(1E)-N-[(3R,5R)-adamantan-1-yl]-N-cyano-2-(2,4-difluorophenoxy)-2-methylpropanimidamide;
(1E)-N-(1-azabicyclo[2.2.2]oct-3-yl)-2-(4-chloro-2-fluorophenoxy)-Y-cyano-2-methylpropanimidamide;
2-(4-chloro-2-fluorophenoxy)-N'-cyano-N-(hexahydro-2,5-methanopentalen-3a(1H)-yl)-2-methylpropanimidamide;
(E)-4-{[(1E)-2-(4-chloro-2-fluorophenoxy)-N-cyano-2-methylpropanimidoyl]amino}adamantane-1-carboxamide;
(E)-4-({(1E)-2-[(5-chloropyridin-2-yl)oxy]-N-cyano-2-methylpropanimidoyl}amino)adamantane-1-carboxamide;
(E)-4-[(2-methyl-2-phenoxypropanimidoyl)amino]adamantane-1-carboxamide;
(1E)-N'-cyano-2-methyl-N-[(E)-5-(methylsulfonyl)adamantan-2-yl]-2-(pyridin-2-yloxy)propanimidamide;
(1E)-N'-cyano-N-[(E)-5-cyanoadamantan-2-yl]-2-(2-fluorophenoxy)-2-methylpropanimidamide;
(1E)-N'-cyano-2-(2-fluorophenoxy)-2-methyl-N-[(E)-5-sulfamoyladamantan-2-yl]propanimidamide;
(1E)-N'-cyano-2-(2-fluorophenoxy)-N-[(E)-5-hydroxyadamantan-2-yl]-2-methylpropanimidamide;
4-{[N-cyano-2-methyl-2-phenoxypropanimidoyl]amino}bicyclo[2.2.1]heptane-1-carboxamide;
4-{[N-cyano-2-methyl-2-phenoxypropanimidoyl]amino}bicyclo[2.2.2]octane-1-carboxamide;
N'-cyano-N-(4-cyanobicyclo[2.2.1]hept-1-yl)-2-methyl-2-phenoxypropanimidamide;
N'-cyano-N-(4-cyanobicyclo[2.2.2]oct-1-yl)-2-methyl-2-phenoxypropanimidamide;
2-(4-chlorophenoxy)-N'-cyano-N-[4-(difluoromethyl)bicyclo[2.2.2]oct-1-yl]-2-methylpropanimidamide;
N'-cyano-N-[4-(difluoromethyl)bicyclo[2.2.2]oct-1-yl]-2-methyl-2-phenoxypropanimidamide;
4-{[N-cyano-2-methyl-2-phenoxypropanimidoyl]amino}bicyclo[2.2.2]octane-1-carboxylic acid;
4-{[2-(4-chlorophenoxy)-N-cyano-2-methylpropanimidoyl]amino}bicyclo[2.2.1]heptane-1-carboxamide;
N'-cyano-N-[4-(difluoromethyl)bicyclo[2.2.1]hept-1-yl]-2-methyl-2-phenoxypropanimidamide;
2-(2-fluorophenoxy)-2-methyl-N-[(E)-5-sulfamoyladamantan-2-yl]propanimidamide;
2-(2-fluorophenoxy)-N-[(E)-5-hydroxyadamantan-2-yl]-2-methylpropanimidamide;
N-[(E)-5-hydroxyadamantan-2-yl]-2-methyl-2-phenoxypropanimidamide;
2-(4-chlorophenoxy)-N'-cyano-N-(4-hydroxybicyclo[2.2.2]oct-1-yl)-2-methylpropanimidamide;
N'-cyano-N-(4-hydroxybicyclo[2.2.2]oct-1-yl)-2-methyl-2-phenoxypropanimidamide;
2-(4-chlorophenoxy)-N'-cyano-N-(4-cyanobicyclo[2.2.2]oct-1-yl)-2-methylpropanimidamide;
N'-cyano-N-(4-hydroxybicyclo[2.2.1]hept-1-yl)-2-methyl-2-phenoxypropanimidamide;
4-({2-[(4-chlorobenzyl)oxy]-N-cyano-2-methylpropanimidoyl}amino)adamantane-1-carboxamide;
4-[(N-cyano-2-methyl-2-{[4-(methylsulfonyl)benzyl]oxy}propanimidoyl)amino]adamantane-1-carboxamide;
4-{[N-cyano-2-methyl-2-(pyridin-2-ylmethoxy)propanimidoyl]amino}adamantane-1-carboxamide;
4-[(N-cyano-2-methyl-2-{[4-(trifluoromethoxy)benzyl]oxy}propanimidoyl)amino]adamantane-1-carboxylic acid;
4-[(N-cyano-2-methyl-2-{[4-(trifluoromethoxy)benzyl]oxy}propanimidoyl)amino]adamantane-1-carboxamide;

4-({N-cyano-2-[(4-cyanobenzyl)oxy]-2-methylpropanimidoyl}amino)adamantane-1-carboxamide;

4-({N-cyano-2-[(4-methoxybenzyl)oxy]-2-methylpropanimidoyl}amino)adamantane-1-carboxamide;

4-[(N-cyano-2-{[2-fluoro-4-(trifluoromethyl)benzyl]oxy}-2-methylpropanimidoyl)amino]adamantane-1-carboxamide;

4-[(N-cyano-2-{[4-(difluoromethoxy)benzyl]oxy}-2-methylpropanimidoyl)amino]adamantane-1-carboxylic acid;

4-[(N-cyano-2-{[4-(difluoromethoxy)benzyl]oxy}-2-methylpropanimidoyl)amino]adamantane-1-carboxamide;

4-({2-[(4-chloro-2-fluorobenzyl)oxy]-N-cyano-2-methylpropanimidoyl}amino)adamantane-1-carboxylic acid;

4-({2-[(4-chloro-2-fluorobenzyl)oxy]-N-cyano-2-methylpropanimidoyl}amino)adamantane-1-carboxamide;

4-({N-cyano-2-[(4-methoxybenzyl)oxy]-2-methylpropanimidoyl}amino)adamantane-1-carboxylic acid;

4-[(N-cyano-2-{[2-fluoro-4-(trifluoromethyl)benzyl]oxy}-2-methylpropanimidoyl)amino]adamantane-1-carboxylic acid;

4-{[N-cyano-2-methyl-2-(pyridin-2-ylmethoxy)propanimidoyl]amino}adamantane-1-carboxylic acid;

4-[(2-{[2-bromo-4-(trifluoromethyl)benzyl]oxy}-N-cyano-2-methylpropanimidoyl)amino]adamantane-1-carboxamide;

4-({N-cyano-2-[(2,6-difluorobenzyl)oxy]-2-methylpropanimidoyl}amino)adamantane-1-carboxylic acid;

4-({N-cyano-2-[(2,3-difluorobenzyl)oxy]-2-methylpropanimidoyl}amino)adamantane-1-carboxylic acid;

4-({N-cyano-2-[(3,4-difluorobenzyl)oxy]-2-methylpropanimidoyl}amino)adamantane-1-carboxamide;

4-{[2-(benzyloxy)-N-cyano-2-methylpropanimidoyl]amino}adamantane-1-carboxamide;

4-({N-cyano-2-[(2,5-difluorobenzyl)oxy]-2-methylpropanimidoyl}amino)adamantane-1-carboxylic acid;

4-({N-cyano-2-[(3,5-difluorobenzyl)oxy]-2-methylpropanimidoyl}amino)adamantane-1-carboxylic acid;

4-({N-cyano-2-[(3-methoxybenzyl)oxy]-2-methylpropanimidoyl}amino)adamantane-1-carboxylic acid;

4-({N-cyano-2-[(2-fluorobenzyl)oxy]-2-methylpropanimidoyl}amino)adamantane-1-carboxylic acid;

4-({N-cyano-2-[(2,6-difluorobenzyl)oxy]-2-methylpropanimidoyl}amino)adamantane-1-carboxamide;

4-({N-cyano-2-[(2-cyanobenzyl)oxy]-2-methylpropanimidoyl}amino)adamantane-1-carboxamide;

4-({N-cyano-2-[(2,3-difluorobenzyl)oxy]-2-methylpropanimidoyl}amino)adamantane-1-carboxamide;

4-({N-cyano-2-[(2-methoxybenzyl)oxy]-2-methylpropanimidoyl}amino)adamantane-1-carboxylic acid;

4-({N-cyano-2-[(4-fluorobenzyl)oxy]-2-methylpropanimidoyl}amino)adamantane-1-carboxylic acid;

4-({2-[(3-chlorobenzyl)oxy]-N-cyano-2-methylpropanimidoyl}amino)adamantane-1-carboxamide;

4-({N-cyano-2-[(4-isopropylbenzyl)oxy]-2-methylpropanimidoyl}amino)adamantane-1-carboxylic acid;

4-[(N-cyano-2-methyl-2-{[3-(trifluoromethyl)benzyl]oxy}propanimidoyl)amino]adamantane-1-carboxylic acid;

4-({N-cyano-2-methyl-2-[(4-methylbenzyl)oxy]propanimidoyl}amino)adamantane-1-carboxylic acid;

methyl 4-[(N-cyano-2-methyl-2-{[4-(trifluoromethyl)benzyl]oxy}propanimidoyl)amino]adamantane-1-carboxylate;

4-{[2-(1,3-benzodioxol-5-ylmethoxy)-N-cyano-2-methylpropanimidoyl]amino}adamantane-1-carboxylic acid;

4-({N-cyano-2-[(2,4-dichlorobenzyl)oxy]-2-methylpropanimidoyl}amino)adamantane-1-carboxylic acid;

4-({N-cyano-2-[(2-methoxybenzyl)oxy]-2-methylpropanimidoyl}amino)adamantane-1-carboxamide;

4-({N-cyano-2-[(3-cyanobenzyl)oxy]-2-methylpropanimidoyl}amino)adamantane-1-carboxamide;

4-({N-cyano-2-[(2-fluorobenzyl)oxy]-2-methylpropanimidoyl}amino)adamantane-1-carboxamide;

4-({2-[(4-tert-butylbenzyl)oxy]-N-cyano-2-methylpropanimidoyl}amino)adamantane-1-carboxamide;

4-({N-cyano-2-[(3-fluorobenzyl)oxy]-2-methylpropanimidoyl}amino)adamantane-1-carboxamide;

4-[(N-cyano-2-methyl-2-{[3-(trifluoromethyl)benzyl]oxy}propanimidoyl)amino]adamantane-1-carboxamide;

4-({N-cyano-2-methyl-2-[(4-methylbenzyl)oxy]propanimidoyl}amino)adamantane-1-carboxamide;

4-({N-cyano-2-[(3,5-difluorobenzyl)oxy]-2-methylpropanimidoyl}amino)adamantane-1-carboxamide;

4-({N-cyano-2-[(3-methoxybenzyl)oxy]-2-methylpropanimidoyl}amino)adamantane-1-carboxamide;

4-({N-cyano-2-methyl-2-[(6-methylpyridin-2-yl)methoxy]propanimidoyl}amino)adamantane-1-carboxylic acid;

4-({N-cyano-2-methyl-2-[(6-methylpyridin-2-yl)methoxy]propanimidoyl}amino)adamantane-1-carboxamide;

4-({N-cyano-2-[(4-fluorobenzyl)oxy]-2-methylpropanimidoyl}amino)adamantane-1-carboxamide;

4-[(N-cyano-2-methyl-2-{[3-(trifluoromethoxy)benzyl]oxy}propanimidoyl)amino]adamantane-1-carboxylic acid;

4-[(N-cyano-2-methyl-2-{[3-(trifluoromethoxy)benzyl]oxy}propanimidoyl)amino]adamantane-1-carboxamide;

4-{[N-cyano-2-methyl-2-(quinolin-2-ylmethoxy)propanimidoyl]amino}adamantane-1-carboxamide;

4-({N-cyano-2-[(2,4-dichlorobenzyl)oxy]-2-methylpropanimidoyl}amino)adamantane-1-carboxamide;
4-{[N-cyano-2-methyl-2-(quinolin-2-ylmethoxy)propanimidoyl]amino}adamantane-1-carboxylic acid;
4-({N-cyano-2-[(4-isopropylbenzyl)oxy]-2-methylpropanimidoyl}amino)adamantane-1-carboxamide;
4-({N-cyano-2-methyl-2-[(3-methylbenzyl)oxy]propanimidoyl}amino)adamantane-1-carboxamide;
4-({N-cyano-2-[(2,5-difluorobenzyl)oxy]-2-methylpropanimidoyl}amino)adamantane-1-carboxamide;
N'-cyano-N-(5-hydroxy-2-adamantyl)-2-{4-[5-(trifluoromethyl)pyridin-2-yl]piperazin-1-yl}ethanimidamide;
N'-cyano-2-(2,6-dimethylmorpholin-4-yl)-N-(5-hydroxy-2-adamantyl)propanimidamide;
N'-cyano-N-(5-hydroxy-2-adamantyl)-2-{4-[5-(trifluoromethyl)pyridin-2-yl]piperazin-1-yl}propanimidamide;
N'-cyano-N-(5-hydroxy-2-adamantyl)-2-(4-hydroxypiperidin-1-yl)propanimidamide;
2-azepan-1-yl-N'-cyano-N-(5-hydroxy-2-adamantyl)propanimidamide;
4-[(N-cyano-2-{4-[5-(trifluoromethyl)pyridin-2-yl]piperazin-1-yl}ethanimidoyl)amino]-1-adamantyl carbamate;
4-[(N-cyano-2-{4-[5-(trifluoromethyl)pyridin-2-yl]piperazin-1-yl}ethanimidoyl)amino]-1-adamantyl acetate;
N-{4-[(N-cyano-2-{4-[5-(trifluoromethyl)pyridin-2-yl]piperazin-1-yl}ethanimidoyl)amino]-1-adamantyl}acetamide;
N'-cyano-N-(5-hydroxy-2-adamantyl)-2-methyl-2-{4-[5-(trifluoromethyl)pyridin-2-yl]piperazin-1-yl}propanimidamide;
N'-cyano-N-(5-fluoro-2-adamantyl)-2-{4-[5-(trifluoromethyl)pyridin-2-yl]piperazin-1-yl}ethanimidamide;
N'-cyano-N-(5-hydroxy-2-adamantyl)-2-[4-(5-methylpyridin-2-yl)piperazin-1-yl]propanimidamide;
2-{[2-(4-chlorophenyl)ethyl]amino}-N'-cyano-N-(5-hydroxy-2-adamantyl)propanimidamide;
2-(4-benzylpiperidin-1-yl)-N'-cyano-N-(5-hydroxy-2-adamantyl)propanimidamide;
N'-cyano-N-(5-hydroxy-2-adamantyl)-2-(6,7,9,10-tetrahydro-8H-[1,3]dioxolo[4,5-g][3]benzazepin-8-yl)propanimidamide;
N'-cyano-N-(5-hydroxy-2-adamantyl)-2-(4-pyridin-2-ylpiperazin-1-yl)propanimidamide;
N'-cyano-2-[4-(4-fluorophenyl)piperazin-1-yl]-N-(5-hydroxy-2-adamantyl)propanimidamide;
N'-cyano-N-(5-hydroxy-2-adamantyl)-2-[4-(4-methoxyphenyl)piperazin-1-yl]propanimidamide;
N'-cyano-2-[4-(5-cyanopyridin-2-yl)piperazin-1-yl]-N-(5-hydroxy-2-adamantyl)propanimidamide;
N'-cyano-2-[4-(2-furoyl)piperazin-1-yl]-N-(5-hydroxy-2-adamantyl)propanimidamide;
N'-cyano-2-(1,3-dihydro-2H-isoindol-2-yl)-N-(5-hydroxy-2-adamantyl)propanimidamide;
N'-cyano-N-(5-hydroxy-2-adamantyl)-2-{4-[4-(trifluoromethyl)phenyl]piperazin-1-yl}propanimidamide;
N'-cyano-N-(5-hydroxy-2-adamantyl)-2-{4-[5-(trifluoromethyl)pyridin-2-yl]piperazin-1-yl}propanimidamide;
2-[3-(4-chlorophenoxy)azetidin-1-yl]-N'-cyano-N-(5-hydroxy-2-adamantyl)propanimidamide;
N'-cyano-2-[4-(2-fluorophenoxy)piperidin-1-yl]-N-(5-hydroxy-2-adamantyl)propanimidamide;
N'-cyano-2-[3-(2-fluorophenoxy)piperidin-1-yl]-N-(5-hydroxy-2-adamantyl)propanimidamide;
N'-cyano-2-[3-(3-fluorophenoxy)pyrrolidin-1-yl]-N-(5-hydroxy-2-adamantyl)propanimidamide;
N'-cyano-2-[[2-(3,4-dichlorophenyl)ethyl](methyl)amino]-N-(5-hydroxy-2-adamantyl)propanimidamide;
2-[[2-(4-chlorophenyl)-1-methylethyl](methyl)amino]-N'-cyano-N-(5-hydroxy-2-adamantyl)propanimidamide;
2-(5-chloro-2,3-dihydro-1H-indol-1-yl)-N'-cyano-N-(5-hydroxy-2-adamantyl)propanimidamide;
2-[4-(6-chloropyridin-3-yl)piperazin-1-yl]-N'-cyano-N-(5-hydroxy-2-adamantyl)propanimidamide;
N'-cyano-N-(5-hydroxy-2-adamantyl)-2-(3-phenylazetidin-1-yl)propanimidamide;
N'-cyano-N-[5-(hydroxymethyl)-2-adamantyl]-2-methyl-2-{4-[5-(trifluoromethyl)pyridin-2-yl]piperazin-1-yl}propanimidamide;
4-[(N-cyano-2-methyl-2-{4-[5-(trifluoromethyl)pyridin-2-yl]piperazin-1-yl}propanimidoyl)amino]-N-methyladamantane-1-carboxamide;
4-[(N-cyano-2-methyl-2-{4-[5-(trifluoromethyl)pyridin-2-yl]piperazin-1-yl}propanimidoyl)amino]-N-methoxyadamantane-1-carboxamide;
4-[(N-cyano-2-methyl-2-{4-[5-(trifluoromethyl)pyridin-2-yl]piperazin-1-yl}propanimidoyl)amino]-N-hydroxyadamantane-1-carboxamide;
N-[5-(aminomethyl)-2-adamantyl]-N-cyano-2-methyl-2-{4-[5-(trifluoromethyl)pyridin-2-yl]piperazin-1-yl}propanimidamide;
4-({N-cyano-2-methyl-2-[2-(trifluoromethyl)pyrrolidin-1-yl]propanimidoyl}amino)adamantane-1-carboxamide;
4-{[N-cyano-2-(3,3-difluoropiperidin-1-yl)-2-methylpropanimidoyl]amino}adamantane-1-carboxamide;
N'-cyano-2-methyl-N-[5-(5-methyl-1,2,4-oxadiazol-3-yl)-2-adamantyl]-2-{4-[5-(trifluoromethyl)pyridin-2-yl]piperazin-1-yl}propanimidamide;
N'-cyano-2-methyl-N-[5-(2H-tetraazol-5-yl)-2-adamantyl]-2-{4-[5-(trifluoromethyl)pyridin-2-yl]piperazin-1-yl}propanimidamide;
4-[(2-{4-[[(4-chlorophenyl)sulfonyl](cyclopropyl)amino]piperidin-1-yl}-N-cyanopropanimidoyl)amino]adamantane-1-carboxamide;
4-[(N-cyano-2-{4-[5-(trifluoromethyl)pyridin-2-yl]piperazin-1-yl}propanimidoyl)amino]adamantane-1-carboxamide;
N'-cyano-N-(5-hydroxy-2-adamantyl)-2-methyl-2-[2-(trifluoromethyl)pyrrolidin-1-yl]propanimidamide;
4-{[N-cyano-2-(3-fluoropyrrolidin-1-yl)-2-methylpropanimidoyl]amino}adamantane-1-carboxamide;
4-{[N-cyano-2-(3-fluoropyrrolidin-1-yl)propanimidoyl]amino}adamantane-1-carboxamide;
4-{[N-cyano-2-(3,3-difluoropiperidin-1-yl)propanimidoyl]amino}adamantane-1-carboxamide;
4-({N-cyano-2-[2-(trifluoromethyl)pyrrolidin-1-yl]propanimidoyl}amino)adamantane-1-carboxamide;
methyl 4-{[N-cyano-2-methyl-2-(4-pyridin-2-ylpiperazin-1-yl)propanimidoyl]amino}adamantane-1-carboxylate;
4-{[N-cyano-2-methyl-2-(4-pyridin-2-ylpiperazin-1-yl)propanimidoyl]amino}adamantane-1-carboxylic acid;
4-{[N-cyano-2-methyl-2-(2-methyl-4-pyridin-2-ylpiperazin-1-yl)propanimidoyl]amino}adamantane-1-carboxylic acid;

4-({2-[4-(5-chloropyridin-2-yl)piperazin-1-yl]-N-cyano-2-methylpropanimidoyl}amino)adamantane-1-carboxylic acid;
4-{[N-cyano-2-(3,3-difluoropiperidin-1-yl)ethanimidoyl]amino}adamantane-1-carboxylic acid;
4-({N-cyano-2-[2-(trifluoromethyl)pyrrolidin-1-yl]ethanimidoyl}amino)adamantane-1-carboxylic acid;
4-[(N-cyano-2-{4-[5-(trifluoromethyl)pyridin-2-yl]piperazin-1-yl}ethanimidoyl)amino]adamantane-1-carboxylic acid;
4-{[N-cyano-2-methyl-2-(4-pyridin-2-ylpiperazin-1-yl)propanimidoyl]amino}adamantane-1-carboxamide;
4-[(N-cyano-2-{4-[5-(trifluoromethyl)pyridin-2-yl]piperazin-1-yl}ethanimidoyl)amino]adamantane-1-carboxamide;
N'-cyano-2-methyl-N-[5-(4H-1,2,4-triazol-3-yl)-2-adamantyl]-2-{4-[5-(trifluoromethyl)pyridin-2-yl]piperazin-1-yl}propanimidamide;
4-{[N-cyano-2-(3,3-difluoropiperidin-1-yl)-2-methylpropanimidoyl]amino}-N-(2-furylmethyl)adamantane-1-carboxamide;
4-{[N-cyano-2-(3,3-difluoropiperidin-1-yl)-2-methylpropanimidoyl]amino}-N-(pyridin-4-ylmethyl)adamantane-1-carboxamide;
4-({2-[4-(4-chlorophenyl)piperidin-1-yl]-N-cyano-2-methylpropanimidoyl}amino)adamantane-1-carboxylic acid;
4-{[N-cyano-2-methyl-2-(4-phenylpiperidin-1-yl)propanimidoyl]amino}adamantane-1-carboxylic acid;
4-{[N-cyano-2-methyl-2-(1,2,4,5-tetrahydro-3H-3-benzazepin-3-yl)propanimidoyl]amino}adamantane-1-carboxylic acid;
4-[(N-cyano-2-methyl-2-{4-[4-(trifluoromethyl)phenyl]piperazin-1-yl}propanimidoyl)amino]adamantane-1-carboxylic acid;
4-({N-cyano-2-[2-(trifluoromethyl)pyrrolidin-1-yl]ethanimidoyl}amino)adamantane-1-carboxamide;
4-{[N-cyano-2-(3,3-difluoropiperidin-1-yl)ethanimidoyl]amino}adamantane-1-carboxamide;
4-({N-cyano-2-methyl-2-[2-methyl-4-(5-methylpyridin-2-yl)piperazin-1-yl]propanimidoyl}amino)adamantane-1-carboxylic acid;
4-{[N-cyano-2-(3-fluoropiperidin-1-yl)propanimidoyl]amino}adamantane-1-carboxamide;
4-[(N-cyano-2-{[4-(trifluoromethyl)benzyl]oxy}propanimidoyl)amino]adamantane-1-carboxylic acid;
4-[(N-cyano-2-{4-[5-(trifluoromethyl)pyridin-2-yl]piperazin-1-yl}propanimidoyl)amino]adamantane-1-carboxamide;
4-[(N-cyano-2-{[4-(trifluoromethyl)benzyl]oxy}propanimidoyl)amino]adamantane-1-carboxylic acid;
4-[(N-cyano-2-{2-(trifluoromethyl)-4-[5-(trifluoromethyl)pyridin-2-yl]piperazin-1-yl}ethanimidoyl)amino]adamantane-1-carboxamide;
4-({N-cyano-2-[4-(5-fluoropyridin-3-yl)-1,4-diazepan-1-yl]-2-methylpropanimidoyl}amino)adamantane-1-carboxamide;
4-[(N-cyano-2-cyclopropyl-2-{4-[5-(trifluoromethyl)pyridin-2-yl]piperazin-1-yl}ethanimidoyl)amino]adamantane-1-carboxylic acid;
4-({N-cyano-2-methyl-2-[4-(3-methylphenyl)-1,4-diazepan-1-yl]propanimidoyl}amino)adamantane-1-carboxylic acid;
4-[(N-cyano-2-methyl-2-phenoxypropanimidoyl)amino]adamantane-1-carboxamide;

4-[(N-cyano-2-methyl-2-{[4-(trifluoromethyl)benzyl]oxy}propanimidoyl)amino]adamantane-1-carboxamide;
4-({2-[7-(5-bromopyridin-2-yl)-3,7-diazabicyclo[3.3.1]non-3-yl]-N-cyano-2-methylpropanimidoyl}amino)adamantane-1-carboxamide;
4-({2-[5-(6-chloropyridin-3-yl)hexahydropyrrolo[3,4-c]pyrrol-2 (1H)-yl]-N-cyano-2-methylpropanimidoyl}amino)adamantane-1-carboxamide;
4-{[N-cyano-2-methyl-2-(3-pyridin-3-yl-3,9-diazabicyclo[4.2.1]non-9-yl)propanimidoyl]amino}adamantane-1-carboxamide;
4-({[(4-{[N-cyano-2-(3,3-difluoropiperidin-1-yl)-2-methylpropanimidoyl]amino}-1-adamantyl)carbonyl]amino}methyl)benzoic acid;
4-[(N-cyano-2-{4-[5-(trifluoromethyl)pyridin-2-yl]piperazin-1-yl}butanimidoyl)amino]adamantane-1-carboxamide;
4-[(N-cyano-2-cyclopropyl-2-{4-[5-(trifluoromethyl)pyridin-2-yl]piperazin-1-yl}ethanimidoyl)amino]adamantane-1-carboxamide;
4-({N-cyano-2-methyl-2-[(2-methylcyclohexyl)oxy]propanimidoyl}amino)adamantane-1-carboxylic acid;
4-({N-cyano-2-methyl-2-[(3-methylcyclohexyl)oxy]propanimidoyl}amino)adamantane-1-carboxylic acid;
4-{[N-cyano-2-(cycloheptyloxy)-2-methylpropanimidoyl]amino}adamantane-1-carboxylic acid;
4-{[N-cyano-2-(cyclohexylmethoxy)-2-methylpropanimidoyl]amino}adamantane-1-carboxylic acid;
4-{[2-(benzyloxy)-N-cyanoethanimidoyl]amino}adamantane-1-carboxylic acid;
4-{[2-(4-chlorophenoxy)-N-cyano-2-methylpropanimidoyl]amino}adamantane-1-carboxylic acid;
4-{[N-cyano-2-(3,3-difluoropiperidin-1-yl)-2-methylpropanimidoyl]amino}-N-(1,3-thiazol-5-ylmethyl)adamantane-1-carboxamide;
4-{[N-cyano-2-(3,3-difluoropiperidin-1-yl)-2-methylpropanimidoyl]amino}-N-(2-methoxybenzyl)adamantane-1-carboxamide;
4-{[N-cyano-2-(3,3-difluoropiperidin-1-yl)-2-methylpropanimidoyl]amino}-N-(3,4-dimethoxybenzyl)adamantane-1-carboxamide;
4-({2-[9-(6-chloropyridin-3-yl)-3,9-diazabicyclo[4.2.1]non-3-yl]-N-cyano-2-methylpropanimidoyl}amino)adamantane-1-carboxamide;
4-[(2-anilino-N-cyano-2-methylpropanimidoyl)amino]adamantane-1-carboxamide;
4-({N-cyano-2-[4-(2,3-dichlorophenyl)piperazin-1-yl]-2-methylpropanimidoyl}amino)adamantane-1-carboxylic acid;
4-{[N-cyano-2-methyl-2-(4-phenylpiperazin-1-yl)propanimidoyl]amino}adamantane-1-carboxylic acid;
4-({N-cyano-2-methyl-2-[4-(4-methylphenyl)piperazin-1-yl]propanimidoyl}amino)adamantane-1-carboxylic acid;
4-({2-[4-(1,3-benzothiazol-2-yl)piperazin-1-yl]-N-cyano-2-methylpropanimidoyl}amino)adamantane-1-carboxylic acid;
4-({N-cyano-2-[4-(3,4-dichlorophenyl)piperazin-1-yl]-2-methylpropanimidoyl}amino)adamantane-1-carboxylic acid;
4-({N-cyano-2-methyl-2-[4-(3-methylphenyl)piperazin-1-yl]propanimidoyl}amino)adamantane-1-carboxylic acid;

4-[(N-cyano-2-methyl-2-{4-[2-(trifluoromethyl)phenyl]piperazin-1-yl}propanimidoyl)amino]adamantane-1-carboxylic acid;
4-({N-cyano-2-[4-(2,4-difluorophenyl)piperazin-1-yl]-2-methylpropanimidoyl}amino)adamantane-1-carboxylic acid;
4-({N-cyano-2-methyl-2-[4-(6-methylpyridin-2-yl)piperazin-1-yl]propanimidoyl}amino)adamantane-1-carboxylic acid;
4-{[N-cyano-2-methyl-2-(4-pyrimidin-2-ylpiperazin-1-yl)propanimidoyl]amino}adamantane-1-carboxylic acid;
4-({N-cyano-2-[4-(4-fluorophenyl)piperazin-1-yl]-2-methylpropanimidoyl}amino)adamantane-1-carboxylic acid;
4-[(N-cyano-2-methyl-2-{4-[3-(trifluoromethyl)phenyl]piperazin-1-yl}propanimidoyl)amino]adamantane-1-carboxylic acid;
4-[(N-cyano-2-methyl-2-{4-[3-(trifluoromethyl)pyridin-2-yl]piperazin-1-yl}propanimidoyl)amino]adamantane-1-carboxylic acid;
4-({2-[4-(3-chlorophenyl)piperazin-1-yl]-N-cyano-2-methylpropanimidoyl}amino)adamantane-1-carboxylic acid;
4-({2-[4-(4-acetylphenyl)piperazin-1-yl]-N-cyano-2-methylpropanimidoyl}amino)adamantane-1-carboxylic acid;
4-[(N-cyano-2-methyl-2-{4-[5-(trifluoromethyl)pyridin-2-yl]piperazin-1-yl}propanimidoyl)amino]-N,N-dimethyladamantane-1-carboxamide;
4-[(N-cyano-2-methyl-2-phenylpropanimidoyl)amino]adamantane-1-carboxylic acid;
4-{[2-(4-chlorophenoxy)-N-cyano-2-methylpropanimidoyl]amino}adamantane-1-carboxamide;
4-({N-cyano-2-methyl-2-[(4-methylcyclohexyl)oxy]propanimidoyl}amino)adamantane-1-carboxamide;
N-{4-[(N-cyano-2-{4-[5-(trifluoromethyl)pyridin-2-yl]piperazin-1-yl}propanimidoyl)amino]-1-adamantyl}acetamide;
4-{[N-cyano-2-methyl-2-(4-pyrimidin-2-ylpiperazin-1-yl)propanimidoyl]amino}adamantane-1-carboxamide;
4-{[N-cyano-2-methyl-2-(4-pyrazin-2-ylpiperazin-1-yl)propanimidoyl]amino}adamantane-1-carboxamide;
4-({N-cyano-2-[4-(4-fluorophenyl)piperazin-1-yl]-2-methylpropanimidoyl}amino)adamantane-1-carboxamide;
4-({N-cyano-2-[4-(3-cyanopyridin-2-yl)piperazin-1-yl]-2-methylpropanimidoyl}amino)adamantane-1-carboxamide;
4-({N-cyano-2-methyl-2-[4-(6-methylpyridin-3-yl)-1,4-diazepan-1-yl]propanimidoyl}amino)adamantane-1-carboxamide;
4-[(2-{4-[3-chloro-5-(trifluoromethyl)pyridin-2-yl]piperazin-1-yl}-N-cyano-2-methylpropanimidoyl)amino]adamantane-1-carboxylic acid;
4-[(N-cyano-2-phenoxypropanimidoyl)amino]adamantane-1-carboxamide;
4-{[2-(benzyloxy)-N-cyano ethanimidoyl]amino}adamantane-1-carboxamide;
4-(2-{[(4-{[N-cyano-2-(3,3-difluoropiperidin-1-yl)-2-methylpropanimidoyl]amino}-1-adamantyl)carbonyl]amino}ethyl)benzoic acid;
4-{[N-cyano-2-(2-methylphenoxy)propanimidoyl]amino}adamantane-1-carboxylic acid;
4-{[N-cyano-2-(4-methylphenoxy)propanimidoyl]amino}adamantane-1-carboxylic acid;
4-{[2-(2-chlorophenoxy)-N-cyano-2-methylpropanimidoyl]amino}adamantane-1-carboxylic acid;
4-[(N-cyano-2-methyl-2-phenylpropanimidoyl)amino]adamantane-1-carboxamide;
N'-cyano-N-{5-[(methylsulfonyl)amino]-2-adamantyl}-2-{4-[5-(trifluoromethyl)pyridin-2-yl]piperazin-1-yl}propanimidamide;
4-{[N-cyano-2-(2-methoxyphenoxy)-2-methylpropanimidoyl]amino}adamantane-1-carboxamide;
4-{[N-cyano-2-(4-methoxyphenoxy)-2-methylpropanimidoyl]amino}adamantane-1-carboxamide;
4-({N-cyano-2-methyl-2-[3-(trifluoromethyl)phenoxy]propanimidoyl}amino)adamantane-1-carboxamide;
N'-cyano-N-[5-(1-hydroxy-1-methylethyl)-2-adamantyl]-2-methyl-2-{4-[5-(trifluoromethyl)pyridin-2-yl]piperazin-1-yl}propanimidamide;
4-{[N-cyano-2-methyl-2-(4-methylphenoxy)propanimidoyl]amino}adamantane-1-carboxamide;
4-{[2-(3-chlorophenoxy)-N-cyano-2-methylpropanimidoyl]amino}adamantane-1-carboxamide;
4-{[N-cyano-2-methyl-2-(tetrahydro-2H-pyran-2-ylmethoxy)propanimidoyl]amino}adamantane-1-carboxylic acid;
4-{[N-cyano-2-methyl-2-(4-phenylpiperazin-1-yl)propanimidoyl]amino}adamantane-1-carboxamide;
4-{[N-cyano-2-(3-methoxyphenoxy)-2-methylpropanimidoyl]amino}adamantane-1-carboxamide;
4-({N-cyano-2-methyl-2-[4-(trifluoromethoxy)phenoxy]propanimidoyl}amino)adamantane-1-carboxamide;
4-({N-cyano-2-[4-(2-methoxyphenyl)piperazin-1-yl]-2-methylpropanimidoyl}amino)adamantane-1-carboxamide;
4-({N-cyano-2-methyl-2-[methyl(phenyl)amino]propanimidoyl}amino)adamantane-1-carboxamide;
4-({N-cyano-2-[4-(2,4-dimethoxyphenyl)piperazin-1-yl]-2-methylpropanimidoyl}amino)adamantane-1-carboxamide;
4-{[N-cyano-2-(cyclohexylmethoxy)-2-methylpropanimidoyl]amino}adamantane-1-carboxamide;
4-({N-cyano-2-[4-(2,3-dicyanophenyl)piperazin-1-yl]-2-methylpropanimidoyl}amino)adamantane-1-carboxamide;
N'-cyano-N-[5-(cyanomethyl)-2-adamantyl]-2-methyl-2-{4-[5-(trifluoromethyl)pyridin-2-yl]piperazin-1-yl}propanimidamide;
4-({N-cyano-2-methyl-2-[4-(4-nitrophenyl)piperazin-1-yl]propanimidoyl}amino)adamantane-1-carboxylic acid;
2-(4-chlorophenoxy)-N'-cyano-N-(5-hydroxy-2-adamantyl)-2-methylpropanimidamide;
4-({N-cyano-2-[4-(2,4-dichlorophenyl)piperazin-1-yl]-2-methylpropanimidoyl}amino)adamantane-1-carboxylic acid;
N-2-adamantyl-2-(4-chlorophenoxy)-N'-cyano-2-methylpropanimidamide;
N-2-adamantyl-N'-cyano-2-methyl-2-phenylpropanimidamide;
{4-[(N-cyano-2-methyl-2-{4-[5-(trifluoromethyl)pyridin-2-yl]piperazin-1-yl}propanimidoyl)amino]-1-adamantyl}acetic acid;
4-({2-[4-(4-chloro-2-fluorophenyl)piperazin-1-yl]-N-cyano-2-methylpropanimidoyl}amino)adamantane-1-carboxylic acid;
4-[(N-cyano-2-methyl-2-{4-[4-(trifluoromethyl)pyrimidin-2-yl]piperazin-1-yl}propanimidoyl)amino]adamantane-1-carboxylic acid;

4-({2-[4-(3-chloro-4-fluorophenyl)piperazin-1-yl]-N-cyano-2-methylpropanimidoyl}amino)adamantane-1-carboxylic acid;

4-({N-cyano-2-[4-(4-cyanophenyl)piperazin-1-yl]-2-methylpropanimidoyl}amino)adamantane-1-carboxylic acid;

4-({2-[4-(4-bromophenyl)piperazin-1-yl]-N-cyano-2-methylpropanimidoyl}amino)adamantane-1-carboxylic acid;

4-({2-[4-(5-chloro-2-methoxyphenyl)piperazin-1-yl]-N-cyano-2-methylpropanimidoyl}amino)adamantane-1-carboxylic acid;

4-({2-[4-(2-chlorophenyl)piperazin-1-yl]-N-cyano-2-methylpropanimidoyl}amino)adamantane-1-carboxylic acid;

4-({N-cyano-2-[4-(2-cyanophenyl)piperazin-1-yl]-2-methylpropanimidoyl}amino)adamantane-1-carboxylic acid;

4-({N-cyano-2-[4-(2-fluorophenyl)piperazin-1-yl]-2-methylpropanimidoyl}amino)adamantane-1-carboxylic acid;

4-({N-cyano-2-methyl-2-[4-(2-methylphenyl)piperazin-1-yl]propanimidoyl}amino)adamantane-1-carboxylic acid;

4-({2-[4-(4-chlorophenyl)piperazin-1-yl]-N-cyano-2-methylpropanimidoyl}amino)adamantane-1-carboxylic acid;

4-({2-[4-(3-chloropyridin-2-yl)piperazin-1-yl]-N-cyano-2-methylpropanimidoyl}amino)adamantane-1-carboxylic acid;

4-[(2-{4-[2-chloro-4-(trifluoromethyl)phenyl]piperazin-1-yl}-N-cyano-2-methylpropanimidoyl)amino]adamantane-1-carboxylic acid;

4-{[N-cyano-2-(3-fluoropyrrolidin-1-yl)-2-methylpropanimidoyl]amino}-N-(pyridin-3-ylmethyl)adamantane-1-carboxamide;

4-({2-[(4-chlorophenyl)thio]-N-cyano-2-methylpropanimidoyl}amino)adamantane-1-carboxylic acid;

4-{[N-cyano-2-methyl-2-(3-phenylpiperidin-1-yl)propanimidoyl]amino}adamantane-1-carboxamide;

4-({2-[4-(2-chloro-4-methylphenyl)piperazin-1-yl]-N-cyano-2-methylpropanimidoyl}amino)adamantane-1-carboxylic acid;

4-{[2-(3-bromophenoxy)-N-cyano-2-methylpropanimidoyl]amino}adamantane-1-carboxylic acid;

4-({N-cyano-2-[4-(2-fluorophenyl)piperidin-1-yl]-2-methylpropanimidoyl}amino)adamantane-1-carboxylic acid;

4-({N-cyano-2-methyl-2-[4-(2-methylphenyl)piperidin-1-yl]propanimidoyl}amino)adamantane-1-carboxylic acid;

4-({2-[4-(2-chloro-4-fluorophenyl)piperazin-1-yl]-N-cyano-2-methylpropanimidoyl}amino)adamantane-1-carboxamide;

4-({[(4-{[2-(4-chlorophenoxy)-N-cyano-2-methylpropanimidoyl]amino}-1-adamantyl)carbonyl]amino}methyl)benzoic acid;

4-{[2-({1-[(benzyloxy)carbonyl]piperidin-4-yl}methoxy)-N-cyano-2-methylpropanimidoyl]amino}adamantane-1-carboxylic acid;

4-({N-cyano-2-[4-(2-furoyl)piperazin-1-yl]-2-methylpropanimidoyl}amino)adamantane-1-carboxylic acid;

4-({2-[4-(2-chloro-4-cyanophenyl)piperazin-1-yl]-N-cyano-2-methylpropanimidoyl}amino)adamantane-1-carboxylic acid;

4-({2-[4-(2-chloro-4-fluorophenyl)piperazin-1-yl]-N-cyano-2-methylpropanimidoyl}amino)adamantane-1-carboxylic acid;

4-{[2-(4-chlorophenyl)-N-cyano-2-methylpropanimidoyl]amino}adamantane-1-carboxamide;

4-{[N-cyano-2-(2,3-dimethylphenoxy)-2-methylpropanimidoyl]amino}adamantane-1-carboxylic acid;

4-[(N-cyano-2-methyl-2-{4-[5-(trifluoromethyl)pyridin-2-yl]piperazin-1-yl}propanimidoyl)amino]-1-adamantyl carbamate;

4-[(2-{4-[(4-chlorophenyl)sulfonyl]piperazin-1-yl}-N-cyano-2-methylpropanimidoyl)amino]adamantane-1-carboxylic acid;

4-{[2-(benzyloxy)-N-cyano-2-methylpropanimidoyl]amino}adamantane-1-carboxylic acid;

4-({N-cyano-2-[4-(2,4-difluorophenyl)piperidin-1-yl]-2-methylpropanimidoyl}amino)adamantane-1-carboxylic acid;

4-({N-cyano-2-[4-(4-cyano-2-fluorophenyl)piperazin-1-yl]-2-methylpropanimidoyl}amino)adamantane-1-carboxylic acid;

N-[4-(aminosulfonyl)benzyl]-4-{[2-(4-chlorophenoxy)-N-cyano-2-methylpropanimidoyl]amino}adamantane-1-carboxamide;

tert-butyl 4-[2-{[5-(aminocarbonyl)-2-adamantyl]amino}-2-(cyanoimino)-1,1-dimethylethoxy]phenylcarbamate;

N-[4-(aminocarbonyl)benzyl]-4-{[2-(4-chlorophenoxy)-N-cyano-2-methylpropanimidoyl]amino}adamantane-1-carboxamide;

[(4-{[2-(4-chlorophenoxy)-N-cyano-2-methylpropanimidoyl]amino}-1-adamantyl)carbonyl]glycine;

3-({[(4-{[2-(4-chlorophenoxy)-N-cyano-2-methylpropanimidoyl]amino}-1-adamantyl)carbonyl]amino}methyl)benzoic acid;

4-[(N-cyano-2-methyl-2-{3-methyl-4-[5-(trifluoromethyl)pyridin-2-yl]piperazin-1-yl}propanimidoyl)amino]adamantane-1-carboxylic acid;

4-({N-cyano-2-[4-(4-cyanophenyl)-3,5-dimethyl-1H-pyrazol-1-yl]-2-methylpropanimidoyl}amino)adamantane-1-carboxylic acid;

4-({N-cyano-2-[4-(4-cyanophenyl)-3,5-dimethyl-1H-pyrazol-1-yl]-2-methylpropanimidoyl}amino)adamantane-1-carboxamide;

4-{[N-cyano-2-methyl-2-(4-pyridin-4-ylphenyl)propanimidoyl]amino}adamantane-1-carboxamide;

4-[(N-cyano-2-methyl-2-thien-2-ylpropanimidoyl)amino]adamantane-1-carboxamide;

4-[(N-cyano-2-methyl-2-thien-3-ylpropanimidoyl)amino]adamantane-1-carboxamide;

4-({N-cyano-2-methyl-2-[5-(trifluoromethyl)pyridin-2-yl]propanimidoyl}amino)adamantane-1-carboxamide;

4-[(N-cyano-2-methyl-2-{4-[5-(trifluoromethyl)pyridin-2-yl]phenyl}propanimidoyl)amino]adamantane-1-carboxamide;

4-({2-[4-chloro-2-(pyrrolidin-1-ylsulfonyl)phenoxy]-N-cyano-2-methylpropanimidoyl}amino)adamantane-1-carboxamide;

4-({N-cyano-2-methyl-2-[4-(methylsulfonyl)phenoxy]propanimidoyl}amino)adamantane-1-carboxamide;

4-({N-cyano-2-methyl-2-[(3-methylphenyl)amino]propanimidoyl}amino)adamantane-1-carboxamide;

tert-butyl 4-[2-{[5-(aminocarbonyl)-2-adamantyl]amino}-2-(cyanoimino)-1,1-dimethylethyl]piperazine-1-carboxylate;

N'-cyano-2-(3-fluoropyrrolidin-1-yl)-N-(5-hydroxy-2-adamantyl)propanimidamide;

4-({N-cyano-2-methyl-2-[2-(methylsulfonyl)phenoxy]
propanimidoyl}amino)adamantane-1-carboxamide;
4-({2-[4-(2-bromophenyl)piperazin-1-yl]-N-cyano-2-
methylpropanimidoyl}amino)adamantane-1-carboxy-
lic acid;
4-{[2-(4-bromophenyl)-N-cyano-2-methylpropanimi-
doyl]amino}adamantane-1-carboxamide;
4-({2-[(3-chlorophenyl)amino]-N-cyano-2-
methylpropanimidoyl}amino)adamantane-1-carboxa-
mide;
4-({N-cyano-2-[(3-methoxyphenyl)amino]-2-
methylpropanimidoyl}amino)adamantane-1-carboxa-
mide;
4-({N-cyano-2-[4-(4-cyanophenyl)-3,5-dimethyl-1H-
pyrazol-1-yl]-2-methylpropanimidoyl}amino)-N-(1,3-
thiazol-5-ylmethyl)adamantane-1-carboxamide;
4-({2-[4-(6-chloropyrimidin-4-yl)piperazin-1-yl]-N-cy-
ano-2-methylpropanimidoyl}amino)adamantane-1-
carboxylic acid;
4-({2-[4-(6-chloropyridazin-3-yl)piperazin-1-yl]-N-cy-
ano-2-methylpropanimidoyl}amino)adamantane-1-
carboxylic acid;
4-({2-[4-(2-chloropyrimidin-4-yl)piperazin-1-yl]-N-cy-
ano-2-methylpropanimidoyl}amino)adamantane-1-
carboxylic acid;
4-[(2-{4-chloro-2-[(diethylamino)sulfonyl]phenoxy}-N-
cyano-2-methylpropanimidoyl)amino]adamantane-1-
carboxamide;
N-[({4-[(N-cyano-2-methyl-2-{4-[5-(trifluoromethyl)py-
ridin-2-yl]piperazin-1-yl}propanimidoyl)amino]-1-
adamantyl}amino)carbonyl]glycine;
4-({N-cyano-2-[4-(5-cyanopyridin-2-yl)piperazin-1-yl]-
2-methylpropanimidoyl}amino)adamantane-1-car-
boxylic acid;
4-({2-[4-(3-chloro-5-cyanopyridin-2-yl)piperazin-1-yl]-
N-cyano-2-methylpropanimidoyl}amino)adamantane-
1-carboxylic acid;
4-({N-cyano-2-methyl-2-[4-(1,3-thiazol-2-yl)piperazin-
1-yl]propanimidoyl}amino)adamantane-1-carboxylic
acid;
4-({2-[(5-bromopyridin-2-yl)oxy]-N-cyano-2-
methylpropanimidoyl}amino)adamantane-1-carboxa-
mide;
4-({N-cyano-2-methyl-2-[4-(pyrrolidin-1-ylsulfonyl)phe-
noxy]propanimidoyl}amino)adamantane-1-carboxam-
ide;
4-({N-cyano-2-[(4-methoxyphenyl)amino]-2-
methylpropanimidoyl}amino)adamantane-1-carboxa-
mide;
4-[(N-cyano-2-{[4-(dimethylamino)phenyl]amino}-2-
methylpropanimidoyl)amino]adamantane-1-carboxa-
mide;
4-[(N-cyano-2-methyl-2-{[4-(trifluoromethyl)phenyl]
amino}propanimidoyl)amino]adamantane-1-carboxa-
mide;
4-[(N-cyano-2-methyl-2-{[3-(trifluoromethyl)phenyl]
amino}propanimidoyl)amino]adamantane-1-carboxa-
mide;
4-{[N-cyano-2-(2-cyanophenoxy)-2-methylpropanimi-
doyl]amino}adamantane-1-carboxamide;
4-({N-cyano-2-[4-(2-hydroxyphenyl)piperazin-1-yl]-2-
methylpropanimidoyl}amino)adamantane-1-carboxy-
lic acid;
2-(2-chloro-4-fluorophenoxy)-N'-cyano-N-(5-hydroxy-2-
adamantyl)-2-methylpropanimidamide;
4-[2-{[5-(aminocarbonyl)-2-adamantyl]amino}-2-(cy-
anoimino)-1,1-dimethylethyl]-N-(tert-butyl)pipera-
zine-1-carboxamide;
4-{[N-cyano-2-(4-hydroxyphenoxy)-2-methylpropanimi-
doyl]amino}adamantane-1-carboxamide;
4-({N-cyano-2-[(4-methoxyphenyl)thio]-2-
methylpropanimidoyl}amino)adamantane-1-carboxa-
mide;
N'-cyano-N-[5-(formylamino)-2-adamantyl]-2-methyl-2-
{4-[5-(trifluoromethyl)pyridin-2-yl]piperazin-1-
yl}propanimidamide;
2-(2-chloro-4-fluorophenoxy)-N-cyano-2-methyl-N-[5-
(2H-tetraazol-5-yl)-2-adamantyl]propanimidamide;
4-({N-cyano-2-methyl-2-[4-(1-methyl-1-pyrazol-4-yl)
phenyl]propanimidoyl}amino)adamantane-1-carboxa-
mide;
2-(2-chloro-4-fluorophenoxy)-N-cyano-2-methyl-N-[5-
(methylthio)-2-adamantyl]propanimidamide;
2-(2-chloro-4-fluorophenoxy)-N-cyano-2-methyl-N-[5-
(methylsulfonyl)-2-adamantyl]propanimidamide;
2-(2-chloro-4-fluorophenoxy)-N-cyano-2-methyl-N-[5-
(methylsulfinyl)-2-adamantyl]propanimidamide;
4-{[2-(3-bromophenyl)-N-cyano-2-methylpropanimi-
doyl]amino}adamantane-1-carboxamide;
4-({N-cyano-2-[4-(3,5-dimethylisoxazol-4-yl)phenyl]-2-
methylpropanimidoyl}amino)adamantane-1-carboxa-
mide;
4-{[N-cyano-2-methyl-2-(4-pyridin-3-ylphenyl)propan-
imidoyl]amino}adamantane-1-carboxamide;
N-[5-(aminosulfonyl)-2-adamantyl]-2-(4-chlorophe-
noxy)-N-cyano-2-methylpropanimidamide;
4-{[({4-[(N-cyano-2-methyl-2-thien-2-ylpropanimidoyl)
amino]-1-adamantyl}carbonyl)amino]methyl}benzoic
acid;
4-({N-cyano-2-methyl-2-[4-(1-pyrazol-4-yl)phenyl]
propanimidoyl}amino)adamantane-1-carboxamide;
4-{[2-(4-chlorophenoxy)-N-cyano-2-methylpropanimi-
doyl]amino}-N-(4-{[(methylsulfonyl)amino]
carbonyl}benzyl)adamantane-1-carboxamide;
4-({N-cyano-2-[(4-methoxyphenyl)sulfinyl]-2-
methylpropanimidoyl}amino)adamantane-1-carboxa-
mide;
4-({N-cyano-2-[(4-methoxyphenyl)sulfonyl]-2-
methylpropanimidoyl}amino)adamantane-1-carboxa-
mide;
2-(4-{[2-(4-chlorophenoxy)-N-cyano-2-methylpropan-
imidoyl]amino}-1-adamantyl)acetamide;
4-{[N-cyano-2-methyl-2-(1,3-thiazol-2-yl)propanimi-
doyl]amino}adamantane-1-carboxamide;
4-{[N-cyano-2-(4-hydroxyphenyl)-2-methylpropanimi-
doyl]amino}adamantane-1-carboxamide;
4-{[N-cyano-2-methyl-2-(4-phenoxyphenyl)propanimi-
doyl]amino}adamantane-1-carboxamide;
(4-{[2-(4-chlorophenoxy)-N-cyano-2-methylpropanimi-
doyl]amino}-1-adamantyl)acetic acid;
2-(4-chlorophenoxy)-N-cyano-2-methyl-N-[5-(2H-tet-
raazol-5-ylmethyl)-2-adamantyl]propanimidamide;
4-{[2-(1-benzothien-3-yl)-N-cyano-2-methylpropanimi-
doyl]amino}adamantane-1-carboxamide;
N-{5-[(aminosulfonyl)methyl]-2-adamantyl}-2-(4-chlo-
rophenoxy)-N-cyano-2-methylpropanimidamide;
4-{[2-(4-chlorophenoxy)-N-cyano-2-methylpropanimi-
doyl]amino}-N-hydroxyadamantane-1-carboximida-
mide;
4-[({[(4-{[2-(4-chlorophenoxy)-N-cyano-2-methylpropa-
nimidoyl]amino}-1-adamantyl)methyl]
sulfonyl}amino)methyl]benzoic acid;

2-(4-chlorophenoxy)-N'-cyano-N-[5-(1H-imidazol-2-yl)-2-adamantyl]-2-methylpropanimidamide;
4-{[N-cyano-2-(5-fluoropyridin-2-yl)-2-methylpropanimidoyl]amino}adamantane-1-carboxamide;
3-(4-{[2-(4-chlorophenoxy)-N-cyano-2-methylpropanimidoyl]amino}-1-adamantyl)acrylic acid;
4-[(N-cyano-2-methyl-2-{[5-(1H-pyrazol-1-yl)pyridin-2-yl]oxy}propanimidoyl)amino]adamantane-1-carboxamide;
2-(4-chlorophenoxy)-N'-cyano-N-(5-isoxazol-5-yl-2-adamantyl)-2-methylpropanimidamide;
4-[(N-cyano-2-methyl-2-quinoxalin-2-ylpropanimidoyl)amino]adamantane-1-carboxamide;
2-(4-chlorophenoxy)-N-cyano-2-methyl-N-{5-[(2-morpholin-4-ylethoxy)methyl]-2-adamantyl}propanimidamide;
N-[5-(amino sulfonyl)-2-adamantyl]-2-(2-chlorophenoxy)-N-cyano-2-methylpropanimidamide;
N-[5-(amino sulfonyl)-2-adamantyl]-Y-cyano-2-methyl-2-(2-methylphenoxy)propanimidamide;
N-[5-(amino sulfonyl)-2-adamantyl]-Y-cyano-2-methyl-2-(4-methylphenoxy)propanimidamide;
N-[5-(amino sulfonyl)-2-adamantyl]-Y-cyano-2-methyl-2-[2-(trifluoromethyl)phenoxy]propanimidamide;
N-[5-(amino sulfonyl)-2-adamantyl]-Y-cyano-2-methyl-2-[2-(trifluoromethoxy)phenoxy]propanimidamide;
N-[5-(amino sulfonyl)-2-adamantyl]-2-(2-chloro-4-fluorophenoxy)-N'-cyano-2-methylpropanimidamide;
N'-cyano-N-[5-(1-hydroxyethyl)-2-adamantyl]-2-methyl-2-{4-[5-(trifluoromethyl)pyridin-2-yl]piperazin-1-yl}propanimidamide;
2-{4-[(N-cyano-2-methyl-2-{4-[5-(trifluoromethyl)pyridin-2-yl]piperazin-1-yl}propanimidoyl)amino]-1-adamantyl}propanoic acid;
4-[(N-cyano-3-methyl-2-{4-[5-(trifluoromethyl)pyridin-2-yl]piperazin-1-yl}butanimidoyl)amino]adamantane-1-carboxamide;   —N-cyano-N-[5-hydroxy-2-adamantyl]-2-{4-[5-(trifluoromethyl)pyridin-2-yl]piperazin-1-yl}butanimidamide;
4-[((2R)—N-cyano-2-{4-[5-(trifluoromethyl)pyridin-2-yl]piperazin-1-yl}propanimidoyl)amino]adamantane-1-carboxylic acid;
4-[((2R)—N-cyano-2-{4-[5-(trifluoromethyl)pyridin-2-yl]piperazin-1-yl}butanimidoyl)amino]adamantane-1-carboxylic acid;
4-[((2R)—N'-cyano-3-methyl-2-{4-[5-(trifluoromethyl)pyridin-2-yl]piperazin-1-yl}butanimidoyl)amino]adamantane-1-carboxylic acid;
4-[((2R)—N-cyano-2-{4-[5-(trifluoromethyl)pyridin-2-yl]piperazin-1-yl}propanimidoyl)amino]-N,N-dimethyladamantane-1-carboxamide;
4-[((2R)—N-cyano-2-{4-[5-(trifluoromethyl)pyridin-2-yl]piperazin-1-yl}butanimidoyl)amino]-N,N-dimethyladamantane-1-carboxamide;
N-{4-[((2R)—N-cyano-2-{4-[5-(trifluoromethyl)pyridin-2-yl]piperazin-1-yl}butanimidoyl)amino]-1-adamantyl}acetamide;
N-{4-[((2R)—N-cyano-3-methyl-2-{4-[5-(trifluoromethyl)pyridin-2-yl]piperazin-1-yl}butanimidoyl)amino]-1-adamantyl}acetamide;
N'-cyano-2-(3,3-difluoropiperidin-1-yl)-N-[5-hydroxy-2-adamantyl]propanimidamide;
N'-cyano-N-[5-hydroxy-2-adamantyl]-2-[(3S)-3-(trifluoromethyl)pyrrolidin-1-yl]ethanimidamide;
4-({N-cyano-2-[(3R)-3-fluoropiperidin-1-yl]propanimidoyl}amino)adamantane-1-carboxamide;
N'-cyano-N-[5-methoxy-2-adamantyl]-2-{4-[5-(trifluoromethyl)pyridin-2-yl]piperazin-1-yl}propanimidamide;
4-[(N-cyano-2-{4-[5-(trifluoromethyl)pyridin-2-yl]piperazin-1-yl}pentanimidoyl)amino]adamantane-1-carboxamide;
4-{[N-cyano-2-methyl-2-(phenylthio)propanimidoyl]amino}adamantane-1-carboxamide;
4-({N-cyano-2-methyl-2-[methyl(phenyl)amino]propanimidoyl}amino)adamantane-1-carboxylic acid;
4-{[N-cyano-2-methyl-2-(2-methylphenoxy)propanimidoyl]amino}adamantane-1-carboxamide;
4-{[N-cyano-2-methyl-2-(3-methylphenoxy)propanimidoyl]amino}adamantane-1-carboxamide;
4-({N-cyano-2-methyl-2-[methyl(phenyl)amino]propanimidoyl}amino)adamantane-1-carboxamide;
4-({2-[(4-chlorophenyl)amino]-N-cyano-2-methylpropanimidoyl}amino)adamantane-1-carboxamide;
4-{[2-(2-chlorophenoxy)-N-cyano-2-methylpropanimidoyl]amino}adamantane-1-carboxamide;
4-{[N-cyano-2-(3,3-difluoropiperidin-1-yl)butanimidoyl]amino}adamantane-1-carboxamide;
4-({2-[4-(2-chloro-4-cyanophenyl)piperazin-1-yl]-N-cyano-2-methylpropanimidoyl}amino)adamantane-1-carboxamide;
N'-cyano-N-[5-hydroxy-2-adamantyl]-2-methyl-2-phenylpropanimidamide;
2-(4-chlorophenyl)-N'-cyano-N-[5-hydroxy-2-adamantyl]-2-methylpropanimidamide;
4-{[2-(4-bromo-3,5-dimethyl-1H-pyrazol-1-yl)-N-cyano-2-methylpropanimidoyl]amino}adamantane-1-carboxamide;
4-{[2-(4-chlorophenoxy)-N-cyano-2-methylpropanimidoyl]amino}-N-methyladamantane-1-carboxamide;
4-{[2-(2-chloro-4-fluorophenoxy)-N-cyano-2-methylpropanimidoyl]amino}adamantane-1-carboxamide;
4-[(N-cyano-2-methyl-2-{[4'-(methylsulfonyl)-1,1'-biphenyl-4-yl]oxy}propanimidoyl)amino]adamantane-1-carboxamide;
4-{[N-cyano-2-(3-cyanopyridin-2-yl)-2-methylpropanimidoyl]amino}adamantane-1-carboxamide;
4-({N-cyano-2-methyl-2-[2-(trifluoromethoxy)phenoxy]propanimidoyl}amino)adamantane-1-carboxamide;
4-({N-cyano-2-methyl-2-[4-(trifluoromethyl)pyridin-2-yl]propanimidoyl}amino)adamantane-1-carboxamide;
4-({2-[(5-bromopyridin-2-yl)oxy]-N-cyano-2-methylpropanimidoyl}amino)adamantane-1-carboxamide;
4-({N-cyano-2-methyl-2-[2-(trifluoromethyl)phenoxy]propanimidoyl}amino)adamantane-1-carboxamide;
4-{[2-(3-bromo-4-methoxyphenoxy)-N-cyano-2-methylpropanimidoyl]amino}adamantane-1-carboxamide;
4-{[2-(2-bromo-4-methoxyphenoxy)-N-cyano-2-methylpropanimidoyl]amino}adamantane-1-carboxamide;
4-{[N-cyano-3-(4-methoxyphenyl)-2,2-dimethyl-3-oxopropanimidoyl]amino}adamantane-1-carboxamide;
4-[(N-cyano-2-methyl-2-{[4-(trifluoromethoxy)phenyl]amino}propanimidoyl)amino]adamantane-1-carboxamide;
4-[(N-cyano-2-methyl-2-{[4-(trifluoromethoxy)phenyl]thio}propanimidoyl)amino]adamantane-1-carboxamide;
4-{[2-(2-chloro-4-fluorophenoxy)-N-cyano-2-methylpropanimidoyl]amino}-N,N-dimethyladamantane-1-carboxamide;

4-({N-cyano-2-methyl-2-[3-(1,3-thiazol-4-ylmethoxy)phenyl]propanimidoyl}amino)adamantane-1-carboxamide;
4-({N-cyano-2-methyl-2-[3-(2-morpholin-4-ylethoxy)phenyl]propanimidoyl}amino)adamantane-1-carboxamide;
N-[5-(5-amino-4H-1,2,4-triazol-3-yl)-2-adamantyl]-2-(4-chlorophenoxy)-N'-cyano-2-methylpropanimidamide;
4-{[N-cyano-2-(6-fluoropyridin-3-yl)-2-methylpropanimidoyl]amino}adamantane-1-carboxamide;
2-(4-chlorophenoxy)-Y-cyano-N-[5-(hydroxymethyl)-2-adamantyl]-2-methylpropanimidamide;
4-{[N-cyano-2-methyl-2-(6-morpholin-4-ylpyridin-3-yl)propanimidoyl]amino}adamantane-1-carboxamide;
4-{[N-cyano-2-(5-fluoropyridin-2-yl)-2-methylpropanimidoyl]amino}adamantane-1-carboxamide;
4-({N-cyano-2-methyl-2-[6-(methylamino)pyridin-3-yl]propanimidoyl}amino)adamantane-1-carboxamide;
4-[(N-cyano-2-{[5-(1H-imidazol-1-yl)pyridin-2-yl]oxy}-2-methylpropanimidoyl)amino]adamantane-1-carboxamide;
4-[(N-cyano-2-methyl-2-{[5-(1H-pyrazol-1-yl)pyridin-2-yl]oxy}propanimidoyl)amino]adamantane-1-carboxamide;
4-[(N-cyano-2-methyl-2-quinoxalin-2-ylpropanimidoyl)amino]adamantane-1-carboxamide;
N-[5-(amino sulfonyl)-2-adamantyl]-2-(3-chlorophenoxy)-N-cyano-2-methylpropanimidamide;
N-[5-(amino sulfonyl)-2-adamantyl]-N-cyano-2-methyl-2-(3-methylphenoxy)propanimidamide;
N-[5-(amino sulfonyl)-2-adamantyl]-N-cyano-2-(2-methoxyphenoxy)-2-methylpropanimidamide;
N-[5-(amino sulfonyl)-2-adamantyl]-N-cyano-2-(3-methoxyphenoxy)-2-methylpropanimidamide;
(2S)-amino (4-{[2-(2-chloro-4-fluorophenoxy)-N-cyano-2-methylpropanimidoyl]amino}-1-adamantyl)acetic acid;
2-[(4-{[2-(2-chloro-4-fluorophenoxy)-N-cyano-2-methylpropanimidoyl]amino}-1-adamantyl)sulfonyl]acetamide;
N'-cyano-N-[5-hydroxy-2-adamantyl]-2-methyl-2-(4-nitrophenyl)propanimidamide;
2-[(4-bromopyridin-2-yl)oxy]-N-cyano-2-methyl-N-[5-(methylsulfonyl)-2-adamantyl]propanimidamide;
(2S)-2-(4-{[2-(2-chloro-4-fluorophenoxy)-N-cyano-2-methylpropanimidoyl]amino}-1-adamantyl)propanoic acid;
N-[5-(amino sulfonyl)-2-adamantyl]-2-(1,1'-biphenyl-2-yloxy)-N-cyano-2-methylpropanimidamide;
4-{[2-(1,1'-biphenyl-2-yloxy)-N-cyano-2-methylpropanimidoyl]amino}adamantane-1-carboxylic acid;
N'-cyano-2-(2,4-dichlorophenoxy)-2-methyl-N-[5-(methylsulfonyl)-2-adamantyl]propanimidamide;
2-(2-bromo-4-fluorophenoxy)-N-cyano-2-methyl-N-[5-(methylsulfonyl)-2-adamantyl]propanimidamide;
N'-cyano-2-methyl-2-(2-methylphenoxy)-N-[5-(methylsulfonyl)-2-adamantyl]propanimidamide;
N'-cyano-2-methyl-2-(4-methylphenoxy)-N-[5-(methylsulfonyl)-2-adamantyl]propanimidamide;
2-(2-chlorophenoxy)-N-cyano-2-methyl-N-[5-(methylsulfonyl)-2-adamantyl]propanimidamide;
2-(4-chlorophenoxy)-N-cyano-2-methyl-N-[5-(methylsulfonyl)-2-adamantyl]propanimidamide;
N'-cyano-2-(4-methoxyphenoxy)-2-methyl-N-[5-(methylsulfonyl)-2-adamantyl]propanimidamide;
N'-cyano-2-(2-cyanophenoxy)-2-methyl-N-[5-(methylsulfonyl)-2-adamantyl]propanimidamide;
N'-cyano-2-(2-methoxyphenoxy)-2-methyl-N-[5-(methylsulfonyl)-2-adamantyl]propanimidamide;
2-[(3-bromopyridin-2-yl)oxy]-N-cyano-2-methyl-N-[5-(methylsulfonyl)-2-adamantyl]propanimidamide;
N-[5-(aminosulfonyl)-2-adamantyl]-2-(2-bromo-4-fluorophenoxy)-N-cyano-2-methylpropanimidamide;
2-(4-chlorophenoxy)-N-cyano-2-methyl-N-{5-[(methylthio)methyl]-2-adamantyl}propanimidamide;
N-[5-(aminosulfonyl)-2-adamantyl]-N-cyano-2-(2,4-dichlorophenoxy)-2-methylpropanimidamide;
N-[5-(aminosulfonyl)-2-adamantyl]-N-cyano-2-(2,4-dimethylphenoxy)-2-methylpropanimidamide;
N-[5-(aminosulfonyl)-2-adamantyl]-N-cyano-2-(4-fluoro-2-methylphenoxy)-2-methylpropanimidamide;
N-[5-(amino sulfonyl)-2-adamantyl]-N-cyano-2-(2,6-dichloro-4-methylphenoxy)-2-methylpropanimidamide;
N-[5-(amino sulfonyl)-2-adamantyl]-N-cyano-2-(2,6-dichloro-4-fluorophenoxy)-2-methylpropanimidamide;
N-[5-(amino sulfonyl)-2-adamantyl]-2-(4-chloro-2-fluorophenoxy)-N-cyano-2-methylpropanimidamide;
N-[5-(amino sulfonyl)-2-adamantyl]-2-(2-chloro-4-methylphenoxy)-N-cyano-2-methylpropanimidamide;
N-[5-(amino sulfonyl)-2-adamantyl]-N-cyano-2-(mesityloxy)-2-methylpropanimidamide;
2-(4-chlorophenoxy)-N-cyano-2-methyl-N-{5-[(methylsulfonyl)methyl]-2-adamantyl}propanimidamide;
N-[5-(amino sulfonyl)-2-adamantyl]-N-cyano-2-(2,4-difluorophenoxy)-2-methylpropanimidamide;
N-[5-(amino sulfonyl)-2-adamantyl]-N-cyano-2-(4-fluorophenoxy)-2-methylpropanimidamide;
N'-cyano-2-(2,4-difluorophenoxy)-2-methyl-N-[5-(methylsulfonyl)-2-adamantyl]propanimidamide;
N'-cyano-2-(2-isopropylphenoxy)-2-methyl-N-[5-(methylsulfonyl)-2-adamantyl]propanimidamide;
N'-cyano-2-(4-fluoro-2-methylphenoxy)-2-methyl-N-[5-(methylsulfonyl)-2-adamantyl]propanimidamide;
N'-cyano-2-(2-fluorophenoxy)-2-methyl-N-[5-(methylsulfonyl)-2-adamantyl]propanimidamide;
N'-cyano-2-methyl-N-[5-(methylsulfonyl)-2-adamantyl]-2-[2-(trifluoromethyl)phenoxy]propanimidamide;
(2S)-2-amino-2-(4-{[2-(2-chloro-4-fluorophenoxy)-N-cyano-2-methylpropanimidoyl]amino}-1-adamantyl)acetamide;
N'-cyano-2-[4-fluoro-2-(1H-pyrazol-1-yl)phenoxy]-2-methyl-N-[5-(methylsulfonyl)-2-adamantyl]propanimidamide;
N'-cyano-2-(2,6-dichloro-4-fluorophenoxy)-2-methyl-N-[5-(methylsulfonyl)-2-adamantyl]propanimidamide;
N'-cyano-2-[4-fluoro-2-(1H-pyrazol-4-yl)phenoxy]-2-methyl-N-[5-(methylsulfonyl)-2-adamantyl]propanimidamide;
N'-cyano-2-methyl-N-[5-(methylsulfonyl)-2-adamantyl]-2-[3-(trifluoromethoxy)phenoxy]propanimidamide;
3-deutero-4-[(N-cyano-2-methyl-2-{[4-(trifluoromethyl)benzyl]oxy}propanimidoyl)amino]adamantane-1-carboxamide;
4-[(N-cyano-2-methyl-2-{[4-(trifluoromethyl)benzyl]oxy}propanimidoyl)amino]-7-deutero-adamantane-1-carboxamide;
N-[1-deutero-4-adamantyl]-N-cyano-2-methyl-2-{[4-(trifluoromethyl)benzyl]oxy}propanimidamide;
3-deutero-4-[(N-cyano-2-methyl-2-{4-[5-(trifluoromethyl)pyridin-2-yl]piperazin-1-yl}propanimidoyl)amino]adamantane-1-carboxamide;

4-[(N-cyano-2-methyl-2-{4-[5-(trifluoromethyl)pyridin-2-yl]piperazin-1-yl}propanimidoyl)amino]-7-deutero-adamantane-1-carboxamide;

N-[1-deutero-4-adamantyl]-N-cyano-2-methyl-2-{4-[5-(trifluoromethyl)pyridin-2-yl]piperazin-1-yl}propanimidamide;

3-[(N-cyano-2-methyl-2-{[4-(trifluoromethyl)benzyl]oxy}propanimidoyl)amino]adamantane-1-carboxamide;

N-1-azabicyclo[2.2.2]oct-3-yl-N-cyano-2-methyl-2-{[4-(trifluoromethyl)benzyl]oxy}propanimidamide; and N-[1-azatricyclo[3.3.1.13,7]dec-4-yl]-N-cyano-2-methyl-2-{4-[5-(trifluoromethyl)pyridin-2-yl]piperazin-1-yl}propanimidamide.

* * * * *